(12) United States Patent
Abraham et al.

(10) Patent No.: US 9,308,207 B2
(45) Date of Patent: Apr. 12, 2016

(54) JAK KINASE MODULATING COMPOUNDS AND METHODS OF USE THEREOF

(71) Applicant: Ambit Biosciences Corp., San Diego, CA (US)

(72) Inventors: Sunny Abraham, San Diego, CA (US); Qi Chao, San Diego, CA (US); Michael J. Hadd, San Diego, CA (US); Mark W. Holladay, San Diego, CA (US); Gang Liu, San Diego, CA (US); Eduardo Setti, San Diego, CA (US)

(73) Assignee: Ambit Biosciences Corp., San Diego, CA (US)

( * ) Notice: Subject to any disclaimer, the term of this patent is extended or adjusted under 35 U.S.C. 154(b) by 0 days.

(21) Appl. No.: 14/558,488

(22) Filed: Dec. 2, 2014

(65) Prior Publication Data

US 2015/0150874 A1 Jun. 4, 2015

Related U.S. Application Data

(60) Continuation of application No. 13/645,406, filed on Oct. 4, 2012, now Pat. No. 8,927,711, which is a division of application No. 12/714,323, filed on Feb. 26, 2010, now Pat. No. 8,349,851.

(60) Provisional application No. 61/156,447, filed on Feb. 27, 2009, provisional application No. 61/294,083, filed on Jan. 11, 2010, provisional application No. 61/294,490, filed on Jan. 13, 2010.

(51) Int. Cl.
| | |
|---|---|
| *C07D 403/12* | (2006.01) |
| *A61K 31/517* | (2006.01) |
| *C07D 401/14* | (2006.01) |
| *C07D 405/14* | (2006.01) |
| *A61K 31/5377* | (2006.01) |
| *A61K 45/06* | (2006.01) |

(52) U.S. Cl.
CPC ............ *A61K 31/517* (2013.01); *A61K 31/5377* (2013.01); *A61K 45/06* (2013.01); *C07D 401/14* (2013.01); *C07D 403/12* (2013.01); *C07D 405/14* (2013.01)

(58) Field of Classification Search
CPC .................................................... C07D 403/12
See application file for complete search history.

(56) References Cited

U.S. PATENT DOCUMENTS

| | | | |
|---|---|---|---|
| 3,536,809 A | 10/1970 | Zaffaroni et al. |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,436,233 A | 7/1995 | Lee et al. |
| 5,591,767 A | 1/1997 | Mohr et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,698,220 A | 12/1997 | Cardinal et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,798,119 A | 8/1998 | Herbig et al. |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |

(Continued)

FOREIGN PATENT DOCUMENTS

| | | |
|---|---|---|
| CN | 101463014 | 6/2009 |
| EP | 00579496 | 7/1992 |

(Continued)

OTHER PUBLICATIONS

Barton, et al., Mol. Canc. Ther. 3(1): 11-20, 2004.

(Continued)

*Primary Examiner* — Brian McDowell
(74) *Attorney, Agent, or Firm* — Jones Day

(57) ABSTRACT

Provided herein are quinazoline compounds of formula (I):

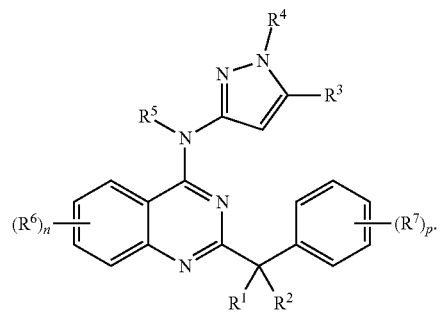

The compounds are useful for treatment of JAK kinase mediated diseases, including JAK2 kinase-, JAK3 kinase- or TYK2 kinase-mediated diseases. Also provided are pharmaceutical compositions comprising the compounds and methods of using the compounds and compositions.

19 Claims, 6 Drawing Sheets

(56) References Cited

U.S. PATENT DOCUMENTS

| | | |
|---|---|---|
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,080,747 A | 6/2000 | Uckun et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,204,267 B1 | 3/2001 | Tang et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,740,634 B1 | 5/2004 | Saikawa et al. |
| 7,087,603 B2 | 8/2006 | Bebbington et al. |
| 7,432,275 B2 | 10/2008 | Bakthavatchalam et al. |
| 2005/0038023 A1 | 2/2005 | Bebbington et al. |
| 2006/0194805 A1 | 8/2006 | Bakthavatchalam et al. |
| 2008/0312258 A1 | 12/2008 | Rodgers et al. |
| 2008/0312259 A1 | 12/2008 | Rodgers et al. |

FOREIGN PATENT DOCUMENTS

| | | |
|---|---|---|
| EP | 00944616 | 11/1996 |
| WO | WO 02/17918 | 3/2002 |
| WO | WO 03/062209 | 7/2003 |
| WO | WO 2004/015142 | 2/2004 |
| WO | WO 2004/020441 | 3/2004 |
| WO | WO 2004/054582 | 7/2004 |
| WO | WO 2004/055003 | 7/2004 |
| WO | WO 2004/080463 | 9/2004 |
| WO | WO 2006/067614 | 6/2006 |
| WO | WO 2008/005310 | 1/2008 |

OTHER PUBLICATIONS

Baxter, et al., Lancet 365, pp. 1054-1056, 2005.
Blume-Jensen, et al., Nature 411 (6836):355-356, 2001.
Borie, et al., Transplantation 79(7): 791-801, 2005.
Bousquet et al., Oncogene 24:7248-7252, 2005.
Bromberg, J. Clin.Invest. 109(9):1139-1142, 2002.
Campbell, et al., Blood 107(5): 2098-2100, 2006.
Erba, et al., J. Chem. Soc., Perkin Trans. 1, pp. 3021-3024, 1997.
Samanta Cancer Res. 66 pp. 6468-6472, 2006.
Tang, Jacs, v124-2870-2871, 2002.
Fabian et al., Nature Biotechnology 23, 329-336, 2005.
Griesinger, et al., Genes Chromosomes Cancer 44:329-333, 2005.
Lacronique, et al., Science 278:1309-1312, 1997.
Lacronique, et al., Blood 95:2076-2083, 2000.
Levine, et al., Blood 107 (10) 4139-4141, 2006.
Mercher et al., Blood 108(8): 2770-2778, 2007.
Middleton et al., J. Org. Chem. 45(14): 2883-2887, 1980.
Milici, et al., Arthritis Research 10(R14):1-9, 2008.
Pakrashi, J. Org. Chem, vol. 36, No. 5, 1971.
Pardanani, et al., Leukemia 21:1658-1668, 2007.
Pardanani, A, Leukemia 22:23-30, 2008.
Rane, et al., Oncogene 19, pp. 5662-5679, 2000.
Santus and Baker, J. Controlled Release, 35, pp. 1-21, 1995.
Sawyers, et al., Cell, 70, pp. 901-910 1992.
Schwaller, et al., Mol. Cell. 6:693-704, 2000.
Scott, et al., N Eng J Med 356(5): 459-468, 2007.
Still, et al., J. Org. Chem. 43:2923-5, 1978.
Tefferi, N. Eng. J. Med. 356 (5) pp. 444-445, 2007.
Verma, et al., Drug Development and Industrial Pharmacy, 26, pp. 695-708, 2000.
Verma, et al., J. Controlled Release, 79, pp. 7-27, 2002.
Wright, et al., Bioorganic & Medicinal Chem Lett. 11:17-21, 2001.
Wright, et al., J. Med. Chem. 45, pp. 3865-3877, 2002.
Zhao, et al., EMBO 21(9):2159-2167, 2002.
Glossary of Terms Used in Medicinal Chemistry (IUPAC Recommendations 1998).
Bendingfield et al., British Journal of Pharmacology, 116: 3323-3329 (1995).
Office Action mailed Oct. 19, 2011 in U.S. Appl. No. 12/714,323.
Office Action mailed Feb. 28, 2012 in U.S. Appl. No. 12/714,323.
Office Action mailed Jul. 5, 2013 in U.S. Appl. No. 13/645,406.
Office Action mailed Jan. 29, 2014 in U.S. Appl. No. 13/645,406.

JAK KINASE MODULATING COMPOUNDS AND METHODS OF USE THEREOF

RELATED APPLICATIONS

This application claims priority under 35 U.S.C. 120 to, and is a continuation of, U.S. patent application Ser. No. 13/645,406, filed Oct. 4, 2012, now allowed, which claims priority under 35 U.S.C. §120 to, and is a divisional of, U.S. patent application Ser. No. 12/714,323, filed Feb. 26, 2010, issued on Jan. 8, 2013 as U.S. Pat. No. 8,349,851, which claims priority to U.S. provisional application Nos. 61/156,447, filed Feb. 27, 2009, 61/294,083, filed Jan. 11, 2010 and 61/294,490, filed Jan. 13, 2010. The disclosures of the above referenced applications are incorporated by reference herein in their entireties.

FIELD

Provided herein are compounds that are modulators of JAK kinases, compositions comprising the compounds and methods of use thereof. The compounds provided are useful in the treatment, prevention, or amelioration of a disease or disorder related to JAK, including JAK2, JAK3 or TYK2 kinases, or one or more symptoms associated with such diseases or disorders. Further provided are methods for treatment of cancer, including blood borne and solid tumors.

BACKGROUND

The JAK kinase family is a cytoplasmic protein kinase family comprising the members JAK1, JAK2, JAK3 and TYK2. Growth factor or cytokine receptors that recruit JAK kinases include the interferon receptors, interleukin receptors (receptors for the cytokines IL-2 to IL-7, IL-9 to IL-13, IL-15, IL-23), various hormone receptors (erythropoietin (Epo) receptor, the thrombopoietin (Tpo) receptor, the leptin receptor, the insulin receptor, the prolactin (PRL) receptor, the Granulocyte Colony-Stimulating Factor (G-CSF) receptor and the growth hormone receptor, receptor protein tyrosine kinases (such as EGFR and PDGFR), and receptors for other growth factors such as leukemia inhibitory factor (LIF), Oncostatin M (OSM), IFNα/β/γ, Granulocyte-macrophage colony-stimulating factor (GM-CSF), Ciliary neurotrophic factor (CNTF), cardiotrophin-1 (CT-1) (See, Rane, S. G. and Reddy E. P., Oncogene 2000 19, 5662-5679).

Phosphorylated receptors serve as docking sites for other SH-2 domain containing signaling molecules that interact with JAKs such as the STAT family of transcription factors, Src family of kinases, MAP kinases, PI3 kinase and protein tyrosine phosphatases (Rane S. G. and Reddy E. P., Oncogene 2000 19, 5662-5679). The family of latent cytoplasmic transcription factors, STATs, is the most well characterized downstream substrates for JAKs. The STAT proteins bind to phosphorylated cytokine receptors through their SH2 domains to become phosphorylated by JAKs, which leads to their dimerization and release and eventual translocation to the nucleus where they activate gene transcription. The various members of STAT which have been identified thus far, are STAT1, STAT2, STAT3, STAT4, STAT5 (including STAT5a and STAT5b) and STAT6.

Since the JAK kinases may play an important signaling role via such receptors, disorders of fat metabolism, growth disorders and disorders of the immune system are all potential therapeutic targets.

The JAK kinases and JAK2 mutations are implicated in myeloproliferative disorders, cancers, including blood borne and solid tumors. Exemplary disorders include chronic myeloid leukemia (CML), polycythemia vera (PV), essential thrombocythemia (ET), primary myelofibrosis (PMF), chronic eosinophilic leukemia (CEL), chronic myelomonocytic leukemia (CMML) and systemic mastocytosis (SM). Myeloproliferative disorders are believed to arise from either gain-of-function mutations to JAK itself or from activation by the oncoprotein BCR-ABL, which specifically activates the JAK2 pathway. Several literature reports describe role of JAK2 mutations in various disorders. See, Samanta et al. Cancer Res 2006, 66(13), 6468-6472, Sawyers et al. Cell, 1992, 70, 901-910, Tefferi N. Eng. J. Med. (2007) 356(5): 444-445) Baxter et al. Lancet (2005) 365:1054-1056, Levine et al. Blood (2006, Jones et al. Blood (2005) 106:2162-2168) 107:4139-4141, Campbell et al. Blood (2006) 107(5): 2098-2100, Scott et al. N Eng J Med 2007 356(5): 459-468, Mercher et al. Blood (2006) 108(8): 2770-2778, Lacronique et al. Science (1997) 278:1309-1312, Lacronique et al. Blood (2000) 95:2535-2540, Griesinger F. et al. Genes Chromosomes Cancer (2005) 44:329-333, Bousquet et al. Oncogene (2005) 24:7248-7252, Schwaller et al. Mol. Cell. 2000 6, 693-704, Zhao et al. EMBO 2002 21(9), 2159-2167.

Literature indicates that JAK may also serve as a target for prostate cancer, including androgen-resistant prostate cancer. See, Barton et al. Mol. Canc. Ther. 2004 3(1), 11-20, Blume-Jensen et al. Nature (2001) 411(6835):355-356 and Bromberg J Clin Invest. (2002) 109(9):1139-1142, Rane Oncogene (2000) 19(49):5662-5679. JAK as a prominent mediator of the cytokine signaling pathway, is considered to be a therapeutic target for inflammation and transplant rejections. See, Borie et al., Transplantation (2005) 79(7):791-801 and Milici et al., Arthritis Research (2008) 10(R14):1-9

Given the multitude of diseases attributed to the dysregulation of JAK signaling, many small molecule inhibitors of JAK are currently being developed. Examples of compounds in preclinical development include TG101209 (TargeGen), examples are compounds being investigated in clinical studies include INCB018424 (Incyte), XL019 (Exelixis) and TG101348 (TargeGen). See, Pardanani et al. Leukemia 2007, 21:1658-1668; and Pardanai, A. Leukemia 2008 22:23-20.

There is, however, an ever-existing need to provide novel classes of compounds that are useful as inhibitors of enzymes in the JAK signaling pathway.

SUMMARY

Provided herein are compounds of formula (I)

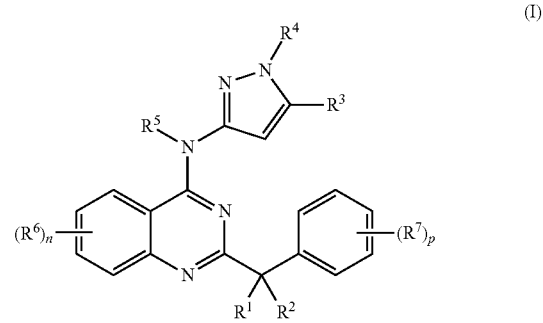

or pharmaceutically acceptable salts, solvates or hydrates thereof, wherein
$R^1$ and $R^2$ are selected from (i), (ii), (iii), (iv) and (v) as follows:
(i) $R^1$ and $R^2$ together form =O, =S, =NR$^9$ or =CR$^{10}$R$^{11}$;
(ii) $R^1$ and $R^2$ are both —OR$^8$, or $R^1$ and $R^2$, together with the carbon atom to which they are attached, form dioxacycloalkyl;

(iii) $R^1$ is hydrogen or halo; and $R^2$ is halo; and (iv) $R^1$ is alkyl, alkenyl, alkynyl, cycloalkyl or aryl, wherein the alkyl, alkenyl, alkynyl, cycloalkyl and aryl is optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$, —$R^xNR^yR^z$ and —C(O)$OR^w$; and $R^2$ is hydrogen, halo or —$OR^8$; and (v) $R^1$ is halo, deutero, —$OR^{12}$, —$NR^{13}R^{14}$, or —$S(O)_qR^{15}$; and $R^2$ is hydrogen, deutero, alkyl, alkenyl, alkynyl, cycloalkyl or aryl, wherein the alkyl, alkenyl, alkynyl, cycloalkyl and aryl is optionally substituted with one or more, in one embodiment, one to four, in one embodiment, one to three, in one embodiment, one, two or three, substituents selected from halo, cyano, alkyl, —$R^xOR^w$, —$R^xS(O)_qR^v$ and —$R^xNR^yR^z$;

$R^3$ is hydrogen, halo, alkyl, cyano, haloalkyl, cycloalkyl, cycloalkylalkyl, hydroxy or alkoxy;

$R^4$ and $R^5$ are each independently hydrogen or alkyl;

each $R^6$ is independently selected from halo, alkyl, alkenyl, alkynyl, haloalkyl, cycloalkyl, —$R^xOR^{18}$, —$R^xNR^{19}R^{20}$, and —$R^xS(O)_qR^v$;

each $R^7$ is independently halo, alkyl, haloalkyl or —$R^x$-$OR^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —C(O)$OR^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)$R^v$, —C(O)$OR^w$ and —C(O)$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:

(i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)$R^v$, —C(O)$OR^w$, —C(O)$NR^yR^z$ and —S(O)$_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or (ii) $R^{13}$ and $R^{14}$, together with the nitrogen atom to which they are attached, form heterocyclyl or heteroaryl wherein the heterocyclyl or heteroaryl are substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)$NR^yR^z$ or —$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxy$C_{2-6}$alkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, alkoxysulfonyl, hydroxycarbonyl, cycloalkyl, heterocyclyl, aryl, heteroaryl, haloaryl and amino;

$R^{19}$ and $R^{20}$ are selected as follows:

(i) $R^{19}$ and $R^{20}$ are each independently hydrogen or alkyl; or (ii) $R^{19}$ and $R^{20}$, together with the nitrogen atom to which they are attached, form a heterocyclyl or heteroaryl which is optionally substituted with 1 to 2 groups each independently selected from halo, alkyl, haloalkyl, hydroxyl and alkoxy;

each $R^x$ is independently alkylene or a direct bond;

$R^v$ is hydrogen, alkyl, alkenyl or alkynyl;

$R^w$ is independently hydrogen, alkyl, alkenyl, alkynyl or haloalkyl;

$R^y$ and $R^z$ are selected as follows:

(i) $R^y$ and $R^z$ are each independently hydrogen, alkyl, alkenyl, alkynyl, cycloalkyl or haloalkyl;

(ii) $R^y$ and $R^z$, together with the nitrogen atom to which they are attached, form a heterocyclyl or heteroaryl which are optionally substituted with 1 to 2 groups each independently selected from halo, alkyl, haloalkyl, hydroxyl and alkoxy;

n is 0-4;

p is 0-5; and each q is independently 0, 1 or 2.

In certain embodiments, the compounds have activity as JAK kinase, including JAK2 kinase, modulators. The compounds are useful in medical treatments, pharmaceutical compositions and methods for modulating the activity of JAK kinase, including wildtype and/or mutated forms of JAK kinase. In certain embodiments, the compounds provided herein have activity as JAK2 kinase modulators. In certain embodiments, the compounds are inhibitors of JAK kinase, including JAK2 kinase.

In one embodiment, the compounds for use in the compositions and methods provided herein are compounds of formula (I).

In one embodiment, the compound provided herein is a compound of formula (I). In one embodiment, the compound provided herein is a pharmaceutically acceptable salt of the compound of formula (I). In one embodiment, the compound provided herein is a solvate of the compound of formula (I). In one embodiment, the compound provided herein is a hydrate of compound of formula (I).

Also provided are pharmaceutical compositions formulated for administration by an appropriate route and means containing effective concentrations of one or more of the compounds provided herein, or pharmaceutically acceptable salts, solvates and hydrates thereof, and optionally comprising at least one pharmaceutical carrier.

Such pharmaceutical compositions deliver amounts effective for the treatment, prevention, or amelioration of diseases or disorders that include without limitation, myeloproliferative disorders such as polycythemia vera (PCV), essential thrombocythemia (ET), primary myelofibrosis (PMF), chronic eosinophilic leukemia (CEL), chronic myelomonocytic leukemia (CMML), systemic mastocytosis (SM) and idiopathic myelofibrosis (IMF); leukemia such as myeloid leukemia including chronic myeloid leukemia (CML), imatinib-resistant forms of CML, acute myeloid leukemia (AML), and a subtype of AML, acute megakaryoblastic leukemia (AMKL); lymphoproliferative diseases such as myeloma; cancer such as cancer of the head and neck, prostate cancer, breast cancer, ovarian cancer, melanoma, lung cancers, brain tumors, pancreatic cancer and renal cancer; and inflammatory diseases or disorders related to immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma chronic obstructive pulmonary disease (COPD) and dry eye syndrome (or keratoconjunctivitis sicca (KCS)). In one embodiment, such diseases or disorders are modulated or otherwise affected by the JAK kinases, including JAK2, JAK3 or TYK2.

Also provided herein are combination therapies using one or more compounds or compositions provided herein, or pharmaceutically acceptable salts, solvates or hydrates thereof, in combination with other pharmaceutically active agents for the treatment of the diseases and disorders described herein.

In one embodiment, such additional pharmaceutical agents include one or more chemotherapeutic agents, anti-proliferative agents, anti-inflammatory agents, immunomodulatory agents or immunosuppressive agents.

The compounds or compositions provided herein, or pharmaceutically acceptable salts, solvates or hydrates thereof, may be administered simultaneously with, prior to, or after administration of one or more of the above agents. Pharmaceutical compositions containing a compound provided herein and one or more of the above agents are also provided.

In certain embodiments, provided herein are methods of treating, preventing or ameliorating a disease or disorder that is modulated or otherwise affected by JAK kinases, including JAK2 kinase such as wild type and/or mutant JAK2 kinase, or one or more symptoms or causes thereof. In another embodiment, provided herein are methods of treating, preventing or ameliorating a disease or disorder by modulating the JAK2 kinase selectively over JAK3 kinase. In yet another embodiment, provided herein are methods of treating, preventing or ameliorating a disease or disorder by modulating the JAK3 kinase selectively over JAK2 kinase. In another embodiment, provided herein are methods of treating, preventing or ameliorating a disease or disorder by modulating both JAK2 and JAK3. In one embodiment, provided are methods for treatment of cancer, including blood borne and solid tumors.

In practicing the methods, effective amounts of the compounds or compositions containing therapeutically effective concentrations of the compounds, which are formulated for systemic delivery, including parenteral, oral, or intravenous delivery, or for local or topical application are administered to an individual exhibiting the symptoms of the disease or disorder to be treated. The amounts are effective to ameliorate or eliminate one or more symptoms of the disease or disorder.

These and other aspects of the subject matter described herein will become evident upon reference to the following detailed description.

DETAILED DESCRIPTION

Figure 1:
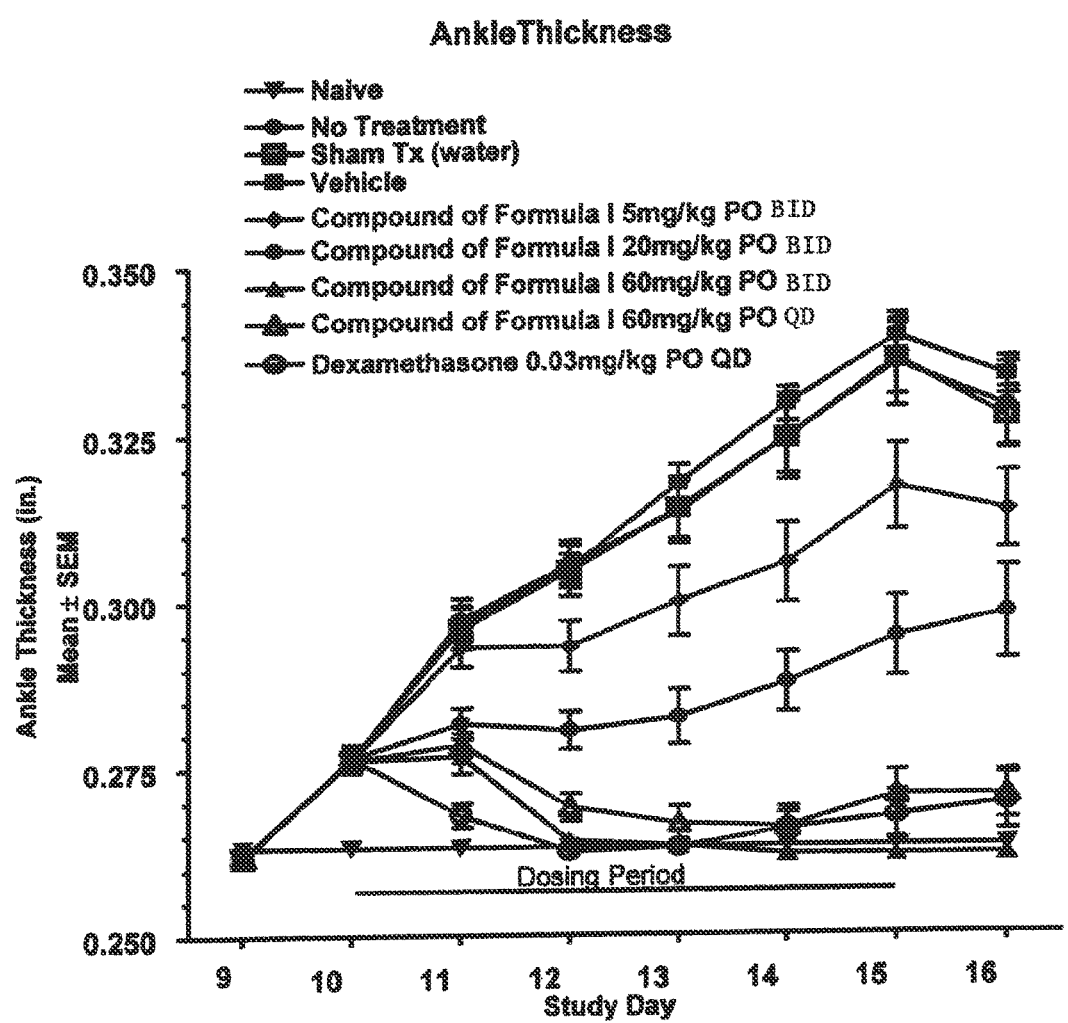
FIG. 1 provides in vivo data to demonstrate dose responsive effects of a compound of Formula I in rat Type II Collagen-Induced Arthritis (CIA) model.

Provided herein are compounds of formula (I) that have activity as JAK kinase, including JAK2 kinase, modulators. Further provided are methods of treating, preventing or ameliorating diseases that are modulated by JAK kinases, including JAK2 kinase, and pharmaceutical compositions and dosage forms useful for such methods. The methods and compositions are described in detail in the sections below.

In certain embodiments, the compounds provided herein are JAK2 selective, i.e., the compounds bind or interact with JAK2 at substantially lower concentrations than they bind or interact with other JAK receptors, including JAK3 receptor, at that same concentration. In certain embodiments, the compounds bind to JAK3 receptor at a binding constant at least about 3-fold higher, about 5-fold higher, about 10-fold higher, about 20-fold higher, about 25-fold higher, about 50-fold higher, about 75-fold higher, about 100-fold higher, about 200-fold higher, about 225-fold higher, about 250 fold higher, or about 300 fold higher than they bind JAK2 receptor.

In certain embodiments, the compounds provided herein are JAK3 selective, i.e., the compounds bind or interact with JAK3 at substantially lower concentrations than they bind or interact with other JAK receptors, including JAK2 receptor, at that same concentration. In certain embodiments, the compounds bind to JAK2 receptor at a binding constant at least about 3-fold higher, about 5-fold higher, about 10-fold higher, about 20-fold higher, about 25-fold higher, about 50-fold higher, about 75-fold higher, about 100-fold higher, about 200-fold higher, about 225-fold higher, about 250 fold higher, or about 300 fold higher than they bind with JAK3 receptor.

In certain embodiments, the compounds provided herein have Kd of greater than about 10 nM, 20 nM, 25 nM, 40 nM, 50 nM, or 70 nM against Aurora B kinase. Methods for determining binding constant against Aurora B kinase are known to one of skill in the art. Exemplary methods are described in U.S. provisional application No. 61/294,413, and Fabian et al., *Nature Biotechnology* 2005, 23, 329-336.

A. DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain group consisting solely of carbon and hydrogen atoms, containing no unsaturation, having from one to ten, one to eight, one to six or one to four carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkenyl" refers to a straight or branched hydrocarbon chain group consisting solely of carbon and hydrogen atoms, containing at least one double bond, in certain embodiment, having from 2 to 10 carbon atoms, from 2 to 8 carbon atoms, or from 2 to 6 carbon atoms, and which is attached to the rest of the molecule by a single bond or a double bond, e.g., ethenyl, prop-1-enyl, but-1-enyl, pent-1-enyl, penta-1,4-dienyl, and the like.

"Alkynyl" refers to a straight or branched hydrocarbon chain group consisting solely of carbon and hydrogen atoms, containing at least one triple bond, having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkoxy" refers to the group having the formula —OR wherein R is alkyl or haloalkyl, where the alkyl may be optionally substituted by one or more substituents, in one embodiment, one, two or three substitutents independently selected from the group consisting of nitro, halo, hydroxyl, alkoxy, oxo, thioxo, amino, carbony, carboxy, azido, cyano, cycloalkyl, heteroaryl, and heterocyclyl.

"Alkoxyalkyl" refers to a group having the formula —$R_h$OR wherein $R_h$ is a straight or branched alkylene chain and OR is alkoxy as defined above.

"Alkylthio" refers to a group having the formula —SR wherein R is alkyl or haloalkyl.

"aryloxy" refers to the group —OR, in which R is aryl, including lower aryl, such as phenyl.

"Amine" or "amino" refers to a group having the formula —NR'R" wherein R' and R" are each independently hydrogen, alkyl, haloalkyl, hydroxyalkyl or alkoxyalkyl or wherein R' and R", together with the nitrogen atom to which they are attached form a heterocyclyl optionally substituted with halo, oxo, hydroxy or alkoxy.

"Aminoalkyl" refers to a group having the formula —$R_h$NR'R" wherein $R_h$ is a straight or branched alkylene chain and wherein NR'R" is amino as defined above.

"Aminocarbonyl" refers to a group having the formula —C(O)NR'R" wherein —NR'R" is amino as defined above.

"Aryl" refers to a group of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene. The term includes both substituted and unsubstituted moieties. The aryl group can be substituted with any described moiety, including, but not limited to, one or more moieties selected from the group consisting of halo (fluoro, chloro, bromo or iodo), alkyl, hydroxyl, amino, alkoxy, aryloxy, nitro and cyano.

"Cycloalkyl" refers to a stable monovalent monocyclic or bicyclic hydrocarbon group consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl, norbornane, norbornene, adamantyl, bicyclo[2.2.2]octane and the like.

"Cycloalkylalkyl" refers to a group of the formula —$R_aR_d$ where $R_a$ is an alkyl group as defined above and $R_d$ is a cycloalkyl group as defined above. The alkyl group and the cycloalkyl group may be optionally substituted as defined herein.

"Deutero" or "deuterium" refers to the hydrogen isotope deuterium having the chemical symbol D.

"Halo", "halogen" or "halide" refers to F, Cl, Br or I.

"Haloalkyl" refers to an alkyl group, in certain embodiments, $C_{1-6}$alkyl group in which one or more of the hydrogen atoms are replaced by halogen. Such groups include, but are not limited to, chloromethyl, trifluoromethyl, 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, 2,2-difluorocyclopropyl, (trifluoromethyl)cyclopropyl, 4,4-difluorocyclohexyl and 2,2,2-trifluoro-1,1-dimethyl-ethyl.

"Heterocyclyl" refers to a stable 3- to 15-membered ring group which consists of carbon atoms and from one to five heteroatoms selected from a group consisting of nitrogen, oxygen and sulfur. In one embodiment, the heterocyclic ring system group may be a monocyclic, bicyclic or tricyclic ring or tetracyclic ring system, which may include fused or bridged ring systems; and the nitrogen or sulfur atoms in the heterocyclic ring system group may be optionally oxidized; the nitrogen atom may be optionally quaternized; and the heterocyclyl group may be partially or fully saturated or aromatic. The heterocyclic ring system may be attached to the main structure at any heteroatom or carbon atom which results in the creation of a stable compound. Exemplary heterocylic radicals include, azetidinyl, benzopyranonyl, benzopyranyl, benzotetrahydrofuranyl, benzotetrahydrothienyl, chromanyl, chromonyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4 dithianyl, isobenzotetrahydrofuranyl, isobenzotetrahydrothienyl, isochromanyl, isocoumarinyl, benzo[1,3]dioxol-5-yl, benzodioxolyl, 1,3-dioxolan-2-yl, dioxolanyl, morpholinyl, octahydroindolyl, octahydroisoindolyl, tetrahydrofuran, oxazolidin-2-onyl, oxazolidinonyl, piperidinyl, piperazinyl, pyranyl, tetrahydrofuryl, tetrahydrofuranyl, tetrahydroisoquinolinyl, tetrahydropyranyl, tetrahydrothienyl, pyrrolidinonyl, oxathiolanyl, and pyrrolidinyl.

"Heteroaryl" refers to a heterocyclyl group as defined above which is aromatic. The heteroaryl group may be attached to the main structure at any heteroatom or carbon atom which results in the creation of a stable compound. Examples of such heteroaryl groups include, but are not limited to: acridinyl, benzimidazolyl, benzindolyl, benzisoxazinyl, benzo[4,6]imidazo[1,2-a]pyridinyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, cinnolinyl, dibenzofuranyl, furanyl, imidazolyl, imidazopyridinyl, imidazothiazolyl, indazolyl, indolizinyl, indolyl, isobenzothienyl, isoindolinyl, isoquinolinyl, isothiazolidinyl, isothiazolyl, naphthyridinyl, octahydroindolyl, octahydroisoindolyl, oxazolidinonyl, oxazolidinyl, oxazolopyridinyl, oxazolyl, isoxazolyl, oxiranyl, perimidinyl, phenanthridinyl, phenanthrolinyl, phenarsazinyl, phenazinyl, phenothiazinyl, phenoxazinyl, phthalazinyl, pteridinyl, purinyl, pyrazinyl, pyrazolyl, pyridazinyl, pyridinyl, pyridopyridinyl, pyrimidinyl, pyrrolyl, quinazolinyl, quinolinyl, quinoxalinyl, tetrazolyl, thiadiazolyl, thiazolyl, thienyl, triazinyl and triazolyl.

"Aralkyl" refers to a group of the formula —$R_aR_b$ where $R_a$ is an alkyl group as defined above, substituted by $R_b$, an aryl group, as defined above, e.g., benzyl. Both the alkyl and aryl groups may be optionally substituted as defined herein.

"Heteroaralkyl" refers to a group of the formula —$R_aR_f$ where $R_a$ is an alkyl group as defined above and $R_f$ is a heteroaryl group as defined herein. The alkyl group and the heteroaryl group may be optionally substituted as defined herein.

"Heterocyclylalkyl" refers to a group of the formula —$R_aR_e$ wherein $R_a$ is an alkyl group as defined above and $R_e$ is a heterocyclyl group as defined herein, where the alkyl group $R_a$ may attach at either the carbon atom or the heteroatom of the heterocyclyl group $R_e$. The alkyl group and the heterocyclyl group may be optionally substituted as defined herein.

"Alkoxycarbonyl" refers to a group having the formula —C(O)OR in which R is alkyl, including lower alkyl.

The term "dioxacycloalkyl" as used herein means a heterocyclic group containing two oxygen ring atoms and two or more carbon ring atoms.

"Oxo" refers to the group =O attached to a carbon atom.

"Thioalkyl" refers to a group having the formula —$R_hSR_i$ where the $R_h$ is a straight or branched alkylene chain and $R_i$ is alkyl or haloalkyl.

"Thioxo" refers to the group =S attached to a carbon atom.

"$IC_{50}$" refers to an amount, concentration or dosage of a particular test compound that achieves a 50% inhibition of a maximal response, such as cell growth or proliferation measured via any the in vitro or cell based assay described herein.

Unless stated otherwise specifically described in the specification, it is understood that the substitution can occur on any atom of the alkyl, alkenyl, alkynyl, cycloalkyl, heterocyclyl, aryl or heteroaryl group.

Pharmaceutically acceptable salts include, but are not limited to, salts of mineral acids, such as hydrochlorides; and salts of organic acids, such as but not limited to mesylate, esylate, tosylate, besylate, brosylate, camphorsulfonate, hydrobromide, phosphate, sulfate, trifluoroacetate, acetate, benzoate, fumarate, malate, maleate, oxalate, succinate and tartrate.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate and the like).

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein. Thus, the compounds provided herein may be enantiomerically pure, or be stereoisomeric or diastereomeric mixtures.

It is to be understood that the compounds provided herein may contain chiral centers. Such chiral centers may be of either the (R) or (S) configuration, or may be a mixture thereof.

Optically active (+) and (−), (R)- and (S)-, or (D)- and (L)-isomers may be prepared using chiral synthons or chiral reagents, or resolved using conventional techniques, such as reverse phase HPLC or by crystallization.

As used herein, the term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the desired enantiomer.

Where the number of any given substituent is not specified (e.g., haloalkyl), there may be one or more substituents present. For example, "haloalkyl" may include one or more of the same or different halogens.

In the description herein, if there is any discrepancy between a chemical name and chemical structure, the structure preferably controls.

As used herein, "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxrubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, and radiation treatment.

"Anti-inflammatory agents" refers to matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate, salicylsalicyclic acid), COX-1 or COX-2 inhibitors), or glucocorticoid receptor agonists such as corticosteroids, methylprednisone, prednisone, or cortisone.

As used herein, the abbreviations for any protective groups, amino acids and other compounds, are, unless indicated otherwise, in accord with their common usage or recognized abbreviations including abbreviations found in *J. Org. Chem.* 2007 72(1): 23A-24A or abbreviations established by the IUPAC-IUB Commission on Biochemical Nomenclature (see, *Biochem.* 1972, 11:942-944).

B. COMPOUNDS

Provided herein are compounds of formula (I) or pharmaceutically acceptable salts, solvates or hydrates thereof, wherein $R^1$ and $R^2$ are selected from (i), (ii), (iii), (iv) and (v) as follows:
  (i) $R^1$ and $R^2$ together form =O, =S, =NR$^9$ or =CR$^{10}$R$^{11}$;
  (ii) $R^1$ and $R^2$ are both —OR$^8$, or $R^1$ and $R^2$, together with the carbon atom to which they are attached, form dioxacycloalkyl;
  (iii) $R^1$ is hydrogen or halo; and $R^2$ is halo; and
  (iv) $R^1$ is alkyl, alkenyl, alkynyl, cycloalkyl or aryl, wherein the alkyl, alkenyl, alkynyl, cycloalkyl and aryl is optionally substituted with one or more substituents selected from halo, alkyl, —R$^x$OR$^w$, —R$^x$S(O)$_q$R$^v$, —R$^x$NR$^y$R$^z$ and —C(O)OR$^w$; and R$^2$ is hydrogen, halo or —OR$^8$; and
  (v) $R^1$ is halo, —OR$^{12}$, —NR$^{13}$R$^{14}$, or —S(O)$_q$R$^{15}$; and $R^2$ is hydrogen, alkyl, alkenyl, alkynyl, cycloalkyl or aryl, wherein the alkyl, alkenyl, alkynyl, cycloalkyl and aryl, is optionally substituted with one or more substituents selected from halo, alkyl, —R$^x$OR$^w$, —R$^x$S(O)$_q$R$^v$ and —R$^x$NR$^y$R$^z$;

$R^3$ is hydrogen, halo, alkyl, cyano, haloalkyl, cycloalkyl, cycloalkylalkyl, hydroxy or alkoxy;
$R^4$ and $R^5$ are each independently hydrogen or alkyl;
each $R^6$ is independently selected from halo, alkyl, alkenyl, alkynyl, haloalkyl, cycloalkyl, R$^x$OR$^{18}$ and —R$^x$NR$^{19}$R$^{20}$;
each $R^7$ is independently halo, alkyl, haloalkyl or —R$^x$-OR$^w$;
$R^8$ is alkyl, alkenyl or alkynyl;

$R^9$ is hydrogen, alkyl, haloalkyl, hydroxy, alkoxy or amino;
$R^{10}$ is hydrogen or alkyl;
$R^{11}$ is hydrogen, alkyl, haloalkyl or —C(O)OR$^8$;
$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)R$^v$, —C(O)OR$^w$ and —C(O)NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;
$R^{13}$ and $R^{14}$ are selected as follows:
  (i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)R$^v$, —C(O)OR$^w$, —C(O)NR$^y$R$^z$ and —S(O)$_q$R$^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio; or
  (ii) $R^{13}$ and $R^{14}$, together with the nitrogen atom to which they are attached, form heterocyclyl or heteroaryl wherein the heterocyclyl or heteroaryl is optionally substituted with one or more substituents independently selected from halo, alkyl, hydroxy, alkoxy, amino and alkylthio and wherein the heterocyclyl is also optionally substituted with oxo;
$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)NR$^y$R$^z$ or —NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;
$R^{18}$ is hydrogen, alkyl, haloalkyl, hydroxyC$_{2-6}$alkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups Q$^1$, each Q$^1$ independently selected from alkyl, hydroxyl, halo, haloalkyl, alkoxy, aryloxy, alkoxyalkyl, alkoxycarbonyl, hydroxycarbonyl, cycloalkyl, heterocyclyl, aryl, heteroaryl, haloaryl and amino;
$R^{19}$ and $R^{20}$ are selected as follows:
  (i) $R^{19}$ and $R^{20}$ are each independently hydrogen or alkyl; or
  (ii) $R^{19}$ and $R^{20}$, together with the nitrogen atom to which they are attached, form a heterocyclyl or heteroaryl which is optionally substituted with 1 to 2 groups each independently selected from halo, alkyl, haloalkyl, hydroxyl and alkoxy;
each $R^x$ is independently alkylene or a direct bond;
$R^v$ is alkyl, alkenyl or alkynyl;
$R^w$ is independently hydrogen, alkyl, alkenyl, alkynyl or haloalkyl;
$R^y$ and $R^z$ are selected as follows:
  (i) $R^y$ and $R^z$ are each independently hydrogen, alkyl, alkenyl, alkynyl, cycloalkyl or haloalkyl;
  (ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy;
n is 0-4;
p is 0-5; and
each q is independently 0, 1 or 2.

In certain embodiments, provided herein are compounds of formula (II)

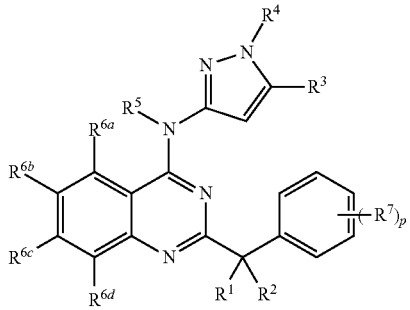

(II)

or pharmaceutically acceptable salts, solvates or hydrates thereof, wherein $R^1$ and $R^2$ are selected from (i), (ii), (iii), (iv) and (v) as follows:
(i) $R^1$ and $R^2$ together form =O, =S, =NR$^9$ or =CR$^{10}$R$^{11}$;
(ii) $R^1$ and $R^2$ are both —OR$^8$, or $R^1$ and $R^2$, together with the carbon atom to which they are attached, form dioxacycloalkyl;
(iii) $R^1$ is hydrogen or halo, and $R^2$ is halo;
(iv) $R^1$ is alkyl, alkenyl, alkynyl, cycloalkyl or aryl, wherein the alkyl, alkenyl, alkynyl, cycloalkyl and aryl is optionally substituted with one or more substitutents selected from halo, alkyl, —R$^x$OR$^w$, —R$^x$S(O)$_q$R$^v$ and —R$^x$NR$^y$R$^z$ and $R^2$ is hydrogen, halo and —OR$^8$; and
(v) $R^1$ is halo, —OR$^{12}$, —NR$^{13}$R$^{14}$, —S(O)$_q$R$^{15}$ or —R$^{17}$C(O)OR$^{12}$, and $R^2$ is hydrogen, alkyl, alkenyl, alkynyl, cycloalkyl or aryl, wherein the alkyl, alkenyl, alkynyl, cycloalkyl and aryl is optionally substituted with one or more substitutents selected from halo, alkyl, —R$^x$OR$^w$, —R$^x$S(O)$_q$R$^v$ and —R$^x$NR$^y$R$^z$;

$R^3$ is hydrogen, alkyl or, cycloalkyl,
$R^4$ and $R^5$ are each independently hydrogen or alkyl;
$R^{6a}$, $R^{6b}$, $R^{6c}$, and $R^{6d}$ are each independently selected from halo, alkyl, haloalkyl —R$^x$S(O)$_q$R$^v$, and —R$^x$OR$^{18}$;

each $R^7$ is independently halo, alkyl, haloalkyl or —R$^x$OR$^w$;
$R^8$ is alkyl, alkenyl or alkynyl;
$R^9$ is hydrogen, alkyl, haloalkyl, hydroxy, alkoxy or amino;
$R^{10}$ is hydrogen or alkyl;
$R^{11}$ is hydrogen, alkyl, haloalkyl or —C(O)OR$^8$;
each $R^{12}$ is independently hydrogen, alkyl, haloalkyl, hydroxyalkyl, alkoxyalkyl, aminoalkyl, thioalkyl, heterocyclylalkyl or —C(O)NR$^y$R$^z$;
$R^{13}$ and $R^{14}$ are selected as follows:
(i) $R^{13}$ is hydrogen or alkyl, and $R^{14}$ is selected from hydrogen, alkyl, haloalkyl, hydroxyalkyl, alkoxyalkyl, aminoalkyl, thioalkyl, heterocyclylalkyl, —C(O)R$^v$, —C(O)OR$^w$, —C(O)NR$^y$R$^z$ and —S(O)$_q$R$^v$; or
(ii) $R^{13}$ and $R^{14}$, together with the nitrogen atom to which they are attached, form heterocyclyl optionally substituted with one more substitutents independently selected from halo, oxo, alkyl, hydroxy, alkoxy, amino and alkylthio;
$R^{15}$ is selected from hydrogen, alkyl, haloalkyl, hydroxyalkyl, alkoxyalkyl, aminoalkyl, thioalkyl, heterocycylalkyl, —C(O)NR$^y$R$^z$ or —NR$^y$R$^z$;

$R^{18}$ is hydrogen, alkyl, haloalkyl, hydroxyalkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, hydroxycarbonyl, cycloalkyl, heterocyclyl, aryl, heteroaryl, haloaryl and amino;
$R^v$ is hydrogen, alkyl, alkenyl or alkynyl;
each $R^x$ is independently alkylene or a direct bond;
$R^w$ is independently hydrogen or alkyl;
$R^y$ and $R^z$ are selected as follows:
(i) $R^y$ and $R^z$ are each independently hydrogen, alkyl, alkenyl, alkynyl, cycloalkyl or haloalkyl;
(ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy; and
each q is independently 0, 1 or 2.

In certain embodiments, provided herein are compounds of formula (III) or (IIIa)

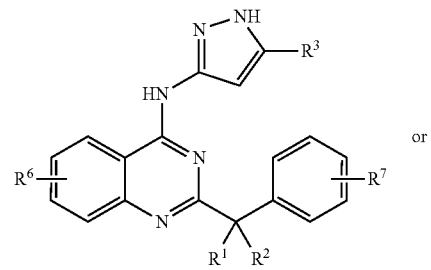

(III)

or

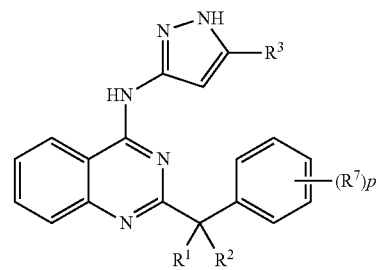

(IIIa)

or pharmaceutically acceptable salts, solvates or hydrates thereof, wherein
$R^3$ is hydrogen, alkyl, haloalkyl or cycloalkyl;
each $R^6$ is independently selected from halo, alkyl, haloalkyl, —R$^x$S(O)$_q$R$^v$ and —R$^x$OR$^{18}$;
each $R^7$ is independently halo, alkyl, haloalkyl or —R$^x$OR$^w$; p is 1 or 2; and other variables are as described elsewhere herein.

In certain embodiments, provided herein are compounds of formula (III), (IIIa) or pharmaceutically acceptable salts, solvates or hydrates thereof, wherein
$R^3$ is hydrogen, alkyl, haloalkyl or cycloalkyl;
each $R^6$ is independently selected from halo, alkyl, haloalkyl, —R$^x$S(O)$_q$R$^v$ and —R$^x$OR$^{18}$;
each $R^7$ is independently halo, alkyl, haloalkyl or —R$^x$OR$^w$; and other variables are as described elsewhere herein.

In certain embodiments, provided herein are compounds of formula (III), (IIIa) or pharmaceutically acceptable salts, solvates or hydrates thereof, wherein $R^3$ is hydrogen or alkyl or cycloalkyl;

each $R^6$ is independently selected from halo, alkyl, haloalkyl, and —$R^xOR^{18}$;

each $R^7$ is independently halo, alkyl, haloalkyl or —$R^xOR^w$; and the other variables are as described elsewhere herein.

In certain embodiments, provided herein are compounds of formula (III), (IIIa) or pharmaceutically acceptable salts, solvates or hydrates thereof, wherein $R^3$ is hydrogen or alkyl;

each $R^6$ is independently selected from halo, alkyl, alkenyl, alkynyl, haloalkyl, cycloalkyl, —$R^xOR^{18}$, —$R^xS(O)_qR^v$ and —$R^xNR^{19}R^{20}$;

each $R^7$ is independently halo, alkyl, haloalkyl or —$R^xOR^w$; p is 1; and the other variables are as described elsewhere herein.

In certain embodiments, provided herein are compounds of formula (III), (IIIa) or pharmaceutically acceptable salts, solvates or hydrates thereof, wherein $R^3$ is hydrogen or alkyl;

each $R^6$ is independently selected from halo, alkyl, haloalkyl, and —$R^xOR^{18}$;

each $R^7$ is independently halo, alkyl, haloalkyl or —$R^xOR^w$; and the other variables are as described elsewhere herein.

In certain embodiments, provided herein are compounds of formula (III), (IIIa) or pharmaceutically acceptable salts, solvates or hydrates thereof, wherein $R^3$ is hydrogen, alkyl or haloalkyl;

each $R^6$ is independently selected from halo, alkyl, haloalkyl, —$R^x(O)_qR^v$ and —$R^xOR^{18}$;

each $R^7$ is independently halo, alkyl, haloalkyl or —$R^xOR^w$; and the other variables are as described elsewhere herein.

In certain embodiments, provided herein are compounds of formula (III), (IIIa) or pharmaceutically acceptable salts, solvates or hydrates thereof, wherein $R^3$ is hydrogen, alkyl, cycloalkyl, hydroxyl or alkoxy;

each $R^6$ is independently selected from halo, alkyl, haloalkyl, and —$R^xOR^{18}$;

each $R^7$ is independently halo, alkyl, haloalkyl or —$R^xOR^w$; and the other variables are as described elsewhere herein.

In certain embodiments, provided herein are compounds of formula (III), (IIIa) or pharmaceutically acceptable salts, solvates or hydrates thereof, wherein $R^3$ is hydrogen, alkyl, cycloalkyl, hydroxyl or alkoxy;

each $R^6$ is independently selected from halo, alkyl, alkenyl, alkynyl, haloalkyl, cycloalkyl, —$R^xOR^{18}$ and —$R^xNR^{19}R^{20}$;

each $R^7$ is independently halo, alkyl, haloalkyl or —$R^xOR^w$; and the other variables are as described elsewhere herein.

In one embodiment, $R^1$ and $R^2$ are selected from (i), (ii), (iii), (iv) and (v) as follows:
(i) $R^1$ and $R^2$ together form =O;
(ii) $R^1$ and $R^2$ are both hydroxy, or $R^1$ and $R^2$, together with the carbon atom to which they are attached, form dioxacycloalkyl;
(iii) $R^1$ is hydrogen or halo; and $R^2$ is halo; and
(iv) $R^1$ is alkyl, alkenyl, alkynyl or cycloalkyl, wherein the alkyl, alkenyl, alkynyl and cycloalkyl is substituted with one or more, in one embodiment, one to four, in one embodiment, one to three, in one embodiment, one, two or three, substitutents selected from halo, cyano, alkyl, —$R^xOR^w$, —$R^xS(O)_qR^v$, —$R^xNR^yR^z$ and —C(O)OR$^w$; and $R^2$ is hydrogen, halo or hydroxy; and
(v) $R^1$ is halo, deutero, hydroxy or amino; and $R^2$ is hydrogen, deutero, alkyl, alkenyl, alkynyl or cycloalkyl, wherein the alkyl, alkenyl, alkynyl and cycloalkyl, is optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$ and —$R^xNR^yR^z$; and the other variables are as described elsewhere herein.

In another embodiment, $R^1$ and $R^2$ are selected from (i), (ii), (iii), (iv) and (v) as follows:
(i) $R^1$ and $R^2$ together form =O;
(ii) $R^1$ and $R^2$ are both hydroxy, or $R^1$ and $R^2$, together with the carbon atom to which they are attached, form dioxacycloalkyl;
(iii) $R^1$ is hydrogen or halo; and $R^2$ is halo; and
(iv) $R^1$ is alkyl, alkenyl, alkynyl or cycloalkyl, wherein the alkyl, alkenyl, alkynyl and cycloalkyl is substituted with one or more, in one embodiment, one to four, in one embodiment, one to three, in one embodiment, one, two or three, substitutents selected from halo, cyano, alkyl, —$R^xOR^w$, —$R^xS(O)_qR^v$, —$R^xNR^yR^z$ and —C(O)OR$^w$; and $R^2$ is hydrogen, halo or hydroxy; and
(v) $R^1$ is halo, deutero, hydroxy or amino; and $R^2$ is hydrogen, deutero, alkyl, alkenyl, alkynyl or cycloalkyl, wherein the alkyl, alkenyl, alkynyl and cycloalkyl, is optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$ and —$R^xNR^yR^z$; and the other variables are as described elsewhere herein.

In one embodiment, $R^1$ and $R^2$ are selected from (i), (ii), (iii), (iv) and (v) as follows:
(i) $R^1$ and $R^2$ together form =O, =S, =NR$^9$ or =CR$^{10}$R$^{11}$;
(ii) $R^1$ and $R^2$ are both alkoxy, or $R^1$ and $R^2$, together with the carbon atom to which they are attached, form dioxacycloalkyl;
(iii) $R^1$ is hydrogen or halo, and $R^2$ is halo;
(iv) $R^1$ is alkyl, alkenyl, alkynyl, cycloalkyl or aryl and $R^2$ is hydrogen, halo hydroxy and alkoxy; and
(v) $R^1$ is deutero, hydroxyl, alkoxy, amino, alkoxycarbonylamino, and —NHC(O)H and $R^2$ is hydrogen, deutero, alkyl, aryl or haloaryl.

In one embodiment, $R^1$ and $R^2$ are selected from (i), (ii), (iii), (iv) and (v) as follows:
(i) $R^1$ and $R^2$ together form =O, =S, =NR$^9$ or =CR$^{10}$R$^{11}$;
(ii) $R^1$ and $R^2$ are both alkoxy, or $R^1$ and $R^2$, together with the carbon atom to which they are attached, form dioxacycloalkyl;
(iii) $R^1$ is hydrogen or halo, and $R^2$ is halo;
(iv) $R^1$ is alkyl, alkenyl, alkynyl, cycloalkyl or aryl and $R^2$ is hydrogen, halo hydroxy and alkoxy; and
(v) $R^1$ is hydroxyl, alkoxy, amino or alkoxycarbonylamino and $R^2$ is hydrogen, alkyl, aryl or haloaryl.

In one embodiment, $R^1$ and $R^2$ are selected from (i), (ii), (iii), (iv) and (v) as follows:
(i) $R^1$ and $R^2$ together form =O, =S, =NR$^9$ or =CR$^{10}$R$^{11}$;
(ii) $R^1$ and $R^2$ are both alkoxy, or $R^1$ and $R^2$, together with the carbon atom to which they are attached, form dioxacycloalkyl;
(iii) $R^1$ is hydrogen or halo, and $R^2$ is halo;

(iv) $R^1$ is alkyl, cyanoalkyl, alkenyl, alkynyl, cycloalkyl or aryl and $R^2$ is hydrogen, halo hydroxy and alkoxy; and (v) $R^1$ is hydroxyl, alkoxy, amino or alkoxycarbonylamino and $R^2$ is hydrogen, alkyl, aryl or haloaryl.

In one embodiment, $R^1$ and $R^2$ are selected from (i), (ii), (iii) and (iv) as follows:

(i) $R^1$ and $R^2$ together form =O;

(ii) $R^1$ and $R^2$ are both alkoxy, or $R^1$ and $R^2$ together with the carbon atom to which they are attached, form dioxacycloalkyl;

(iii) $R^1$ is hydrogen or halo, and $R^2$ is halo; and (iv) $R^1$ is hydroxyl, alkoxy, amino or alkoxycarbonylamino and $R^2$ is hydrogen, alkyl, aryl or haloaryl.

In one embodiment, $R^1$ and $R^2$ together form =O.

In one embodiment, $R^1$ is hydrogen, halo or deutero and $R^2$ is halo or deutero.

In one embodiment, $R^1$ and $R^2$ are selected from (i) and (ii) as follows:

(i) $R^1$ and $R^2$ are both alkoxy or $R^1$ and $R^2$, together form =O; and (ii) $R^1$ is hydroxyl, $-OR^{12}$ or $-NR^{13}R^{14}$; and $R^2$ is hydrogen, alkyl, aryl or haloaryl;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, $-C(O)R^v$, $-C(O)OR^w$ and $-C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;

$R^{13}$ and $R^{14}$ are selected as follows:

(i) $R^{13}$ is hydrogen or alkyl, and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, $-C(O)R^v$, $-C(O)OR^w$, $-C(O)NR^yR^z$ and $-S(O)_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio; or (ii) $R^{13}$ and $R^{14}$, together with the nitrogen atom to which they are attached, form heterocyclyl or heteroaryl, wherein the heterocyclyl or heteroaryl is optionally substituted with one or more substituents independently selected from halo, alkyl, hydroxy, alkoxy, amino and alkylthio, and wherein the heterocyclyl is also optionally substituted with oxo;

$R^v$ is hydrogen, alkyl, alkenyl or alkynyl;

$R^w$ is independently hydrogen, alkyl, alkenyl, alkynyl or haloalkyl;

$R^y$ and $R^z$ are selected as follows:

(i) $R^y$ and $R^z$ are each independently hydrogen, alkyl, alkenyl, alkynyl, cycloalkyl or haloalkyl;

(ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy; and each q is independently 0, 1 or 2.

In one embodiment, $R^1$ and $R^2$ are selected from (i) and (ii) as follows:

(i) $R^1$ and $R^2$ are both alkoxy or $R^1$ and $R^2$, together form =O; and (ii) $R^1$ is hydroxyl, $-OR^{12}$ or $-NR^{13}R^{14}$; and $R^2$ is hydrogen, alkyl, aryl or haloaryl;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, $-C(O)R^v$, $-C(O)OR^w$ and $-C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;

$R^{13}$ and $R^{14}$ are selected as follows:

(i) $R^{13}$ is hydrogen or alkyl, and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, $-C(O)R^v$, $-C(O)OR^w$, $-C(O)NR^yR^z$ and $-S(O)_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio; or (ii) $R^{13}$ and $R^{14}$, together with the nitrogen atom to which they are attached, form heterocyclyl or heteroaryl, wherein the heterocyclyl or heteroaryl is optionally substituted with one or more substituents independently selected from halo, alkyl, hydroxy, alkoxy, amino and alkylthio, and wherein the heterocyclyl is also optionally substituted with oxo;

$R^v$ is alkyl, alkenyl or alkynyl;

$R^w$ is independently hydrogen, alkyl, alkenyl, alkynyl or haloalkyl;

$R^y$ and $R^z$ are selected as follows:

(i) $R^y$ and $R^z$ are each independently hydrogen, alkyl, alkenyl, alkynyl, cycloalkyl or haloalkyl;

(ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy; and each q is independently 0, 1 or 2.

In another embodiment, $R^{12}$ is hydrogen or alkyl; $R^{13}$ is hydrogen or alkyl and $R^{14}$ is alkyl, cycloalkyl, $-C(O)R^v$ or $-C(O)OR^w$, where $R^v$ and $R^w$ are each independently hydrogen or alkyl.

In another embodiment, $R^{12}$ is hydrogen or alkyl; $R^{13}$ is hydrogen or alkyl and $R^{14}$ is alkyl, cycloalkyl or $-C(O)OR^w$, where $R^v$ and $R^w$ are each independently hydrogen or alkyl.

In one embodiment, $R^1$ and $R^2$ are selected from (i), (ii) and (iii) as follows:

(i) $R^1$ and $R^2$ together form =O;

(ii) $R^1$ and $R^2$ are both alkoxy; and (iii) $R^1$ is hydroxy or alkoxy and $R^2$ is hydrogen.

In one embodiment, $R^1$ and $R^2$ are selected from (i) and (ii) as follows:

(i) $R^1$ and $R^2$ together form =O; and (ii) $R^1$ is hydroxy or alkoxy and $R^2$ is hydrogen.

In one embodiment, $R^1$ is $-OR^{12}$ or $-NR^{13}R^{14}$ and $R^2$ is hydrogen, wherein $R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, $-C(O)R^v$, $-C(O)OR^w$ and $-C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;

$R^{13}$ and $R^{14}$ are selected as follows:
(i) $R^{13}$ is hydrogen or alkyl and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)$R^v$, —C(O)O$R^w$, —C(O)N$R^y R^z$ and —S(O)$_q R^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio; or
(ii) $R^{13}$ and $R^{14}$, together with the nitrogen atom to which they are attached, form heterocyclyl or heteroaryl wherein the heterocyclyl and heteroaryl is optionally substituted with one or more substituents independently selected from halo, alkyl, hydroxy, alkoxy, amino and alkylthio, and wherein the heterocyclyl is also optionally substituted with oxo;
$R^v$ is alkyl, alkenyl or alkynyl;
$R^w$ is independently hydrogen, alkyl, alkenyl, alkynyl or haloalkyl;
$R^y$ and $R^z$ are selected as follows:
(i) $R^y$ and $R^z$ are each independently hydrogen, alkyl, alkenyl, alkynyl, cycloalkyl or haloalkyl;
(ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy; and
each q is independently 0, 1 or 2.

In another embodiment, $R^{12}$ is hydrogen or alkyl; $R^{13}$ and $R^{14}$ are selected as follows: (i) $R^{13}$ is hydrogen or alkyl and $R^{14}$ is alkyl, cycloalkyl or —C(O)O$R^w$; or (ii) $R^{13}$ and $R^{14}$, together with the nitrogen atom to which they are attached, form a heterocyclyl.

In another embodiment, $R^{12}$ is hydrogen or alkyl; $R^{13}$ is hydrogen or alkyl and $R^{14}$ is alkyl, cycloalkyl, —C(O)$R^v$ or —C(O)O$R^w$, where $R^v$ and $R^w$ are each independently hydrogen or alkyl.

In another embodiment, $R^{12}$ is hydrogen or alkyl; $R^{13}$ is hydrogen or alkyl and $R^{14}$ is alkyl, cycloalkyl or —C(O)O$R^w$. In one embodiment, $R^1$ and $R^2$, together with the carbon atom to which they are attached, form dioxacycloalkyl.

In one embodiment, $R^1$ is hydrogen or halo, and $R^2$ is halo. In one embodiment, $R^1$ is hydrogen or fluoro, and $R^2$ is fluoro. In one embodiment, $R^1$ is fluoro and $R^2$ is fluoro.

In one embodiment, $R^1$ is hydroxyl, alkoxy, amino or alkoxycarbonylamino and $R^2$ is hydrogen, alkyl, aryl or haloaryl. In one embodiment, $R^1$ is hydroxyl or alkoxy and $R^2$ is hydrogen. In one embodiment, $R^1$ is hydroxyl and $R^2$ is hydrogen. In one embodiment, $R^1$ is alkoxy and $R^2$ is hydrogen. In one embodiment, $R^1$ is hydroxyl, methoxy, amino or methoxycarbonylamino and $R^2$ is hydrogen, phenyl or fluorophenyl.

In one embodiment, $R^3$ is hydrogen, alkyl, cycloalkyl or alkoxy. In another embodiment, $R^3$ is hydrogen, alkyl or cycloalkyl. In one embodiment, $R^3$ is hydrogen, alkyl or alkoxy. In yet another embodiment, $R^3$ is hydrogen or alkyl. In another embodiment, $R^3$ is hydrogen or methyl. In one embodiment, $R^3$ is hydrogen, methyl or cyclopropyl.

In one embodiment, $R^3$ is alkyl, cycloalkyl or cyano. In one embodiment, $R^3$ is methyl, cyclopropyl or cyano. In one embodiment, $R^3$ is alkyl or cycloalkyl. In one embodiment, $R^3$ is methyl or cyclopropyl.

In one embodiment, each $R^6$ is independently selected from halo, alkyl alkenyl, alkynyl, haloalkyl, cycloalkyl and —O$R^{18}$, where $R^{18}$ is hydrogen, alkyl, haloalkyl, hydroxyalkyl, alkenyl, alkynyl, cycloalkyl, cycloalkylalkyl, heterocyclyl, cycloalkylalkyl, heterocyclyl or heterocyclylalkyl; wherein $R^{18}$ is optionally substituted with 1 to 3 groups $Q^1$, each $Q^1$ independently selected from alkyl, hydroxyl, cyano, halo, haloalkyl, alkoxy, aryloxy, alkoxyalkyl, alkoxycarbonyl, hydroxycarbonyl, cycloalkyl, heterocyclyl, aryl, heteroaryl, haloaryl and amino.

In one embodiment, each $R^6$ is independently selected from halo, alkyl alkenyl, alkynyl, haloalkyl, hydroxyalkyl; cycloalkyl, —$R^x$S(O)$_q R^v$ and —O$R^{18}$, where $R^x$ is direct bond or alkylene; $R^v$ is hydrogen or alkyl; q is 1 or 2; $R^{18}$ is hydrogen, alkyl, haloalkyl, hydroxyalkyl, alkenyl, alkynyl, cycloalkyl, cycloalkylalkyl, heterocyclyl or heterocyclylalkyl; wherein $R^{18}$ is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, hydroxycarbonyl, cycloalkyl, heterocyclyl, aryl, heteroaryl, haloaryl and amino.

In one embodiment, each $R^6$ is independently selected from halo, alkyl, haloalkyl and —O$R^{18}$; where $R^{18}$ is hydrogen, alkyl, hydroxyalkyl, alkoxyalkyl, heterocyclylalkyl or heterocyclyl, wherein $R^{18}$ is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, hydroxycarbonyl, cycloalkyl, heterocyclyl, aryl, heteroaryl, haloaryl and amino. In one embodiment, $R^{18}$ is hydrogen, alkyl, haloalkyl, hydroxy$C_{2-6}$alkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, hydroxycarbonyl, cycloalkyl, heterocyclyl, aryl, heteroaryl, haloaryl and amino.

In one embodiment, each $R^6$ is independently selected from halo, alkyl, haloalkyl and —$R^x$O$R^{18}$; where $R^{18}$ is hydrogen, alkyl, haloalkyl, hydroxyalkyl or heterocyclyl; wherein $R^{18}$ is optionally substituted with group $Q^1$, where $Q^1$ is selected from hydroxyl, cyano, alkoxy, alkoxycarbonyl, hydroxycarbonyl, heterocyclyl and amino. In one embodiment, $R^{18}$ is hydrogen or alkyl. In another embodiment, $R^{18}$ is hydrogen or methyl.

In one embodiment, each $R^6$ is independently selected from hydrogen, alkyl, halo, hydroxy or alkoxy. In one embodiment, each $R^6$ is independently selected from fluoro, iodo, methyl, trifluoromethyl and —O$R^{18}$; where $R^{18}$ is hydrogen, methyl, hydroxyethyl, hydroxypropyl, morpholinoethyl, methoxyethyl, tert-butyloxycarbonylmethyl, hydroxycarbonylmethyl or piperidinyl.

In one embodiment, $R^{6a}$ is hydrogen or halo. In one embodiment, $R^{6b}$ is hydrogen or alkoxy. In one embodiment, $R^{6c}$ is hydrogen, halo, alkyl, haloalkyl, —$R^x$O$R^{18}$, —$R^x$S(O)$_q R^v$, where $R^x$ is direct bond or alkylene; $R^v$ is hydrogen or alkyl; q is 1 or 2; $R^{18}$ is hydrogen, alkyl, haloalkyl, hydroxyalkyl or heterocyclyl; wherein $R^{18}$ is optionally substituted with group $Q^1$, where $Q^1$ is selected from hydroxy, alkoxy, alkoxycarbonyl, hydroxycarbonyl, heterocyclyl and amino. In one embodiment, $R^{6c}$ is hydrogen, halo, alkyl, hydroxy or alkoxy. In one embodiment, $R^{6d}$ is hydrogen or halo.

In one embodiment, $R^{6a}$ is hydrogen or halo. In one embodiment, $R^{6b}$ is hydrogen or alkoxy. In one embodiment, $R^{6c}$ is hydrogen, halo, alkyl, haloalkyl, —$R^x$O$R^{18}$; where $R^{18}$ is hydrogen, alkyl, haloalkyl, hydroxyalkyl or heterocyclyl; wherein $R^{18}$ is optionally substituted with group $Q^1$, where $Q^1$ is selected from hydroxy, alkoxy, alkoxycarbonyl, hydroxycarbonyl, heterocyclyl and amino. In one embodiment, $R^{6c}$ is hydrogen, halo, alkyl, hydroxy or alkoxy. In one embodiment, $R^{6d}$ is hydrogen or halo.

In one embodiment, $R^{6a}$ is hydrogen or halo. In one embodiment, $R^{6a}$ is hydrogen or fluoro. In one embodiment, $R^{6b}$ is hydrogen or methoxy. In one embodiment, $R^{6c}$ is hydrogen, fluoro, iodo, methyl, trifluoromethyl or —$OR^{18}$; where $R^{18}$ is hydrogen, methyl, hydroxyethyl, hydroxypropyl, morpholinoethyl, methoxyethyl, tert-butyloxycarbonylmethyl, hydroxycarbonylmethyl or piperidinyl. In one embodiment, $R^{6d}$ is hydrogen or fluoro.

In one embodiment, $R^7$ is halo, alkyl, haloalkyl or —$R^x$-$OR^w$, where $R^w$ is hydrogen or alkyl. In one embodiment, $R^7$ is fluoro or methoxy. In one embodiment, $R^7$ is halo. In one embodiment, $R^7$ is fluoro.

In one embodiment, $R^x$ is a direct bond. In one embodiment, n is 0-4. In one embodiment, n is 0, 1, 2 or 3. In one embodiment, n is 1. In one embodiment, n is 0. In one embodiment, n is 2. In one embodiment, p is 0, 1 or 2. In one embodiment, p is 1 or 2. In one embodiment, p is 1.

In certain embodiments, provided herein are compounds of formula (III) or (IIIa), wherein $R^1$ and $R^2$ are selected from (i), (ii), (iii) and (iv) as follows:
(i) $R^1$ and $R^2$ together form =O;
(ii) $R^1$ and $R^2$, are both —$OR^8$, or $R^1$ and $R^2$, together with the carbon atom to which they are attached, form dioxacycloalkyl;
(iii) $R^1$ is hydrogen or halo, and $R^2$ is halo; and
(iv) $R^1$ is hydroxyl, alkoxy, cyanoalkyl, amino, alkoxycarbonylamino or —NHC(O)H, and $R^2$ is hydrogen, alkyl, aryl or haloaryl;

$R^3$ is hydrogen or alkyl;

each $R^6$ is independently selected from halo, alkyl, haloalkyl and —$R^xOR^{18}$; where $R^{18}$ is hydrogen, alkyl, haloalkyl, hydroxyalkyl or heterocyclyl; wherein $R^{18}$ is optionally substituted with group $Q^1$, where $Q^1$ is selected from hydroxyl, alkoxy, alkoxycarbonyl, hydroxycarbonyl, heterocyclyl and amino;

each $R^6$ is independently halo, alkyl, haloalkyl, hydroxy or alkoxy; and $R^8$ is alkyl, alkenyl or alkynyl.

In certain embodiments, provided herein are compounds of formula (III) or (IIIa), wherein $R^1$ and $R^2$ are selected from (i), (ii), (iii) and (iv) as follows:
(i) $R^1$ and $R^2$ together form =O;
(ii) $R^1$ and $R^2$, are both —$OR^8$, or $R^1$ and $R^2$, together with the carbon atom to which they are attached, form dioxacycloalkyl;
(iii) $R^1$ is hydrogen or halo, and $R^2$ is halo; and
(iv) $R^1$ is hydroxyl, alkoxy, amino or alkoxycarbonylamino, and $R^2$ is hydrogen, alkyl, aryl or haloaryl;

$R^3$ is hydrogen or alkyl;

each $R^6$ is independently selected from halo, alkyl, haloalkyl and —$R^xOR^{18}$; where $R^{18}$ is hydrogen, alkyl, haloalkyl, hydroxyalkyl or heterocyclyl; wherein $R^{18}$ is optionally substituted with group $Q^1$, $Q^1$ is selected from hydroxyl, alkoxy, alkoxycarbonyl, hydroxycarbonyl, heterocyclyl and amino;

each $R^7$ is independently halo, alkyl, haloalkyl, hydroxy or alkoxy; and $R^8$ is alkyl, alkenyl or alkynyl.

In certain embodiments, provided herein are compounds of formula (III) or (IIIa), wherein $R^1$ and $R^2$ are selected from (i), (ii), and (iii) as follows:
(i) $R^1$ and $R^2$ together form =O;
(ii) $R^1$ is hydrogen or halo, and $R^2$ is halo; and
(iii) $R^1$ is hydroxyl, alkoxy, amino, —NHCH(O) or alkoxycarbonylamino, and $R^2$ is hydrogen or alkyl;

$R^3$ is hydrogen or alkyl;

each $R^6$ is independently selected from halo, alkyl, haloalkyl, —$R^xOR^{18}$, and —$R^xS(O)_qR^v$, where $R^x$ is direct bond or alkylene; $R^v$ is hydrogen or alkyl; q is 2; $R^{18}$ is hydrogen, alkyl, haloalkyl, hydroxyalkyl or heterocyclyl; wherein $R^{18}$ is optionally substituted with group $Q^1$, $Q^1$ is selected from hydroxyl, alkoxy, alkoxycarbonyl, hydroxycarbonyl, heterocyclyl and amino;

$R^7$ is halo; and p is 1.

In certain embodiments, provided herein are compounds of formula (III) or (IIIa), wherein $R^1$ and $R^2$ are selected from (i), (ii), and (iii) as follows:
(i) $R^1$ and $R^2$ together form =O;
(ii) $R^1$ is hydrogen or halo, and $R^2$ is halo; and
(iii) $R^1$ is hydroxyl, alkoxy, amino, —NHCH(O) or alkoxycarbonylamino, and $R^2$ is hydrogen or alkyl;

$R^3$ is hydrogen or alkyl;

each $R^6$ is independently selected from halo, alkyl, haloalkyl, —$R^xOR^{18}$, and —$R^xS(O)_qR^v$, where $R^x$ is direct bond or alkylene; $R^v$ is alkyl; q is 2; $R^{18}$ is hydrogen, alkyl, haloalkyl, hydroxyalkyl or heterocyclyl; wherein $R^{18}$ is optionally substituted with group $Q^1$, where $Q^1$ is selected from hydroxyl, alkoxy, alkoxycarbonyl, hydroxycarbonyl, heterocyclyl and amino;

$R^7$ is halo; and p is 1.

In certain embodiments, provided herein are compounds of formula (IV) of (IVa)

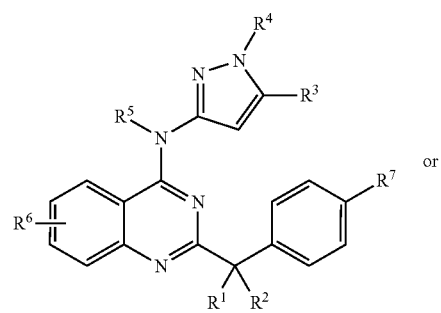

(IV)

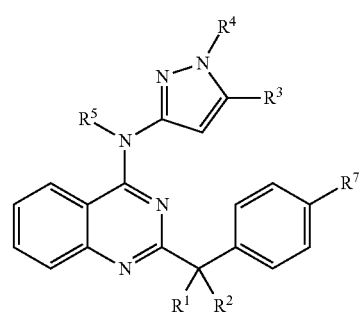

(IVa)

or pharmaceutically acceptable salts, solvates or hydrates thereof, where the variables are as described elsewhere herein. In one embodiment, $R^7$ is fluoro.

In certain embodiments, provided herein are compounds of formula (V) or (Va)

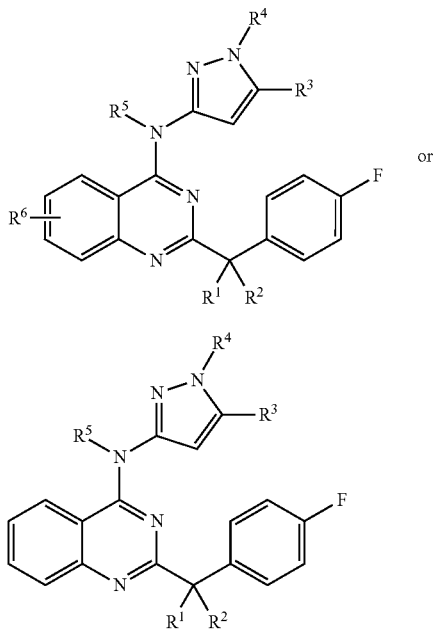

or pharmaceutically acceptable salts, solvates or hydrates thereof, where the variables are as described elsewhere herein. In certain embodiments, provided herein are compounds of formula (V) or (Va), wherein $R^1$ and $R^2$ are selected from (i), (ii), and (iii) as follows:
(i) $R^1$ and $R^2$ together form =O;
(ii) $R^1$ is hydrogen or halo, and $R^2$ is halo; and
(iii) $R^1$ is hydroxyl, alkoxy, amino, —NHCH(O) or alkoxycarbonylamino, and $R^2$ is hydrogen or alkyl;
$R^3$ is hydrogen or alkyl; and
$R^4$ is hydrogen;
$R^5$ is hydrogen;
each $R^6$ is independently selected from halo, alkyl, haloalkyl, —$R^xOR^{18}$, and —$R^xS(O)_qR^v$, where $R^x$ is direct bond or alkylene; $R^v$ is alkyl; q is 2; $R^{18}$ is hydrogen, alkyl, haloalkyl, hydroxyalkyl or heterocyclyl; wherein $R^{18}$ is optionally substituted with group $Q^1$, where $Q^1$ is selected from hydroxyl, alkoxy, alkoxycarbonyl, hydroxycarbonyl, heterocyclyl and amino.

In certain embodiments, provided herein are compounds of formula (VI)

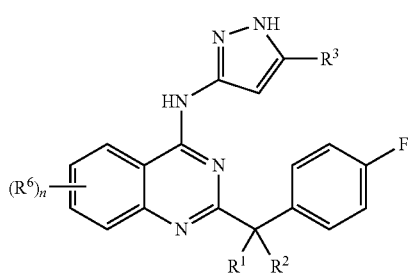

or pharmaceutically acceptable salts, solvates or hydrates thereof, where the variables are as described elsewhere herein. In one embodiment, $R^1$ is hydroxyl, amino, alkoxy, or alkoxycarbonylamino; $R^2$ is hydrogen, halo or haloaryl; $R^6$ is selected from halo, alkyl, haloalkyl, —$R^xS(O)_qR^v$, and —$R^xOR^{18}$; where $R^x$ is direct bond or alkylene; $R^v$ is hydrogen or alkyl; q is 1 or 2; $R^{18}$ is hydrogen, alkyl, haloalkyl, hydroxyalkyl or heterocyclyl; $R^{18}$ is optionally substituted with group $Q^1$ selected from hydroxyl, alkoxy, alkoxycarbonyl, hydroxycarbonyl, heterocyclyl and amino; n is 0 or 1; and $R^3$ is hydrogen or alkyl. In one embodiment, $R^1$ is hydroxyl; and $R^2$ is hydrogen; n is 0, and $R^3$ is alkyl.

In certain embodiments, provided herein are compounds of formula (VII)

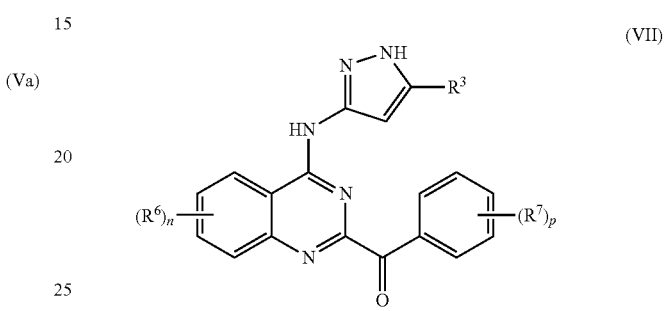

or pharmaceutically acceptable salts, solvates or hydrates thereof, where the variables are as described elsewhere herein. In one embodiment, each $R^6$ is independently selected from halo, alkyl, haloalkyl, —$R^xS(O)_qR^v$, and —$R^xOR^{18}$; where $R^x$ is direct bond or alkylene; $R^v$ is hydrogen or alkyl; q is 1 or 2; where $R^{18}$ is hydrogen, alkyl, haloalkyl, hydroxyalkyl or heterocyclyl; $R^{18}$ is optionally substituted with group $Q^1$ selected from hydroxyl, alkoxy, alkoxycarbonyl, hydroxycarbonyl, heterocyclyl and amino; n is 0 or 1; each $R^7$ is independently halo, alkyl, haloalkyl, hydroxy or alkoxy; p is 1; and $R^3$ is hydrogen, alkyl or alkoxy.

In certain embodiments, provided herein are compounds of formula (VII) or pharmaceutical acceptable salts, solvates or hydrates thereof, where n is 0 and the other variables are as described elsewhere herein.

In certain embodiments, provided herein are compounds of formula (VIII)

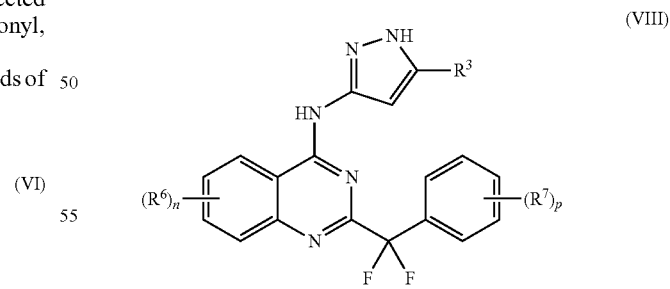

or pharmaceutically acceptable salts, solvates or hydrates thereof, where the variables are as described elsewhere herein. In one embodiment, each $R^6$ is independently selected from halo, alkyl, haloalkyl, —$R^xS(O)_qR^v$, and —$R^xOR^{18}$; where $R^x$ is direct bond or alkylene; $R^v$ is hydrogen or alkyl; q is 1 or 2; where $R^{18}$ is hydrogen, alkyl, haloalkyl, hydroxyalkyl or heterocyclyl; $R^{18}$ is optionally substituted with group $Q^1$ selected from hydroxyl, alkoxy, alkoxycarbonyl, hydroxycarbonyl, heterocyclyl and amino; n is 0 or 1; $R^7$ is halo, alkyl, haloalkyl, hydroxy or alkoxy; p is 1; and $R^3$ is hydrogen, alkyl or cycloalkyl.

In certain embodiments, provided herein are compounds of formula (IX)

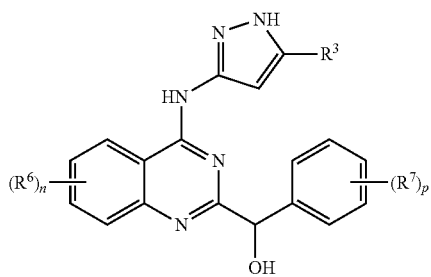

(IX)

or pharmaceutically acceptable salts, solvates or hydrates thereof, where the variables are as described elsewhere herein. In one embodiment, each $R^6$ is independently selected from halo, alkyl, haloalkyl, —$R^xS(O)_qR^v$, and —$R^xOR^{18}$; where $R^x$ is direct bond or alkylene; $R^v$ is hydrogen or alkyl; q is 1 or 2; where $R^{18}$ is hydrogen, alkyl, haloalkyl, hydroxyalkyl or heterocyclyl; $R^{18}$ is optionally substituted with group $Q^1$ selected from hydroxyl, alkoxy, alkoxycarbonyl, hydroxycarbonyl, heterocyclyl and amino; n is 0 or 1; each $R^7$ is independently halo, alkyl, haloalkyl, hydroxy or alkoxy; p is 1; and $R^3$ is hydrogen or alkyl. In one embodiment, provided herein are compounds of formula (IX) or pharmaceutically acceptable salts, solvates or hydrates thereof, where $R^3$ is alkyl; $R^7$ is halo; n is 0 and p is 1.

In certain embodiments, provided herein are compounds of formula (X)

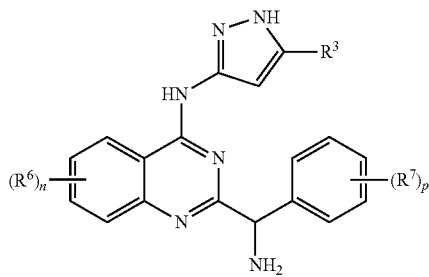

(X)

or pharmaceutically acceptable salts, solvates or hydrates thereof, where the variables are as described elsewhere herein. In one embodiment, each $R^6$ is independently selected from halo, alkyl, haloalkyl, —$R^xS(O)_qR^v$, and —$R^xOR^{18}$; where $R^x$ is direct bond or alkylene; $R^v$ is hydrogen or alkyl; q is 1 or 2; where $R^{18}$ is hydrogen, alkyl, haloalkyl, hydroxyalkyl or heterocyclyl; $R^{18}$ is optionally substituted with group $Q^1$ selected from hydroxyl, alkoxy, alkoxycarbonyl, hydroxycarbonyl, heterocyclyl and amino; n is 0 or 1; each $R^7$ is independently halo, alkyl, haloalkyl, hydroxy or alkoxy; p is 1; and $R^3$ is hydrogen or alkyl.

In certain embodiments, provided herein are compounds of formula (XI)

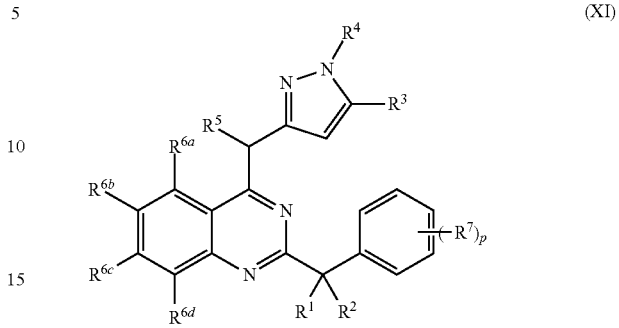

(XI)

or pharmaceutically acceptable salts, solvates or hydrates thereof, wherein $R^1$ and $R^2$ are selected from (i), (ii), (iii), (iv) and (v) as follows:
 (i) $R^1$ and $R^2$ together form =O, =S, =$NR^9$ or =$CR^{10}R^{11}$;
 (ii) $R^1$ and $R^2$ are both —$OR^8$, or $R^1$ and $R^2$, together with the carbon atom to which they are attached, form dioxacycloalkyl;
 (iii) $R^1$ is hydrogen or halo; and $R^2$ is halo; and
 (iv) $R^1$ is alkyl, alkenyl, alkynyl, cycloalkyl or aryl, wherein the alkyl, alkenyl, alkynyl, cycloalkyl and aryl is optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$, —$R^xNR^yR^z$ and —$C(O)OR^w$; and $R^2$ is hydrogen, halo or —$OR^8$; and
 (v) $R^1$ is halo, deutero, —$OR^{12}$, —$NR^{13}R^{14}$, or —$S(O)_qR^{15}$; and $R^2$ is hydrogen, deutero, alkyl, alkenyl, alkynyl, or cycloalkyl, wherein the alkyl, alkenyl, alkynyl and cycloalkyl is optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$ and —$R^xNR^yR^z$;

$R^3$ is halo, alkyl, haloalkyl, hydroxy or alkoxy;
$R^4$ and $R^5$ are each independently hydrogen or alkyl;
$R^{6a}$, $R^{6b}$, $R^{6c}$, and $R^{6d}$ are each independently selected from hydrogen, halo, alkyl, alkenyl, alkynyl, haloalkyl, cycloalkyl, —$R^xOR^{18}$, —$R^xNR^{19}R^{20}$, and —$R^xS(O)_qR^v$;
$R^7$ is halo, alkyl, haloalkyl or —$R^xOR^w$;
$R^8$ is alkyl, alkenyl or alkynyl;
$R^9$ is hydrogen, alkyl, haloalkyl, hydroxy, alkoxy or amino;
$R^{10}$ is hydrogen or alkyl;
$R^{11}$ is hydrogen, alkyl, haloalkyl or —$C(O)OR^8$;
$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —$C(O)R^v$, —$C(O)OR^w$ and —$C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;
$R^{13}$ and $R^{14}$ are selected as follows:
 (i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)$R^v$, —C(O)O$R^w$, —C(O)N$R^y R^z$ and —S(O)$_q R^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or (ii) $R^{13}$ and $R^{14}$, together with the nitrogen atom to which they are attached, form heterocyclyl or heteroaryl wherein the heterocyclyl or heteroaryl is optionally substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is also optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)N$R^y R^z$ or —N$R^y R^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxyC$_{2-6}$alkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, alkoxysulfonyl, hydroxycarbonyl, cycloalkyl, heterocyclyl, aryl, heteroaryl, haloaryl and amino;

$R^{19}$ and $R^{20}$ are selected as follows:
(i) $R^{19}$ and $R^{20}$ are each independently hydrogen or alkyl; or
(ii) $R^{19}$ and $R^{20}$, together with the nitrogen atom to which they are attached, form a heterocyclyl or heteroaryl which is optionally substituted with 1 to 2 groups each independently selected from halo, alkyl, haloalkyl, hydroxyl and alkoxy;

each $R^x$ is independently alkylene or a direct bond;
$R^v$ is hydrogen, alkyl, alkenyl or alkynyl;
$R^w$ is independently hydrogen, alkyl, alkenyl, alkynyl or haloalkyl;
$R^y$ and $R^z$ are selected as follows:
(i) $R^y$ and $R^z$ are each independently hydrogen, alkyl, alkenyl, alkynyl, cycloalkyl or haloalkyl;
(ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy;

p is 0-5; and
each q is independently 0, 1 or 2; with the proviso that when $R^1$ and $R^2$ together form =O, then $R^{6a}$ and $R^{6d}$ are hydrogen, $R^{6b}$ is selected from hydrogen, alkyl, alkenyl, alkynyl, haloalkyl, cycloalkyl, —$R^x$O$R^{18}$, —$R^x$N$R^{19}R^{20}$, and —$R^x$S(O)$_q R^v$, $R^{6c}$ is selected from hydrogen, alkyl, alkenyl, alkynyl, cycloalkyl, hydroxy, —$R^x$N$R^{19}R^{20}$, and —$R^x$S(O)$_q R^v$ and the other variables are as described elsewhere herein.

In another embodiment, when $R^1$ and $R^2$ together form =O, then $R^{6a}$ and $R^{6d}$ are hydrogen, $R^{6b}$ and $R^{6c}$ are each independently selected from hydrogen, alkyl, alkenyl, alkynyl, cycloalkyl, hydroxy, —$R^x$N$R^{19}R^{20}$, and —$R^x$S(O)$_q R^v$ and the other variables are as described elsewhere herein.

In another embodiment, when $R^1$ and $R^2$ together form =O, then $R^{6a}$, $R^{6b}$ and $R^{6d}$ are hydrogen, and $R^{6c}$ is selected from hydrogen, alkyl, alkenyl, alkynyl, cycloalkyl, hydroxy, —$R^x$N$R^{19}R^{20}$, and —$R^x$S(O)$_q R^v$ and the other variables are as described elsewhere herein.

In another embodiment, when $R^1$ and $R^2$ together form =O, then $R^{6a}$, $R^{6b}$ and $R^{6d}$ are hydrogen, and $R^{6c}$ is selected from hydrogen, alkyl, cycloalkyl and hydroxy.

In another embodiment, $R^{6a}$ is hydrogen and $R^{6b}$, $R^{6c}$ and $R^{6d}$ are each independently selected from hydrogen, halo, alkyl, alkenyl, alkynyl, haloalkyl, cycloalkyl, —$R^x$O$R^{18}$, —$R^x$N$R^{19}R^{20}$, and —$R^x$S(O)$_q R^v$ with the proviso that when $R^1$ and $R^2$ together form =O, then $R^{6b}$ and $R^{6d}$ are hydrogen and $R^{6c}$ is selected from hydrogen, alkyl, alkenyl, alkynyl, cycloalkyl, —$R^x$O$R^{18}$, —$R^x$N$R^{19}R^{20}$, and —$R^x$S(O)$_q R^v$, and the other variables are as described elsewhere herein.

In another embodiment, $R^{6a}$, $R^{6b}$ and $R^{6d}$ are each hydrogen, and $R^{6c}$ independently selected from hydrogen, alkyl, alkenyl, alkynyl, cycloalkyl, $R^x$O$R^{18}$, —$R^x$N$R^{19}R^{20}$, and —$R^x$S(O)$_q R^v$ and the other variables are as described elsewhere herein. In yet another embodiment, $R^{6a}$, $R^{6b}$ and $R^{6d}$ are each hydrogen and $R^{6c}$ is hydrogen, alkyl, cycloalkyl or —$R^x$O$R^{18}$ and the other variables are as described elsewhere herein. In another embodiment, $R^{6a}$, $R^{6b}$, $R^{6c}$, and $R^{6d}$ are hydrogen. In another embodiment, p is 2 and $R^7$ is selected from halo, hydroxy and alkoxy. In yet another embodiment, p is 1 and $R^7$ is halo.

In one embodiment, $R^{6a}$ and $R^{6d}$ are hydrogen and $R^{6b}$ and $R^{6c}$ are each independently selected from hydrogen, halo, alkyl, alkenyl, alkynyl, haloalkyl, cycloalkyl, —$R^x$O$R^{18}$, —$R^x$N$R^{19}R^{20}$, and —$R^x$S(O)$_q R^v$ with the proviso that when $R^1$ and $R^2$ together form =O, $R^{6c}$ is selected from hydrogen, alkyl, alkenyl, alkynyl, cycloalkyl, —$R^x$O$R^{18}$, —$R^x$N$R^{19}R^{20}$, and —$R^x$S(O)$_q R^v$, where the other variables are as described elsewhere herein.

In certain embodiments, provided herein are compounds of formula (XII)

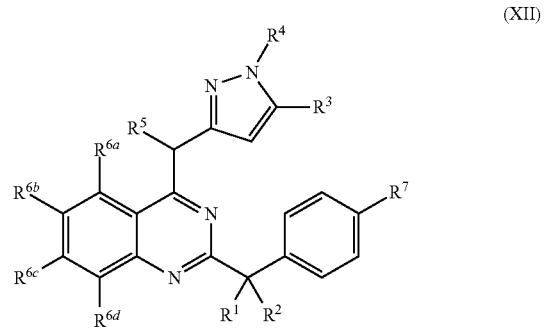

(XII)

or pharmaceutical acceptable salts, solvates or hydrates thereof, where the other variables are as described elsewhere herein.

In certain embodiments, provided herein are compounds of formula (XIII)

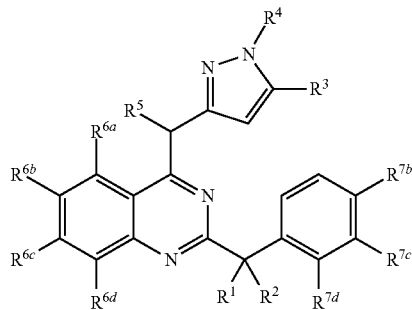

or pharmaceutical acceptable salts, solvates or hydrates thereof, where
$R^1$ and $R^2$ are selected from (i), (ii), (iii), (iv) and (v) as follows:
- (i) $R^1$ and $R^2$ together form =O, =S, =NR$^9$ or =CR$^{10}$R$^{11}$;
- (ii) $R^1$ and $R^2$ are both —OR$^8$, or $R^1$ and $R^2$, together with the carbon atom to which they are attached, form dioxacycloalkyl;
- (iii) $R^1$ is hydrogen or halo; and $R^2$ is halo; and
- (iv) $R^1$ is alkyl, alkenyl, alkynyl, cycloalkyl or aryl, wherein the alkyl, alkenyl, alkynyl, cycloalkyl and aryl is optionally substituted with one or more, in one embodiment, one to four, in one embodiment, one to three, in one embodiment, one, two or three, substitutents selected from halo, cyano, alkyl, —R$^x$OR$^w$, —R$^x$S(O)$_q$R$^v$, —R$^x$NR$^y$R$^z$ and —C(O)OR$^w$; and $R^2$ is hydrogen, halo or —OR$^8$; and
- (v) $R^1$ is halo, deutero, —OR$^{12}$, —NR$^{13}$R$^{14}$, or —S(O)$_q$R$^{15}$; and $R^2$ is hydrogen, deutero, alkyl, alkenyl, alkynyl or cycloalkyl, wherein the alkyl, alkenyl, alkynyl and cycloalkyl, is optionally substituted with one or more, in one embodiment, one to four, in one embodiment, one to three, in one embodiment, one, two or three, substitutents selected from halo, cyano, alkyl, —R$^x$OR$^w$, —R$^x$S(O)$_q$R$^v$ and —R$^x$NR$^y$R$^z$;

$R^3$ is halo, alkyl, haloalkyl, cycloalkyl, cycloalkylalkyl, hydroxy or alkoxy;

$R^4$ and $R^5$ are each independently hydrogen or alkyl;

$R^{6a}$, $R^{6b}$, $R^{6c}$ and $R^{6d}$ are each independently selected from hydrogen, halo, alkyl, alkenyl, alkynyl, haloalkyl, cycloalkyl, —R$^x$OR$^{18}$, —R$^x$NR$^{19}$R$^{20}$, and —R$^x$S(O)$_q$R$^v$;

$R^{7b}$, $R^{7c}$ and $R^{7d}$ are each independently selected from hydrogen, halo, alkyl, haloalkyl or —R$^x$OR$^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —C(O)OR$^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)R$^v$, —C(O)OR$^w$ and —C(O)NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:
- (i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)R$^v$, —C(O)OR$^w$, —C(O)NR$^y$R$^z$ and —S(O)$_q$R$^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or
- (ii) $R^{13}$ and $R^{14}$, together with the nitrogen atom to which they are attached, form heterocyclyl or heteroaryl wherein the heterocyclyl or heteroaryl is optionally substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is also optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —C(O)NR$^y$R$^z$ or —NR$^y$R$^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{18}$ is hydrogen, alkyl, haloalkyl, hydroxyC$_{2-6}$alkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups Q$^1$, each Q$^1$ independently selected from alkyl, hydroxyl, halo, haloalkyl, alkoxy, aryloxy, alkoxyalkyl, alkoxycarbonyl, alkoxysulfonyl, hydroxycarbonyl, cycloalkyl, heterocyclyl, aryl, heteroaryl, haloaryl and amino;

$R^{19}$ and $R^{20}$ are selected as follows:
- (i) $R^{19}$ and $R^{20}$ are each independently hydrogen or alkyl; or
- (ii) $R^{19}$ and $R^{20}$, together with the nitrogen atom to which they are attached, form a heterocyclyl or heteroaryl which is optionally substituted with 1 to 2 groups each independently selected from halo, alkyl, haloalkyl, hydroxyl and alkoxy;

each R$^x$ is independently alkylene or a direct bond;

R$^v$ is hydrogen, alkyl, alkenyl or alkynyl;

R$^w$ is independently hydrogen, alkyl, alkenyl, alkynyl or haloalkyl;

R$^y$ and R$^z$ are selected as follows:
- (i) R$^y$ and R$^z$ are each independently hydrogen, alkyl, alkenyl, alkynyl, cycloalkyl or haloalkyl;
- (ii) R$^y$ and R$^z$, together with the nitrogen atom to which they are attached, form a heterocyclyl or heteroaryl which is optionally substituted with 1 to 2 groups each independently selected from halo, alkyl, haloalkyl, hydroxyl and alkoxy;

p is 0-5; and each q is independently 0, 1 or 2; and with the proviso that when $R^1$ and $R^2$ together form =O, then $R^{7d}$ is not —OR$^w$. In one embodiment, $R^{7d}$ is hydrogen. In one embodiment, $R^{7d}$ is hydrogen and $R^{7b}$ and $R^{7c}$ are each independently selected from hydrogen, halo, alkyl, haloalkyl or —R$^x$OR$^w$.

In another embodiment, provided herein are compounds of formula (XIV)

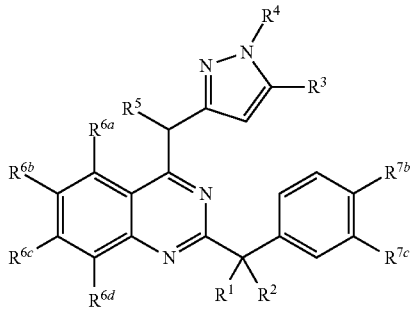

(XIV)

or pharmaceutically acceptable salts, solvates or hydrates thereof, wherein:

$R^1$ and $R^2$ are selected from (i), (ii), (iii), (iv) and (v) as follows:
  (i) $R^1$ and $R^2$ together form =O, =S, =$NR^9$ or =$CR^{10}R^{11}$;
  (ii) $R^1$ and $R^2$ are both —$OR^8$, or $R^1$ and $R^2$, together with the carbon atom to which they are attached, form dioxacycloalkyl;
  (iii) $R^1$ is hydrogen or halo; and $R^2$ is halo; and
  (iv) $R^1$ is alkyl, alkenyl, alkynyl, cycloalkyl or aryl, wherein the alkyl, alkenyl, alkynyl, cycloalkyl and aryl is optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$, —$R^xNR^yR^z$ and —$C(O)OR^w$; and $R^2$ is hydrogen, halo or —$OR^8$; and
  (v) $R^1$ is halo, deutero, —$OR^{12}$, —$NR^{13}R^{14}$, or —$S(O)_qR^{15}$; and $R^2$ is hydrogen, deutero, alkyl, alkenyl, alkynyl or cycloalkyl, wherein the alkyl, alkenyl, alkynyl and cycloalkyl, is optionally substituted with one or more, in one embodiment, one to four, in one embodiment, one to three, in one embodiment, one, two or three, substitutents selected from halo, cyano, alkyl, —$R^xOR^w$, —$R^xS(O)_qR^v$ and —$R^xNR^yR^z$;

$R^3$ is hydrogen, halo, alkyl, haloalkyl, cycloalkyl, hydroxy or alkoxy;
$R^4$ and $R^5$ are each independently hydrogen or alkyl;
$R^{6a}$, $R^{6b}$, $R^{6d}$ are hydrogen;
$R^{6c}$ is hydrogen, halo, alkyl, hydroxy, hydroxyalkyl, alkoxyalkyl, alkylsulfonylalkyl, alkoxy, hydroxyalkoxy or alkoxyalkoxy,
$R^{7b}$ is halo and $R^{7c}$ is halo, hydroxy or alkoxy;
$R^8$ is alkyl, alkenyl or alkynyl;
$R^9$ is hydrogen, alkyl, haloalkyl, hydroxy, alkoxy or amino;
$R^{10}$ is hydrogen or alkyl;
$R^{11}$ is hydrogen, alkyl, haloalkyl or —$C(O)OR^8$;
$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —$C(O)R^v$, —$C(O)OR^w$ and —$C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

$R^{13}$ and $R^{14}$ are selected as follows:
  (i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —$C(O)R^v$, —$C(O)OR^w$, —$C(O)NR^yR^z$ and —$S(O)_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio; or
  (ii) $R^{13}$ and $R^{14}$, together with the nitrogen atom to which they are attached, form heterocyclyl or heteroaryl wherein the heterocyclyl or heteroaryl is optionally substituted with one or more, in one embodiment, one to four, in one embodiment, one to three, in one embodiment, one, two or three, substituents independently selected from halo, alkyl, hydroxy, alkoxy, amino and alkylthio and wherein the heterocyclyl is also optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —$C(O)NR^yR^z$ or —$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more, in one embodiment, one to four, in one embodiment, one to three, in one embodiment, one, two or three, substituents independently selected from halo, oxo, alkyl, hydroxy, alkoxy, amino and alkylthio;

each $R^x$ is independently alkylene or a direct bond;
$R^v$ is hydrogen, alkyl, alkenyl or alkynyl;
$R^w$ is independently hydrogen, alkyl, alkenyl, alkynyl or haloalkyl;
$R^y$ and $R^z$ are selected as follows:
  (i) $R^y$ and $R^z$ are each independently hydrogen, alkyl, alkenyl, alkynyl, cycloalkyl or haloalkyl;
  (ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy;
with the proviso that when $R^3$ is hydrogen, $R^{6c}$ is not halo.

In another embodiment, $R^3$ is halo, alkyl, cycloalkyl, haloalkyl, hydroxy or alkoxy. In yet another embodiment, $R^3$ is alkyl, haloalkyl, cycloalkyl, hydroxy or alkoxy. In yet another embodiment, $R^3$ is alkyl, cycloalkyl or alkoxy. In another embodiment, $R^{6c}$ is hydrogen, fluoro, chloro, hydroxy, alkyl, hydroxyalkyl, alkoxyalkyl, alkylsulfonylalkyl, alkoxy, hydroxyalkoxy or alkoxyalkoxy. In another embodiment, $R^{6c}$ is hydrogen, fluoro, chloro, hydroxy, methyl, hydroxymethyl, hydroxyethyl, methoxymethyl, ethoxymethyl, methylsulfonylmethyl, ethylsulfonylmethyl, methoxy, ethoxy, propyloxy, hydroxypropyloxy, hydroxyethoxy, hydroxymethoxy, methoxymethoxy or methoxyethoxy. In yet another embodiment, $R^{6a}$ is hydrogen, alkyl, hydroxy, hydroxyalkyl, alkoxyalkyl, alkylsulfonylalkyl, hydroxyalkoxy or alkoxyalkoxy.

In one embodiment, provided herein is a compound selected from
(4-chloroquinazolin-2-yl)(3-fluorophenyl)methanone;
(4-(1H-pyrazol-3-ylamino)quinazolin-2-yl)(3-fluorophenyl) methanone;
(4-fluorophenyl)(4-(5-methyl-1H-pyrazol-3-ylamino) quinazolin-2-yl)methanone;
(4-(1H-pyrazol-3-ylamino)quinazolin-2-yl)(4-fluorophenyl) methanone;

(4-(1H-pyrazol-3-ylamino)quinazolin-2-yl)(2-methoxyphenyl)methanone;
(4-(1H-pyrazol-3-ylamino)quinazolin-2-yl)(4-fluorophenyl)methanol;
2-(fluoro(4-fluorophenyl)methyl)-N-(1H-pyrazol-3-yl)quinazolin-4-amine;
2-(difluoro(4-fluorophenyl)methyl)-N-(5-methyl-1H-pyrazol-3-yl)quinazolin-4-amine;
2-(difluoro(4-fluorophenyl)methyl)-N-(1H-pyrazol-3-yl)quinazolin-4-amine;
N-(5-cyclopropyl-1H-pyrazol-3-yl)-2-(difluoro(4-fluorophenyl)methyl)quinazolin-4-amine;
3-(2-(4-fluorobenzoyl)quinazolin-4-ylamino)-1H-pyrazole-5-carbonitrile;
(4-fluorophenyl)(4-(5-methyl-1H-pyrazol-3-ylamino)quinazolin-2-yl)methanol;
2-((4-fluorophenyl)(methoxy)methyl)-N-(5-methyl-1H-pyrazol-3-yl)quinazolin-4-amine;
2-(amino(4-fluorophenyl)methyl)-N-(5-methyl-1H-pyrazol-3-yl)quinazolin-4-amine;
3-(2-((4-fluorophenyl)(hydroxy)methyl)quinazolin-4-ylamino)-1H-pyrazole-5-carbonitrile;
(5-fluoro-4-(5-methyl-1H-pyrazol-3-ylamino)quinazolin-2-yl)(4-fluorophenyl)methanol
(4-fluorophenyl)(4-(5-methyl-1H-pyrazol-3-ylamino)-7-(trifluoromethyl)quinazolin-2-yl)methanone;
(4-fluorophenyl)(4-(5-methyl-1H-pyrazol-3-ylamino)-7-(trifluoromethyl)quinazolin-2-yl);
(7-fluoro-4-(5-methyl-1H-pyrazol-3-ylamino)quinazolin-2-yl)(4-fluorophenyl)methanone;
2-(difluoro(4-fluorophenyl)methyl)-7-fluoro-N-(5-methyl-1H-pyrazol-3-yl)quinazolin-4-amine;
2-(difluoro(4-fluorophenyl)methyl)-7-fluoro-N-(1H-pyrazol-3-yl)quinazolin-4-amine;
(4-(1H-pyrazol-3-ylamino)-7-iodoquinazolin-2-yl)(4-fluorophenyl)methanone;
(4-(1H-pyrazol-3-ylamino)-7-iodoquinazolin-2-yl)(4-fluorophenyl)methanol;
(4-fluorophenyl)(7-methyl-4-(5-methyl-1H-pyrazol-3-ylamino)quinazolin-2-yl)methanone;
(4-fluorophenyl)(7-methyl-4-(5-methyl-1H-pyrazol-3-ylamino)quinazolin-2-yl)methanol;
2-(difluoro(4-fluorophenyl)methyl)-7-methyl-N-(5-methyl-1H-pyrazol-3-yl)quinazolin-4-amine;
2-(difluoro(4-fluorophenyl)methyl)-7-methyl-N-(1H-pyrazol-3-yl)quinazolin-4-amine;
(4-(1H-pyrazol-3-ylamino)-7-methoxyquinazolin-2-yl)(4-fluorophenyl)methanone;
(4-(1H-pyrazol-3-ylamino)-7-methoxyquinazolin-2-yl)(4-fluorophenyl)methanol;
(4-fluorophenyl)(7-methoxy-4-(5-methyl-1H-pyrazol-3-ylamino)quinazolin-2-yl)methanone;
(4-fluorophenyl)(7-methoxy-4-(5-methyl-1H-pyrazol-3-ylamino)quinazolin-2-yl)methanol;
2-(difluoro(4-fluorophenyl)methyl)-7-methoxy-N-(5-methyl-1H-pyrazol-3-yl)quinazolin-4-amine;
2-(difluoro(4-fluorophenyl)methyl)-7-methoxy-N-(1H-pyrazol-3-yl)quinazolin-4-amine;
2-(difluoro(4-fluorophenyl)methyl)-8-fluoro-N-(5-methyl-1H-pyrazol-3-yl)quinazolin-4-amine;
(4-(1H-pyrazol-3-ylamino)-8-methoxyquinazolin-2-yl)(4-fluorophenyl)methanone;
2-((4-fluorophenyl)(hydroxy)methyl)-4-(5-methyl-1H-pyrazol-3-ylamino)quinazolin-7-ol;
(4-fluorophenyl)(7-hydroxy-4-(5-methyl-1H-pyrazol-3-ylamino)quinazolin-2-yl)methanone;
(4-fluorophenyl)(4-(5-methyl-1H-pyrazol-3-ylamino)-7-(2-morpholinoethoxy)quinazolin-2-yl)methanol;
2-(2-((4-fluorophenyl)(hydroxy)methyl)-4-(5-methyl-1H-pyrazol-3-ylamino)quinazolin-7-yloxy)ethanol;
3-(2-((4-fluorophenyl)(hydroxy)methyl)-4-(5-methyl-1H-pyrazol-3-ylamino)quinazolin-7-yloxy)propan-1-ol;
(4-fluorophenyl)(4-(5-methyl-1H-pyrazol-3-ylamino)-7-(piperidin-4-yloxy)quinazolin-2-yl)methanol;
(4-fluorophenyl)(7-(2-methoxyethoxy)-4-(5-methyl-1H-pyrazol-3-ylamino)quinazolin-2-yl)methanol;
tert-butyl 2-(2-((4-fluorophenyl)(hydroxy)methyl)-4-(5-methyl-1H-pyrazol-3-ylamino)quinazolin-7-yloxy)acetate;
2-(2-((4-fluorophenyl)(hydroxy)methyl)-4-(5-methyl-1H-pyrazol-3-ylamino)quinazolin-7-yloxy)acetic acid;
{(4-fluoro-phenyl)-[4-(5-methyl-1H-pyrazol-3-ylamino)-quinazolin-2-yl]-methyl}-carbamic acid methyl ester; and
bis-(4-fluoro-phenyl)-[4-(5-methyl-1H-pyrazol-3-ylamino)-quinazolin-2-yl]-methanol.

In one embodiment, provided herein is a compound selected from
(R,S)-methyl (4-fluorophenyl)(4-(5-methyl-4H-pyrazol-3-ylamino)quinazolin-2-yl)methylcarbamate;
(R,S)-(4-fluorophenyl)(8-methyl-4-(5-methyl-1H-pyrazol-3-ylamino)quinazolin-2-yl)methanol;
(R,S)-(7-fluoro-4-(5-methyl-1H-pyrazol-3-ylamino)quinazolin-2-yl)(4-fluorophenyl)methanol;
(4-(1H-pyrazol-3-ylamino)quinazolin-2-yl)bis(4-fluorophenyl)methanol;
(2-(difluoro(4-fluorophenyl)methyl)-4-(5-methyl-1H-pyrazol-3-ylamino)quinazolin-7-yl)methanol;
2-(difluoro(4-fluorophenyl)methyl)-N-(5-methyl-1H-pyrazol-3-yl)-7-(methylsulfonylmethyl)quinazolin-4-amine;
2-(Difluoro(4-fluorophenyl)methyl)-7-(ethoxymethyl)-N-(5-methyl-1H-pyrazol-3-yl)quinazolin-4-amine;
(R,S) (7-chloro-4-(5-methyl-1H-pyrazol-3-ylamino)quinazolin-2-yl)(4-fluorophenyl)methanol;
(6-fluoro-4-(5-methyl-1H-pyrazol-3-ylamino)quinazolin-2-yl)(4-fluorophenyl)methanone(R,S)-(6-fluoro-4-(5-methyl-1H-pyrazol-3-ylamino)quinazolin-2-yl)(4-fluorophenyl)methanol;
(R,S)-(4-(1H-pyrazol-3-ylamino)-6-fluoroquinazolin-2-yl)(4-fluorophenyl)methanol;
(7-bromo-4-(5-methyl-1H-pyrazol-3-ylamino)quinazolin-2-yl)(4-fluorophenyl)methanone;
(7-bromo-4-(5-methyl-1H-pyrazol-3-ylamino)quinazolin-2-yl)(4-fluorophenyl)methanol;
(R,S)-(4-(1H-pyrazol-3-ylamino)-7-bromo quinazolin-2-yl)(4-fluorophenyl)methanol;
2-(2-(4-fluorophenyl)-1,3-dioxolan-2-yl)-N-(5-methyl-1H-pyrazol-3-yl)quinazolin-4-amine;
(8-fluoro-4-(5-methyl-1H-pyrazol-3-ylamino)quinazolin-2-yl)(4-fluorophenyl)methanone;
(R,S)-(8-fluoro-4-(5-methyl-1H-pyrazol-3-ylamino)quinazolin-2-yl)(4-fluorophenyl)methanol;
(2-methoxyphenyl)(4-(5-methyl-1H-pyrazol-3-ylamino)quinazolin-2-yl)methanone;
(R,S)-(2-methoxyphenyl)(4-(5-methyl-1H-pyrazol-3-ylamino)quinazolin-2-yl)methanol;
(3-fluorophenyl)(4-(5-methyl-1H-pyrazol-3-ylamino)quinazolin-2-yl)methanol;
N-((4-fluorophenyl)(4-(5-methyl-1H-pyrazol-3-ylamino)quinazolin-2-yl)methyl)formamide;
(R,S)-(3,4-difluorophenyl)(4-(5-methyl-1H-pyrazol-3-ylamino)quinazolin-2-yl)methanol;
(3-chloro-4-fluorophenyl)(4-(5-methyl-1H-pyrazol-3-ylamino)quinazolin-2-yl)methanol;

3-(4-fluorophenyl)-3-(4-(5-methyl-1H-pyrazol-3-ylamino) quinazolin-2-yl)propanenitrile;
2-((cyclopropylamino)(4-fluorophenyl)methyl)-N-(5-methyl-1H-pyrazol-3-yl)quinazolin-4-amine;
2-(1-(4-fluorophenyl)-2-(methylsulfonyl)ethyl)-N-(5-methyl-1H-pyrazol-3-yl)quinazolin-4-amine;
2-(3-amino-1-(4-fluorophenyl)propyl)-N-(5-methyl-1H-pyrazol-3-yl)quinazolin-4-amine;
(R,S) (4-fluorophenyl)(4-(5-methyl-1H-pyrazol-3-ylamino) quinazolin-2-yl)methanol-1-d; (4-fluorophenyl)(4-(5-methoxy-1H-pyrazol-3-ylamino)quinazolin-2-yl)methanone;
(R,S)-(4-(5-ethyl-1H-pyrazol-3-ylamino)quinazolin-2-yl) (4-fluorophenyl)methanol;
(4-Fluorophenyl)(4-(5-methoxy-1H-pyrazol-3-ylamino) quinazolin-2-yl)methanol;
(4-fluoro-3-methoxyphenyl)(4-(5-methyl-1H-pyrazol-3-ylamino)quinazolin-2-yl)methanone;
(4-fluoro-3-hydroxyphenyl)(4-(5-methyl-1H-pyrazol-3-ylamino)quinazolin-2-yl)methanone;
(R,S)-(2-fluoro-5-(hydroxy(4-(5-methyl-1H-pyrazol-3-ylamino)quinazolin-2-yl)methyl)phenol acetate.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

C. FORMULATION OF PHARMACEUTICAL COMPOSITIONS

Provided herein are pharmaceutical compositions comprising a compound provided herein, e.g., a compound of Formula I, as an active ingredient, or a pharmaceutically acceptable salt, solvate or hydrate thereof in combination with a pharmaceutically acceptable vehicle, carrier, diluent, or excipient, or a mixture thereof.

The compound provided herein may be administered alone, or in combination with one or more other compounds provided herein. The pharmaceutical compositions that comprise a compound provided herein, e.g., a compound of Formula I, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise a compound provided herein, e.g., a compound of Formula I, or a pharmaceutically acceptable salt, solvate or hydrate thereof; and one or more pharmaceutically acceptable excipients or carriers.

In another embodiment, the pharmaceutical compositions are provided in a dosage form for parenteral administration, which comprise a compound provided herein, e.g., a compound of Formula I, or a pharmaceutically acceptable salt, solvate or hydrate thereof; and one or more pharmaceutically acceptable excipients or carriers.

In yet another embodiment, the pharmaceutical compositions are provided in a dosage form for topical administration, which comprise a compound provided herein, e.g., a compound of Formula I, or a pharmaceutically acceptable salt, solvate or hydrate thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In one embodiment, the therapeutically effective dose is from about 0.1 mg to about 2,000 mg per day of a compound provided herein. The pharmaceutical compositions therefore should provide a dosage of from about 0.1 mg to about 2000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

Oral Administration

The pharmaceutical compositions provided herein can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, troches, lozenges, pastilles, cachets, pellets, medicated chewing gum, bulk powders, effervescent or non-effervescent powders or granules, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein can be formulated as immediate or modified release dosage forms, including delayed-, sustained, pulsed-, controlled, targeted-, and programmed-release forms.

The pharmaceutical compositions provided herein can be co-formulated with other active ingredients which do not impair the desired therapeutic action, or with substances that supplement the desired action.

Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein can be formulated as immediate or modified release dosage forms, including delayed-, sustained-, pulsed-, controlled, targeted-, and programmed-release forms.

The pharmaceutical compositions can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration can further comprise a suitable flavor, such as menthol and levomenthol, or sweeteners, such as saccharin or saccharin sodium.

The pharmaceutical compositions provided herein for topical administration can be formulated to be immediate release or modified release, including delayed-, sustained-, pulsed-, controlled-, targeted, and programmed release.

Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate, and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form can be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol, organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

D. EVALUATION OF THE ACTIVITY OF THE COMPOUNDS

Standard physiological, pharmacological and biochemical procedures are available for testing the compounds to identify those that possess biological activities that modulate the activity of JAK kinases, including wild type and mutant JAK kinases. Such assays include, for example, biochemical assays such as binding assays, see, Fabian et al., *Nature Biotechnology* 2005, 23, 329-336, radioactivity incorporation assays, as well as a variety of cell based assays.

Exemplary cell based assay methodologies include measurement of STAT5A phosphorylation, for example, by ELISA or the measurement of proliferation in leukemic cell lines such as TF-1 or HEL-2, for example, by BrdU incorporation, by fluorescent staining or by a reporter assay activated by the transcription factor STATS. Cells useful in the assays include cells with wildtype JAK such as TF-1 or mutated JAK such as the cell line HEL-2 which express a constitutively active JAK2 carrying the V617F mutation. Suitable cells include those derived through cell culture from patient samples as well as cells derived using routine molecular biology techniques, e.g., retroviral transduction, transfection, mutagenesis, etc.

E. METHODS OF USE OF THE COMPOUNDS AND COMPOSITIONS

Also provided herein are methods of using the disclosed compounds and compositions, or pharmaceutically acceptable salts, solvates or hydrates thereof, for the treatment, prevention, or amelioration of a disease or disorder that is mediated or otherwise affected via JAK kinase, including JAK2 kinase activity or one or more symptoms of diseases or disorders that are mediated or otherwise affected via JAK kinase, including JAK2 kinase, activity. JAK kinase can be wild type and/or mutant form of JAK2 kinase. Consistent with the description above, such diseases or disorders include without limitation: myeloproliferative disorders such as polycythemia vera (PCV), essential thrombocythemia and idiopathic myelofibrosis (IMF); leukemia such as myeloid leukemia including chronic myeloid leukemia (CML), imatinib-resistant forms of CML, acute myeloid leukemia (AML), and a subtype of AML, acute megakaryoblastic leukemia (AMKL); lymphoproliferative diseases such as myeloma; cancer including head and neck cancer, prostate cancer, breast cancer, ovarian cancer, melanoma, lung cancer, brain tumor, pancreatic cancer and renal carcinoma; and inflammatory diseases or disorders related to immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD) and dry eye syndrome (or keratoconjunctivitis sicca (KCS)).

In certain embodiments, provided herein are methods of using the disclosed compounds and compositions, or pharmaceutically acceptable salts, solvates or hydrates thereof, for the treatment, prevention, or amelioration of a disease or disorder selected from myeloproliferative disorders such as polycythemia vera (PCV), essential thrombocythemia and idiopathic myelofibrosis (IMF) and hypereosinophilic syndrome (HES); leukemia such as myeloid leukemia including chronic myeloid leukemia (CML), imatinib-resistant forms of CML, acute myeloid leukemia (AML), acute lymphoblastic leukemia (ALL) and a subtype of AML, acute megakaryoblastic leukemia (AMKL); lymphoproliferative diseases such as myeloma; cancer including head and neck cancer, prostate cancer, breast cancer, ovarian cancer, melanoma, lung cancer, brain cancer, pancreatic cancer, gastric cancer, thyroid cancer, renal carcinoma, Kaposi's sarcoma, Castleman's disease, melanoma; and inflammatory diseases or disorders related to immune dysfunction, immunodeficiency or immunomodulation, such as tissue transplant rejection, graft-versus-host disease, wound healing, kidney disease; autoimmune diseases such as multiple sclerosis, thyroiditis, type 1 diabetes, sarcoidosis, psoriasis, allergic rhinitis, atopic dermatitis, myasthenia gravis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD), inflammatory diseases of the eye including conjunctivitis, uveitis, iritis, scleritis, inflammatory diseases of the respiratory tract including the upper respiratory tract such as rhinitis and sinusitis and inflammatory diseases of the lower reparatory tract including bronchitis; inflammatory myopathy such as myocarditis, other inflammatory diseases such as ischemia reperfusion injuries related to an inflammatory ischemic event such as a stroke or cardiac arrest, and other inflammatory conditions such as systemic inflammatory response syndrome (SIRS) and sepsis.

In certain embodiments, JAK-mediated diseases and disorders include restenosis, fibrosis and scleroderma. In certain embodiments, JAK-mediated diseases include viral diseases such as Epstein Barr virus (EBV), hepatitis (hepatitis B or hepatitis C), human immunodeficiency virus (HIV), Human T-lymphotropic virus type 1 (HTLV-1), varicella-zoster virus and the human papilloma virus (HPV).

F. COMBINATION THERAPY

Furthermore, it will be understood by those skilled in the art that the compounds, isomers, and pharmaceutically acceptable salts, solvates or hydrates provided herein, including pharmaceutical compositions and formulations containing these compounds, can be used in a wide variety of combination therapies to treat the conditions and diseases described above. Thus, also contemplated herein is the use of compounds, isomers and pharmaceutically acceptable salts, solvates or hydrates provided herein in combination with other active pharmaceutical agents for the treatment of the disease/conditions described herein.

In one embodiment, such additional pharmaceutical agents include without limitation anti-cancer agents, including chemotherapeutic agents and anti-proliferative agents; anti-inflammatory agents and immunomodulatory agents or immunosuppressive agents.

In certain embodiments, the anti-cancer agents include anti-metabolites (e.g., 5-fluoro-uracil, cytarabine, methotrexate, fludarabine and others), antimicrotubule agents (e.g., vinca alkaloids such as vincristine, vinblastine; taxanes such as paclitaxel and docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, satraplatin and CI-973), anthracyclines (e.g., doxrubicin and daunorubicin), antitumor antibiotics (e.g., mitomycin, idarubicin, adriamycin and daunomycin), topoisomerase inhibitors (e.g., etoposide and camptothecins), anti-angiogenesis agents (e.g. Sutent®, sorafenib and Bevacizumab) or any other cytotoxic agents, (e.g. estramustine phosphate, prednimustine), hormones or hormone agonists, antagonists, partial agonists or partial antagonists, kinase inhibitors (such as imatinib), and radiation treatment.

In certain embodiments, the anti-inflammatory agents include matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate and salicylsalicyclic acid), COX-1 or COX-2 inhibitors, or glucocorticoid receptor agonists such as corticosteroids, methylprednisone, prednisone, or cortisone.

The compound or composition provided herein, or pharmaceutically acceptable salts, solvates or hydrates thereof, may be administered simultaneously with, prior to, or after administration of one or more of the above agents.

Pharmaceutical compositions containing a compound provided herein or pharmaceutically acceptable salts, solvates or hydrates thereof, and one or more of the above agents are also provided.

Also provided is a combination therapy that treats or prevents the onset of the symptoms, or associated complications of cancer and related diseases and disorders comprising the administration to a subject in need thereof, of one of the compounds or compositions disclosed herein, or pharmaceutically acceptable salts, solvates or hydrates thereof, with one or more anti-cancer agents.

G. PREPARATION OF COMPOUNDS

Starting materials in the synthesis examples provided herein are either available from commercial sources or via literature procedures (e.g., March *Advanced Organic Chemistry: Reactions, Mechanisms, and Structure*, (1992) 4th Ed.; Wiley Interscience, New York). All commercially available compounds were used without further purification unless otherwise indicated. 300 MHz Proton ($^1$H) nuclear magnetic resonance (NMR) spectra were recorded on a Bruker Avance 300 NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low resolution mass spectra (MS) were obtained as electrospray ionization (ESI) mass spectra, which were recorded on a Shimadzu HPLC/MS instrument using reverse-phase conditions (acetonitrile/water, 0.05% acetic acid). Preparative reverse phase HPLC was typically performed using a Varian HPLC system equipped with a Phenomenex phenylhexyl, a Phenomenex Luna C18, or a Varian Pursuit diphenyl reverse phase column; typical elution conditions utilized a gradient containing an increasing composition of organic cosolvent (0.05% HOAc/CH$_3$CN or 0.05% HOAc/MeOH) to aqueous cosolvent (0.05% aq HOAc). Silica gel chromatography was either performed manually, typically following the published procedure for flash chromatography (Still et al. (1978) *J. Org. Chem.* 43:2923), or on an automated system (for example, Biotage SP instrument) using pre-packed silica gel columns.

It is understood that in the following description, combinations of substituents and/or variables of the depicted formulae are permissible only if such contributions result in stable compounds under standard conditions.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1991), 2nd Ed., Wiley-Interscience.

One of ordinary skill in the art could readily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that the compounds provided herein could exist as one or more isomers, that is E/Z isomers, enantiomers and/or diastereomers.

Compounds of formula (I) may be generally prepared as depicted in the following schemes, unless otherwise noted, the various substituents are as defined elsewhere herein.

Standard abbreviations and acronyms as defined in *J. Org. Chem.* 2007 72(1): 23A-24A are used herein. Other abbreviations and acronyms used herein are as follows:

| | |
|---|---|
| DCM | dichloromethane |
| DIEA | diisopropylethylamine |
| EDCI | N-(3-Dimethylaminopropyl)-N'-ethylcarbodiimide hydrochloride |
| EtOAc | ethyl acetate |
| EtOH | ethanol |
| FBS | fetal bovine serum |
| HATU | O-(7-Azabenzotriazol-1-yl)-N,N,N',N'-tetramethyluronium hexafluorophosphate |
| HOAc | acetic acid |
| HOBt | N-hydroxybenzotriazole |
| MeOH | methanol |
| TEA | Triethylamine |
| Trityl | Triphenylmethyl |

Compounds provided herein are synthesized according to the following schemes and descriptions. Scheme 1 illustrates a general route to key synthetic intermediates and compounds provided herein via substituted anthranilimides 5. Starting from a substituted benzoic acid, nitration under standard conditions, for example, treatment with nitric acid under acidic conditions with heating as necessary, provides the corresponding nitrobenzoic acid 2, which is separated from any undesired regioisomers by chromatography or crystallization. Reduction of the nitro group under standard conditions, for example, using hydrogen gas and noble metal catalyst in a solvent such as water, a lower alcohol, EtOAc, or DMF; metallic Sn or Fe under acid conditions; or SnCl$_2$ in a solvent such as EtOH or DMF, affords the corresponding anthranilic acid 4. Conversion of the carboxyl group of 4 to the carboxamide group of 5 is accomplished by any of a variety of standard methods, including treatment with ammonia or ammonium chloride in the presence of coupling reagents such as HATU, EDCI, (Benzotriazol-1-yloxy)tris(dimethylamino)phosphonium hexafluorophosphate, dicyclohexyl carbodiimide, and the like, or alternatively, via the acid chloride by treatment of the acid with thionyl chloride or phosphoryl chloride or the like, followed by addition of a suitable form of ammonia, such as ammonia in MeOH or ammonium hydroxide. Anthranilamide 5 is then condensed with a suitably activated carboxylic acid derivative 6 followed by dehydrative cyclization, promoted for example, with heat or with TMSCl in the presence of a tertiary amine base such as TEA, DIEA, or pyridine to form 4-hydroxyquinazolines 8. The hydroxyl group of 4-hydroxyquinazoline 8 is next converted to a leaving group. Examples of this transformation include treatment with a halogenating agent such as phosphoryl halide to produce quinazoline 9 (Z=halo), or with a sulfonyl chloride to produce quinazoline 9 (Z=a sulfonyloxy derivative), or with a halogenating agent followed by an organic mercaptan followed by sulfur oxidation to produce compound 7 (Z=a sulfinyl derivative). Quinazoline 9 is then allowed to react with a suitable pyrazole amine (pyrazole-NH$_2$) in a suitable solvent such as DMF or dimethylacetamide, optionally in the presence of a source of iodide ion, for example potassium iodide or tetrabutylammonium iodide, optionally with heating, to afford, after isolation, compound 10.

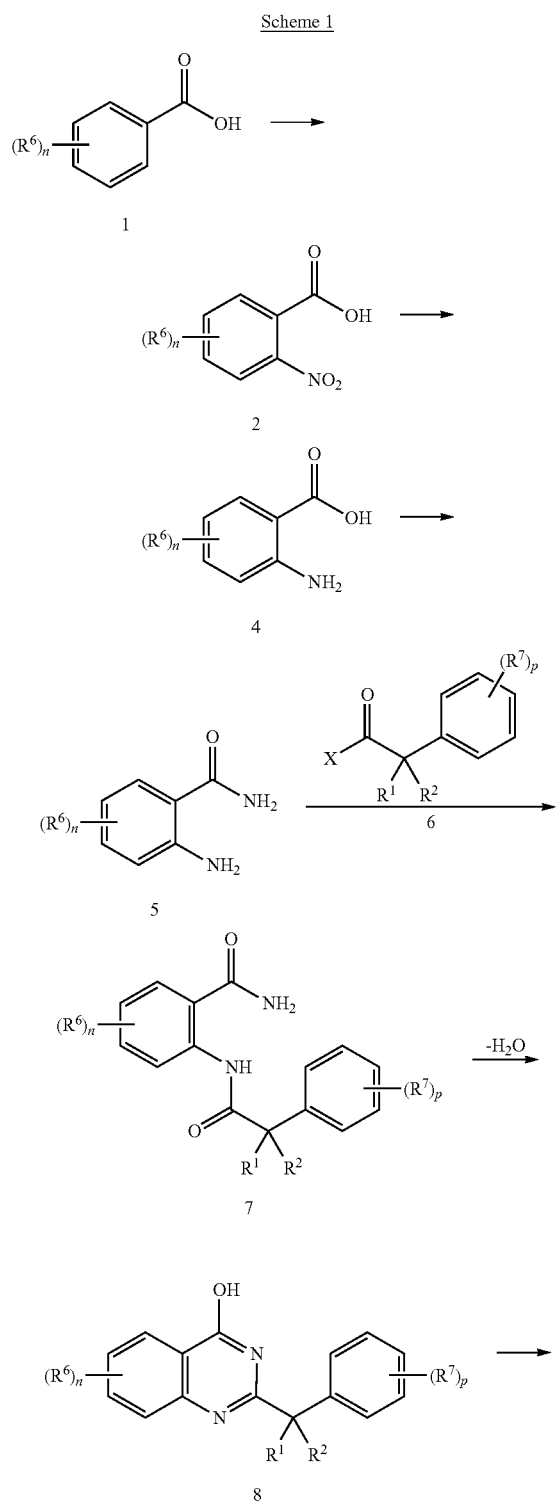

Scheme 1

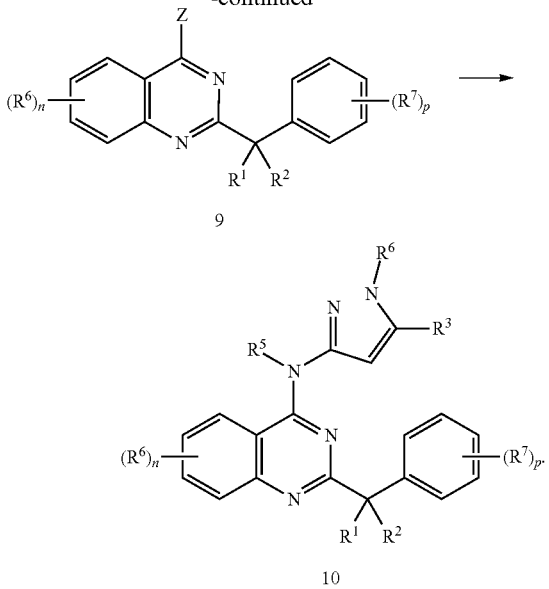

It is understood that at suitable stages of a synthetic process such as that illustrated in Scheme 1, one or more R$^6$ groups of formulae 1-10 may serve as a precursor to a modified R$^6$ group in the final compound provided herein. For example, if in compound I, R$^6$=CO$_2$Me, the methoxycarbonyl group may be transformed at a suitable stage of the synthesis, to, for example, a carboxyl group by hydrolysis, to an amide by hydrolysis followed by carboxy group activation and treatment with an amine, to a hydroxymethyl group by reduction, to a tertiary carbinol by treatment with two equivalents of a Grignard reagent, to an aminomethyl group by reduction to a hydroxymethyl group followed by oxidation to an aldehyde followed by reductive amination with a suitable amine in the presence of a selective reducing agent such as sodium triacetoxyborohydride. Similarly, if R$^6$=OCH$_2$Ph, then R$^6$ may be transformed to OH, by hydrogenolytic cleavage of the benzyl group, followed by alkylation of the resulting phenolic hydroxyl group with an optionally substituted alkyl halide or an optionally substituted alkyl sulfonate to form a corresponding aromatic ether.

Similarly, certain R groups in intermediates 8, 9, or 10 may be incorporated as shown in Scheme 1 and then converted to alternative R groups.

In Scheme 2, an anthranilamide 5 prepared according to Scheme 1 is treated with an activated oxalic acid derivative such as a dialkyl oxalate either neat or in a suitable solvent such as EtOH or HOAc; or anthranilamide 5 is treated with an oxalic acid monoalkyl ester chloride in a suitable solvent such as DCM in the presence of a base such as TEA and optionally in the presence of a catalyst such as DMAP; or anthranilamide 5 is treated with a cyano oxoacetate monoalkyl ester with heating in a suitable solvent such as acetonitrile or DMF in the presence of a base such as TEA. Analogously to the methods described in Scheme 1, subsequent treatment under dehydrating conditions, for example, heating with or without TMSCl in the presence of a suitable base such as DIEA in a suitable solvent such as DCE affords the bicyclic product 11. In addition, a slightly modified procedure to intermediates 11 is reported in patent application WO2004/20441, incorporated by reference in its entirety. The alkoxycarbonyl group at the 2-position of the quinazoline ring of compound 12 or compound 14 can treated with a metalloarene, for example an aryl lithium or an aryl Grignard reagent in a suitable solvent such diethyl ether, THF, or other ether solvent, to produce ketone 13 or 15, respectively. Although not shown in Scheme 2, intermediate 11 also may be analogously treated with a metalloarene to form the corresponding aryl ketone.

halide reagent affords a tertiary carbinol 17. Alternatively, treatment of ketone 15 with an O-substituted or O-unsubstituted hydroxylamine in a suitable solvent such as an alcohol or alcohol/water mixture, optionally in the presence of an acidic or basic catalyst, affords an oxime 18. The oxime may

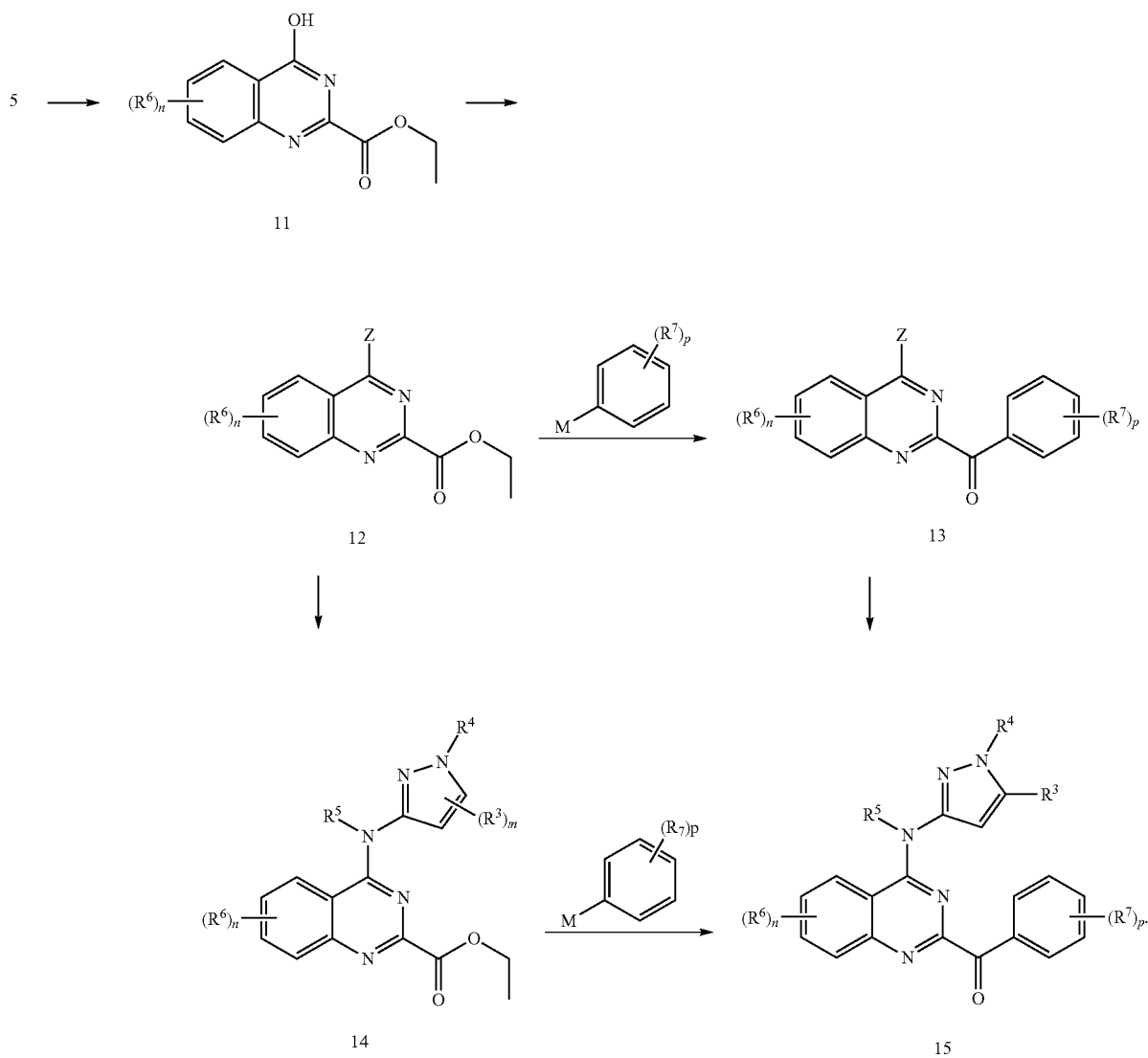

M is a metal

Methods are illustrated in Scheme 3 for the conversion of ketones 15 prepared according to Scheme 2 to further compounds provided herein. Treatment of a compound 15 with a suitable reducing agent, for example a hydride reagent such as sodium borohydride in an alcohol solvent, or lithium borohydride in an ether solvent, or a related borohydride or aluminum hydride reagent in an appropriate solvent system, reduces the ketone to the corresponding carbinol 16. Treatment of ketone 15 with an alkyl or aryl lithium or magnesium be further treated under reducing conditions, for example a borane-amine complex in the presence of a strong acid and heat for prolonged reaction times or hydrogenolysis conditions ($H_2$, noble metal catalyst, optionally in the presence of an organic or mineral acid) for prolonged periods to afford the amine 19. Alternatively, use of milder conditions such as lower temperature, shorter reaction times or milder acid, when present, afford the alkoxylamine or hydroxylamine 20.

Scheme 3

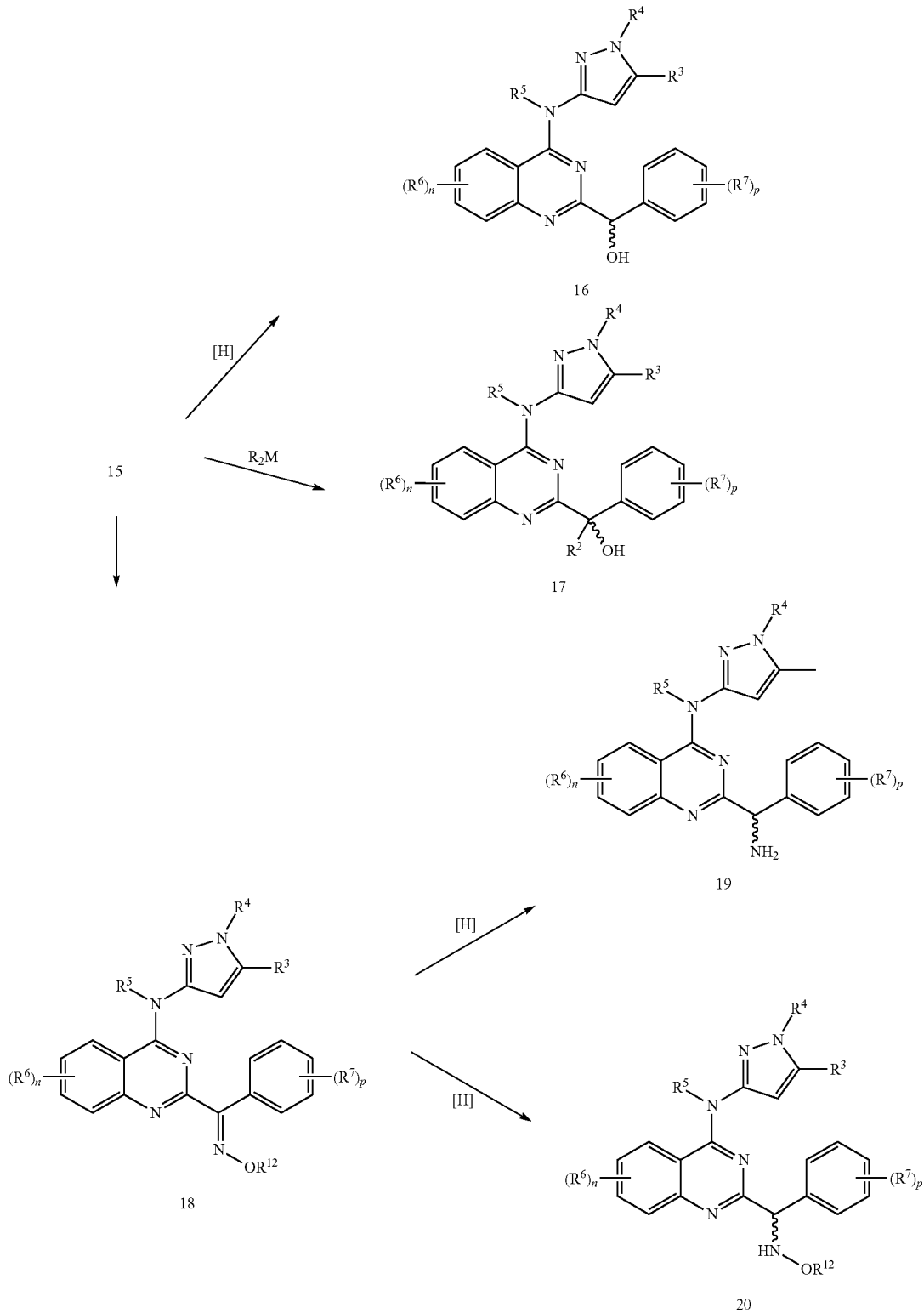

Alternatively, amines 19 may be prepared according to the synthetic sequence illustrated in Scheme 4. In Scheme 4, the hydroxyl group in carbinol 16 is converted to a leaving group Z by treatment with, for example, a phosphorus halide to afford compound 21 (Z=halo) or by treatment with a sulfonyl halide in a suitable solvent such as DCM and in the presence of a hydrogen halide scavenger such as a tertiary amine, for example DIEA or pyridine, to afford compound 21 (Z=a sulfonyloxy derivative). For the last reaction, in the event of adventitious sulfonylation at one or more other sites of the molecule, the extraneous sulfonyl groups are removed at a later stage by treatment with a nucleophile such as hydroxide, ammonia, or hydrazine.

As shown in Scheme 4, intermediate 21 is further transformed to an azide 22 by displacement of leaving group Z with azide ion, for example by treatment of 21 with an alkali metal azide in a suitable solvent such as a dipolar aprotic solvent, for example DMF or DMSO, at a temperature between about 0° C. and about 100° C. Reduction of the azide with a reducing system, for example triphenylphosphine followed by hydrolysis or hydrogenolysis conditions ($H_2$, noble metal catalyst) in a suitable solvent such as an alcohol or DMF, affords amine 23.

Scheme 4 also illustrates that amines 23 can be further modified to form products of the invention 24, where one of the hydrogen atoms of the amino group has been substituted with a group $R^{14}$. Treatment of amine 23 with an acylating agent such as an acid chloride or acid anhydride usually in the presence of base and optionally in the presence of an acylation catalyst such as DMAP or pyridine in a suitable solvent such as EtOAc, DCM, DMF, or THF, affords products 24 ($R^{14}$=acyl). Alternatively, amine 23 is treated with an alkyl chloroformate, for example ethyl or isopropyl chloroformate, in the presence of base and optionally in the presence of an acylation catalyst such as DMAP or pyridine in a suitable solvent such as EtOAc, DCM, DMF, or THF to afford the corresponding carbamate 24 ($R^{14}$=—C(O)O$R^{12}$). Alternatively, amine 23 is treated with a sulfonyl halide, for example methane or benzene sulfonyl chloride, in the presence of base and optionally in the presence of an acylation catalyst such as DMAP or pyridine in a suitable solvent such as EtOAc, DCM, DMF, or THF to afford the corresponding sulfonamide 23 ($R^{14}$=—SO$_2R^{12}$). Alternatively, amine 23 in a suitable solvent such as MeOH, EtOH, or DME is treated with an aldehyde under dehydrating conditions, for example in the presence of molecular sieves or trimethyl orthoformate, optionally in the presence of an acid catalyst such as acetic acid or hydrochloric acid to form an intermediate imine, and the mixture is treated either concurrently or subsequently with a selective reducing agent such as sodium cyanoborohydride or sodium triacetoxyborohydride, or (especially in the case of pretreatment with aldehyde) sodium borohydride to afford a new amine 23 ($R^{14}$=alkyl or aryl, each of which is optionally substituted).

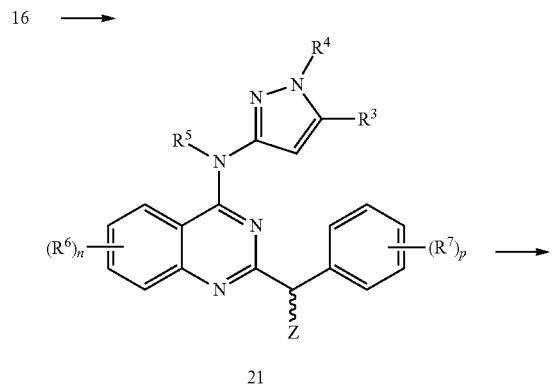

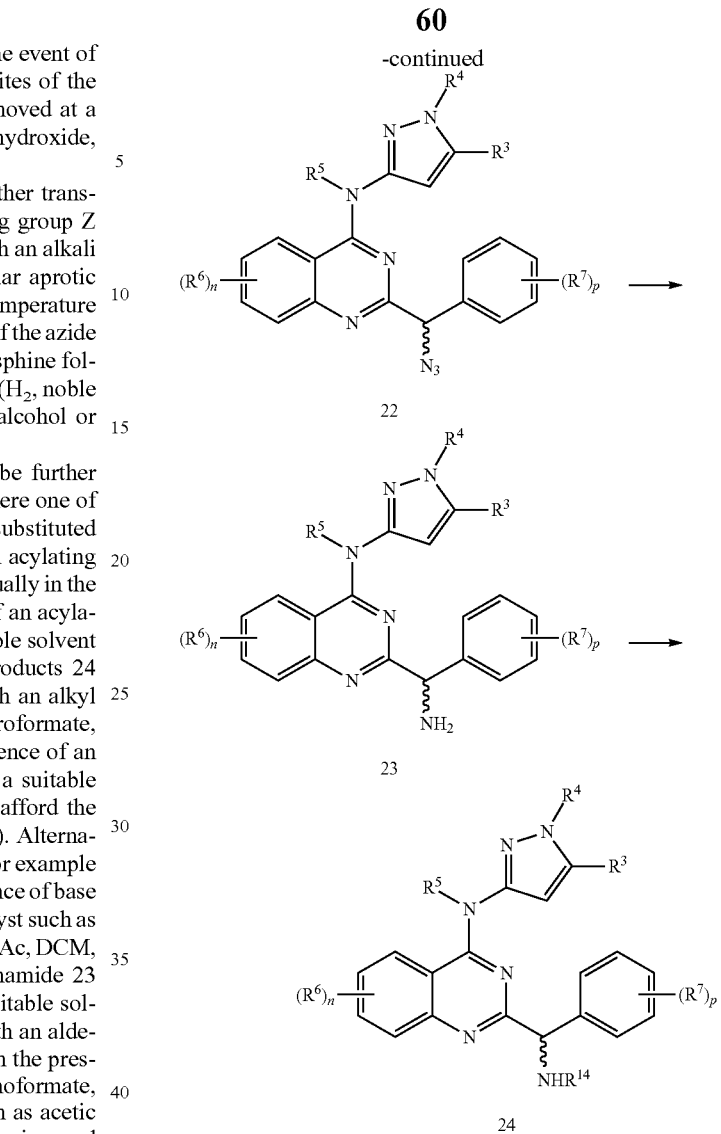

A representative method is illustrated in Scheme 5 for the conversion of ketone 15 to additional compounds provided herein. Ketone 15 in a suitable solvent such as THF, DME, diglyme, or DMSO is treated with the anion generated from treatment of a trialkylphosphonoacetate with a strong base such as sodium hydride, a lithium amide, dimsyl (DMSO) anion, or the like, at a suitable temperature between about 0° C. and about 100° C. to provide, following work-up and isolation, α,β-unsaturated ester 25. Treatment of compound 25 under suitable reducing conditions, for example with $H_2$ in the presence of a noble metal catalyst in a suitable solvent such as an alcohol or DMF affords ester 26. Reduction of the ester moiety of compound 19 may be effected by treatment with a hydride reducing system such as LiAlH$_4$/THF, LiBH$_4$/THF, or Ca(BH$_4$)$_2$/EtOH/THF to afford primary alcohol 27. The hydroxyl group of alcohol 27 is converted to a leaving group Z using method well known in the art, for example treatment of 20 with a phosphoryl halide to afford 28 (Z=halide) or treatment of 27 with a sulfonyl halide to afford 28 (Z=a sulfonyloxy derivative). Intermediate 28 may then been treated with a nucleophile to afford compound 29. For example, treatment of compound 28 with a mercaptide nucleophile affords compound 29 (Y=S); treatment of compound 28 with an alkoxide nucleophile affords 29 (Y=O);

treatment of compound 28 with an amine nucleophile affords compound 29 (Y=NH or NR$^x$).

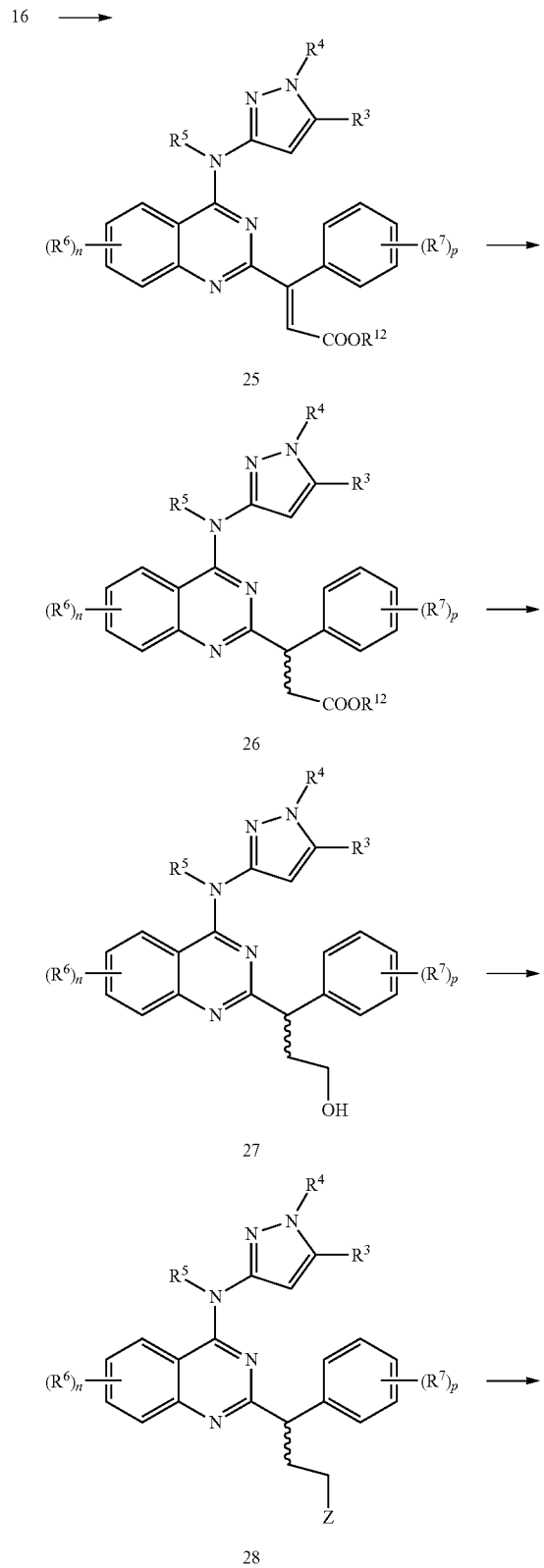

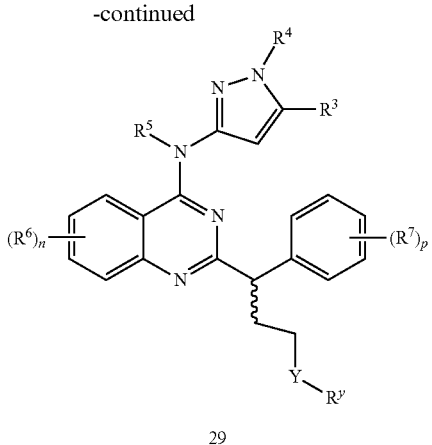

A complementary approach to conversion of alcohol 27 to compounds provided herein is illustrated in Scheme 6. Alcohol 27 is first treated with a suitable oxidizing system such as pyridinium chlorochromate/DCM or Swern reagent (DMSO/oxalyl chloride/TEA/DCM) or DMSO/pyridine-sulfur trioxide complex/TEA or Dess-Martin periodinane (1,1,1-trisacetoxy)-1,1-dihydro-1,2-benziodoxol-3-(1H)-one/DCM) to afford aldehyde 30. Treatment of aldehyde 30 with a primary or secondary amine in the presence of a selective reducing agent such as sodium triacetoxyborohydride or sodium cyanoborohydride in a suitable solvent such as an alcohol, optionally in the presence of catalytic a catalytic quantity acid such as acetic acid, affords amine 31.

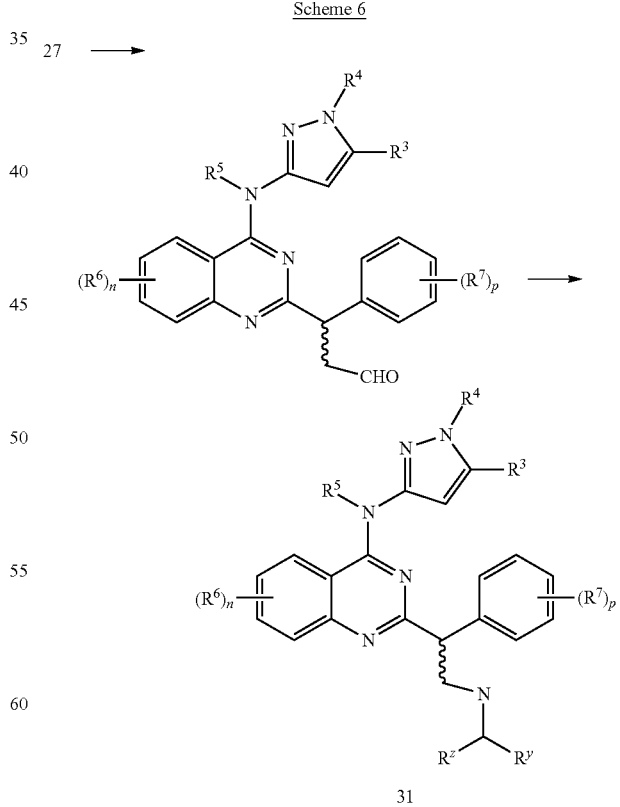

The subject matter has been described in an illustrative manner, and it is to be understood that the terminology used is

EXAMPLES

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

Example 1

Preparation of (3-fluorophenyl)(4-(5-methyl-1H-pyrazol-3-ylamino)quinazolin-2-yl)methanone

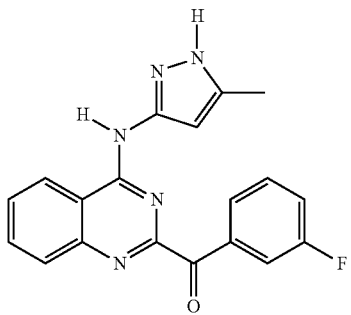 [SMILES: Cc1cc(Nc2nc(C(=O)c3cccc(F)c3)nc3ccccc23)n[nH]1]

Step A

To a suspension of ethyl 4-chloroquinazoline-2-carboxylate (237 mg, 1 mmol) in THF (5 mL) was added dropwise a 1M solution of 3-fluorophenylmagnesium bromide in THF (2 mL, 2 mmol) at −20° C. The reaction mixture was stirred at −20° C. for 4 h. The mixture was quenched by adding 0.5 N HCl solution (5 mL) and the biphasic mixture was extracted with EtOAc (2×10 mL). The combined organic layers were washed with brine and dried over MgSO$_4$. (4-chloroquinazolin-2-yl)(3-fluorophenyl)methanone was obtained as a yellow solid (190 mg, 66%). LC-MS (ESI) m/z 287 (M+H)$^+$.

Step B (3-fluorophenyl)(4-(5-methyl-1H-pyrazol-3-ylamino)quinazolin-2-yl)methanone was obtained following the same procedure described for synthesis of (4-fluorophenyl)(4-(5-methyl-1H-pyrazol-3-ylamino)quinazolin-2-yl)methanone in Example 3 using (4-chloroquinazolin-2-yl)(3-fluorophenyl)methanone as a starting material. Purification was performed on HPLC without work-up (26% yield). $^1$H NMR (300 MHz, DMSO-d$_6$) δ 2.19 (s, 3H), 6.54 (s, 1H), 7.60 (m, 2H), 7.70 (m, 1H), 7.83-7.92 (m, 4H), 8.75 (m, 1H), 10.73 (s, 1H), 12.24 (s, 1H); LC-MS (ESI) m/z 348 (M+H)$^+$.

Example 2

Preparation of (4-(1H-pyrazol-3-ylamino)quinazolin-2-yl)(3-fluorophenyl)methanone

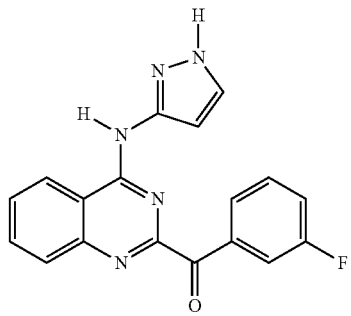 [SMILES: O=C(c1cccc(F)c1)c1nc(Nc2cc[nH]n2)c2ccccc2n1]

To a solution of (4-chloroquinazolin-2-yl)(3-fluorophenyl)methanone from Example 1 (57 mg, 0.20 mmol) in DMF (3 mL), DIEA (0.069 mL, 0.4 mmol) and 1H-pyrazol-3-amine (83 mg, 1 mmol) were added. The mixture was stirred at 50° C. for 2 h. The reaction was quenched by adding water and the precipitate was filtered. The crude solid was purified on preparative TLC using DCM/MeOH as mobile phase to afford (4-(1H-pyrazol-3-ylamino)quinazolin-2-yl)(3-fluorophenyl)methanone (18 mg, 27%). $^1$H NMR (300 MHz, DMSO-d$_6$) δ 6.80 (s, 1H), 7.67-7.61 (m, 4H), 7.92-7.84 (m, 4H), 8.78 (m, 1H), 10.82 (s, 1H), 12.54 (s, 1H); LC-MS (ESI) m/z 334 (M+H)$^+$.

Example 3

Preparation of (4-fluorophenyl)(4-(5-methyl-1H-pyrazol-3-ylamino)quinazolin-2-yl)methanone

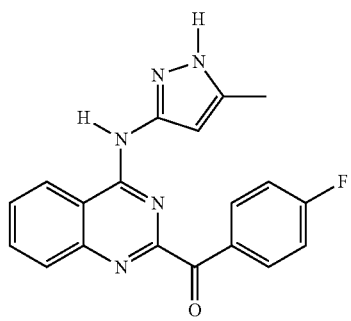 [SMILES: Cc1cc(Nc2nc(C(=O)c3ccc(F)cc3)nc3ccccc23)n[nH]1]

Step A

To a solution of ethyl 4-chloroquinazoline-2-carboxylate (0.6 g, 2.53 mmol) in THF (6 mL) at −40° C., was added dropwise a 1 M solution of 4-fluorophenylmagnesium bromide in THF (3 mL, 3.0 mmol, 1.2 eq). The mixture was stirred at −40 C for 4 h. The reaction was quenched by adding 0.5 N HCl solution (5 mL) and the mixture was extracted with EtOAc (2×10 mL). The combined organic layers were washed with brine and dried over MgSO$_4$. The crude product was purified on a silica gel column using a mixture of EtOAc-hexanes as eluent. (4-chloroquinazoline-2-yl)(4-fluorophenyl)methanone was obtained as a light yellow solid (440 mg, 60%). $^1$H NMR (300 MHz, DMSO-d$_6$) δ 7.45-740 (m, 2H), 8.07-8.03 (m, 1H), 8.17-8.13 (m, 2H), 8.23 (m, 2H), 8.42 (d, 1H); LC-MS (ESI) m/z 287 (M+H)$^+$.

Step B

To a solution of (4-chloroquinazolin-2-yl)(4-fluorophenyl)methanone (84 mg, 0.30 mmol) in DMF (3 mL) were added DIEA (0.103 mL, 0.6 mmol) and 5-methyl-1H-pyrazol-3-amine (88 mg, 0.9 mmol at rt. The reaction mixture was heated at 40° C. overnight. The reaction was quenched by adding water and the yellow precipitate was collected by filtration and washed with water. The crude product was purified by silica gel chromatography eluting with DCM/MeOH to give (4-fluorophenyl)(4-(5-methyl-1H-pyrazol-3-ylamino)quinazolin-2-yl)methanone (30 mg, 29%). $^1$H NMR (300 MHz, DMSO-$d_6$) δ 2.19 (s, 3H), 6.54 (s, 1H), 7.40 (m, 2H), 7.68 (t, 1H), 7.9-7.7 (m, 2H), 8.08 (m, 2H), 8.74 (d, 1H), 10.66 (s, 1H), 12.20 (s, 1H); LC-MS (ESI) m/z 348 (M+H)$^+$.

Example 4

Preparation of (4-(1H-pyrazol-3-ylamino)quinazolin-2-yl)(4-fluorophenyl)methanone

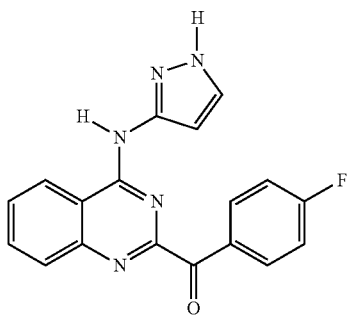 [SMILES: O=C(c1ccc(F)cc1)c1nc(Nc2cc[nH]n2)c2ccccc2n1]

(4-(1H-pyrazol-3-ylamino)quinazolin-2-yl)(4-fluorophenyl)methanone was obtained following the procedure described in Example 3 for synthesis of (4-fluorophenyl)(4-(5-methyl-1H-pyrazol-3-ylamino)quinazolin-2-yl)methanone, substituting 5-methyl-1H-pyrazol-3-amine in Example 3 with 1H-pyrazol-3-amine (30% yield). $^1$H NMR (300 MHz, DMSO-$d_6$) δ 6.78 (s, 1H), 7.39 (t, 2H), 7.70 (m, 2H), 7.90 (m, 2H), 8.10 (m, 2H), 8.77 (d, 1H), 10.84 (s, 1H), 12.56 (s, H); LC-MS (ESI) m/z 334.3 (M+H)$^+$.

Example 5

Preparation of (4-(1H-pyrazol-3-ylamino)quinazolin-2-yl)(2-methoxyphenyl)methanone

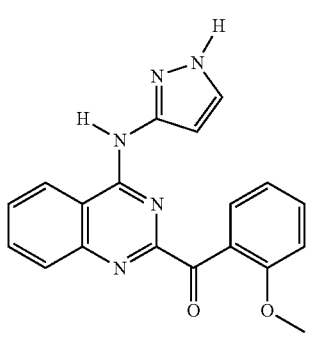 [SMILES: COc1ccccc1C(=O)c1nc(Nc2cc[nH]n2)c2ccccc2n1]

Step A

To a solution of ethyl 4-chloroquinazoline-2-carboxylate (0.250 g, 1.05 mmol) in DMF (2.5 mL) at rt under argon were added potassium iodide (0.192 g, 1.16 mmol), DIEA (0.238 mL, 1.37 mmol), and 1H-pyrazol-3-amine (0.113 g, 1.37 mmol). The mixture was stirred at rt for 5 h and diluted with H$_2$O (5 mL). The precipitate was collected by filtration, washed with H$_2$O, and dried under high vacuum for several hours to afford ethyl 4-(1H-pyrazol-3-ylamino)quinazoline-2-carboxylate as a tan solid (0.190 g, 64%). $^1$H NMR (300 MHz, DMSO-$d_6$) δ 12.52 (s, 1H), 10.58 (s, 1H), 8.72 (d, 1H), 7.90 (d, 2H), 7.78 (s, 1H), 7.68 (m, 1H), 7.18 (s, 1H), 4.48 (q, 2H), 1.48 (t, 3H); LC-MS (ESI) m/z 284 (M+H)$^+$.

Step B

To a suspension of ethyl 4-(1H-pyrazol-3-ylamino)quinazoline-2-carboxylate (0.110 g, 0.39 mmol) in THF (5 mL) under argon at −40° C. was added (2-methoxyphenyl)magnesium bromide (0.5 M solution in THF; 2.32 mL, 1.16 mmol). The mixture was stirred at −40° C. for 3 h and quenched with 0.5 N HCl (10 mL). The organic layer was separated. The aqueous layer was washed with 10% MeOH/CH$_2$Cl$_2$ (50 mL×2). The combined organic layers were washed with brine (25 mL), dried over anhydrous Na$_2$SO$_4$, filtered, and concentrated under reduced pressure. The residue was purified on preparative HPLC (Phenomenex phenyl-hexyl reverse phase column, eluted with gradient of solvent B=0.05% HOAc/CH$_3$CN and solvent A=0.05% HOAc/H$_2$O) to afford (4-(1H-pyrazol-3-ylamino)quinazolin-2-yl)(2-methoxyphenyl)methanone as a yellow solid (0.023 g, 17%). $^1$H NMR (300 MHz, DMSO-$d_6$) δ 3.50 (s, 3H), 6.58 (s, 1H), 7.15 (m, 2H), 7.70-7.50 (m, 4H), 7.88 (m, 2H), 8.75 (d, 1H), 10.68 (s, 1H), 12.42 (s, 1H); LC-MS (ESI) m/z 346 (M+H)$^+$.

Example 6

Preparation of (R,S)-(4-(1H-pyrazol-3-ylamino)quinazolin-2-yl)(4-fluorophenyl)methanol

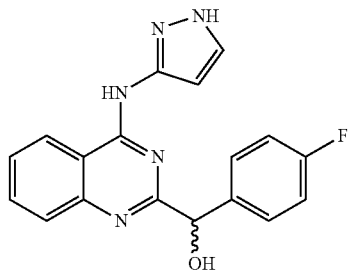 [SMILES: OC(c1ccc(F)cc1)c1nc(Nc2cc[nH]n2)c2ccccc2n1]

To a solution of (4-(1H-pyrazol-3-ylamino)quinazolin-2-yl)(4-fluorophenyl)methanone from Example 4 (375 mg, 1.12 mmol) in a mixture of 1:1 MeOH/THF (10 mL) at 0° C. was added NaBH$_4$ (64 mg, 1.69 mmol). The reaction mixture was stirred at 0° C. for 3 h. The reaction mixture was quenched by adding water, and the solid was collected by filtration. The crude product was purified by reverse-phase HPLC to afford (R,S)-(4-(1H-pyrazol-3-ylamino)quinazolin-2-yl)(4-fluorophenyl)methanol as a white solid (130 mg, 34%). $^1$H NMR (300 MHz, DMSO-$d_6$) δ 5.67 (m, 1H), 5.79 (m, 1H), 6.85 (s, 1H), 7.11 (t, 2H), 7.55 (m, 3H), 7.70 (s, 1H), 7.80 (m, 2H), 8.61 (d, 1H), 10.50 (s, 1H), 12.46 (s, 1H); LC-MS (ESI) m/z 336 (M+H)$^+$.

Example 7

Preparation of (R,S)-2-(fluoro(4-fluorophenyl)methyl)-N-(1H-pyrazol-3-yl)quinazolin-4-amine

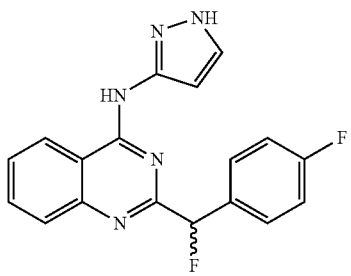 [SMILES: Fc1ccc(C(F)c2nc(Nc3cc[nH]n3)c3ccccc3n2)cc1]

To a solution of (R,S)-(4-(1H-pyrazol-3-ylamino)quinazolin-2-yl)(4-fluorophenyl)methanol from Example 6 (88 mg, 0.238 mmol) in a mixture of DCM/THF (18 mL, 2:1), bis(2-methoxyethyl)-amino)sulfur trifluoride (0.066 mL, 0.22 mmol) was added at rt. The reaction mixture was stirred at 50° C., overnight. The reaction mixture was quenched by adding acetone (0.1 mL), the solvent was evaporated and the residue was purified on HPLC. (R,S)-2-(Fluoro(4-fluorophenyl)methyl)-N-(1H-pyrazol-3-yl)quinazolin-4-amine was obtained as a white powder (12 mg, 15%). $^1$H NMR (300 MHz, DMSO-d$_6$) δ 6.46 (s, 1H), 6.61 (s, 1H), 6.86 (s, 1H), 7.22 (t, 2H), 7.64-7.56 (m, 2H), 7.70 (s, 1H), 7.82 (m, 2H), 8.65 (d, 1H), 10.63 (s, 1H), 12.50 (s, 1H); LC-MS (ESI) m/z 338 (M+H)$^+$.

Example 8

Preparation of 2-(difluoro(4-fluorophenyl)methyl)-N-(5-methyl-1H-pyrazol-3-yl)quinazolin-4-amine

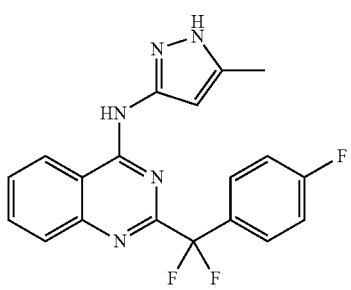 [SMILES: Cc1cc(Nc2nc(C(F)(F)c3ccc(F)cc3)nc3ccccc23)n[nH]1]

Step A 2,2-Difluoro-2-(4-fluorophenyl)acetic acid was prepared according to Middleton et al., J. Org. Chem., 1980, 45(14): 2883-2887) by reaction of ethyl 2-(4-fluorophenyl)-2-oxoacetate with (diethylamino)sulfur trifluoride followed by ester saponification.

Step B

To a solution of 2,2-difluoro-2-(4-fluorophenyl)acetic acid (1.33 g, 7.0 mmol) in DCM (50 mL) was added oxalyl chloride (0.640 mL, 7.5 mmol) and a catalytic amount of DMF. After stirring for 3 h, the mixture was concentrated under reduced pressure to afford 2,2-difluoro-2-(4-fluorophenyl)acetyl chloride. To a solution of 2-aminobenzamide (0.857 g, 6.3 mmol) and TEA (1.04 mL, 0.0075 mol) in DCE (100 mL) at rt was added 2,2-difluoro-2-(4-fluorophenyl)acetyl chloride from above in DCE (100 mL) and the reaction mixture was stirred overnight. After adding EtOAc (200 mL) the mixture was washed with 1 N HCl, sat. NaHCO$_3$ and brine. The organic solution was concentrated to yield an off-white solid (0.989 mg, 51%). $^1$H NMR (300 MHz, DMSO-d$_6$) δ 7.15 (t, 1H), 7.27 (m, 2H), 7.54 (m, 1H), 7.74 (m, 2H), 7.92 (m, 2H), 8.44 (d, 2H), 13.37 (s, 1H).

Step C

To a solution of 2-(2,2-difluoro-2-(4-fluorophenyl)acetamido)benzamide (0.95 g, 3.08 mmol) in DCE (25 mL), TEA (17.2 mL, 0.123 mol) and chlorotrimethylsilane (5.84 mL, 0.0462 mol) were added at rt. The reaction mixture was stirred at 85° C. overnight. After cooling to rt, the solid was filtered and the filtrate was concentrated to dryness. The residue was purified on a silica gel column, using DCM/MeOH as eluent. 2-(Difluoro(4-fluorophenyl)methyl)quinazolin-4-ol was obtained as an off white solid (0.668 g, 75%). $^1$H NMR (300 MHz, DMSO-d$_6$) δ 7.39 (t, 2H), 7.62 (m, 1H), 7.78-7.71 (m, 3H), 7.84 (m, 1H), 8.16 (m, 1H), 13.11 (s, 1H).

Step D

4-Chloro-2-(difluoro(4-fluorophenyl)methyl)quinazoline was obtained according to the procedure described in Example 26 for preparation of 4-chloro-2-(difluoro(4-fluorophenyl)methyl)-7-methylquinazoline, substituting 2-(difluoro(4-fluorophenyl)methyl)-7-methylquinazolin-4-ol in Example 26 with 2-(difluoro(4-fluorophenyl)methyl)quinazolin-4-ol (95% yield). LC-MS (ESI) m/z 308 (M+H)$^+$.

Step E

To a solution of 4-chloro-2-(difluoro(4-fluorophenyl)methyl)quinazoline (0.150 g, 0.487 mmol) in DMF (2 mL) at rt were added potassium iodide (0.081 g, 0.487 mmol), DIEA (0.093 mL, 0.535 mmol) and 5-methyl-1H-pyrazol-3-amine (0.048 g, 0.487 mmol). After stirring the reaction mixture at rt overnight, the reaction was quenched by adding water (15 mL). The precipitate was collected by filtration and washed with H$_2$O. The crude solid was triturated with MeOH. 2-(Difluoro(4-fluorophenyl)methyl)-N-(5-methyl-1H-pyrazol-3-yl)quinazolin-4-amine was obtained as an off-white solid (0.125 g, 69%). $^1$H NMR (300 MHz, DMSO-d$_6$) δ 2.24 (s, 3H), 6.31 (s, 1H), 7.34 (m, 2H), 7.68 (m, 3H), 7.87 (m, 2H), 8.68 (m, 1H), 10.69 (s, 1H), 12.20 (s, 1H); LC-MS (ESI) m/z 370 (M+H)$^+$.

Example 9

Preparation of 2-(difluoro(4-fluorophenyl)methyl)-N-(1H-pyrazol-3-yl)quinazolin-4-amine

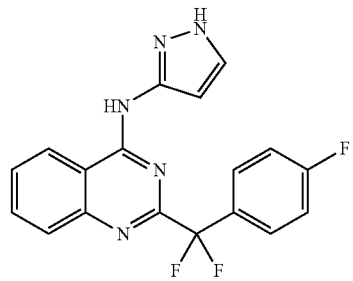 [SMILES: Fc1ccc(C(F)(F)c2nc(Nc3cc[nH]n3)c3ccccc3n2)cc1]

2-(Difluoro(4-fluorophenyl)methyl)-N-(1H-pyrazol-3-yl)quinazolin-4-amine was prepared using a procedure analogous to that described in Example 8, substituting 1H-pyrazol-3-amine for the 5-methyl-1H-pyrazol-3-amine used in Example 8 Step E (61% yield). $^1$H NMR (300 MHz, DMSO-$d_6$) δ 6.77 (s, 1H), 7.32 (t, 2H), 7.77-7.63 (m, 4H), 7.88 (m, 2H), 8.71 (d, 1H), 10.82 (s, 1H), 12.55 (s, 1H); LC-MS (ESI) m/z 356 (M+H)$^+$.

Example 10

Preparation of N-(5-cyclopropyl-1H-pyrazol-3-yl)-2-(difluoro(4-fluorophenyl)methyl)quinazolin-4-amine

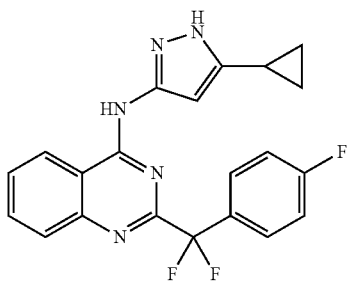 [SMILES: Fc1ccc(C(F)(F)c2nc(Nc3cc(C4CC4)[nH]n3)c3ccccc3n2)cc1]

N-(5-cyclopropyl-1H-pyrazol-3-yl)-2-(difluoro(4-fluorophenyl)methyl)quinazolin-4-amine was prepared using a procedure analogous to that described in Example 8, substituting 5-cyclopropyl-1H-pyrazol-3-amine for the 5-methyl-1H-pyrazol-3-amine used in Example 8 Step E (68% yield). $^1$H NMR (300 MHz, DMSO-$d_6$) δ 0.637 (m, 2H), 0.96 (m, 2H), 1.91 (m, 1H), 6.20 (s, 1H), 7.70 (m, 2H), 7.80 (m, 3H), 7.90 (m, 4H), 8.70 (d, 1H), 10.68 (s, 1H), 12.20 (s, 1H); LC-MS (ESI) m/z 396 (M+H)$^+$ Example 11

Preparation of 3-(2-(4-fluorobenzoyl)quinazolin-4-ylamino)-1H-pyrazole-5-carbonitrile

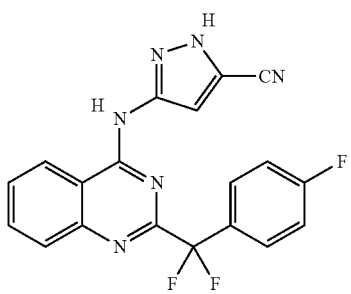

Step A

To a solution of 5-nitro-3-pyrazolecarboxylic acid (6.28 mg, 40 mmol) in DMF (30 mL) was added carbonyldiimidazole (12.96 mg, 80 mmol) The mixture was allowed to stir for 30 min, and ammonia in MeOH (2M, 60 mL) was added. The reaction mixture was stirred at rt overnight. The mixture was concentrated under reduced pressure to afford the crude product which was then washed with ether to afford 3-nitro-1H-pyrazole-5-carboxamide (3.0 g, 48%), which was used directly in the next step without further purification. LC-MS (ESI) m/z 155 (M−H)$^-$.

Step B 3-nitro-1H-pyrazole-5-carboxamide (3.0 g, 19.2 mmol) in pyridine (30 mL) was treated with phosphorus oxychloride (5.9 g) and the resultant solution was stirred for 3 h at rt. The reaction mixture was diluted with ice, then extracted with DCM (100 mL), dried over sodium sulfate, filtered and concentrated under reduced pressure to afford the crude 3-nitro-1H-pyrazole-5-carbonitrile, which was used directly in the next step without further purification. LC-MS (ESI) m/z 137 (M−H)$^-$.

Step C

To a solution of 3-nitro-1H-pyrazole-5-carbonitrile (1000 mg, 7.24 mmol) in AcOH (10 mL) and $H_2O$ (2 mL) was added zinc powder (2.35 mg, 36.24 mmol) at 0° C. The resultant solution was stirred at rt for 3 h. The reaction mixture was filtered, the pH was adjusted to 8 with ammonium hydroxide, and then the mixture was extracted with EtOAc (30 mL). The organic layer was dried over sodium sulfate, filtered and concentrated under reduced pressure to afford the crude product 3-amino-1H-pyrazole-5-carbonitrile (200 mg, 28%), which was used directly in the next step without further purification. LC-MS (ESI) m/z 107 (M+H)$^+$.

Step D

A mixture of (4-chloroquinazoline-2-yl)(4-fluorophenyl)methanone from Example 3 (580 mg, 2.02 mmol), and 3-amino-1H-pyrazole-5-carbonitrile (218 mg, 2.02 mmol) in DMF (5 mL) was stirred at rt overnight. MeOH (10 mL) was then added to this mixture, and the precipitate was filtered washed with MeOH, and dried to afford 3-(2-(4-fluorobenzoyl)quinazolin-4-ylamino)-1H-pyrazole-5-carbonitrile (170 mg, 23.4%) $^1$H NMR (300 MHz, DMSO-$d_6$) δ 6.89 (s, 1H), 7.40 (d, 2H), 7.83 (s, 1H), 7.98 (m, 2H), 8.11 (m, 2H), 8.56 (s, 1H), 11.18 (s, 1H), 13.84 (s, 1H); LC-MS (ESI) m/z 359 (M+H)$^+$.

Example 12

Preparation of (R,S)-(4-fluorophenyl)(4-(5-methyl-1H-pyrazol-3-ylamino)quinazolin-2-yl)methanol hydrochloride

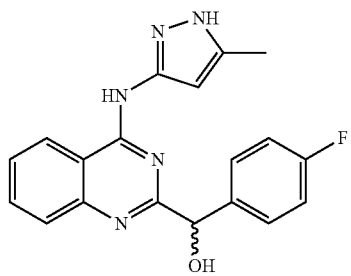 [SMILES: Cc1cc(Nc2nc(C(O)c3ccc(F)cc3)nc3ccccc23)n[nH]1]

To a solution of 4-fluorophenyl)(4-(5-methyl-1H-pyrazol-3-ylamino)quinazolin-2-yl)methanone from Example 3 (60 mg, 0.172 mmol) in 1:1 MeOH/THF (10 mL) at 0° C., was added NaBH$_4$ (64 mg, 1.69 mmol). The reaction mixture was stirred at 0° C. for 1.5 h. The reaction mixture was quenched by adding a few drops of acetone and concentrated to dryness. The crude solid was purified on HPLC to afford (4-fluorophenyl)(4-(5-methyl-1H-pyrazol-3-ylamino)quinazolin-2-yl)methanol (18 mg, 30%); $^1$H NMR (300 MHz, DMSO-d$_6$) δ 2.25 (s, 3H), 5.67 (s, 1H), 5.83 (bs, 1H), 6.40 (bs, 1H), 7.13 (m, 2H), 7.55-7.53 (m, 3H), 7.79 (s, 2H), 8.57 (bs, 1H), 10.43 (s, 1H), 12.12 (bs, 1H); LC-MS (ESI) m/z 350 (M+H)$^+$.

To a suspension of (4-fluorophenyl)(4-(5-methyl-1H-pyrazol-3-ylamino)quinazolin-2-yl)methanone (2.3 g) in 30% MeOH/DCM (60 mL) at 0° C. was added dropwise 4M HCl/1,4-dioxane (10 mL). After all solid material had dissolved, the mixture was concentrated under reduced pressure, and to the residue was added 30% CH3CN/H2O (80 mL) and the mixture was sonicated until all solid material had dissolved. The mixture was frozen and lyophilized overnight to afford (4-fluorophenyl)(4-(5-methyl-1H-pyrazol-3-ylamino)quinazolin-2-yl)methanol hydrochloride (100%). $^1$H NMR (300 MHz, DMSO-d$_6$) δ 2.25 (s, 3H), 6.02 (s, 1H), 6.20 (s, 1H), 7.27 (t, 2H), 7.60 (qt, 2H), 7.80 (t, 1H), 8.08 (t, 1H), 8.23 (d, 1H), 8.83 (d, 1H), 12.16 (s, 1H), 14.51 (b, 1H); LC-MS (ESI) m/z 350 (M+H)$^+$.

Example 13

Preparation of (R,S)-2-((4-fluorophenyl)(methoxy)methyl)-N-(5-methyl-1H-pyrazol-3-yl)quinazolin-4-amine

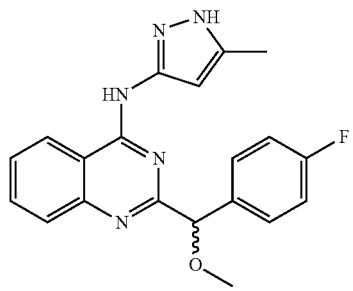 [SMILES: COC(c1ccc(F)cc1)c1nc(Nc2cc(C)[nH]n2)c2ccccc2n1]

Step A

To a solution of (R,S)-2-bromo-2-(4-fluorophenyl)acetic acid (2.02 g, 8.66 mmol) in DCM (15 mL) and DMF (0.15 mL) was added oxalyl chloride (0.8 mL, 9.1 mmol), then the mixture was allowed to stir for 30 min at rt. The reaction mixture was then cooled to 0° C. and 2-aminobenzamide (1.12 g, 8.23 mmol) in pyridine (2 mL) was added slowly. The mixture was warmed to rt over ~1 h and then evaporated. Trituration with a mixture of 2N HCl/methanol/water gave a crude (R,S)-2-(2-bromo-2-(4-fluorophenyl)acetamido)benzamide which was used without further purification (2.13 g, 73%). LC-MS (ESI) m/z 351 (M+H)$^+$.

Step B

To (R,S)-2-(2-bromo-2-(4-fluorophenyl)acetamido)benzamide (0.52 g, 1.48 mmol) in MeOH (4 mL) was added sodium methoxide in MeOH (25%, 0.64 mL, 2.96 mmol), and the resultant solution was stirred overnight at 65° C. The reaction was partitioned between EtOAc and 2 N HCl, the EtOAc layer was dried with sodium sulfate and then evaporated. The crude product was then triturated with ether to give (R,S)-2-((4-fluorophenyl)(methoxy)methyl)quinazolin-4-ol which was used without further purification (260 mg, 62%). LC-MS (ESI) m/z 285 (M+H)$^+$.

Step C

To a solution of (R,S)-2-((4-fluorophenyl)(methoxy)methyl)quinazolin-4-ol (200 mg, 0.7 mmol) in DCM (2 mL) was added DMAP (8 mg, 0.07 mmol), and TEA (0.39 mL, 2.8 mmol), followed by 2,4,6-triisopropylbenzene-1-sulfonyl chloride (211 mg, 0.91 mmol) and the reaction was stirred for 30 min at rt. The crude mixture was purified by silica gel chromatography, eluting with 0-50% EtOAc and hexanes to give (R,S)-2-((4-fluorophenyl)(methoxy)methyl)quinazolin-4-yl-2,4,6-triisopropylbenzenesulfonate (320 mg, 83%). LC-MS (ESI) m/z 573 (M+Na)$^+$.

Step D

To (R,S)-2-((4-fluorophenyl)(methoxy)methyl)quinazolin-4-yl-2,4,6-triisopropylbenzenesulfonate (77 mg, 0.14 mmol), in DMF (2 mL) was added 5-methyl-1H-pyrazol-3-amine (20 mg, 0.2 mmol), TEA (0.02 mL, 0.14 mmol), and potassium iodide (33 mg, 0.2 mmol) and the reaction mixture was stirred at 50° C. for 1 h, followed by heating at 70° C. for 2 h. Additional 5-methyl-1H-pyrazol-3-amine (45 mg) was then added and the mixture was heated at 50° C. overnight. The mixture was evaporated and purified by silica gel chromatography, eluting with 0-12% MeOH in DCM. The purified fractions were evaporated and then further purified by preparative HPLC (Phenomenex C-18 reverse phase column, eluted with gradient of solvent B=0.05% HOAc/CH$_3$CN and solvent A=0.05% HOAc/H$_2$O), followed by preparative thin layer chromatography (10% MeOH in DCM) to afford (R,S)-2-((4-fluorophenyl)(methoxy)methyl)-N-(5-methyl-1H-pyrazol-3-yl)quinazolin-4-amine (5 mg, 10%) $^1$H NMR (300 MHz, DMSO-d$_6$) δ 2.28 (s, 3H), 3.32 (s, 3H), 5.37 (s, 1H), 6.56 (s, 1H), 7.15 (d, 2H), 7.57 (m, 3H), 7.81 (m, 2H), 8.59 (d, 1H), 10.48 (s, 1H), 12.09 (s, 1H); LC-MS (ESI) m/z 364 (M+H)$^+$.

Example 14

Preparation of (R,S)-2-(amino(4-fluorophenyl)methyl)-N-(5-methyl-1H-pyrazol-3-yl)quinazolin-4-amine

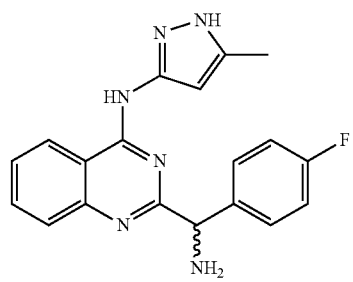 [SMILES: Cc1cc(Nc2nc(C(N)c3ccc(F)cc3)nc3ccccc23)n[nH]1]

Step A

To a solution of 2-amino-2-(4-fluorophenyl)acetic acid (5 g, 29.5 mmol) in THF (50 mL) at 50° C. was added triphosgene (8.77 g, 29.5 mmol), then heating was continued for 3 h. The reaction mixture was then filtered and evaporated to a volume of about 10 mL, followed by addition of 150 mL of hexanes. The mixture was heated slightly, and then cooled to −20° C. for 1 h. The crude slurry was filtered to give 4-(4-fluorophenyl)oxazolidine-2,5-dione (5.03 g, 87%) which was used without further purification.

Step B

To a solution of 4-(4-fluorophenyl)oxazolidine-2,5-dione (2.5 g, 12.8 mmol) in THF (30 mL) cooled to −25° C. was added benzyl chloroformate (2.3 mL, 16.6 mmol), followed by the slow addition (~10 min) of N-methylmorpholine (2.11 mL, 19.2 mmol) as a solution in THF (5 mL). The solution was stirred at this temperature for 1 h. and then allowed to warm to rt overnight. The resulting solution was filtered through Celite, and the filtrate was concentrated. The resulting crude material was recrystallized from 2:2:1 t-butyl methyl ether:hexanes:THF to give benzyl 4-(4-fluorophenyl)-2,5-dioxooxazolidine-3-carboxylate (2.7 g, 64%) which was used without further purification.

Step C

To a solution of 2-aminobenzamide (591 mg, 4.34 mmol) in THF (10 mL) was added benzyl 4-(4-fluorophenyl)-2,5-dioxooxazolidine-3-carboxylate (1.43 g, 4.34 mmol) and the reaction was heated at 50° C. for 2 h. An additional 5 mL of THF was added and heating was continued for another 0.5 h. Then sodium methoxide in MeOH (25%, 1.87 mL, 8.68 mmol) was added and the reaction was heated to 65° C. for 2 h. Then HOAc (0.4 mL) was added, the solution was evaporated, and the crude mixture was purified by silica gel chromatography eluting with 0-10% MeOH in DCM to give (R,S)-(4-fluorophenyl)(4-hydroxyquinazolin-2-yl)methylcarbamate (1.1 g, 63%). LC-MS (ESI) m/z 404 (M+Na)$^+$.

Step D

To a solution of (R,S)-(4-fluorophenyl)(4-hydroxyquinazolin-2-yl)methylcarbamate (451 mg, 1.11 mmol) in DCM (5 mL) were added DMAP (7 mg, 0.05 mmol), TEA (0.61 mL, 4.4 mmol) and 2,4,6-triisopropylbenzene-1-sulfonyl chloride (440 mg, 1.45 mmol). The reaction was stirred at rt for 0.5 h and then evaporated. The residue was purified by silica gel chromatography eluting with 0-50% EtOAc in hexanes to give (R,S)-2-((benzyloxycarbonylamino)(4-fluorophenyl)methyl)quinazolin-4-yl-2,4,6-triisopropylbenzenesulfonate (580 mg, 75%). LC-MS (ESI) m/z 692 (M+Na)$^+$.

Step E

To (R,S)-2-((benzyloxycarbonylamino)(4-fluorophenyl)methyl)quinazolin-4-yl-2,4,6-triisopropylbenzenesulfonate (216 mg, 0.32 mmol), in DMA (2 mL) were added 5-methyl-1H-pyrazol-3-amine (198 mg, 2.04 mmol) and potassium iodide (140 mg, 0.83 mmol), and the mixture was stirred at 55° C. for 4 h. The crude mixture was partitioned between EtOAc and a saturated sodium hydrogen carbonate solution. The EtOAc layer was dried with sodium sulfate and then evaporated to an oil. Half of this crude oil was dissolved in MeOH (5 mL) and 10% palladium hydroxide on carbon (50 mg) was added. The resulting solution was stirred under an atmosphere of hydrogen for 6 h, then filtered. Purification by preparative HPLC (Varian diphenyl and then Phenomenex C-18 reverse phase columns, eluted with gradient of solvent B=0.05% HOAC/CH$_3$CN and solvent A=0.05% HOAc/H$_2$O) gave (R,S)-2-(amino(4-fluorophenyl)methyl)-N-(5-methyl-1H-pyrazol-3-yl)quinazolin-4-amine as its acetate salt (5 mg, 9%) $^1$H NMR (300 MHz, DMSO-d$_6$) δ 1.89 (s, 3H), 2.25 (s, 3H), 5.07 (s, 1H), 6.35 (s, 1H), 7.12 (t, 2H), 7.51 (m, 3H), 7.77 (m, 2H), 8.56 (d, 1H), 10.55 (s, 1H); LC-MS (ESI) m/z 349 (M+H)$^+$.

Example 15

Preparation of (R,S)-3-(2-((4-fluorophenyl)(hydroxy)methyl)quinazolin-4-ylamino)-1H-pyrazole-5-carbonitrile

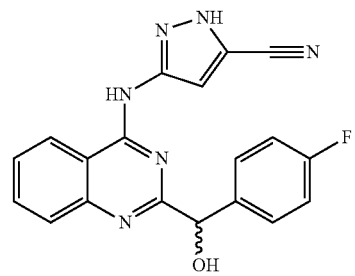 [SMILES: N#Cc1cc(Nc2nc(C(O)c3ccc(F)cc3)nc3ccccc23)n[nH]1]

To a solution of 3-(2-(4-fluorobenzoyl)quinazolin-4-ylamino)-1H-pyrazole-5-carbonitrile from Example 11 (107 mg, 0.3 mmol) in MeOH (4 mL) and THF (4 mL) was added sodium borohydride (22.7 mg, 0.6 mmol) at 0° C., and the mixture was stirred overnight at rt. The mixture was poured into H$_2$O (20 mL), whereupon a precipitate formed. Filtration afforded a solid which was purified by preparative HPLC to yield (R,S)-3-(2-((4-fluorophenyl)(hydroxy)methyl)quinazolin-4-ylamino)-1H-pyrazole-5-carbonitrile (30 mg, 29%) $^1$H NMR (300 MHz, DMSO-d$_6$) δ 5.81 (s, 1H), 6.34 (bs, 1H), 6.88 (s, 1H), 7.17 (t, 2H), 7.58 (m, 3H), 7.81 (s, 2H), 8.37 (m, 1H); LC-MS (ESI) m/z 361 (M+H)$^+$.

Example 16

Preparation of (R,S)-(5-fluoro-4-(5-methyl-1H-pyrazol-3-ylamino)quinazolin-2-yl)(4-fluorophenyl)methanol

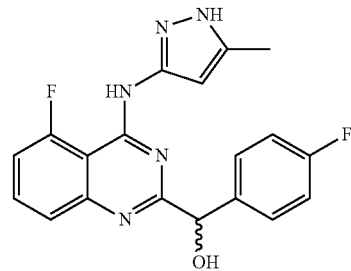 [SMILES: Cc1cc(Nc2nc(C(O)c3ccc(F)cc3)nc3cccc(F)c23)n[nH]1]

Step A 5-(4-fluorophenyl)-1,3-dioxolane-2,4-dione was prepared according to JACS, 2002 2870-2871. To 2-amino-6-fluorobenzamide (550 mg, 3.5 mmol) in THF (15 mL) was added 5-(4-fluorophenyl)-1,3-dioxolane-2,4-dione (1049 mg, 5.35 mmol) and the mixture was heated at 50° C. overnight. The solvent was evaporated to afford crude 2-(2,2-difluoro-2-(4-fluorophenyl)acetamido)-4-methoxybenzamide and the crude mixture was dissolved in ethanol (12 mL), added aq potassium carbonate solution and heated the reaction mixture at 80° C. for overnight. The crude mixture was extracted with EtOAc and water and the EtOAc layer was concentrated in vacuum to afford (R,S)-5-fluoro-2-((4-fluorophenyl)(hydroxyl)methyl)quinazolin-4-ol (650 mg, %). LC-MS (ESI) m/z 290 (M+Na)+.

Step B

To (R,S)-5-fluoro-2-((4-fluorophenyl)(hydroxy)methyl)quinazolin-4-ol (650 mg, 2.25 mmol) was added Dess-Martin periodinane (1140 mg, 2.7 mmol) in acetonitrile (15 mL) and the mixture was stirred at rt for 30 min. To the crude mixture was added aq sodium bicarbonate solution and the mixture was stirred for 0.5 h. The resulting brown precipitate was collected and washed with diethyl ether (650 mg, quantitative) LC-MS (ESI) m/z 287 (M+Na)+.

Step C

To phosphorus oxychloride (7 mL) was added (5-fluoro-4-hydroxyquinazolin-2-yl)(4-fluorophenyl)methanone (650 mg, 2.26 mmol) followed by DMA (1 drop). The solution was heated at 85° C. for 3 h, and then the mixture was concentrated. The residue was cooled in a −20° C. cooling bath and diluted with cold EtOAc. The solution was washed with saturated aq sodium bicarbonate and brine. Removal of the solvent resulted in a brown solid. Purification by chromatography (elution gradient of 0-40% EtOAc in hexanes) afforded a yellow solid (300 mg, 44%) LC-MS (ESI) m/z 305 (M+Na)+.

Step D

To (4-chloro-5-fluoroquinazolin-2-yl)(4-fluorophenyl)methanone (300 mg, 0.98 mmol) in dimethyl formamide (8.0 mL) was added DIEA (0.17 mL, 0.98 mmol), 5-methyl-1H-pyrazol-3-amine (240 mg, 2.5 mmol), and potassium iodide (162 mg, 0.98 mmol) and the mixture was stirred at rt for 1 h. To the reaction mixture was added water and the precipitate was collected by filtration. The precipitate was washed with diethyl ether to give a yellow solid (280 mg, 78%) LC-MS (ESI) m/z 366 (M+Na)+.

Step E

To (5-fluoro-4-(5-methyl-1H-pyrazol-3-ylamino)quinazolin-2-yl)(4-fluorophenyl)methanone (280 mg, 0.76 mmol) in a 1:1 mixture of MeOH and THF (8 mL) at 0° C. was added NaBH4 (43 mg, 1.14 mmol). After 1 h of stirring at 0° C., 10 drops of water were added. The solvents were removed under vacuum and the residue was dissolved in EtOAc (15 mL), washed with brine and dried over Na2SO4. The crude product was purified on reverse-phase preparative HPLC (elution gradient of 40-90% acetonitrile in water with 0.05% acetic acid) to afford (R,S)-(5-fluoro-4-(5-methyl-1H-pyrazol-3-ylamino)quinazolin-2-yl)(4-fluorophenyl)methanol as a white solid. $^1$H NMR (300 MHz, DMSO-d$_6$) δ ppm 2.2 (s, 3H) 5.7 (s, 1H) 5.9 (s, 1H) 6.55 (s, 1H) 7.1-7.2 (m, 2H) 7.35-7.9 (m, 4H) 8.9 (s, 1H) 12.25 (s, 1H) LC-MS (ESI) m/z 368 (M+H)+

Example 17

Preparation of (4-fluorophenyl)(4-(5-methyl-1H-pyrazol-3-ylamino)-7-(trifluoromethyl)quinazolin-2-yl)methanone

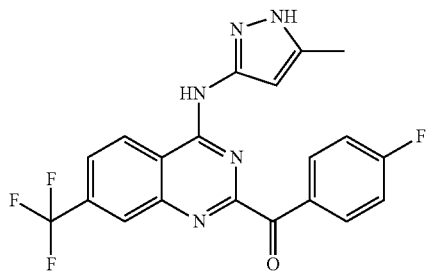 [SMILES: Cc1cc(Nc2nc(C(=O)c3ccc(F)cc3)nc3cc(C(F)(F)F)ccc23)n[nH]1]

Step A

To 2-nitro-4-(trifluoromethyl)benzamide (1000 mg, 4.27 mmol), in MeOH (15 mL) was added palladium hydroxide 20% by weight (230 mg) and the mixture was stirred at rt overnight. The reaction mixture was filtered through Celite washing with MeOH. The crude mixture was concentrated in vacuo to afford 2-amino-4-(trifluoromethyl)benzamide (840 mg, 96%). LC-MS (ESI) m/z 205 (M+Na)+.

Step B

To 2-amino-4-(trifluoromethyl)benzamide (840 mg, 4.16 mmol), in THF (15 mL) was added 5-(4-fluorophenyl)-1,3-dioxolane-2,4-dione from Example 16 (1225 mg, 6.24 mmol) and the mixture was heated at 50° C. for 4 h. The solvent was evaporated and the crude 2-(2-(4-fluorophenyl)-2-hydroxyacetamido)-4-(trifluoromethyl)benzamide was dissolved in MeOH (10 mL), added 0.5 M sodium methoxide in MeOH (2.5 mL, 1.25 mmol) and the reaction mixture was heated at 50° C. for 1 h. The solvent was evaporated and then 1N hydrochloric acid was added. The mixture was extracted with EtOAc and the organic phase was dried over sodium sulfate and concentrated in vacuo to afford crude 2-(((4-fluorophenyl)(hydroxy)methyl)-7-(trifluoromethyl)quinazolin-4-ol, which was used in next reaction without purification. LC-MS (ESI) m/z 339 (M+Na)+.

Step D

To 2-((4-fluorophenyl)(hydroxy)methyl)-7-(trifluoromethyl)quinazolin-4-ol (2000 mg, 5.89 mmol) was added Dess-Martin periodinane (3000 mg, 7.07 mmol) in acetonitrile (25 mL) and the mixture was stirred at rt for 2 h. To the crude mixture was added aq sodium bicarbonate solution and the mixture was stirred for 0.5 h. The resulting brown precipitate was collected, washed with diethyl ether and dried under high vacuum to afford (4-fluorophenyl)(4-hydroxy-7-(trifluoromethyl)quinazolin-2-yl)methanone (2.57 g, quantitative yield) LC-MS (ESI) m/z 336 (M+Na)+.

Step E

To phosphorus oxychloride (6 mL) was added (4-fluorophenyl)(4-hydroxy-7-(trifluoromethyl)quinazolin-2-yl)methanone (1280 mg, 3.80 mmol) followed by DMA (1 drop). The solution was heated at 85° C. overnight, and then the mixture was concentrated. The crude (4-chloro-7-(trifluoromethyl)quinazolin-2-yl)(4-fluorophenyl)methanone was taken to next step without purification. LC-MS (ESI) m/z 305 (M+Na)⁺.

Step F

To (4-chloro-7-(trifluoromethyl)quinazolin-2-yl)(4-fluorophenyl)methanone (1 g, 2.82 mmol) in DMF (10 mL) were added DIEA (0.49 mL, 2.82 mmol), 5-methyl-1H-pyrazol-3-amine (823 mg, 8.47 mmol), and potassium iodide (468 mg, 2.82 mmol) and the mixture was stirred at rt for 2 h. To the reaction mixture was added water followed by extraction with EtOAc. The organic phases were dried over sodium sulfate. The solvent was concentrated and the residue was dried under high vacuum overnight. The crude solid (240 mg) was purified on reverse-phase preparative HPLC (elution gradient of 40-90% acetonitrile in water with 0.05% acetic acid) to afford (4-fluorophenyl)(4-(5-methyl-1H-pyrazol-3-ylamino)-7-(trifluoromethyl)quinazolin-2-yl)methanone as a yellow solid (40 mg, 16%). ¹H NMR (300 MHz, DMSO-$d_6$) δ ppm 2.2 (s, 3H) 6.55 (s, 1H) 7.35-7.5 (m, 3H) 7.9-8.0 (m, 1H) 8.05-8.3 (m, 4H) 11.1 (s, 1H) 12.25 (s, 1H) LC-MS (ESI) m/z 416 (M+H)⁺.

Example 18

Preparation of (R,S)-(4-fluorophenyl) (4-(5-methyl-1H-pyrazol-3-ylamino)-7-(trifluoromethyl) quinazolin-2-yl) methanol

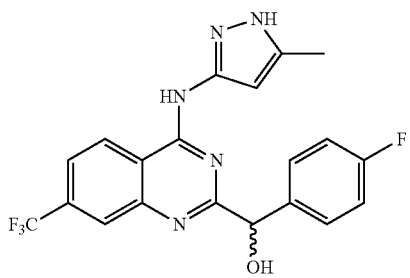

To (4-fluorophenyl)(4-(5-methyl-1H-pyrazol-3-ylamino)-7-(trifluoromethyl)quinazolin-2-yl)methanone (500 mg, 1.2 mmol) in a 1:1 mixture of MeOH/THF (10 mL) at 0° C. was added NaBH₄ (68 mg, 1.79 mmol). After 10 min of stirring at 0° C., 10 drops of water were added. The solvents were removed under vacuum and the residue was dissolved in a mixture of 1:1 of water EtOAc (20 mL), washed with brine and dried over sodium sulfate. The crude product (360 mg) was purified on reverse-phase preparative HPLC (elution gradient of 40-90% acetonitrile in water with 0.05% acetic acid) to afford (4-fluorophenyl)(4-(5-methyl-1H-pyrazol-3-ylamino)-7-(trifluoromethyl)quinazolin-2-yl)methanol as white solid (140 mg, 40%). ¹H NMR (300 MHz, DMSO-$d_6$) δ ppm 2.2 (s, 3H) 5.9 (s, 1H) 6.55 (s, 1H) 7.35-7.5 (m, 3H) 7.9-8.0 (m, 1H) 8.05-8.3 (m, 4H) 11.1 (br. s, 1H) 12.25 (br. s., 1H) LC-MS (ESI) m/z 418 (M+H)⁺.

Example 19

Preparation of (7-fluoro-4-(5-methyl-1H-pyrazol-3-ylamino)quinazolin-2-yl)(4-fluorophenyl)methanone

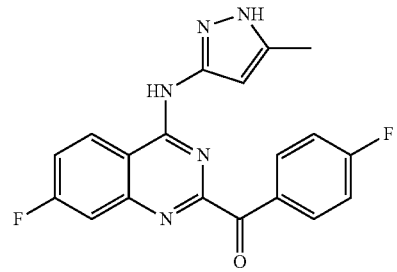

Step A

To a solution of 2-bromo-2-(4-fluorophenyl)acetic acid (425 mg, 1.82 mmol) in DCM (5 mL) and DMF (0.05 mL) was added oxalyl chloride (0.17 mL, 1.91 mmol) and the solution was stirred for 0.75 h. The solution was then cooled to 0° C. and a solution of 2-amino-4-fluorobenzamide (267 mg, 1.73 mmol) in pyridine (1 mL) was added. The solution was stirred at rt for 1 h and then evaporated. The crude residue was partitioned between EtOAc and 2 N HCl. The EtOAc layer was evaporated to give 2-(2-bromo-2-(4-fluorophenyl)acetamido)-4-fluorobenzamide as a crude oil which was used without further purification. (420 mg, 62%). LC-MS (ESI) m/z 369 (M–H)—.

Step B

To 2-(2-bromo-2-(4-fluorophenyl)acetamido)-4-fluorobenzamide (420 mg, 1.1 mmol) in diglyme (5 mL), was added 1 mL of 10% aq potassium carbonate and the solution was heated at 95° C. for 6 h, then at 60° C. overnight. The crude residue was partitioned between EtOAc and 2 N HCl. The EtOAc layer was evaporated and the crude mixture was purified by silica gel chromatography (0-10% MeOH in DCM) to give benzyl 7-fluoro-2-((4-fluorophenyl)(hydroxy)methyl)quinazolin-4-ol (98 mg, 31%). LC-MS (ESI) m/z 289 (M+H)⁺.

Step C

To a solution of 7-fluoro-2-((4-fluorophenyl)(hydroxy)methyl)quinazolin-4-ol (98 mg, 0.33 mmol) in acetonitrile (4 mL) was added Dess-Martin periodinane (168 mg, 0.4 mmol), and the reaction was stirred at rt for 0.75 h. Saturated sodium hydrogen carbonate solution was then added and the solution was stirred for 1 h. This solution was then filtered and the resulting solid dried. To this crude solid was added phosphorus oxychloride (2 mL) and DMA (0.02 mL) and the resulting solution was heated at 85° C. for 0.75 h. The solvent was evaporated and then DCM was added and the solution filtered through a plug of silica gel, washing with DCM. The solvent was evaporated to give (4-chloro-7-fluoroquinazolin- 2-yl)(4-fluorophenyl)methanone (27 mg, 27%) which was used without further purification. LC-MS (ESI) m/z 305 (M+H)+.

Step D

A solution of 5-methyl-1H-pyrazol-3-amine (13 mg, 0.13 mmol), potassium iodide (15 mg, 0.088 mmol), and DIEA (0.016 mL, 0.088 mmol) in DMF (2 mL) was added to (4-chloro-7-fluoroquinazolin-2-yl)(4-fluorophenyl)methanone (0.027 mg, 0.088 mmol). The resulting solution was stirred at rt overnight and then purified by preparative HPLC (Varian diphenyl reverse phase column, eluted with gradient of solvent B=0.05% HOAC/CH$_3$CN and solvent A=0.05% HOAc/H$_2$O) to give (7-fluoro-4-(5-methyl-1H-pyrazol-3-ylamino)quinazolin-2-yl)(4-fluorophenyl)methanone (10 mg, 31%). $^1$H NMR (300 MHz, DMSO-d$_6$) δ 2.18 (s, 3H), 6.48 (s, 1H), 7.36 (t, 2H), 7.60 (m, 2H), 8.09 (m, 2H), 8.29 (t, 1H), 10.78 (s, 1H), 12.23 (s, 1H); LC-MS (ESI) m/z 366 (M+H)+.

Example 20

Preparation of 2-(difluoro(4-fluorophenyl)methyl)-7-fluoro-N-(5-methyl-1H-pyrazol-3-yl)quinazolin-4-amine

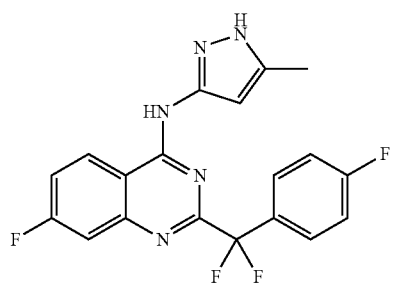 [SMILES: Cc1cc(Nc2nc(C(F)(F)c3ccc(F)cc3)nc3cc(F)ccc23)n[nH]1]

Step A 2,2-difluoro-2-(4-fluorophenyl)acetyl chloride was prepared as described in Example 8 Step B. To a solution of 2-amino-4-fluorobenzamide (0.330 g, 2.14 mmol) and TEA (0.395 mL, 2.83 mmol) in DCE (15 mL) was added a solution of 2,2-difluoro-2-(4-fluorophenyl)acetyl chloride (0.460 mg, 2.2 mmol) in DCE (4 mL) at rt and the reaction mixture was stirred overnight. After adding EtOAc (20 mL) the mixture was washed with water, saturated aq NaHCO$_3$ and brine solution. The organic solution was concentrated to yield an off-white solid (0.650 g, 84%). LC-MS (ESI) m/z 327 (M+H)+.

Step B

To a solution of 2-(2,2-difluoro-2-(4-fluorophenyl)acetamido)-4-fluorobenzamide (0.650 g, 1.9 mmol) in DCE (14 mL) were added TEA (10.6 mL, 76 mmol) and chlorotrimethylsilane (3.78 mL, 29.9 mmol) at rt. The reaction mixture was stirred at 85° C. overnight. After cooling to rt, the solid was filtered and the filtrate was concentrated to dryness. The residue was dissolved in a mixture of EtOAc/THF (1:1) and washed with water and brine. The organic phase was dried over MgSO$_4$. The crude product was purified on silica gel column using a mixture of DCM/MeOH as eluent to afford 2-(difluoro(4-fluorophenyl)-7-fluoroquinazolin-4-ol (0.668 g, 75%). $^1$H NMR (300 MHz, DMSO-d$_6$) δ 7.40 (t, 2H), 7.48 (dt, 1H), 7.56 (dd, 1H), 7.77 (dd, 2H), 8.21 (dd, 1H), 13.25 (s, 1H).

Step C

A solution of 2-(difluoro(4-fluorophenyl)-7-fluoroquinazolin-4-ol (0.350 g, 1.13 mmol) in POCl$_3$ (5 mL) was heated at 105° C. for 4 h. The reaction mixture was concentrated to dryness under reduced pressure and the residue was dissolved in anhydrous toluene. The toluene was concentrated under reduced pressure. The residue was dissolved in a small volume of DCM and passed through a short pad of silica gel, eluting with DCM. 4-Chloro-2-(difluoro(4-fluorophenyl)methyl)-7-fluoroquinazoline was obtained as a pale yellow solid (325 mg, 88.5%). LC-MS (ESI) m/z 327 (M+H)+

Step D

To a solution of 4-chloro-2-(difluoro(4-fluorophenyl)methyl)-7-fluoroquinazoline (0.160 g, 0.492 mmol) in DMF (2 mL) at rt were added potassium iodide (0.082 g, 0.492 mmol), DIEA (0.094 mL, 0.541 mmol) and 5-methyl-1H-pyrazol-3-amine (0.048 g, 0.492 mmol). After stirring the reaction mixture at 50° C. overnight, the mixture was cooled to rt and H$_2$O (15 mL) was added. The precipitate was collected by filtration and washed with H$_2$O. The crude product was purified on HPLC (Phenomenex phenylhexyl reverse phase column, eluted with gradient of solvent B=0.05% HOAc/CH$_3$CN and solvent A=0.05% HOAc/H$_2$O) to afford 2-(difluoro(4-fluorophenyl)methyl)-7-fluoro-N-(5-methyl-1H-pyrazol-3-yl)quinazolin-4-amine as a white powder (36 mg, 19%). $^1$H NMR (300 MHz, DMSO-d$_6$) δ 2.26 (s, 3H), 6.27 (s, 1H), 7.35 (t, 2H), 7.56 (m, 1H), 7.72-763 (m, 3H), 8.78 (m, 1H), 10.82 (s, 1H), 12.23 (s, 1H); LC-MS (ESI) m/z 388 (M+H)+.

Example 21

Preparation of 2-(difluoro(4-fluorophenyl)methyl)-7-fluoro-N-(1H-pyrazol-3-yl)quinazolin-4-amine

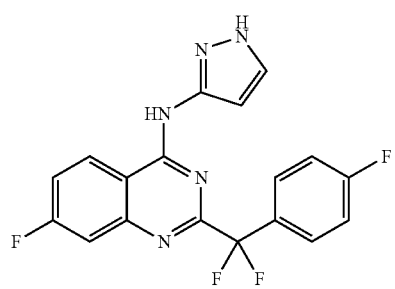 [SMILES: Fc1ccc(C(F)(F)c2nc(Nc3cc[nH]n3)c3ccc(F)cc3n2)cc1]

2-(Difluoro(4-fluorophenyl)methyl)-7-fluoro-N-(1H-pyrazol-3-yl)quinazolin-4-amine was obtained according to procedure described in Example 20 for preparation of 2-(difluoro(4-fluorophenyl)methyl)-7-fluoro-N-(5-methyl-1H-pyrazol-3-yl)quinazolin-4-amine, substituting 5-methyl-1H-pyrazol-3-amine in Example 20 with 1H-pyrazol-3-amine (11% yield). $^1$H NMR (300 MHz, DMSO-d$_6$) δ 6.74 (s, 1H), 7.32 (t, 2H), 7.72-7.55 (m, 5H), 8.81 (m, 1H), 10.95 (s, 1H), 12.58 (s, 1H); LC-MS (ESI) m/z 374 (M+H)⁺.

Example 22

Preparation of (4-(1H-pyrazol-3-ylamino)-7-iodoquinazolin-2-yl)(4-fluorophenyl)methanone

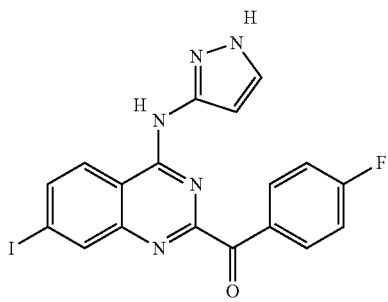

Step A

To a solution of 2-amino-4-iodobenzoic acid (2.5 g, 9.50 mmol) in DMF (10 mL) at rt under argon were added EDCI (2.18 g, 11.40 mmol), 1-hydroxybenzotriazole (1.54 g, 11.40 mmol), DIEA (1.98 mL, 11.40 mmol), and ammonia (7.0 N solution in MeOH, 1.90 mL, 13.30 mmol). The dark solution was stirred at rt overnight and diluted with H₂O until precipitate formed. The precipitate was separated by filtration, washed with H₂O, and dried under high vacuum for several hours to afford 2-amino-4-iodobenzamide as a tan solid (1.3 g, 52%). LC-MS (ESI) m/z 263 (M+H)⁺.

Step B

To a solution of 2-amino-4-iodobenzamide (1.0 g, 3.61 mmol) in glacial acetic acid (10 mL) at rt was added diethyl oxalate (5 mL). The mixture was heated at 120° C. for 24 h. The mixture was cooled to rt and diluted with H₂O until a precipitate formed. The precipitate was removed by filtration, washed with H₂O, and dried under high vacuum for several hours to afford ethyl 7-iodo-4-oxo-3,4-dihydroquinazoline-2-carboxylate (1.0 g, 76%) as a tan solid. ¹H NMR (300 MHz, DMSO-d₆) δ 1.36 (t, 3H), 4.48 (q, 2H), 7.90 (d, 1H), 7.95 (d, 1H), 8.20 (d, 1H), 8.28 (s, 1H), 12.78 (s, 1H); LC-MS (ESI) m/z 330 (M+H)⁺.

Step C

A suspension of ethyl 7-iodo-4-oxo-3,4-dihydroquinazoline-2-carboxylate (1.0 g, 2.90 mmol) in phosphorus oxychloride (10 mL) was heated at 110° C. under argon for 12 h. The reaction mixture was cooled to rt and concentrated under reduced pressure. The residue was purified by column chromatography using silica gel eluting with 30% EtOAc/hexanes to afford ethyl 4-chloro-7-iodoquinazoline-2-carboxylate as a white solid (0.510 g, 48%). ¹H NMR (300 MHz, DMSO-d₆) δ 1.32 (t, 3H), 4.48 (q, 2H), 7.88 (d, 1H), 7.92 (d, 1H), 8.25 (s, 1H); LC-MS (ESI) m/z 363 (M+H)⁺.

Step D

To a solution of ethyl 4-chloro-7-iodoquinazoline-2-carboxylate (0.138 g, 0.38 mmol) in DMF (2 mL) at rt under argon were added potassium iodide (0.069 g, 0.42 mmol), DIEA (0.079 mL, 0.45 mmol), and 1H-pyrazol-3-amine (0.038 g, 0.46 mmol). The mixture was stirred at rt overnight then diluted with H₂O (15 mL). The precipitate was collected by filtration, washed with H₂O, and dried under high vacuum for several hours to afford ethyl 4-(1H-pyrazol-3-ylamino)-7-iodoquinazoline-2-carboxylate as a yellow solid (0.130 g, 84%). ¹H NMR (300 MHz, DMSO-d₆) δ 1.34 (t, 3H), 4.38 (q, 2H), 7.14 (m, 1H), 7.72 (m, 1H), 7.94 (d, 1H), 8.28 (d, 1H), 8.48 (d, 1H), 10.92 (s, 1H), 12.58 (s, 1H); LC-MS (ESI) m/z 410 (M+H)⁺.

Step E

To a suspension of ethyl 4-(1H-pyrazol-3-ylamino)-7-iodoquinazoline-2-carboxylate (0.130 g, 0.31 mmol) in THF (5 mL) at −40° C. was added (4-fluorophenyl)magnesium bromide (1.0 M solution in THF, 0.797 mL, 0.79 mmol). The mixture was stirred at −40° C. for 5 h, quenched with 1.0 N HCl (2.0 mL), and concentrated under reduced pressure. The residue wad purified on preparative HPLC (Phenomenex phenylhexyl reverse phase column, eluted with gradient of solvent B=0.05% HOAc/CH₃CN and solvent A=0.05% HOAc/H₂O) to afford (4-(1H-pyrazol-3-ylamino)-7-iodoquinazolin-2-yl)(4-fluorophenyl)methanone as a yellow solid (0.050 g, 34%). ¹H NMR (300 MHz, DMSO-d₆) δ 6.72 (s, 1H), 7.35 (t, 2H), 7.64 (s, 1H), 8.00 (d, 1H), 8.08 (dd, 2H), 8.28 (s, 1H), 8.55 (d, 1H), 10.88 (s, 1H), 12.55 (s, 1H); LC-MS (ESI) m/z 460 (M+H)⁺.

Example 23

Preparation of (R,S)-(4-(1H-pyrazol-3-ylamino)-7-iodoquinazolin-2-yl)(4-fluorophenyl)methanol

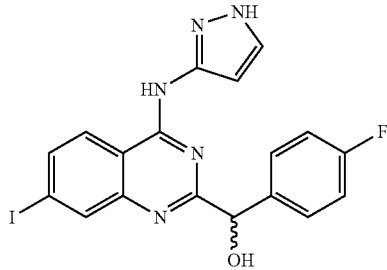 [SMILES: OC(c1ccc(F)cc1)c1nc(Nc2cc[nH]n2)c2ccc(I)cc2n1]

To a suspension of (4-(1H-pyrazol-3-ylamino)-7-iodoquinazolin-2-yl)(4-fluorophenyl)methanone from Example 22 (0.032 g, 0.07 mmol) in a mixture of 1:1 THF:MeOH (2 mL) at 0° C. under argon was added NaBH₄ (0.004 g, 0.10 mmol). The mixture was stirred at 0° C. for 3 h, quenched by adding two drops of acetone and concentrated in reduced pressure. The residue was purified on preparative HPLC (Phenomenex phenylhexyl reverse phase column, eluted with gradient of solvent B=0.05% HOAc/CH₃CN and solvent A=0.05% HOAc/H₂O) to afford (R,S)-(4-(1H-pyrazol-3-ylamino)-7-iodoquinazolin-2-yl)(4-fluorophenyl) methanol as a white solid (0.020 g, 63%). ¹H NMR (300 MHz, DMSO-d₆) δ 5.64 (s, 1H), 5.88 (bs, 1H), 6.80 (bs, 1H), 7.15 (t, 2H), 7.52 (m, 2H), 7.65 (s, 1H), 7.80 (d, 1H), 8.12 (bs, 1H), 8.35 (bs, 1H), 10.62 (bs, 1H), 12.50 (bs, 1H); LC-MS (ESI) m/z 462 (M+H)⁺.

Example 24

Preparation of (4-fluorophenyl)(7-methyl-4-(5-methyl-1H-pyrazol-3-ylamino)quinazolin-2-yl)methanone

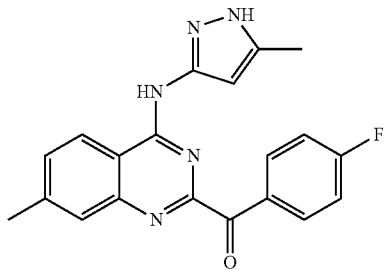 [SMILES: Cc1ccc2c(Nc3cc(C)[nH]n3)nc(C(=O)c3ccc(F)cc3)nc2c1]

Step A

To a solution of 2-amino-4-methylbenzamide (3 g, 20.0 mmol) in THF (40 mL) was added 5-(4-fluorophenyl)-1,3-dioxolane-2,4-dione from Example 16 (4.7 g, 24 mmol) and the solution was stirred for 2 h at 50° C. Sodium methoxide in MeOH (25%, 5.2 mL, 24 mmol) was then added and the solution was stirred at 50° C. overnight. The reaction mixture solution was concentrated, 2N HCl was added and the mixture was filtered. The collected solid was dried to give 2-(((4-fluorophenyl)(hydroxy)methyl)-7-methylquinazolin-4-ol (5.14 g, 91%) which was used without further purification. LC-MS (ESI) m/z 285 (M+H)$^+$.

Step B

To a solution of 2-((4-fluorophenyl)(hydroxy)methyl)-7-methylquinazolin-4-ol (3 g, 10.56 mmol) in acetonitrile (45 mL) was added Dess-Martin periodinane (5.37 g, 12.67 mmol), and the mixture was stirred at rt for 5 h. Saturated sodium hydrogen carbonate solution was then added and the mixture was stirred at rt overnight. This suspension was then filtered and the resulting solid dried to give crude (4-fluorophenyl)(4-hydroxy-7-methylquinazolin-2-yl)methanone (2.65 g, 89%). LC-MS (ESI) m/z 283 (M+H)$^+$.

Step C

To a solution of (4-fluorophenyl)(4-hydroxy-7-methylquinazolin-2-yl)methanone (650 mg, 2.3 mmol) in DCM (4 mL) were added TEA (1.23 mL, 9.2 mmol), DMAP (15 mg, 0.05 mmol), and 2,4,6-triisopropylbenzene-1-sulfonyl chloride (905 mg, 3.0 mmol) and the mixture was stirred at rt for 0.5 h. The crude mixture was concentrated and the residue was purified by silica gel chromatography eluting with 0-50% EtOAc in hexanes to give 2-(4-fluorobenzoyl)-7-methylquinazolin-4-yl-2,4,6-triisopropylbenzenesulfonate (790 mg, 63%) which was used without further purification. LC-MS (ESI) m/z 571 (M+Na)$^+$.

Step D

A solution of 5-methyl-1H-pyrazol-3-amine (225 mg, 2.31 mmol), potassium iodide (188 mg, 0.088 mmol), and 2-(4-fluorobenzoyl)-7-methylquinazolin-4-yl-2,4,6-triisopropylbenzenesulfonate (380 mg, 0.69 mmol) in DMA (2 mL) was stirred at 50° C. for 6 h, then water was added and the solution was filtered. The solid was then dried and triturated with acetonitrile to give (4-fluorophenyl)(7-methyl-4-(5-methyl-1H-pyrazol-3-ylamino)quinazolin-2-yl)methanone (36 mg, 14%). $^1$H NMR (300 MHz, DMSO-d$_6$) δ 2.18 (s, 3H), 2.50 (s, 3H), 6.53 (s, 1H), 7.38 (t, 2H), 7.51 (d, 2H), 7.66 (s, 1H), 8.08 (m, 2H), 8.62 (d, 1H), 10.57 (s, 1H), 12.18 (s, 1H); LC-MS (ESI) m/z 362 (M+H)$^+$.

Example 25

Preparation of (R,S)-(4-fluorophenyl)(7-methyl-4-(5-methyl-1H-pyrazol-3-ylamino)quinazolin-2-yl)methanol

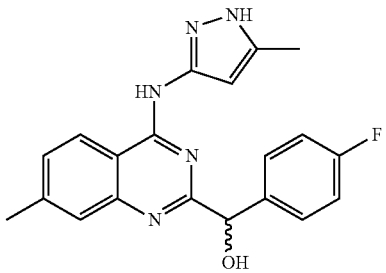 [SMILES: Cc1ccc2c(Nc3cc(C)[nH]n3)nc(C(O)c3ccc(F)cc3)nc2c1]

To a suspension of (4-fluorophenyl)(7-methyl-4-(5-methyl-1H-pyrazol-3-ylamino)quinazolin-2-yl)methanone (40 mg, 0.11 mmol) in MeOH (2 mL), cooled to 0° C. was added sodium borohydride (30 mg, 0.8 mmol). The solution was allowed to warm to rt slowly and stirred for 2 h. Then 1 N HCl was added, the solution was stirred for 10 min, and then filtered. The crude solid was purified by preparative HPLC (Varian diphenyl reverse phase column, eluted with gradient of solvent B=0.05% HOAC/CH$_3$CN and solvent A=0.05% HOAc/H$_2$O) to give (R,S)-(4-fluorophenyl)(7-methyl-4-(5-methyl-1H-pyrazol-3-ylamino)quinazolin-2-yl)methanol (17 mg, 42%) $^1$H NMR (300 MHz, DMSO-d$_6$) δ 2.24 (s, 3H), 2.47 (s, 3H), 5.64, (s, 1H), 5.82 (bs, 1H), 6.36 (s, 1H), 7.14 (t, 2H), 7.34 (d, 1H), 7.54 (m, 3H), 8.45 (d, 1H), 10.39 (s, 1H), 12.18 (s, 1H); LC-MS (ESI) m/z 364 (M+H)$^+$.

Example 26

Preparation of 2-(difluoro(4-fluorophenyl)methyl)-7-methyl-N-(5-methyl-1H-pyrazol-3-yl)quinazolin-4-amine

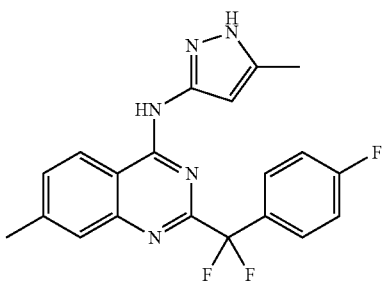

Step A 2,2-difluoro-2-(4-fluorophenyl)acetyl chloride was prepared as described in Example 8 Step B. To a solution of 2-amino-4-methylbenzamide (4.0 g, 0.026 mol) and TEA (4.35 mL, 0.0312 mol) in DCE (60 mL), a solution of 2,2-difluoro-2-(4-fluorophenyl)acetyl chloride (4.90 g, 0.025 mol) in DCE (10 mL) was added at rt and the reaction mixture was stirred overnight. After adding EtOAc (200 mL) the mixture was washed with water, saturated aq NaHCO₃ and brine solution. The organic solution was concentrated to yield an off-white solid (5.85 g, 69%). LC-MS (ESI) m/z 305 (M+H)⁺.

Step B

To a solution of 2-(2,2-difluoro-2-(4-fluorophenyl)acetamido)-4-methylbenzamide (5.85 g, 0.0181 mol) in DCE (120 mL) were added TEA (91.5 mL, 0.724 mol) and chlorotrimethylsilane (34.4 mL, 0.272 mol) at rt. The reaction mixture was stirred at 85° C. overnight. After cooling to rt, the solid was filtered and the filtrate was concentrated to dryness. The residue was taken in a mixture of EtOAc/THF (1:1) and washed with water and brine. Pure product was obtained after crystallization from hot EtOAc (2.02 g, 37%); LC-MS (ESI) m/z 305 (M+H)⁺.

Step C

A solution of 2-(difluoro(4-fluorophenyl)methyl)-7-methylquinazolin-4-ol (0.304 g, 1 mmol) in POCl₃ (5 mL) was heated at 105° C. overnight. The reaction mixture was concentrated to dryness under reduced pressure and the residue was dissolved in anhydrous toluene. The toluene was concentrated under reduced pressure. The residue was dissolved in a small volume of DCM and passed through a short pad of silica gel, using DCM as solvent. 4-Chloro-2-(difluoro(4-fluorophenyl)methyl)-7-fluoroquinazoline was obtained as a pale yellow solid (308 mg, 95%). ¹H NMR (300 MHz, DMSO-d₆) δ 2.61 (s, 3H), 7.33 (t, 2H), 7.73 (m, 2H), 7.82 (dd, 1H), 8.01 (s, 1H), 8.23 (d, 1H).

Step D 2-(Difluoro(4-fluorophenyl)methyl)-7-methyl-N-(5-methyl-1H-pyrazol-3-yl)quinazolin-4-amine was obtained according to the procedure described in Example 20 for preparation of 2-(difluoro(4-fluorophenyl)methyl)-7-fluoro-N-(5-methyl-1H-pyrazol-3-yl)quinazolin-4-amine, substituting 4-chloro-2-(difluoro(4-fluorophenyl)methyl)-7-fluoroquinazoline in Example 20 with 4-chloro-2-(difluoro(4-fluorophenyl)methyl)-7-methylquinazoline (13% yield). ¹H NMR (300 MHz, DMSO-d₆) δ 2.26 (s, 3H), 2.50 (s, 3H), 6.30 (s, 1H), 7.34 (t, 2H), 7.47 (m, 1H), 7.71-7.66 (m, 3H), 8.56 (d, 1H), 10.59 (s, 1H), 12.20 (bs, 1H); LC-MS (ESI) m/z 384 (M+H)⁺.

Example 27

Preparation of 2-(difluoro(4-fluorophenyl)methyl)-7-methyl-N-(1H-pyrazol-3-yl)quinazolin-4-amine

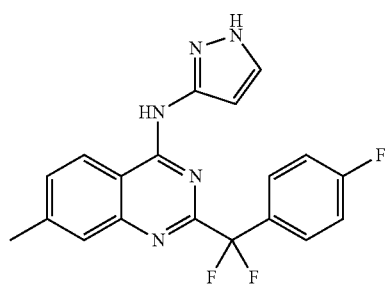 [SMILES: Cc1ccc2c(Nc3cc[nH]n3)nc(C(F)(F)c3ccc(F)cc3)nc2c1]

2-(Difluoro(4-fluorophenyl)methyl)-7-methyl-N-(1H-pyrazol-3-yl)quinazolin-4-amine was obtained according to procedure described in Example 20 for preparation of 4-chloro-2-(difluoro(4-fluorophenyl)methyl)-7-fluoroquinazoline, substituting 4-chloro-2-(difluoro(4-fluorophenyl)methyl)-7-fluoroquinazoline in Example 20 with 4-chloro-2-(difluoro(4-fluorophenyl)methyl)-7-methylquinazoline and 5-methyl-1H-pyrazol-3-amine in Example 20 with 1H-pyrazol-3-amine (6% yield). ¹H NMR (300 MHz, DMSO-d₆) δ 2.50 (s, 3H), 6.75 (s, 1H), 7.32 (t, 2H), 7.48 (m, 1H), 7.71-7.66 (m, 4H), 8.69 (d, 1H), 10.72 (s, 1H), 12.51 (s, 1); LC-MS (ESI) m/z 370 (M+H)⁺.

Example 28

Preparation of (4-(1H-pyrazol-3-ylamino)-7-methoxyquinazolin-2-yl)(4-fluorophenyl)methanone

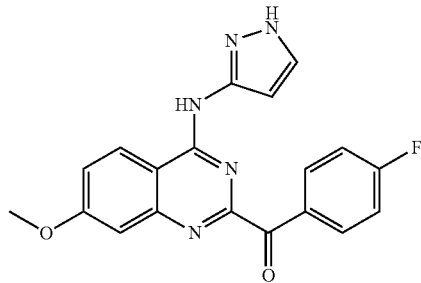 [SMILES: COc1ccc2c(Nc3cc[nH]n3)nc(C(=O)c3ccc(F)cc3)nc2c1]

Step A

To 2-amino-4-methoxybenzoic acid (10.00 g, 59.82 mmol) in DMF (150 mL) at rt were added DIEA (16.2 mL, 71.79 mmol), 2 N ammonia in MeOH (41.8 mL, 83.75 mmol), 1-EDCI (13.76 g, 71.79 mmol), and 1-hydroxybenzotriazole (9.70 g, 71.79 mmol). The solution was stirred at rt under argon. After 20 h the solution was concentrated, diluted with water, and extracted seven times with EtOAc. The EtOAc volume was reduced and the solution was washed with brine. The EtOAc fraction was concentrated and diluted with diethyl ether. The resulting precipitate was collected and dried in vacuo to give a tan solid (9.8 grams, 91%). ¹H NMR (300 MHz, DMSO-d₆) δ ppm 3.69 (s, 3H) 6.06 (dd, J=8.76, 2.54 Hz, 1H) 6.19 (d, J=2.64 Hz, 1H) 6.72 (bs, 2H) 7.48 (d, J=8.67 Hz, 1H) LC-MS (ESI) m/z 167 (M+H)⁺.

Step B

To 2-amino-4-methoxybenzamide (6.0 g, 36.11 mmol) in DCM (200 mL) was added DIEA (8.2 mL, 46.94 mmol). The solution was cooled to 0° C. followed by dropwise addition of ethyl chloroglyoxylate (4.44 mL, 39.72 mmol) in DCM (50 mL). Then DMAP (20 mg) was added followed by removal of the cooling bath. After stirring for 20 h at rt under Ar, the mixture was concentrated and addition of water led to a precipitate which was filtered and washed with water. Drying in vacuo gave a solid (6.9 g, 72%). ¹H NMR (300 MHz, DMSO-d₆) δ ppm 1.31 (t, 3H) 3.82 (s, 3H) 4.30 (q, J=7.10 Hz, 2H) 6.80 (dd, J=8.85, 2.64 Hz, 1H) 7.64 (br. s., 1H) 7.89 (d, J=8.85 Hz, 1H) 8.20 (d, J=2.64 Hz, 2H) 13.53 (s, 1H) LC-MS (ESI) m/z 250, 289, 330.

Step C

To ethyl 2-(2-carbamoyl-5-methoxyphenylamino)-2-oxoacetate (6.9 g, 25.92 mmol) in DCE (300 mL) at rt was added TEA (144 mL, 1.04 mol) followed by the addition of trimethylsilyl chloride (49 mL, 388.7 mmol). The heterogeneous mixture was heated to reflux under Ar. After 20 h the solution was cooled and poured into ice/water. The organic layer was separated and concentrated, then added to the aqueous fraction. The mixture was acidified to pH 4 and the precipitate was collected and dried in vacuo to give a tan white solid (5.4 g, 85%). $^1$H NMR (300 MHz, DMSO-$d_6$) δ ppm 1.35 (t, J=7.16 Hz, 3H) 3.92 (s, 3H) 4.38 (q, J=7.16 Hz, 2H) 7.21 (dd, J=8.76, 2.54 Hz, 1H) 7.30 (d, J=2.64 Hz, 1H) 8.07 (d, J=8.67 Hz, 1H) 12.48 (br. s., 1H) LC-MS (ESI) m/z 249 (M+H)$^+$.

Step D

To phosphorus oxychloride (5 mL) was added ethyl 7-methoxy-4-oxo-3,4-dihydroquinazoline-2-carboxylate (1.0 g, 4.03 mmol) followed by dimethylformamide (4 drops). The solution was heated to 85° C. for 2 h and then concentrated. The residue was cooled in a −20° C. cooling bath and diluted with cold EtOAc. The cold solution was washed with cold water, saturated aq sodium bicarbonate, and brine. Removal of the solvent resulted in a white solid (1.2 g, 100%.) LC-MS (ESI) m/z 267 (M+H)$^+$.

Step E

To ethyl 4-chloro-8-methoxyquinazoline-2-carboxylate (500 mg, 1.88 mmol) in DMF (20 mL) were added DIEA (0.720 mL, 4.14 mmol), 3-aminopyrazole (309 mg, 3.76 mmol), and potassium iodide (312 mg, 1.88 mmol) at rt. After stirring for 18 h and 6 h at 40° C., the solution was concentrated. Addition of water led to a precipitate which was collected and washed with water. Drying in vacuo gave a solid (475 mg, 81%) $^1$H NMR (300 MHz, DMSO-$d_6$) δ ppm 1.36 (t, 3H) 3.94 (s, 3H) 4.39 (q, 2H) 7.16 (s, 1H) 7.28 (m, 1H) 7.34 (m, 1H) 7.74 (br. s., 1H) 8.65 (m, 1H) 10.65 (s, 1H) 12.50 (s, 1H) LC-MS (ESI) m/z 314 (M+H)$^+$.

Step F

To ethyl 4-(1H-pyrazol-3-ylamino)-7-methoxyquinazoline-2-carboxylate (30 mg, 0.10 mmol) in dry DMA (2.5 mL) cooled in a −20° C. cooling bath was added dropwise 1N 4-fluorophenylmagnesium bromide in THF (0.306 mL, 0.306 mmol). After 2 h additional 1 N 4-fluorophenyl magnesium bromide (0.050 mL) was added. After 2 h, the reaction mixture was quenched by addition of a saturated ammonium chloride solution. The solution was concentrated and H$_2$O was added. The precipitate was washed with water and purified by preparative thin layer chromatography on silica gel eluting with 10% MeOH/DCM to give a solid (21 mg, 60%). $^1$H NMR (300 MHz, DMSO-$d_6$) δ ppm 3.93 (s, 3H) 6.73 (br. s., 1H) 7.29 (m., 2H) 7.38 (m, 2H) 7.63 (br. s., 1H) 8.08 (m, 2H) 8.64 (m., 1H) 10.63 (br. s., 1H) 12.47 (br. s., 1H) LC-MS (ESI) m/z 364 (M+H)$^+$.

Example 29

Preparation of (R,S)-(4-(1H-pyrazol-3-ylamino)-7-methoxyquinazolin-2-yl)(4-fluorophenyl)methanol

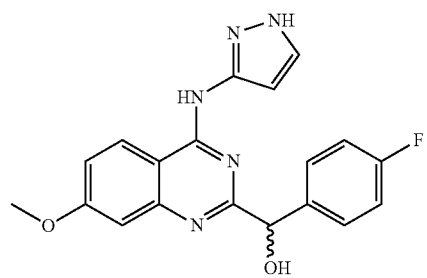 [SMILES: COc1ccc2c(Nc3cc[nH]n3)nc(C(O)c3ccc(F)cc3)nc2c1]

To (4-(1H-pyrazol-3-ylamino)-7-methoxyquinazolin-2-yl)(4-fluorophenyl)methanone (50 mg, 0.14 mmol) in 2:1 MeOH/DMF (4.5 mL) at rt was added sodium borohydride (8 mg, 0.21 mmol) in one portion. After stirring for 40 min, a solution of LiOH (60 mg) in H$_2$O (1 mL) was added and stirring was continued for 45 min. The solution was concentrated and diluted with water which led to the formation of a white precipitate (32 mg). The precipitate was collected and purified by silica preparative thin layer chromatography eluting with 10% MeOH/DCM to afford (R,S)-(4-(1H-pyrazol-3-ylamino)-7-methoxyquinazolin-2-yl)(4-fluorophenyl)methanol as a white solid (10 mg, 20%). $^1$H NMR (300 MHz, DMSO-$d_6$) δ ppm 3.91 (s, 3H) 5.64 (m, 1H) 5.77 (br. s., 1H) 6.80 (br. s., 1H) 7.12 (m, 4H) 7.19 (br. s., 1H) 7.54 (m, 2H) 7.66 (br. s., 1H) 8.49 (m., 1H) 10.38 (br. s., 1H) 12.44 (br. s., 1H) LC-MS (ESI) m/z 366 (M+H)$^+$.

Example 30

Preparation of (4-fluorophenyl)(7-methoxy-4-(5-methyl-1H-pyrazol-3-ylamino)quinazolin-2-yl)methanone

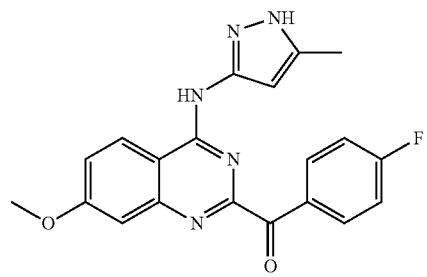 [SMILES: COc1ccc2c(Nc3cc(C)[nH]n3)nc(C(=O)c3ccc(F)cc3)nc2c1]

Step A

To ethyl 4-chloro-7-methoxyquinazoline-2-carboxylate (600 mg, 2.26 mmol) in DMF (8 mL) were added DIEA (0.864 mL, 4.96 mmol), 5-methyl-1H-pyrazol-3-amine (657 mg, 6.77 mmol), and potassium iodide (374 mg, 2.26 mmol) at rt. After stirring for 18 h at 40° C. the solution was concentrated, and the addition of water led to a precipitate which was collected and washed with water. Drying in vacuo gave a solid (570 mg, 77%) $^1$H NMR (300 MHz, DMSO-$d_6$) δ ppm 1.37 (t, 3H) 2.27 (s, 3) 3.93 (s, 3H) 4.36 (q, 2H) 6.93 (s, 1H) 7.25 (m, 1H) 7.32 (br. s., 1H) 8.62 (m, 1H) 10.53 (s, 1H) 12.18 (s, 1H) LC-MS (ESI) m/z 328 (M+H)$^+$.

Step B

To ethyl 7-methoxy-4-(5-methyl-1H-pyrazol-3-ylamino) quinazoline-2-carboxylate (379 mg, 1.16 mmol) in dry DMA (16 mL) cooled in a −30° C. bath was added dropwise 1N 4-fluorophenylmagnesium bromide in THF (4.05 mL, 4.05 mmol). After 4 h the reaction mixture was quenched by addition of a saturated ammonium chloride solution. The solution was concentrated and H$_2$O was added. The precipitate was washed with water and diethyl ether to give a yellow solid (415 mg, 95%). $^1$H NMR (300 MHz, DMSO-$d_6$) δ ppm 2.18 (br. s., 3H) 3.92 (br. s., 3H) 6.48 (br. s., 1H) 7.27 (br. s., 2H) 7.39 (br. s., 2H) 8.07 (br. s., 2H) 8.62 (br. s., 1H) 10.50 (br. s., 1H) 12.15 (br. s., 1H) LC-MS (ESI) m/z 378 (M+H)$^+$.

Example 31

Preparation of (R,S)-(4-fluorophenyl)(7-methoxy-4-(5-methyl-1H-pyrazol-3-ylamino)quinazolin-2-yl) methanol

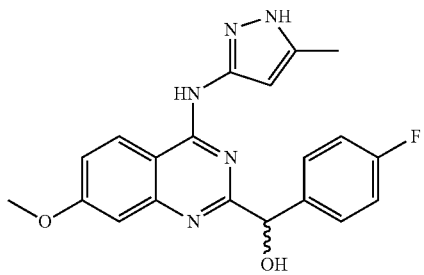 [SMILES: COc1ccc2c(Nc3cc(C)[nH]n3)nc(C(O)c3ccc(F)cc3)nc2c1]

To (4-fluorophenyl)(7-methoxy-4-(5-methyl-1H-pyrazol-3-ylamino)quinazolin-2-yl)methanone (150 mg, 0.40 mmol) in a solution of 2:1 MeOH/DMF (8 mL) cooled to 0° C. was added sodium borohydride (23 mg, 0.60 mmol) in one portion. After stirring for two h at rt the solution was cooled to 0° C. and quenched by addition of 1 N HCl. The solution was concentrated and diluted with water which led to the formation of a white precipitate (130 mg). The precipitate was collected and purified on silica eluting with 3 to 15% MeOH/DCM which gave a white solid (20 mg, 13%). $^1$H NMR (300 MHz, DMSO-$d_6$) δ ppm 2.25 (s, 3H) 3.91 (s, 3H) 5.62 (m., 1H) 5.74 (m, 1H) 6.43 (s, 1H) 6.96-7.19 (m, 4H) 7.51-7.55 (m, 2H) 8.49 (m, 1H) 10.22 (s, 1H) 12.08 (br. s., 1H) LC-MS (ESI) m/z 380 (M+H)$^+$.

Example 32

Preparation of 2-(difluoro(4-fluorophenyl)methyl)-7-methoxy-N-(5-methyl-1H-pyrazol-3-yl)quinazolin-4-amine

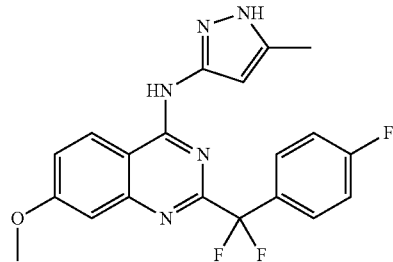 [SMILES: COc1ccc2c(Nc3cc(C)[nH]n3)nc(C(F)(F)c3ccc(F)cc3)nc2c1]

Step A 2,2-difluoro-2-(4-fluorophenyl)acetyl chloride was prepared as described in Example 8 Step B. To a solution of 2-amino-4-methoxybenzamide (0.415 g, 2.5 mmol) and TEA (0.418 mL, 3 mmol) in DCE (15 mL) was added a solution of 2,2-difluoro-2-(4-fluorophenyl)acetyl chloride (0.579 mg, 2.78 mmol) in DCE (5 mL) at rt and the reaction mixture was stirred overnight. After adding EtOAc (200 mL) the mixture was washed with 1 N HCl, saturated aq NaHCO$_3$ and brine solution. The organic solution was concentrated to yield an off-white solid (371 g, 44%). LC-MS (ESI) m/z 339 (M+H)$^+$.

Step B 2-(Difluoro(4-fluorophenyl)methyl)-7-methoxyquinazolin-4-ol was prepared according to the procedure described in Example 20 for preparation of 2-(difluoro(4-fluorophenyl)-7-fluoroquinazolin-4-ol, substituting 2-(2,2-difluoro-2-(4-fluorophenyl)acetamido)-4-fluorobenzamide in Example 20 with 2-(2,2-difluoro-2-(4-fluorophenyl)acetamido)-4-methoxybenzamide. The crude product (~100% yield) was taken directly to the next step. $^1$H NMR (300 MHz, DMSO-$d_6$) δ 3.89 (s, 3H), 7.16 (m, 2H), 7.39 (t, 2H), 7.75 (m, 2H), 8.04 (d, 1H), 12.96 (s, 1H); LC-MS (ESI) m/z 321 (M+H)$^+$.

Step C

4-Chloro-2-(difluoro(4-fluorophenyl)methyl)-7-methoxyquinazoline was obtained according to the procedure described in Example 26 for synthesis of 4-chloro-2-(difluoro (4-fluorophenyl)methyl)-7-methylquinazoline, substituting 2-(difluoro(4-fluorophenyl)methyl)-7-methylquinazolin-4-ol in Example 26 with 2-(difluoro(4-fluorophenyl)methyl)-7-methoxyquinazolin-4-ol. 4-Chloro-2-(difluoro(4-fluorophenyl)methyl)-7-methoxyquinazoline was isolated as a light yellow solid (0.290 g, 89%). LC-MS (ESI) m/z 339 (M+H)$^+$.

Step D 2-(Difluoro(4-fluorophenyl)methyl)-7-methoxy-N-(5-methyl-1H-pyrazol-3-yl)-quinazolin-4-amine was obtained according to the procedure described in Example 20 for preparation of 2-(difluoro(4-fluorophenyl)methyl)-7-fluoro-N-(5-methyl-1H-pyrazol-3-yl)quinazolin-4-amine, substituting 4-chloro-2-(difluoro(4-fluorophenyl)methyl)-7-fluoroquinazoline in Example 20 with 4-chloro-2-(difluoro(4-fluorophenyl)methyl)-7-methoxyquinazoline (36% yield). ¹H NMR (300 MHz, DMSO-d₆) δ 2.27 (s, 3H), 3.93 (s, 3H), 6.28 (s, 1H), 7.37-7.20 (m, 4H), 7.71-7.66 (m, 1H), 8.58 (d, 2H), 10.53 (s, 1H); LC-MS (ESI) m/z 400 (M+H)⁺.

Example 33

Preparation of 2-(difluoro(4-fluorophenyl)methyl)-7-methoxy-N-(1H-pyrazol-3-yl)quinazolin-4-amine

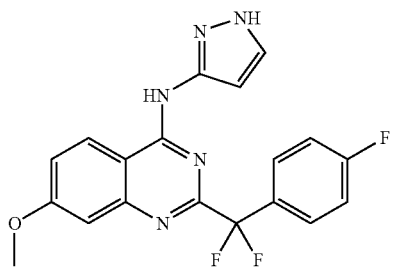 [SMILES: COc1ccc2c(Nc3cc[nH]n3)nc(C(F)(F)c3ccc(F)cc3)nc2c1]

2-(difluoro(4-fluorophenyl)methyl)-7-methoxy-N-(1H-pyrazol-3-yl)quinazolin-4-amine was obtained according to the procedure described in Example 20 for preparation of 2-(difluoro(4-fluorophenyl)methyl)-7-fluoro-N-(5-methyl-1H-pyrazol-3-yl)quinazolin-4-amine, substituting 4-chloro-2-(difluoro(4-fluorophenyl)methyl)-7-fluoroquinazoline in Example 20 with 4-chloro-2-(difluoro(4-fluorophenyl)methyl)-7-methoxyquinazoline and 5-methyl-1H-pyrazol-3-amine in Example 20 with 1H-pyrazol-3-amine (24% yield). ¹H NMR (300 MHz, DMSO-d₆) δ 4.17 (s, 3H), 6.75 (s, 1H), 7.43-7.22 (m, 4H), 7.71-7.67 (m, 3H), 8.60 (d, 1H), 10.70 (s, 1H), 12.50 (s, 1H); LC-MS (ESI) m/z 386 (M+H)⁺.

Example 34

Preparation of 2-(difluoro(4-fluorophenyl)methyl)-8-fluoro-N-(5-methyl-1H-pyrazol-3-yl)quinazolin-4-amine

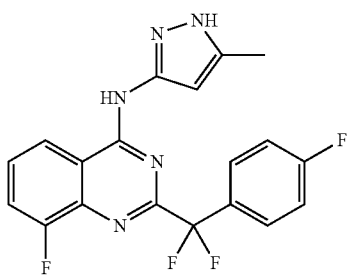 [SMILES: Cc1cc(Nc2nc(C(F)(F)c3ccc(F)cc3)nc3c(F)cccc23)n[nH]1]

Step A 2-(2,2-Difluoro-2-(4-fluorophenyl)acetamido)-3-fluorobenzamide was prepared according to the procedure described in Example 32 for preparation of 2-(2,2-difluoro-2-(4-fluorophenyl)acetamido)-4-methoxybenzamide, substituting 2-amino-4-methoxybenzamide in Example 32 with 2-amino-3-fluorobenzamide. The product was purified on silica gel column using DCM/MeOH as eluent (20%); LC-MS (ESI) m/z 327 (M+H)⁺.

Step B

A solution of 2-(2,2-difluoro-2-(4-fluorophenyl)acetamido)-3-fluorobenzamide (0.235 g, 0.72 mmol) in acetic acid (2 mL) was heated at 120° C. for 3 h. The reaction mixture was allowed to warm to rt and then water was added. The solid was collected by filtration and washed with H₂O. 2-(Difluoro(4-fluorophenyl)methyl-8-fluoroquinazolin-4-ol was obtained as an off-white solid (0.135 g, 61%). ¹H NMR (300 MHz, DMSO-d₆) δ 7.38 (m, 2H), 7.61 (m, 1H), 7.80-7.74 (m, 3H), 7.97 (m, 1H), 13.43 (s, 1H); LC-MS (ESI) m/z 309 (M+H)⁺.

Step C

4-Chloro-2-(difluoro(4-fluorophenyl)methyl)-8-fluoroquinazoline was obtained according to the procedure described in Example 26 for preparation of 4-chloro-2-(difluoro(4-fluorophenyl)methyl)-7-methylquinazoline, substituting 2-(difluoro(4-fluorophenyl)methyl)-7-methylquinazolin-4-ol in Example 26 with 2-(difluoro(4-fluorophenyl)methyl)-8-fluoroquinazolin-4-ol (94% yield). LC-MS (ESI) m/z 327 (M+H)⁺.

Step D 2-(Difluoro(4-fluorophenyl)methyl)-8-fluoro-N-(5-methyl-1H-pyrazol-3-yl)quinazolin-4-amine was obtained according to the procedure described in Example 20 for preparation of 2-(difluoro(4-fluorophenyl)methyl)-7-fluoro-N-(5-methyl-1H-pyrazol-3-yl)quinazolin-4-amine, substituting 4-chloro-2-(difluoro(4-fluorophenyl)methyl)-7-fluoroquinazoline in Example 20 with 4-chloro-2-(difluoro(4-fluorophenyl)methyl)-8-fluoroquinazoline. Pure compound was obtained after trituration with MeOH (34%). ¹H NMR (300 MHz, DMSO-d₆) δ 2.24 (s, 3H), 6.27 (s, 1H), 7.34 (t, 2H), 7.64 (m, 1H), 7.78-7.69 (m, 3H), 8.51 (d, 1H), 10.85 (s, 1H), 12.25 (s, 1H); LC-MS (ESI) m/z 388 (M+H)⁺.

Example 35

Preparation of (4-(1H-pyrazol-3-ylamino)-8-methoxyquinazolin-2-yl)(4-fluorophenyl)methanone

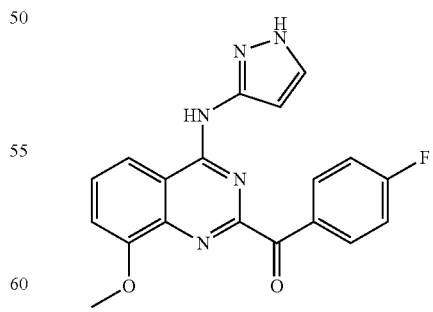

Step A

To 2-amino-3-methoxybenzoic acid (8.11 g, 48.52 mmol) in DMF (150 mL) at rt were added DIEA (13.2 mL, 58.22 mmol), 2 N ammonia in MeOH (33.96 mL, 67.92 mmol), EDCI (11.16 g, 58.22 mmol), and 1-hydroxybenzotriazole (7.87 g, 58.22 mmol). The solution was stirred at rt under argon. After 20 h the solution was diluted with water and extracted ten times with EtOAc. The EtOAc volume was reduced and washed with brine. The EtOAc fraction was concentrated and diluted with diethyl ether. The resulting tan solid was collected and dried in vacuo to give 2-amino-3-methoxybenzamide (6.08 g, 76%). $^1$H NMR (300 MHz, DMSO-$d_6$) δ 3.79 (s, 3H), 6.26 (bs, 2H), 6.48 (m, 1H), 6.88 (d, J=7.9 hz, 1H), 7.12 (bs, 1H), 7.19 (dd, J=8.2, 1.0 Hz, 1H), 7.70 (bs, 1H) LC-MS (ESI) m/z 167 (M+H)$^+$.

Step B

To 2-amino-3-methoxybenzamide (1 g, 6.02 mmol) in DCM (20 mL) was added DIEA (1.37 mL, 7.82 mmol). The solution was cooled to 0° C. followed by addition of ethylchloroglyoxalate (0.808 mL, 7.22 mmol) in DCM (5 mL) dropwise. After addition dimethylaminopyridine was added (10 mg) followed by removal of the cooling bath. After stirring 20 h at rt under Ar, the mixture was washed with water and chromatographed on silica eluting with EtOAc/DCM (20 to 60%) and MeOH/DCM (2 to 15%) to give a white solid (770 mg, quant.) $^1$H NMR (300 MHz, DMSO-$d_6$) δ ppm 1.30 (t, J=7.16 Hz, 3H) 3.79 (s, 3H) 4.29 (q, J=7.03 Hz, 2H) 7.16 (dd, J=17.2, 1.2 Hz, 1H) 7.21 (dd, J=17.8, 1.2 Hz, 1H) 7.27-7.39 (m, 1H) 7.44 (bs, 1H) 7.67 (br. s., 1H) 10.14 (bs, 1H) LC-MS (ESI) m/z 250 (M−16)$^+$.

Step C

To ethyl 2-(2-carbamoyl-6-methoxyphenylamino)-2-oxoacetate (3.4 g, 12.77 mmol) in DCE (50 mL) at rt was added TEA (71 mL, 511 mmol) followed by fast addition of trimethylsilylchloride (21 mL, 191 mmol) over twenty seconds. The heterogeneous solution was heated to reflux under Ar. After 18 h the solution was cooled and poured into ice/water. The resulting mixture was acidified to pH 3-4 and the precipitated product was collected by filtration. The acidic layer was extracted four times with EtOAc. The aqueous layer was basified to pH 7 with saturated sodium bicarbonate and extracted with EtOAc. The organic extracts were combined, washed with brine, and concentrated to 50 mL. Diethyl ether (10 mL) was added and the resulting precipitate was collected. Combination of both precipitates gave a tan solid (3.85 g, quant.) $^1$H NMR (300 MHz, DMSO-$d_6$) δ ppm 1.36 (t, J=7.06 Hz, 3H) 3.94 (s, 3H) 4.39 (q, J=6.97 Hz, 2H) 7.44 (d, J=8.10 Hz, 1H) 7.58 (t, J=8.01 Hz, 1H) 7.72 (d, J=7.91 Hz, 1H) 12.56 (br. s., 1H) LC-MS (ESI) m/z 249 (M+H)$^+$.

Step D

To phosphorus oxychloride (2 mL) was added ethyl 8-methoxy-4-oxo-3,4-dihydroquinazoline-2-carboxylate (100 mg, 0.403 mmol) followed by dimethylformamide (2 drops). The solution was heated at 80° C. for 1.5 h, and then concentrated. The residue was cooled in a −20° C. cooling bath and diluted with cold EtOAc. The cold solution was washed with cold water, saturated aq sodium bicarbonate, and brine. Removal of the solvent resulted in a white solid (98 mg, 91%) $^1$H NMR (300 MHz, DMSO-$d_6$) δ ppm 1.38 (t, J=7.06 Hz, 3H) 4.06 (s, 3H) 4.45 (q, J=7.03 Hz, 2H) 7.51-7.76 (m, 1H) 7.76-8.12 (m, 2H).

Step E

To ethyl 4-chloro-8-methoxyquinazoline-2-carboxylate (550 mg, 2.07 mmol) in dimethylformamide (6 mL) were added DIEA (0.468 mL, 2.69 mmol), 3-aminopyrazole (221 mg, 2.69 mmol), and potassium iodide (343 mg, 2.07 mmol) at rt. After stirring for 18 h, additional 3-aminopyrazole (100 mg) was added and stirring was continued for 5 h. The solution was poured into water and filtered and the solid was washed with diethyl ether to give a yellow solid (510 mg, 79% yield) $^1$H NMR (300 MHz, DMSO-$d_6$) δ ppm 137 (t, 3H) 3.97 (s, 3H) 4.38 (q, J=7.16 Hz, 2H) 7.18 (br. s., 1H) 7.38 (d, J=7.72 Hz, 1H) 7.60 (m, 1H) 7.75 (br. s., 1H) 8.25 (d, J=8.29 Hz, 1H) 10.65 (s, 1H) 12.53 (br. s., 1H) LC-MS (ESI) m/z 314 (M+H)$^+$.

Step F

To ethyl 4-(1H-pyrazol-3-ylamino)-8-methoxyquinazoline-2-carboxylate (200 mg, 0.64 mmol) in dry THF (8 mL) cooled to −40° C. was added dropwise over 2 min 1N 4-fluorophenylmagnesium bromide in THF (2.17 mL, 2.17 mmol). After 1.5 h the reaction mixture was quenched by addition of saturated aq ammonium chloride. The solution was concentrated and H$_2$O was added. The precipitate was washed with water and diethyl ether to give (4-(1H-pyrazol-3-ylamino)-8-methoxyquinazolin-2-yl)(4-fluorophenyl)methanone as a yellow solid (74 mg, 87% purity by LC/MS) $^1$H NMR (300 MHz, DMSO-$d_6$) δ ppm 3.94 (s, 3H) 6.75 (s, 1H) 7.35-7.41 (m, 3H) 7.58-7.65 (m, 2H) 8.07-8.12 (m, 2H) 8.2 (d, J=8.48 Hz, 1H) 10.64 (br. s., 1H) 12.51 (br. s., 1H) LC-MS (ESI) m/z 364 (M+H)$^+$.

Example 36

Preparation of (R,S)-2-((4-fluorophenyl)(hydroxy)methyl)-4-(5-methyl-1H-pyrazol-3-ylamino)quinazolin-7-ol

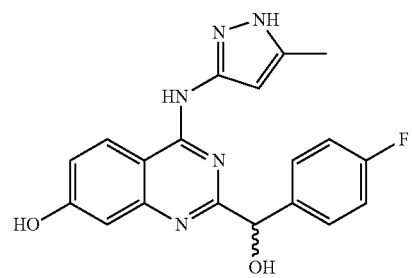 [SMILES: Cc1cc(Nc2nc(C(O)c3ccc(F)cc3)nc3cc(O)ccc23)n[nH]1]

Step A

To 2-amino-4-methoxybenzamide (7.0 g, 42 mmol) in 1,2-dichloroethane (100 mL) was added boron tribromide (25 g, 100 mmol) at rt. After heating for 40° C. for 20 h, 1 N boron tribromide in THF (40 mL) was added, and the reaction was heated to 50° C. for 20 h. The mixture was cooled and quenched by addition of aq. sodium bicarbonate. The resulting precipitate was collected by filtration to afford 2-amino-4-hydroxybenzamide as a white solid (2.0 g). The mother liquors were concentrated, diluted with MeOH., filtered and concentrated. The residue was again diluted with MeOH, filtered and concentrated, and the resulting residue was chromatographed on silica gel eluting with 5-15% MeOH/DCM to give 2-amino-4-hydroxybenzamide as a white solid (4.7 grams). The solids were combined for a total yield of 6.7 g (quantitative). $^1$H NMR (300 MHz, DMSO-d$_6$) δ ppm 5.91 (dd, J=8.67, 2.26 Hz, 1H) 6.03 (d, J=2.45 Hz, 1H) 6.62 (br. s., 2H) 7.38 (d, J=8.67 Hz, 1H) 9.45 (s, 1H). LC-MS (ESI) m/z 153 (M+H)$^+$.

Step B

To a solution of 95% NaH (1.82 g, 72.30 mmol) in DMF (100 mL) at 10° C. was added 2-amino-4-hydroxybenzamide (10.0 g, 66.72 mmol) in portions, maintaining the internal temperature at ca. 15° C. The cooling bath was removed, and the solution was allowed to warm to 40° C. over 25 min. The mixture was cooled to 10° C. and a solution of benzyl bromide (7.8 mL, 66.72 mmol) in DMF (20 mL) was added dropwise, and the mixture was allowed to warm to rt. After stirring for 20 h at rt, the mixture was cooled in an ice bath and quenched by addition of aq ammonium chloride. The solution was concentrated and diluted with water. The precipitate was collected by filtration, and the filtrate was extracted with EtOAc. The precipitate from above and the ethyl acetate extracts were combined and chromatographed on silica gel eluting with 20-80% EtOAc/DCM to afford 2-amino-4-(benzyloxy)benzamide as a solid (6.8 g, 43%). $^1$H NMR (300 MHz, DMSO-d$_6$) δ ppm 5.04 (s, 2H) 6.14 (dd, J=8.76, 2.54 Hz, 1H) 6.27 (d, J=2.64 Hz, 1H) 6.71 (bs, 2H) 7.26-7.58 (m, 6H). LC-MS (ESI) m/z 243 (M+H)$^+$.

Step C

To a solution of 2-amino-4-(benzyloxy)benzamide (4.0 g, 16.5 mmol) in THF (60 mL) was added a solution of 5-(4-fluorophenyl)-1,3-dioxolane-2,4-dione (3.65 g, 18.6 mmol) from Example 16 in THF (20 mL) portionwise at rt. After heating to 63° C. for 18 h, the solution was cooled and concentrated. After addition of H$_2$O, the solution was extracted twice with DCM. The combined organic phases were washed with brine and dried over sodium sulfate. Chromatography on silica gel eluting with 10 to 80% EtOAc/DCM afforded 4-(benzyloxy)-2-(2-(4-fluorophenyl)-2-hydroxyacetamido) benzamide as a foamy solid (4.1 g, 64%). $^1$H NMR (300 MHz, DMSO-d$_6$) δ ppm 5.06 (m, 1H), 5.12 (s, 2H) 6.68-6.74 (m, 1H) 7.14-7.20 (m, 2H) 7.32-7.51 (m, 6H) 7.77 (d, J=8.85 Hz, 1H) 8.05 (br. s., 1H) 8.30 (d, J=2.64 Hz, 1H) 12.73 (s, 1H). LC-MS (ESI) m/z 392 (M−2).

Step D

To 4-(benzyloxy)-2-(2-(4-fluorophenyl)-2-hydroxyacetamido)benzamide (4.1 g, 10.4 mmol) in absolute EtOH (50 mL) was added 20% aq potassium carbonate (5 mL). After heating and stirring at 80° C. for 20 h, the solution was cooled and concentrated to a solid. The solid was washed with water and dried under vacuum to afford 7-(benzyloxy)-2-((4-fluorophenyl)(hydroxy)methyl)quinazolin-4(3H)-one as a white solid (3.51 g, 90%). $^1$H NMR (300 MHz, DMSO-d$_6$) δ ppm 5.25 (s, 2H) 5.55 (s, 1H) 7.10-7.21 (m, 4H) 7.36-7.48 (m, 5H) 7.56-7.61 (m, 2H) 7.97 (d, J=8.67 Hz, 1H). LC-MS (ESI) m/z 377 (M+H)$^+$.

Step E

To 4-(benzyloxy)-2-((4-fluorophenyl)(hydroxy)methyl)quinazolin-4(3H)-one (3.5 g, 9.3 mmol) in DMSO (15 mL) and CHCl$_3$ (30 mL) at 0° C. was added portionwise Dess-Martin periodinane (5.52 g, 13.02 mmol). After stirring for 6 h, a 1:1 mixture of 10% aq sodium thiosulfate pentahydrate and saturated aq sodium bicarbonate was added. Upon shaking with DCM, a precipitate formed which was collected by filtration. The filtrate was extracted three times with DCM, and the combined organic fractions were washed with brine and dried over magnesium sulfate. Concentration and combination with the initial precipitate gave 7-(benzyloxy)-2-(4-fluorobenzoyl)quinazolin-4(3H)-one As a white solid (3.0 g, 86%). LC-MS (ESI) m/z 375 (M+H)$^+$.

Step F

To phosphorous oxychloride (10 mL) cooled to 5° C. was added portionwise 7-(benzyloxy)-2-(4-fluorobenzoyl) quinazolin-4(3H)-one (500 mg, 1.34 mmol) followed by the addition of DMF (4 drops). The mixture was warmed to 56° C. over 10 min and held at this temperature for 2 min, then the heating bath was removed. The mixture was concentrated, and the residue was diluted with EtOAc, then the solution was and washed with cold water, saturated sodium bicarbonate (aq), brine, and dried over sodium sulfate. The solution was concentrated to afford (7-(benzyloxy)-4-chloroquinazolin-2-yl)(4-fluorophenyl)methanone as an off-white solid (380 mg, 72%). $^1$H NMR (300 MHz, DMSO-d$_6$) δ ppm 5.40 (s, 2H) 7.37-7.45 (m, 5H) 7.52-7.55 (m, 2H) 7.66-7.71 (m, 2H) 8.09-8.14 (m, 2H) 8.31 (d, J=9.04 Hz, 1H). LC-MS (ESI) m/z 393 (M+H)$^+$.

Step G

To (7-(benzyloxy)-4-chloroquinazolin-2-yl)(4-fluorophenyl)methanone (380 mg, 0.97 mmol) in DMF (10 mL) at rt were added DIEA (500 uL, 2.90 mmol), 5-methyl-1H-pyrazol-3-amine (280 mg, 2.90 mmol), and KI (161 mg, 0.97 mmol). After stirring at 40° C. for 18 h, the solution was cooled and diluted with water. After standing at 0° C. for 1 h, the precipitate was collected by filtration and dried under reduced pressure to afford (7-(benzyloxy)-4-(5-methyl-1H-pyrazol-3-ylamino)quinazolin-2-yl)(4-fluorophenyl)methanone as a yellow solid (365 mg, 83%) $^1$H NMR (300 MHz, DMSO-d$_6$) δ ppm 2.18 (s, 3H) 5.30 (s, 2H) 6.48 (s, 1H) 7.33-7.44 (m, 8H) 7.50-7.52 (m, 2H) 8.07 (m, 2H) 8.65 (m, 1H) 10.53 (s, 1H) 12.18 (s, 1H). LC-MS (ESI) m/z 454 (M+H)$^+$ Step H To 10% Pd/C (200 mg) was added a solution of (7-(benzyloxy)-4-(5-methyl-1H-pyrazol-3-ylamino)quinazolin-2-yl) (4-fluorophenyl)methanone (390 mg, 0.99 mmol) in DMF (30 mL). After stirring under H$_2$ at 1 atm for 18 h, the mixture was filtered and the filtrate was concentrated. The residue was passed through on a short column of silica gel, eluting first with 10 to 30% EtOAc/DCM followed by 1-5% AcOH/9-5% MeOH 1/90% DCM. The fractions containing product were combined and washed with sodium bicarbonate followed by evaporation to afford (R,S)-2-((4-fluorophenyl)(hydroxy) methyl)-4-(5-methyl-1H-pyrazol-3-ylamino)quinazolin-7-ol as a white solid (130 mg, 36%). $^1$H NMR (300 MHz, DMSO-d$_6$) δ ppm 2.24 (s, 3H) 5.59 (bs., 1H) 5.73 (m, 1H)

6.38 (m, 1H) 6.99 (bs, 2H) 7.14 (m, 2H) 7.53 (m, 2H) 8.39 (bs., 1H) 10.11 (bs., 1H) 12.06 (bs., 1H). LC-MS (ESI) m/z 366 (M+H)+.

Example 37

Preparation of (4-fluorophenyl)(7-hydroxy-4-(5-methyl-1H-pyrazol-3-ylamino)quinazolin-2-yl)methanone

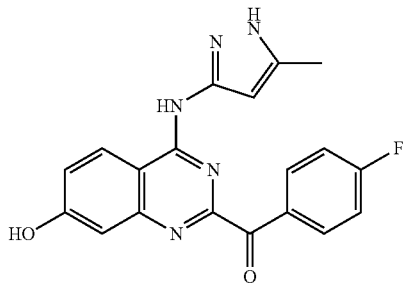

To 2-((4-fluorophenyl)(hydroxy)methyl)-4-(5-methyl-1H-pyrazol-3-ylamino)quinazolin-7-ol (50 mg, 0.14 mmol) in 1:3 DMSO/DCM was added Dess-Martin periodinane (81 mg, 0.19 mmol) in one portion. After stirring for 1 h at rt, the solution was cooled to 0° C. and quenched by addition of a 1:1 mixture of 10% sodium thiosulfate pentahydrate and saturated sodium bicarbonate. The resulting dark precipitate was collected and chromatographed on silica eluting with 2 to 10% MeOH/DCM. Trituration of the colored solid with MeOH afforded (4-fluorophenyl)(7-hydroxy-4-(5-methyl-1H-pyrazol-3-ylamino)quinazolin-2-yl)methanone as a white solid (7 mg, 14%). $^1$H NMR (300 MHz, DMSO-$d_6$) δ ppm 2.27 (s, 3H), 6.47 (bs, 1H), 7.06 (m, 2H), 7.13 (m, 1H), 7.38 (m, 2H), 8.06 (m, 2H), 8.57 (m, 2H), 10.41 (bs, 1H), 10.60 (bs, 1H), 12.15 (bs, 1H). LC-MS (ESI) m/z 364 (M+H)+.

Example 38

Preparation of (R,S)-(4-fluorophenyl)(4-(5-methyl-1H-pyrazol-3-ylamino)-7-(2-morpholinoethoxy)quinazolin-2-yl)methanol

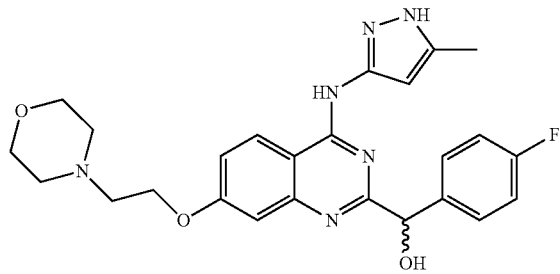 [SMILES: Cc1cc(Nc2nc(C(O)c3ccc(F)cc3)nc3cc(OCCN4CCOCC4)ccc23)n[nH]1]

To (R,S)-2-((4-fluorophenyl)(hydroxy)methyl)-4-(5-methyl-1H-pyrazol-3-ylamino)quinazolin-7-ol (50 mg, 0.14 mmol) in DMF (2 mL) were added 4-(2-chloroethyl)morpholine (51 mg, 0.27 mmol) and cesium carbonate (134 mg, 0.41 mmol) at rt. After heating at 40° C. for 18 h the solution was diluted with EtOAc and washed with water and brine, and dried over sodium sulfate. Chromatography on silica gel eluting with 2 to 10% MeOH/DCM afforded (R,S)-(4-fluorophenyl)(4-(5-methyl-1H-pyrazol-3-ylamino)-7-(2-morpholinoethoxy)quinazolin-2-yl)methanol as a solid (26 mg, 40%). $^1$H NMR (300 MHz, DMSO-$d_6$) δ ppm 2.25 (bs, 3H) 2.75 (m 3H) 3.59 (m, 6H) 4.26 (m, 3H) 5.63 (m, 1H) 5.75 (m, 1H) 6.43 (bs, 1H) 7.10-7.20 (m, 4H) 7.53 (m, 2H) 8.47 (m., 1H) 10.23 (bs., 1H) 12.09 (bs., 1H). LC-MS (ESI) m/z 479 (M+H)+.

Example 39

Preparation of (R,S)-2-(2-((4-fluorophenyl)(hydroxy)methyl)-4-(5-methyl-1H-pyrazol-3-ylamino)quinazolin-7-yloxy)ethanol

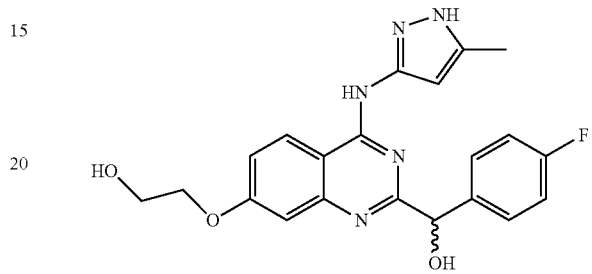

(R,S)-(7-(2-(tert-butyldimethylsilyloxy)ethoxy)-4-(5-methyl-1H-pyrazol-3-ylamino)quinazolin-2-yl)(4-fluorophenyl)methanol was obtained following the procedure described in Example 38 for the synthesis of (R,S)-(4-fluorophenyl)(4-(5-methyl-1H-pyrazol-3-ylamino)-7-(2-morpholinoethoxy)quinazolin-2-yl)methanol, substituting 4-(2-chloroethyl)morpholine in Example 38 with (2-bromoethoxy)(tert-butyl)dimethylsilane to afford 150 mg of crude impure solid. To the crude solid (150 mg) in THF (1 mL) was added tetrabutylammonium fluoride (1.0 mL) dropwise at rt. After 18 h the solution was concentrated, diluted with EtOAc, and washed with water. Chromatography of the residue on silica gel eluting with 2-8% 1% NH4OH.9% MeOH/DCM afforded (R,S)-2-(2-((4-fluorophenyl)(hydroxy)methyl)-4-(5-methyl-1H-pyrazol-3-ylamino)quinazolin-7-yloxy)ethanol as a solid (31 mg, 18%). $^1$H NMR (300 MHz, DMSO-$d_6$) δ ppm 2.31 (s, 3H) 3.84 (q, J=5.09 Hz, 2H) 4.22 (t, J=4.71 Hz, 2H) 5.01 (t, J=5.46 Hz, 1H) 5.69 (m, 1H) 5.83 (bs, 1H) 6.47 (bs, 1H) 7.17-7.25 (m, 4H) 7.59 (m, 2H) 8.54 (d, J=9.04 Hz, 1H) 10.30 (bs, 1H) 12.15 (bs, 1H). LC-MS (ESI) m/z 410 (M+H)+.

Example 40

Preparation of (R,S)-3-(2-((4-fluorophenyl)(hydroxy)methyl)-4-(5-methyl-1H-pyrazol-3-ylamino)quinazolin-7-yloxy)propan-1-ol

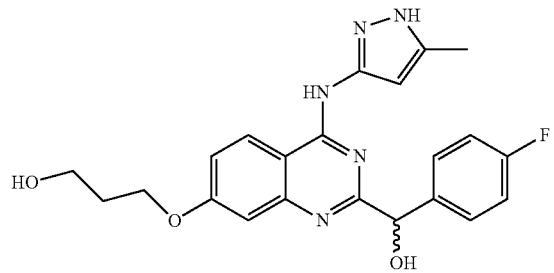 [SMILES: Cc1cc(Nc2nc(C(O)c3ccc(F)cc3)nc3cc(OCCCO)ccc23)n[nH]1]

(R,S)-3-(2-((4-fluorophenyl)(hydroxy)methyl)-4-(5-methyl-1H-pyrazol-3-ylamino)quinazolin-7-yloxy)propan-1-ol was obtained following the procedure described in Example 38 for the synthesis of (R,S)-(4-fluorophenyl)(4-(5-methyl-1H-pyrazol-3-ylamino)-7-(2-morpholinoethoxy)quinazolin-2-yl)methanol, substituting 4-(2-chloroethyl)morpholine in Example 38 with 3-chloropropan-1-ol (35 mg, 30%) $^1$H NMR (300 MHz, DMSO-$d_6$) δ ppm 1.96 (m, 2H) 2.24 (s, 3H) 3.60 (m, 2H) 4.26 (t, J=6.41 Hz, 2H) 5.97 (s, 1H) 6.15 (s, 1H) 7.24-7.41 (m, 4H) 7.60 (m, 2H) 7.70 (bs, 1H) 8.73 (d, J=9.42 Hz, 4H) 11.87 (bs, 1H) 12.56 (bs, 1H) 14.21 (bs, 1H). LC-MS (ESI) m/z 424 (M+H)$^+$.

Example 41

Preparation of (4-fluorophenyl)(4-(5-methyl-1H-pyrazol-3-ylamino)-7-(piperidin-4-yloxy)quinazolin-2-yl)methanol

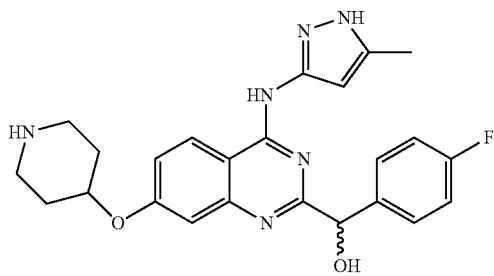 [SMILES: Cc1cc(Nc2nc(C(O)c3ccc(F)cc3)nc3cc(OC4CCNCC4)ccc23)n[nH]1]

Intermediate compound (R,S)-tert-butyl 4-(2-(4-fluorophenyl)(hydroxy)methyl)-4-(5-methyl-1H-pyrazol-3-ylamino)quinazolin-7-yloxy)piperidine-1-carboxylate was obtained (105 mg) following the procedure described in Example 38 for the synthesis of (R,S)-(4-fluorophenyl)(4-(5-methyl-1H-pyrazol-3-ylamino)-7-(2-morpholinoethoxy)quinazolin-2-yl)methanol, substituting 4-(2-chloroethyl)morpholine in Example 38 with tert-butyl 4-(methylsulfonyloxy)piperidine-1-carboxylate. To the crude tert-butyl 4-(2-(((4-fluorophenyl)(hydroxy)methyl)-4-(5-methyl-1H-pyrazol-3-ylamino)quinazolin-7-yloxy)piperidine-1-carboxylate (100 mg, 18.2 mmol) in a flask at 0° C. was added 4N HCl/dioxane (5 mL). After stirring for 20 h, the solvent was removed and the residue was shaken with DCM and aq sodium bicarbonate. The solvents were removed, and the remaining residue was extracted with MeOH/DCM. The extracts were concentrated and the residue was chromatographed on reverse phase HPLC to afford (4-fluorophenyl)(4-(5-methyl-1H-pyrazol-3-ylamino)-7-(piperidin-4-yloxy)quinazolin-2-yl)methanol as a white solid (32 mg, 21%). $^1$H NMR (300 MHz, DMSO-$d_6$) δ ppm 1.54 (m, 2H) 1.89 (s, 13H) 1.89 (s., 3H) 1.98 (m, 2H) 2.68 (m, 2H) 2.99 (m, 2H) 4.66 (m, 4H) 5.62 (s, 1H) 5.76 (s, 1H) 6.36 (b., 1H) 7.08-7.18 (m, 4H) 7.52 (m, 2H) 8.45 (m., 1H), 10.29 (bs, 1H). LC-MS (ESI) m/z 449 (M+H)$^+$.

Example 42

Preparation of (R,S)-(4-fluorophenyl)(7-(2-methoxyethoxy)-4-(5-methyl-1H-pyrazol-3-ylamino)quinazolin-2-yl)methanol

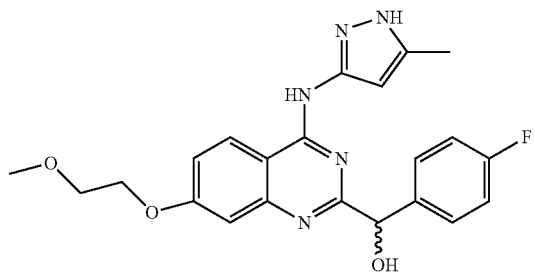 [SMILES: COCCOc1ccc2c(Nc3cc(C)[nH]n3)nc(C(O)c3ccc(F)cc3)nc2c1]

(R,S)-(4-fluorophenyl)(7-(2-methoxyethoxy)-4-(5-methyl-1H-pyrazol-3-ylamino)quinazolin-2-yl)methanol was obtained (35 mg, 25%) following the procedure described in Example 38 for the synthesis of (4-fluorophenyl)(4-(5-methyl-1H-pyrazol-3-ylamino)-7-(2-morpholinoethoxy)quinazolin-2-yl)methanol, substituting 4-(2-chloroethyl)morpholine in Example 38 with 1-bromo-2-methoxyethane. $^1$H NMR (300 MHz, DMSO-$d_6$) δ ppm 2.24 (s, 3H), 3.71 (m, 2H), 4.26 (m, 2H), 5.63 (bs, 1H), 5.77 (bs, 1H), 6.40 (bs, 1H), 7.14 (m, 4H), 7.53 (m, 2H), 8.47 (m, 1H), 10.25 (bs, 1H), 12.09 (bs, 1H). LC-MS (ESI) m/z 424 (M+H)$^+$.

Example 43

Preparation of (R,S)-tert-butyl 2-(2-((4-fluorophenyl)(hydroxy)methyl)-4-(5-methyl-1H-pyrazol-3-ylamino)quinazolin-7-yloxy)acetate

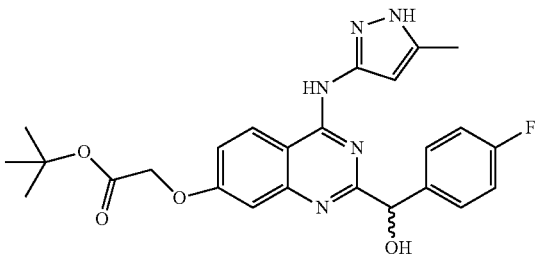 [SMILES: Cc1cc(Nc2nc(C(O)c3ccc(F)cc3)nc3cc(OCC(=O)OC(C)(C)C)ccc23)n[nH]1]

(R,S)-Tert-butyl 2-(2-((4-fluorophenyl)(hydroxy)methyl)-4-(5-methyl-1H-pyrazol-3-ylamino)quinazolin-7-yloxy)acetate was prepared (70 mg, 30%) following the procedure described in Example 38 for the synthesis of (4-fluorophenyl)(4-(5-methyl-1H-pyrazol-3-ylamino)-7-(2-morpholinoethoxy)quinazolin-2-yl)methanol, substituting 4-(2-chloroethyl)morpholine in Example 38 with tert-butyl 2-bromoacetate. $^1$H NMR (300 MHz, DMSO-$d_6$) δ ppm 1.43 (s, 9H), 2.25 (s, 3H), 4.86 (s, 2H), 5.62 (m, 1H), 5.77 (m, 1H), 7.09-7.16 (m, 4H), 7.52 (m, 2H), 8.50 (m, 1H), 10.26 (bs, 1H), 12.09 (bs, 1H). LC-MS (ESI) m/z 424 (M+H)⁺.

Example 44

Preparation of (R,S)-2-(2-((4-fluorophenyl)(hydroxy)methyl)-4-(5-methyl-1H-pyrazol-3-ylamino)quinazolin-7-yloxy)acetic acid

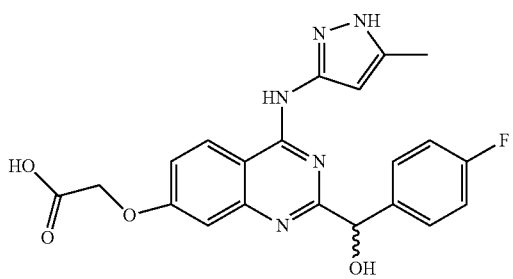 [SMILES: Cc1cc(Nc2nc(C(O)c3ccc(F)cc3)nc3cc(OCC(=O)O)ccc23)n[nH]1]

To (R,S)-tert-butyl 2-(2-((4-fluorophenyl)(hydroxy)methyl)-4-(5-methyl-1H-pyrazol-3-ylamino)quinazolin-7-yloxy)acetate (26 mg, 0.05 mmol) from Example 43 in DCM (1 mL) at 0° C. was added TFA (1 mL). After stirring for 18 h at 0° C. the solvent was removed and the residue was triturated with DCM to give (R,S)-2-(2-((4-fluorophenyl)(hydroxy)methyl)-4-(5-methyl-1H-pyrazol-3-ylamino)quinazolin-7-yloxy)acetic acid as a solid (20 mg, 87%) $^1$H NMR (300 MHz, DMSO-d₆) δ ppm 2.27 (s, 3H), 5.93 (s, 1H), 6.15 (s, 1H), 7.22-7.43 (m, 4H), 7.59 (m, 3H), 8.71 (m, 1H) LC-MS (ESI) m/z 424 (M+H)⁺.

Example 45

Preparation of (R,S)-methyl (4-fluorophenyl)(4-(5-methyl-4H-pyrazol-3-ylamino)quinazolin-2-yl)methylcarbamate

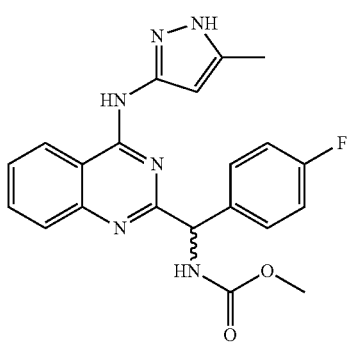 [SMILES: COC(=O)NC(c1ccc(F)cc1)c1nc(Nc2cc(C)[nH]n2)c2ccccc2n1]

Step A

To (4-fluorophenyl)(4-(5-methyl-4H-pyrazol-3-ylamino)quinazolin-2-yl)methanone from Example 3 (0.700 g, 2.15 mmol) in EtOH (10 mL) was added methoxyamine hydrochloride (0.336 g, 4.02 mmol) and the mixture was heated to 60° C. for 30 min. Water was added and the yellow precipitate was collected by filtration and washed with MeOH to afford (4-fluorophenyl)(4-(5-methyl-1H-pyrazol-3-ylamino)quinazolin-2-yl)methanone O-methyloxime (0.88 g). LC-MS (ESI) m/z 377 (M+H)⁺.

Step B

To a solution of (4-fluorophenyl)(4-(5-methyl-1H-pyrazol-3-ylamino)quinazolin-2-yl)methanone O-methyloxime (0.88 g, 2.33 mmol) in acetic acid (25 mL) was added zinc dust (3.0 g, 46 mmol), and the mixture was stirred at rt overnight then filtered through Celite. The filtrate was concentrated and the residue was purified by reverse-phase preparative HPLC eluting with 30-50% CH₃CN/H₂O containing 0.05% HOAc to afford (R,S)-2-(amino(4-fluorophenyl)methyl)-N-(5-methyl-1H-pyrazol-3-yl)quinazolin-4-amine as a light yellow solid (105 mg, 40%). LC-MS (ESI) m/z 349 (M+H)⁺.

Step C

To a solution of (R,S)-2-(amino(4-fluorophenyl)methyl)-N-(5-methyl-1H-pyrazol-3-yl)quinazolin-4-amine (0.105 g, 0.3 mmol) in dry THF (3 mL) was added dropwise methyl chloroformate (0.02 mL, 0.3 mmol). DIEA (0.06 mL, 0.36 mmol) was added and the mixture was stirred at 0° C. for 10 min. The mixture was allowed to warm to rt and stir for 5 min. The mixture was partitioned between water and EtOAc and the organic layer was dried over Na₂SO₄, filtered and concentrated. The residue was purified by reverse-phase preparative HPLC eluting with CH₃CN/H₂O containing 0.05% HOAc to afford (R,S)-methyl (4-fluorophenyl)(4-(5-methyl-1H-pyrazol-3-ylamino)quinazolin-2-yl)methylcarbamate as a white powder (35 mg, 29% yield). $^1$H NMR (300 MHz, DMSO-d₆) δ 2.2 (s, 3H) 3.57 (s, 3H) 5.8 (s, 1H) 6.4 (s, 1H) 7.1-7.2 (m, 2H) 7.4-7.5 (m, 3H) 7.7-7.9 (m, 3H) 8.5 (s, 1H) 10.42 (s, 1H) 12.25 (s, 1H); LC-MS (ESI) m/z 407 (M+H)⁺.

Example 46

Preparation of (R,S)-(4-fluorophenyl)(8-methyl-4-(5-methyl-1H-pyrazol-3-ylamino)quinazolin-2-yl)methanol

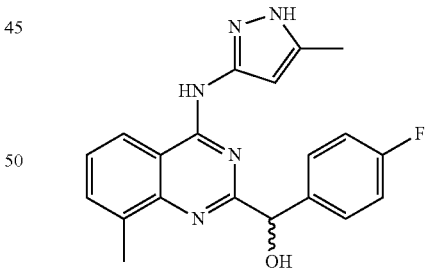

Step A

To solution of 2-amino-3-methylbenzoic acid (4.0 g, 26.5 mmol) in degassed DMF (40 mL) were added HOBt (4.28 g, 31.7 mmol), DIEA (5.52 mL, 31.7 mmol), and 2N NH₃/MeOH (19 mL, 37.1 mmol). The solution was stirred at rt for 16 h, then the mixture was concentrated under reduced pressure and the residue was purified by silica gel chromatography eluting with 10-60% EtOAc/hexanes to afford 2-amino-3-methylbenzamide as a solid (2.52 g, 63%). $^1$H NMR (300

MHz, DMSO-d$_6$) δ 2.07 (s, 3H), 6.40-6.47 (m, 3H), 7.06 (m, 2H), 7.42 (d, 1H), 7.72 (br d, 1H).

Step B

To a solution of 2-amino-3-methylbenzamide (1.50 g, 10.0 mmol) and DIEA (2.61 mL, 15 mmol) in THF (50 mL) at 0° C. was added ethyl chlorooxoacetate (1.23 mL, 11.0 mmol). The solution was allowed to warm to rt and stir for 16 h, then was concentrated under reduced pressure. The residue was purified by silica gel chromatography eluting with 20-100% EtOAc/hexanes to afford ethyl 2-(2-carbamoyl-6-methylphenylamino)-2-oxoacetate as a solid (490 mg, 20%). $^1$H NMR (300 MHz, DMSO-d$_6$) δ 1.31 (t, J=7.1 Hz, 3H), 2.17 (s, 3H), 4.30 (q, J=7.1 Hz, 2H), 7.28 (t, 1H), 7.33-7.57 (m, 3H), 7.82 (s, 1H), 10.67 (s, 1H).

Step C

To a solution of ethyl 2-(2-carbamoyl-6-methylphenylamino)-2-oxoacetate (490 mg, 1.96 mmol) and TEA (10.4 mL, 75 mmol) in DCE (20 mL) was added TMS-Cl (3.6 mL, 29 mmol) and the solution was stirred at 80° C. for 16 h. The mixture was concentrated under reduced pressure and the residue was partitioned between DCM (100 mL) and saturated aq NaHCO$_3$. The separated aqueous phase was extracted with DCM (2×100 mL) and the combined organic layers were dried over MgSO$_4$, filtered, and concentrated. The residue was purified by silica gel chromatography eluting with 10-40% EtOAc/hexanes to afford ethyl 4-hydroxy-8-methylquinazoline-2-carboxylate as a solid (330 mg, 72%). $^1$H NMR (300 MHz, DMSO-d$_6$) δ 1.36 (t, J=7.2 Hz, 3H), 2.58 (s, 3H), 4.39 (q, J=7.2 Hz, 2H), 7.46-7.64 (m, 1H), 7.64 (m, 1H), 8.02 (m, 1H), 12.62 (br s, 1H).

Step D

A mixture of ethyl 4-hydroxy-8-methylquinazoline-2-carboxylate (330 mg, 1.39 mmol), POCl$_3$ (20 mL), and DMF (3 drops) was stirred at 80° C. for 48 h. The mixture was concentrated under reduced pressure and the solid residue was partitioned between DCM (100 mL) and cold H$_2$O (100 mL). The separated aqueous phase was extracted with DCM (2×100 mL) and the combined organic layers were dried over MgSO$_4$, filtered, and concentrated. The residue was purified by silica gel chromatography eluting with EtOAc/hexanes to afford ethyl 4-chloro-8-methylquinazoline-2-carboxylate as a solid (320 mg, 90%). $^1$H NMR (300 MHz, DMSO-d$_6$) δ 1.39 (t, J=7.1 Hz, 3H), 2.76 (s, 3H), 4.45 (q, J=7.1 Hz, 2H), 7.90 (m, 1H), 8.1 (m, 1H), 8.2 (m, 1H).

Step E

To a solution of ethyl 4-chloro-8-methylquinazoline-2-carboxylate (320 mg, 0.43 mmol) in THF (10 mL) at −40° C. was added 1M 4-fluorophenylmagnesium bromide (1.55 mL, 1.55 mmol), and the mixture was stirred at −40° C. for 1 h. The reaction was quenched with saturated aq NH$_4$Cl and the mixture was concentrated under reduced pressure, and the residue was partitioned between DCM (100 mL) and H$_2$O (100 mL). The separated aqueous phase was extracted with DCM (2×100 mL) and the combined organic layers were dried over MgSO$_4$, filtered, and concentrated to afford a solid (370 mg, 1.22 mmol). A solution of the above solid (370 mg) and KI (224 mg, 1.35 mmol) in DMF (10 mL) was stirred at rt for 30 min, and then 5-methyl-1H-pyrazol-3-amine (257 mg, 2.63 mmol) and DIEA (275 uL, 1.60 mmol) were added and the mixture was stirred at 50° C. for 24 h. Water was added and the precipitated solid was collected by filtration and washed several times with water. The crude product was purified by HPLC eluting with 10-80% ACN/H$_2$O containing 0.05% HOAc to provide (4-fluorophenyl)(8-methyl-4-(5-methyl-1H-pyrazol-3-ylamino)quinazolin-2-yl)methanone as a solid (64 mg, 14%). $^1$H NMR (300 MHz, DMSO-d$_6$) δ 2.20 (s, 3H), 2.59 (s, 3H), 6.56 (br s, 1H), 7.40 (t, J=8.7 Hz, 2H), 7.56 (t, J=7.6 Hz, 1H), 7.77 (d, J=6.8 Hz, 1H), 8.16 (t, J=6.3 Hz, 2H), 8.56 (d, J=7.7 Hz, 1H), 10.59 (br s, 1H), 12.20 (br s, 1H).

Step F

A mixture of (4-fluorophenyl)(8-methyl-4-(5-methyl-1H-pyrazol-3-ylamino)quinazolin-2-yl)methanone (64 mg, 0.177 mmol) and NaBH$_4$ (15 mg, 0.355 mmol) in MeOH (3 mL) was stirred at rt for 24 h. 1M HCl was added dropwise until the a homogeneous mixture was obtained, and the mixture was stirred for 5 min. Then saturated aq NaHCO$_3$ was added until a solid precipitate formed. The solid was collected by filtration washing with H$_2$O to afford (R,S)-(4-fluorophenyl)(8-methyl-4-(5-methyl-1H-pyrazol-3-ylamino)quinazolin-2-yl)methanol as a solid (42 mg, 66%). $^1$H NMR (300 MHz, DMSO-d$_6$) δ 2.25 (s, 3H), 2.65 (s, 3H), 5.68 (s, 1H), 5.78 (s, 1H), 6.41 (s, 1H), 7.15 (m, 2H), 7.41 (m, 1H), 7.56 (m, 2H), 7.68 (m, 1H), 8.42 (m, 1H), 10.31 (br s, 1H), 12.11 (br s, 1H); LC-MS (ESI) m/z 364 (M+H)$^+$.

Example 47

Preparation of (R,S)-(7-fluoro-4-(5-methyl-1H-pyrazol-3-ylamino)quinazolin-2-yl)(4-fluorophenyl)methanol

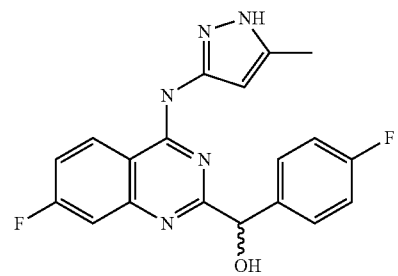 [SMILES: Cc1cc(Nc2nc(C(O)c3ccc(F)cc3)nc3cc(F)ccc23)n[nH]1]

Step A

To solution of 2-amino-4-fluorobenzoic acid (4.0 g, 25.8 mmol) in degassed DMF (50 mL) were added HOBt (4.19 g, 31 mmol), DIEA (5.4 mL, 31 mmol), EDCI (5.94 g, 31 mmol) and 2N NH$_3$/MeOH (18 mL, 36.1 mmol). The solution was stirred at rt for 48 h, and then concentrated under reduced pressure. The residue was purified by silica gel chromatography to afford 2-amino-4-fluorobenzamide as a solid (2.89 g, 66%). $^1$H NMR (300 MHz, DMSO-d$_6$) δ 6.28 (m, 1H), 6.44 (m, 1H), 6.90 (br s, 2H), 7.08 (m, 1H), 7.58 (m, 1H), 7.71 (br d, 1H).

Step B

A solution of 2-amino-4-fluorobenzamide (750 mg, 4.40 mmol), diethyl oxalate (20 mL), and AcOH (8 mL) was stirred at 140° C. for 16 h. The solid was collected by filtration and dried under reduced pressure to afford ethyl 7-fluoro-4-hydroxyquinazoline-2-carboxylate as a solid (235 mg, 22%). $^1$H NMR (300 MHz, DMSO-d$_6$) δ 1.36 (t, J=7.08 Hz, 2H), 4.39 (q, J=7.08 Hz, 2H), 7.52 (m, 1H), 7.67 (m, 1H), 8.25 (m, 1H), 11.97 (br s, 1H), 12.77 (br s, 1H).

Step C

A mixture of ethyl 7-fluoro-4-hydroxyquinazoline-2-carboxylate (235 mg, 1.38 mmol), POCl$_3$ (15 mL), and DMF (3 drops) was stirred at 80° C. for 24 h. The mixture was concentrated under reduced pressure and the residue was partitioned between cold H$_2$O (100 mL) and DCM (50 mL). The separated aqueous phase was extracted with DCM (2×50 mL) and the combined organic layers were dried over MgSO$_4$, filtered, and concentrated under reduced pressure. The residue was purified by silica gel chromatography eluting with 20-80% EtOAc/hexanes to afford. ethyl 4-chloro-7-fluoroquinazoline-2-carboxylate as a solid (128 mg, 37%). $^1$H NMR (300 MHz, DMSO-d$_6$) δ 1.38 (t, J=7.10 Hz, 3H), 4.45 (q, J=7.10 Hz, 2H), 7.92 (m, 1H), 8.15 (m, 1H), 8.37-8.65 (m, 1H).

Step D

To a solution of ethyl 4-chloro-7-fluoroquinazoline-2-carboxylate (122 mg, 0.479 mmol) in 5 mL THF at −40° C. was added 1M 4-fluorophenylmagnesium bromide/THF (0.58 mL, 0.58 mmol) and the mixture was stirred at −40° C. for 2 h. Saturated aq NH$_4$Cl was added and the mixture was concentrated under reduced pressure. The residue was partitioned between H$_2$O (100 mL) and DCM (50 mL). The separated aqueous phase was extracted with DCM (2×50 mL) and the combined organic layers were dried over MgSO$_4$, filtered, and concentrated under reduced pressure to afford a solid (130 mg) containing (4-chloro-7-fluoroquinazolin-2-yl)(4-fluorophenyl)methanone. A solution of the solid (130 mg, ca. 0.43 mmol) and KI (78 mg, 0.47 mmol) in DMF (6 mL) was stirred at rt for 30 min, and then 5-methyl-1H-pyrazol-3-amine (88 mg, 0.88 mmol) and DIEA (96 uL, 0.56 mmol) were added. The mixture was stirred at rt for 24 h, and then water was added. The precipitated solid was collected by filtration washing with water. The solid was purified by preparative reverse-phase HPLC eluting with 10-80% ACN/H$_2$O containing 0.05% HOAC to afford (7-fluoro-4-(5-methyl-1H-pyrazol-3-ylamino)quinazolin-2-yl)(4-fluorophenyl) methanone as a solid (96 mg, 45%). $^1$H NMR (300 MHz, DMSO-d$_6$) δ ppm 2.18 (s, 3H), 6.48 (s, 1H), 7.39 (m, 2H), 7.63 (m, 2H), 8.13 (m, 2H), 8.84 (m, 1H), 10.80 (s, 1H), 12.08 (br s, 1H).

Step E

A solution of (7-fluoro-4-(5-methyl-1H-pyrazol-3-ylamino)quinazolin-2-yl)(4-fluorophenyl)methanone (96 mg, 0.26 mmol) and NaBH$_4$ (21 mg, 0.53 mmol) in MeOH (3 mL) was stirred at rt for 24 h, and then 1M HCl was added dropwise until a homogeneous mixture was obtained. The mixture was stirred for 5 min, and then saturated aq NaHCO$_3$ was added until a precipitate formed. The solid was collected by filtration and washed with H$_2$O to afford (R,S)-(7-fluoro-4-(5-methyl-1H-pyrazol-3-ylamino)quinazolin-2-yl)(4-fluorophenyl)methanol as a solid (62 mg, 64%). $^1$H NMR (300 MHz, DMSO-d$_6$) (one or more impurities present) δ 2.25 (s), 5.66 (1H), 5.84 (1H), 6.44 (br s, 1H), 7.14 (m), 7.37-7.50 (m), 7.47-7.68 (m), 8.56-8.91 (m, 1H), 10.50 (br s, 1H), 12.15 (br s, 1H); LC-MS (ESI) m/z 368 (M+H)$^+$.

Example 48

Preparation of (4-(1H-pyrazol-3-ylamino)quinazolin-2-yl)bis(4-fluorophenyl)methanol

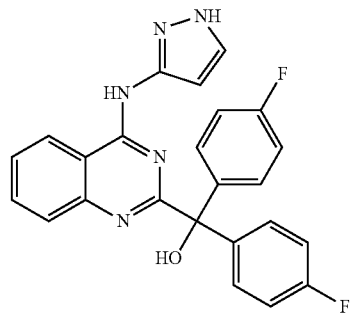 [SMILES: OC(c1ccc(F)cc1)(c1ccc(F)cc1)c1nc(Nc2cc[nH]n2)c2ccccc2n1]

Step A

A stirred mixture of ethyl 4-chloroquinazoline-2-carboxylate (709 mg, 3 mmol), 3-aminopyrazole (274 mg, 3.3 mmol), potassium iodide (498 mg, 3 mmol), and DIEA (574 µL, 3.3 mmol) in N,N-dimethylformamide (5 mL) was heated at 50° C. for 2 h and then stirred at rt overnight. Water was added to the mixture and the precipitated solid was filtered, washed with water and dried under high vacuum at 50° C. for 3 h to afford ethyl 4-(1H-pyrazol-3-ylamino)quinazoline-2-carboxylate (595 mg, 70%). LC-MS (ESI) m/z 284 (M+H)$^+$.

Step B

To a stirred solution of ethyl 4-(1H-pyrazol-3-ylamino) quinazoline-2-carboxylate (595 mg, 2.1 mmol) in THF (15 mL) at −40° C., was added dropwise a 2 M solution of 4-fluorophenylmagnesium bromide in THF (4.2 mL, 8.4 mmol). The mixture was stirred at −40° C. for 2 h and then stored at −30° C. for 18 h. The reaction was quenched by adding 0.5 N HCl at 0° C. and the mixture was extracted with EtOAc (2×20 mL). The solid precipitate from the combined organic layers was removed by filtration and the resulting filtrate was washed with brine. The organic phase was dried over MgSO$_4$, filtered, and concentrated under reduced pressure. The crude product was purified by silica gel chromatography eluting with 0-5% MeOH/DCM to afford (4-(1H-pyrazol-3-ylamino)quinazolin-2-yl)bis(4-fluorophenyl)methanol as a solid (75 mg, 8%). $^1$H NMR (300 MHz, DMSO-d$_6$) δ 12.50 (s, 1H), 10.66 (s, 1H), 8.67 (d, J=8.1, 1H), 7.81-7.87 (m, 2H), 7.60-7.62 (m, 2H), 7.42-7.47 (m, 4H), 7.07-7.13 (m, 4H), 6.66 (s, 1H), 6.26 (s, 1H); LC-MS (ESI) m/z 430 (M+H)+.

Example 49

Preparation of (2-(difluoro(4-fluorophenyl)methyl)-4-(5-methyl-1H-pyrazol-3-ylamino)quinazolin-7-yl)methanol

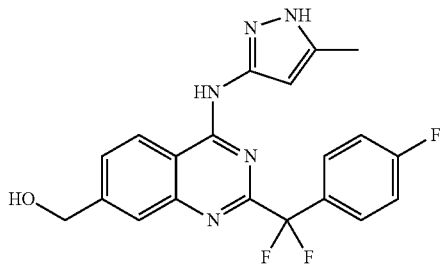 [SMILES: Cc1cc(Nc2nc(C(F)(F)c3ccc(F)cc3)nc3cc(CO)ccc23)n[nH]1]

Step A

A mixture of 4-(methoxycarbonyl)-3-nitrobenzoic acid (200 mg) and concentrated NH$_4$OH (30 mL) in sealed tube was heated at 105° C. overnight. After cooling to rt the mixture was concentrated under reduced pressure and then 2N HCl (5 mL) was added. The mixture was extracted with EtOAc (3×50 mL) and the combined organic extracts were washed with brine (50 mL), dried over Na$_2$SO$_4$, filtered and concentrated under reduced pressure. To the residue in MeOH (20 mL) was added dropwise thionyl chloride (0.2 mL), and the mixture was heated at reflux for 6 h. The mixture was concentrated under reduced pressure, and the residue was partitioned between saturated aq NaHCO3 (50 mL) and EtOAc (50 mL), the separated aqueous phase was extracted with EtOAc (2×50 mL). The combined organic layers were washed with brine (50 mL), dried over Na$_2$SO$_4$, filtered, and concentrated under reduced pressure. To the residue in EtOH (30 mL) was add 10% Pd/C (10 mg), and the mixture was stirred at rt under H$_2$ (1 atm) for 4 h. The mixture was filtered through Celite washing with MeOH. The filtrate was concentrated under reduced pressure and the residue was purified by silica gel chromatography eluting with 5% MeOH/DCM to afford methyl 3-amino-4-carbamoylbenzoate as a white solid (142 mg, 82.5%). $^1$H NMR (300 MHz, DMSO-d$_6$) δ 3.82 (s, 3H), 6.75 (s, 2H), 7.01 (d, 1H), 7.28 (s, 1H), 7.34 (s, 1H), 7.62 (d, 1H) 7.89 (s, 1H); LC-MS (ESI) m/z 211 (M+H)+.

Step B

To a solution of methyl 4-carbamoyl-3-(2,2-difluoro-2-(4-fluorophenyl)acetamido)benzoate (1.3 g, 3.5 mmol) in DCE (20 mL) were added triethylamine (20 mL, 142 mmol) and trimethylsilyl chloride (6.7 mL, 53.2 mmol and the mixture was heated 85° C. overnight. The mixture was allowed to cool to rt, and then was concentrated under reduced pressure. The residue was partitioned between EtOAc (150 mL) and H$_2$O (100 mL), and the separated aqueous phase was extracted with EtOAc (3×150 mL). The combined organic layers were washed with brine (100 mL), dried over Na$_2$SO$_4$, filtered, and concentrated under reduced pressure. The residue was treated with MeOH with sonication, and the solid was collected by filtration to afford methyl 2-(difluoro(4-fluorophenyl)methyl)-4-hydroxyquinazoline-7-carboxylate (1.1 g, 89%). $^1$H NMR (300 MHz, DMSO-d$_6$) δ 3.91 (s, 3H), 7.39 (t, 2H), 7.78 (t, 2H), 8.06 (d, 1H), 8.16 (s, 1H), 8.27 (d, 1H), 13.34 (s, 1H); LC-MS (ESI) m/z 349 (M+H)+.

Step C

A mixture of methyl 2-(difluoro(4-fluorophenyl)methyl)-4-hydroxyquinazoline-7-carboxylate (1.1 g, 3.2 mmol) and phosphorus oxychloride (15 mL) was heated at reflux overnight. The mixture was concentrated under reduced pressure, and then toluene (20 mL) was added and evaporated under reduced pressure (2×). The residue in DCM was filtered through a pad of silica gel eluting with DCM. The filtrate was concentrated under reduced pressure to afford methyl 4-chloro-2-(difluoro(4-fluorophenyl)methyl)quinazoline-7-carboxylate (1 g, 86%). $^1$H NMR (300 MHz, DMSO-d$_6$) δ 3.98 (s, 3H), 7.37 (t, 2H), 7.75 (t, 2H), 8.39 (d, 1H), 8.49 (s, 1H), 8.64 (d, 1H).

Step D

A mixture of methyl 4-chloro-2-(difluoro(4-fluorophenyl)methyl)quinazoline-7-carboxylate (1 g, 2.7 mmol), 5-methyl-1H-pyrazol-3-amine (0.32 g, 3.27 mmol), DIEA (0.62 mL, 3.5 mmol), and KI (0.5 g, 3 mmol) in DMF (20 mL) was stirred at rt for 20 h. The mixture was diluted with H$_2$O and stirred for 1 h, and then the precipitated solid was collected by filtration, washed with H$_2$O, and dried to afford methyl 2-(difluoro(4-fluorophenyl)methyl)-4-(5-methyl-1H-pyrazol-3-ylamino)quinazoline-7-carboxylate (1.17 g, 100%). $^1$H NMR (300 MHz, DMSO-d$_6$) δ 2.24 (s, 3H), 3.97 (s, 3H), 6.31 (s, 1H), 7.15-7.50 (m, 2H), 7.62-7.90 (m, 2H), 7.99-8.13 (m, 1H), 8.20-8.55 (m, 1H), 8.69-9.04 (m, 1H), 10.96 (s, 1H), 12.28 (s, 1H); LC-MS (ESI) m/z 428 (M+H)+.

Step E

To a suspension of LAH (0.26 g, 6.84 mmol) in THF (50 mL) at 0° C. was slowly added a suspension of methyl 2-(difluoro(4-fluorophenyl)methyl)-4-(5-methyl-1H-pyrazol-3-ylamino)quinazoline-7-carboxylate (1.17 g, 2.74 mmol) in THF (30 mL). The mixture was stirred at 0° C. for 0.5 h and then at rt for 4 h. The mixture was cooled to 0° C., and water (0.26 mL) was added dropwise and the mixture was stirred for 30 min. Then 15% NaOH (0.39 mL) was added and the mixture was stirred for 1 h. Then water (1.3 mL) was added and the mixture was stirred at rt overnight. The mixture was filtered through Celite washing with 20% MeOH/DCM (500 mL), and the filtrate was concentrated under reduced pressure. The residue was partitioned between water (200 mL) and EtOAc (150 mL), and the separated aqueous phase was extracted with EtOAc (2×150 mL). The combined organic layers were washed with brine (200 mL), dried over Na$_2$SO$_4$, filtered, and concentrated under reduced pressure. The residue was purified by preparative reverse phase HPLC to afford a (2-(difluoro(4-fluorophenyl)methyl)-4-(5-methyl-1H-pyrazol-3-ylamino)quinazolin-7-yl)methanol as a white solid (901 mg, 82%). $^1$H NMR (300 MHz, DMSO-d$_6$) δ 2.24 (s, 3H), 4.70 (s, 2H), 5.49 (s, 1H), 6.31 (s, 1H), 7.35 (t, 2H), 7.56 (d, 2H), 7.70 (t, 2H), 7.77 (s, 1H), 8.63 (d, 1H), 10.64 (s, 1H), 12.18 (s, 1H); LC-MS (ESI) m/z 400 (M+H)+.

Example 50

Preparation 2-(difluoro(4-fluorophenyl)methyl)-N-(5-methyl-1H-pyrazol-3-yl)-7-(methylsulfonylmethyl)quinazolin-4-amine

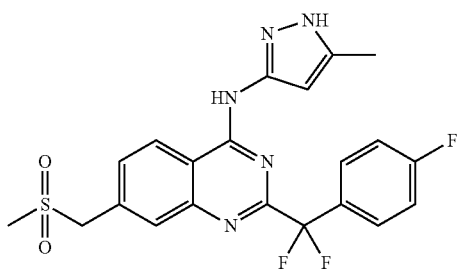 [SMILES: Cc1cc(Nc2nc(C(F)(F)c3ccc(F)cc3)nc3cc(CS(C)(=O)=O)ccc23)n[nH]1]

To a suspension of (2-(difluoro(4-fluorophenyl)methyl)-4-(5-methyl-1H-pyrazol-3-ylamino)quinazolin-7-yl)methanol from Example 49 (150 mg, 0.38 mmol) in DCM (20 mL) was added PBr$_3$ (203 mg, 0.75 mmol) while the mixture was warmed at 60° C. The resulting mixture was stirred at 60° C. for 30 min, then cooled to rt and concentrated under reduced pressure. Then sodium thiomethoxide (133 mg, 1.90 mmol) and DMF (10 mL) were added, and the mixture was stirred at rt for 2 d. Saturated aq NaHCO$_3$ (50 mL) was added, and the mixture was extracted with EtOAc (3×50 mL). The combined organic layers were washed with brine (3×80 mL), dried over Na$_2$SO$_4$, filtered, and concentrated under reduced pressure. To the residue in DCM (50 mL) was added 4-chloroperbenzoic acid (655 mg, 3.80 mmol) and the mixture was stirred at rt for 4 h. Saturated aq NaHCO$_3$ (50 mL) was added and the mixture was extracted with DCM (3×50 mL). The combined organic layers were washed with brine (60 mL), dried over Na$_2$SO$_4$, filtered and concentrated. The residue was purified by preparative reverse phase HPLC to give 2-(difluoro(4-fluorophenyl)methyl)-N-(5-methyl-1H-pyrazol-3-yl)-7-(methylsulfonylmethyl)quinazolin-4-amine as a white solid (11.3 mg, 6.5%). $^1$H NMR (300 MHz, DMSO-d$_6$) δ 2.24 (s, 3H), 2.96 (s, 3H), 4.73 (s, 2H), 6.32 (s, 1H), 7.35 (t, 2H), 7.63-7.73 (m, 3H), 7.92 (s, 1H), 8.70 (d, 1H), 10.79 (s, 1H), 12.23 (s, 1H); LC-MS (ESI) m/z 462 (M+H)$^+$.

Example 51

Preparation 2-(Difluoro(4-fluorophenyl)methyl)-7-(ethoxymethyl)-N-(5-methyl-1H-pyrazol-3-yl)quinazolin-4-amine

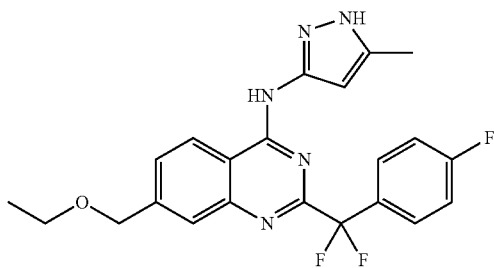 [SMILES: CCOCc1ccc2c(Nc3cc(C)[nH]n3)nc(C(F)(F)c3ccc(F)cc3)nc2c1]

To a suspension of (2-(difluoro(4-fluorophenyl)methyl)-4-(5-methyl-1H-pyrazol-3-ylamino)quinazolin-7-yl)methanol from Example 49 (150 mg, 0.38 mmol) in DCM (20 mL) was added PBr$_3$ (203 mg, 0.75 mmol) while warming the mixture at 60° C. The mixture was stirred at 60° C. for 30 min, allowed to cool to rt and concentrated under reduced pressure. To the residue were added EtOH (20 mL) and 21% NaOEt/EtOH (3 mL), and the mixture was heated under reflux for 15 h. The mixture was allowed to cool to rt and then the mixture was concentrated under reduced pressure. Water (50 mL) was added and then 1N HCl was added slowly to adjust the pH to <4, and then saturated aq NaHCO$_3$ (50 mL) was added. The mixture was extracted with EtOAc (3×80 mL), and the combined organic layers were washed with brine (80 mL), dried over Na$_2$SO$_4$, filtered, and concentrated under reduced pressure. The residue was purified by preparative reverse phase HPLC to afford 2-(Difluoro(4-fluorophenyl)methyl)-7-(ethoxymethyl)-N-(5-methyl-1H-pyrazol-3-yl)quinazolin-4-amine as a white solid (11.3 mg, 6.5%). $^1$H NMR (300 MHz, DMSO-d$_6$) δ 1.21 (t, 3H), 2.23 (s, 3H), 3.56 (qt, 2H), 4.66 (s, 2H), 6.31 (s, 1H), 7.38 (t, 2H), 7.56 (d, 1H), 7.70 (qt, 2H), 7.76 (s, 1H), 8.65 (d, 1H), 10.69 (s, 1H), 12.20 (s, 1H); LC-MS (ESI) m/z 428 (M+H)$^+$.

Example 52

Preparation of (R,S) (7-chloro-4-(5-methyl-1H-pyrazol-3-ylamino)quinazolin-2-yl)(4-fluorophenyl)methanol

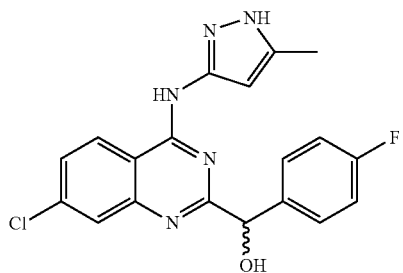 [SMILES: Cc1cc(Nc2nc(C(O)c3ccc(F)cc3)nc3cc(Cl)ccc23)n[nH]1]

Step A

To solution of 2-amino-4-chlorobenzoic acid (4.4 g, 25.8 mmol) in degassed DMF (75 mL) were added successively HOBt (4.19 g, 31 mmol), DIEA (5.4 mL, 31 mmol), EDCI (5.37 g, 28 mmol), and 2N NH$_3$/MeOH (18 mL, 36 mmol), and the solution was stirred at rt for 4 d. The mixture was concentrated under reduced pressure and the residue was partitioned between H$_2$O (200 mL) and DCM (200 mL). The separated aqueous phase was extracted with DCM (2×200 mL) and the combined organic layers were dried over MgSO$_4$, filtered, and concentrated under reduced pressure. The residue was purified by silica gel chromatography eluting with 10-50% EtOAc/hexanes to afford 2-amino-4-chlorobenzamide as a solid (2.91 g, 66%). $^1$H NMR (300 MHz, DMSO-d$_6$) δ 6.50 (dd, J=8.48, 2.26 Hz, 1H), 6.75 (d, J=2.26 Hz, 1H), 6.84 (br s, 2H), 7.18 (br s, 1H), 7.48-7.63 (m, 1H), 7.80 (br s, 1H).

Step B

To a solution of 2-amino-4-chlorobenzamide (393 mg, 2.30 mmol) and DIEA (0.60 mL, 3.45 mmol) in THF (15 mL) at 0° C. was added ethyl chlorooxoacetate (0.28 mL, 2.53 mmol). The solution was allowed to warm to rt and stir for 2 h. The mixture was concentrated under reduced pressure and the residue was purified by silica gel chromatography eluting with 10-50% EtOAc/hexanes to afford ethyl 2-(2-carbamoyl-5-chlorophenylamino)-2-oxoacetate as a solid (545 mg, 88%). $^1$H NMR (300 MHz, DMSO-d$_6$) δ 1.32 (t, J=6.97 Hz, 3H), 4.31 (q, J=6.97 Hz, 2H), 7.34 (d, J=8.48 Hz, 1H), 7.86-8.03 (m, 2H), 8.44 (br s, 1H), 8.62 (s, 1H), 13.24 (s, 1H)

Step C

To a solution of ethyl 2-(2-carbamoyl-5-chlorophenylamino)-2-oxoacetate (545 mg, 2.02 mmol) and TEA (11 mL, 80 mmol) in DCE (20 mL) was added trimethylsilyl chloride (3.8 mL, 30 mmol) and the solution was stirred at 80° C. for 16 h. The mixture was concentrated under reduced pressure and the residue was partitioned between saturated aq NaHCO$_3$ and DCM (100 mL). The separated aqueous phase was extracted with DCM (2×100 mL) and the combined organic layers were dried over MgSO$_4$, filtered, and concentrated under reduced pressure. The residue was purified by silica gel chromatography eluting with 10-60% EtOAc/hexanes to afford ethyl 7-chloro-4-hydroxyquinazoline-2-carboxylate as a solid (321 mg, 63%). $^1$H NMR (300 MHz, DMSO-d$_6$) δ 1.36 (t, J=7.06 Hz, 3H), 4.39 (q, J=7.10 Hz, 2H), 7.60-7.74 (m, 1H), 7.85-7.98 (m, 1H), 8.11-8.23 (m, 1H), 12.82 (br s, 1H).

Step D (R,S)-(7-Chloro-4-(5-methyl-1H-pyrazol-3-ylamino)quinazolin-2-yl)(4-fluorophenyl)methanol was prepared as a solid using procedures analogous to those described in Example 46 Steps D-F, substituting ethyl 7-chloro-4-hydroxyquinazoline-2-carboxylate for the ethyl 4-hydroxy-8-methylquinazoline-2-carboxylate used in Example 46 Step D. $^1$H NMR (300 MHz, DMSO-d$_6$) δ 2.25 (s, 3H), 5.69 (d, J=1.00 Hz, 1H), 5.82 (d, J=1.00 Hz, 1H), 6.43 (s, 1H), 7.07-7.23 (m, 2H), 7.46-7.62 (m, 3H), 7.81 (s, 1H), 8.57-8.69 (m, 1H), 10.53 (br. s, 1H), 12.18 (br. s, 1H). LC-MS (ESI) m/z 384 (M+H)$^+$.

Example 53

Preparation of (6-fluoro-4-(5-methyl-1H-pyrazol-3-ylamino)quinazolin-2-yl)(4-fluorophenyl)methanone

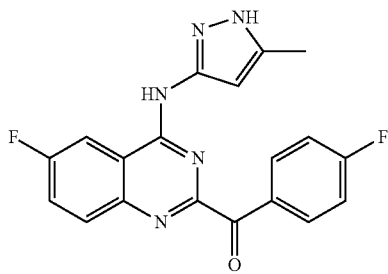 [SMILES: Cc1cc(Nc2nc(C(=O)c3ccc(F)cc3)nc3ccc(F)cc23)n[nH]1]

Step A

A stirred mixture of methyl 2-amino-5-fluorobenzoate (1 g, 5.92 mmol) and ethyl carbonocyanidate (1.17 g, 11.8 mmol) in HOAc (8 mL) was treated with a 12 N aq solution of hydrochloric acid (0.8 mL). The resulting mixture was heated at 70° C. for 3 h. After cooling to rt, the solvent was removed under reduced pressure. The residue was suspended in water and treated with a saturated aq solution of NaHCO$_3$ until pH=7. The solid was filtered, washed with water/diethyl ether and dried under reduced pressure to afford ethyl 6-fluoro-4-oxo-3,4-dihydroquinazoline-2-carboxylate (1.2 g, 86%). $^1$H NMR (300 MHz, DMSO-d$_6$) δ 12.79 (s, 1H), 7.76-7.95 (m, 3H), 4.39 (q, J=7.0 Hz, 2H), 1.36 (t, J=7.0 Hz, 3H); LC-MS (ESI) m/z 237 (M+H)$^+$.

Step B

A stirred solution of ethyl 6-fluoro-4-oxo-3,4-dihydroquinazoline-2-carboxylate (1.2 g, 5.08 mmol) in phosphorus oxychloride (15 mL) was heated at 105° C. for 6 h. After cooling to rt, the reaction mixture was concentrated to dryness under reduced pressure and the residue was dissolved in anhydrous toluene. The toluene was concentrated under reduced pressure. The residue was dissolved in a small volume of DCM and it was passed through a short pad of silica gel eluting with DCM. Ethyl 4-chloro-6-fluoroquinazoline-2-carboxylate was obtained as a solid (1.3 g, 100%). LC-MS (ESI) m/z 255 (M+H)$^+$.

Step C

To a stirred solution of ethyl 4-chloro-6-fluoroquinazoline-2-carboxylate (1.06 g, 4.5 mmol) in THF (15 mL) at −40° C., was added dropwise 1 M 4-fluorophenylmagnesium bromide/THF (5.85 mL, 5.85 mmol). The mixture was stirred at −40° C. for 2 h. The reaction was quenched by adding 0.5 N HCl at 0° C. and then the mixture was extracted with EtOAc (2×20 mL). The solid that precipitated from the combined organic layers was removed by filtration and the filtrate was washed with brine. The organic phase was dried over MgSO$_4$, filtered, and concentrated under reduced pressure. The residue was purified by silica gel chromatography to afford (4-chloro-6-fluoroquinazolin-2-yl)(4-fluorophenyl)methanone as a solid (950 mg, 69%). $^1$H NMR (300 MHz, DMSO-d$_6$) δ 8.32-8.36 (m, 1H), 8.13-8.21 (m, 4H), 7.43 (t, J=8.2 Hz, 2H); LC-MS (ESI) m/z 305 (M+H)$^+$.

Step D (6-Fluoro-4-(5-methyl-1H-pyrazol-3-ylamino)quinazolin-2-yl)(4-fluorophenyl)methanone was prepared from (4-chloro-6-fluoroquinazolin-2-yl)(4-fluorophenyl)methanone (306 mg, 1 mmol) and 5-methyl-1H-pyrazol-3-amine (194 mg, 2 mmol) using a procedure analogous to that described in Example 48 Step A. The crude product was triturated with MeOH to afford (6-fluoro-4-(5-methyl-1H-pyrazol-3-ylamino)quinazolin-2-yl)(4-fluorophenyl)methanone (310 mg, 85%). $^1$H NMR (300 MHz, DMSO-d$_6$) δ 12.24 (s, 1H), 10.71 (s, 1H), 8.64 (d, J=9.6 Hz, 1H), 7.95-8.09 (m, 2H), 7.93-7.95 (m, 1H), 7.80-7.86 (m, 1H), 7.39 (t, J=8.6 Hz, 2H), 6.53 (s, 1H), 1.91 (s, 3H); LC-MS (ESI) m/z 366 (M+H)$^+$.

Example 54

Preparation of (R,S)-(6-fluoro-4-(5-methyl-1H-pyrazol-3-ylamino)quinazolin-2-yl)(4-fluorophenyl)methanol

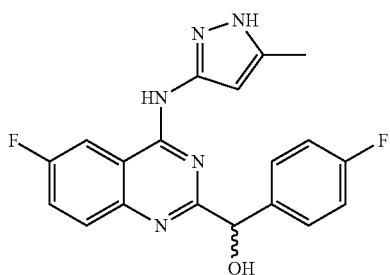 [SMILES: Cc1cc(Nc2nc(C(O)c3ccc(F)cc3)nc3ccc(F)cc23)n[nH]1]

To a stirred suspension of (6-fluoro-4-(5-methyl-1H-pyrazol-3-ylamino)quinazolin-2-yl)(4-fluorophenyl)methanone from Example 53 Step D (200 mg, 0.55 mmol) in 4:1 MeOH/THF (10 mL) was added sodium borohydride (33 mg, 0.88 mmol) and the mixture was stirred at rt for 2 h. Water (8 mL) was added and the precipitated solid was collected by filtration, washed with MeOH, and purified twice by preparative reverse-phase HPLC to afford (R,S)-(6-fluoro-4-(5-methyl-1H-pyrazol-3-ylamino)quinazolin-2-yl)(4-fluorophenyl) methanol as a solid (72.5 mg, 36%). $^1$H NMR (300 MHz, DMSO-$d_6$) δ 12.15 (s, 1H), 10.41 (s, 1H), 8.49 (d, J=9.8 Hz, 1H), 7.84-7.88 (m, 1H), 7.70-7.76 (m, 1H), 7.52-7.56 (m, 2H), 7.14 (t, J=8.5 Hz, 2H), 6.45 (s, 1H), 5.84 (br s, 1H), 5.68 (br s, 1H), 2.25 (s, 3H); LC-MS (ESI) m/z 368 (M+H)$^+$.

Example 55

Preparation of (R,S)-(4-(1H-pyrazol-3-ylamino)-6-fluoroquinazolin-2-yl)(4-fluorophenyl)methanol

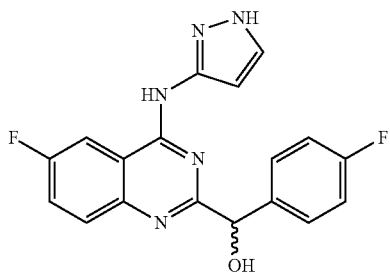 [SMILES: OC(c1ccc(F)cc1)c1nc(Nc2cc[nH]n2)c2cc(F)ccc2n1]

Step A (4-(1H-Pyrazol-3-ylamino)-6-fluoroquinazolin-2-yl)(4-fluorophenyl)methanone was obtained from (4-chloro-6-fluoroquinazolin-2-yl)(4-fluorophenyl)methanone from Example 53 Step C (304 mg, 1 mmol) and 1H-pyrazol-3-amine (166 mg, 2 mmol) using a procedure analogous to that described in Example 48 Step A. The crude product was triturated with MeOH to afford (4-(1H-pyrazol-3-ylamino)-6-fluoroquinazolin-2-yl)(4-fluorophenyl)methanone as a solid (275 mg, 78%). $^1$H NMR (300 MHz, DMSO-$d_6$) δ 12.56 (s, 1H), 10.84 (s, 1H), 8.67 (d, J=9.9 Hz, 1H), 8.08-8.13 (m, 2H), 7.95-7.99 (m, 1H), 7.82-7.87 (m, 1H), 7.67 (s, 1H), 7.36-7.41 (m, 2H), 6.78 (s, 1H); LC-MS (ESI) m/z 352 (M+H)$^+$.

Step B (4-(1H-Pyrazol-3-ylamino)-6-fluoroquinazolin-2-yl)(4-fluorophenyl)methanol was obtained from (4-(1H-pyrazol-3-ylamino)-6-fluoroquinazolin-2-yl)(4-fluorophenyl)methanone (200 mg, 0.57 mmol) using a procedure analogous to that described in Example 54 to afford (R,S)-(4-(1H-pyrazol-3-ylamino)-6-fluoroquinazolin-2-yl)(4-fluorophenyl)methanol as a solid (59 mg, 29%). $^1$H NMR (300 MHz, DMSO-$d_6$) δ 12.50 (s, 1H), 10.53 (s, 1H), 8.53 (d, J=9.8 Hz, 1H), 7.85-7.89 (m, 1H), 7.71-7.77 (m, 2H), 7.52-7.57 (m, 2H), 7.12 (t, J=8.5 Hz, 2H), 6.88 (s, 1H), 5.84 (br s, 1H), 5.69 (br s, 1H); LC-MS (ESI) m/z 354 (M+H)$^+$.

Example 56

Preparation of (7-bromo-4-(5-methyl-1H-pyrazol-3-ylamino)quinazolin-2-yl)(4-fluorophenyl)methanone

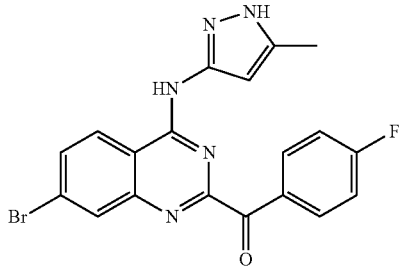

Step A

Methyl 2-amino-4-bromobenzoate was prepared from the corresponding acid by Fischer esterification. A mixture of methyl 2-amino-4-bromobenzoate (1.1 g, 4.8 mmol) and ethyl carbonocyanidate (0.95 g, 9.66 mmol) in HOAc (4 mL) was treated with a s12 N HCl (0.4 mL) and the resulting mixture was stirred at 70° C. for 3 h. After cooling to rt, water was added followed by addition of aq sodium hydrogen carbonate to pH ~5. The precipitated solid was filtered and washed thoroughly with water and diethyl ether to afford ethyl 7-bromo-4-oxo-3,4-dihydroquinazoline-2-carboxylate (825 mg, 58%). $^1$H NMR (300 MHz, DMSO-$d_6$) δ 12.82 (s, 1H), 8.06-8.09 (m, 2H), 7.81 (d, J=8.4 Hz, 1H), 4.38 (q, J=7.0 Hz, 2H), 1.35 (t, J=7.0 Hz, 3H); LC-MS (ESI) m/z 296 (M+H)$^+$.

Step B

Ethyl 7-bromo-4-chloroquinazoline-2-carboxylate was prepared in 69% yield using a procedure analogous to that described in Example 53 Step B, substituting ethyl 7-bromo-4-oxo-3,4-dihydroquinazoline-2-carboxylate (825 mg, 2.78 mmol) for the ethyl 6-fluoro-4-oxo-3,4-dihydroquinazoline-2-carboxylate used in Example 53. LC-MS (ESI) m/z 315 and 317 (M+H)$^+$.

Step C (7-Bromo-4-chloroquinazolin-2-yl)(4-fluorophenyl)methanone was prepared in 43% yield using a procedure analogous to that described in Example 53 Step C, substituting ethyl 7-bromo-4-oxo-3,4-dihydroquinazoline-2-carboxylate (605 mg, 1.92 mmol) for the ethyl 4-chloro-6-fluoroquinazoline-2-carboxylate used in Example 53. LC-MS (ESI) m/z 387 (M+Na)$^+$.

Step D (7-Bromo-4-(5-methyl-1H-pyrazol-3-ylamino)quinazolin-2-yl)(4-fluorophenyl)methanone was prepared using a procedure analogous to that described in Example 48 Step A, substituting (7-bromo-4-chloroquinazolin-2-yl)(4-fluorophenyl)methanone (300 mg, 0.82 mmol) for the ethyl 4-chloroquinazoline-2-carboxylate used in Example 48. A portion of the crude product (90 mg) was purified by preparative reverse-phase HPLC to afford (7-bromo-4-(5-methyl-1H-pyrazol-3-ylamino)quinazolin-2-yl)(4-fluorophenyl)methanone as a solid (12 mg, 11%). $^1$H NMR (300 MHz, DMSO-$d_6$) δ 12.23 (s, 1H), 10.85 (s, 1H), 8.69 (d, J=8.0 Hz, 1H), 8.07-8.11 (m, 3H), 7.84 (d, J=9.0 Hz, 1H), 7.36-7.42 (m, 2H), 6.49 (s, 1H), 2.18 (s, 3H); LC-MS (ESI) m/z 426 (M+H)$^+$.

Example 57

Preparation of (7-bromo-4-(5-methyl-1H-pyrazol-3-ylamino)quinazolin-2-yl)(4-fluorophenyl)methanol

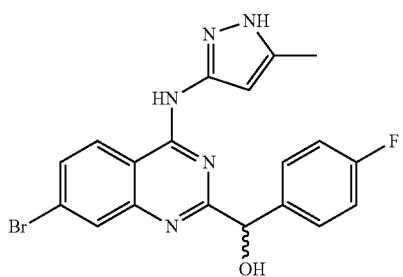

(7-Bromo-4-(5-methyl-1H-pyrazol-3-ylamino)quinazolin-2-yl)(4-fluorophenyl)methanol was prepared using a procedure analogous to that described in Example 54 substituting (7-bromo-4-(5-methyl-1H-pyrazol-3-ylamino)quinazolin-2-yl)(4-fluorophenyl)methanone from Example 56 (240 mg, 0.56 mmol) for the (6-fluoro-4-(5-methyl-1H-pyrazol-3-ylamino)quinazolin-2-yl)(4-fluorophenyl)methanone used in Example 54 (31 mg, 13%). $^1$H NMR (300 MHz, DMSO-$d_6$) δ 12.17 (s, 1H), 10.55 (s, 1H), 8.54 (br s, 1H), 7.97 (br s, 1H), 7.67 (d, J=8.4 Hz, 1H), 7.52-7.56 (m, 2H), 7.12-7.17 (m, 2H), 6.44 (s, 1H), 5.84 (s, 1H), 5.66 (s, 1H), 2.25 (s, 3H); LC-MS (ESI) m/z 428 (M+H)$^+$.

Example 58

Preparation of (R,S)-(4-(1H-pyrazol-3-ylamino)-7-bromoquinazolin-2-yl)(4-fluorophenyl)methanol

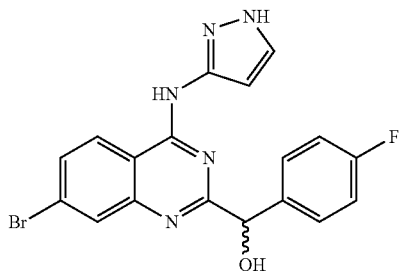

Step A (4-(1H-Pyrazol-3-ylamino)-7-bromoquinazolin-2-yl)(4-fluorophenyl)methanone (270 mg, 80%) was prepared using a procedure analogous to that described in Example 48 Step A, substituting (7-bromo-4-chloroquinazolin-2-yl)(4-fluorophenyl)methanone from Example 56 (300 mg, 0.82 mmol) for the ethyl 4-chloroquinazoline-2-carboxylate used in Example 48. $^1$H NMR (300 MHz, DMSO-$d_6$) δ 12.57 (s, 1H), 10.97 (s, 1H), 8.72 (d, J=8.3 Hz, 1H), 8.10 (t, J=8.3 Hz, 3H), 7.86 (d, J=8.5 Hz, 1H), 7.67 (br s, 1H), 7.36 (t, J=8.0 Hz, 2H), 6.75 (br s, 1H); LC-MS (ESI) m/z 412 (M+H)$^+$.

Step B (R,S)-(4-(1H-Pyrazol-3-ylamino)-7-bromoquinazolin-2-yl)(4-fluorophenyl)methanol (37 mg, 18%) was prepared using a procedure analogous to that described in Example 54, substituting (4-(1H-pyrazol-3-ylamino)-7-bromoquinazolin-2-yl)(4-fluorophenyl)methanone (200 mg, 0.49 mmol) for the (6-fluoro-4-(5-methyl-1H-pyrazol-3-ylamino)quinazolin-2-yl)(4-fluorophenyl)methanone used in Example 54. $^1$H NMR (300 MHz, DMSO-$d_6$) δ 12.47 (s, 1H), 10.70 (s, 1H), 8.57 (d, J=8.9 Hz, 1H), 7.99 (s, 1H), 7.69-7.72 (m, 2H), 7.54 (t, J=6.4 Hz, 2H), 7.12 (t, J=8.2 Hz, 2H), 6.82 (s, 1H), 5.86 (br s, 1H), 5.68 (br s, 1H); LC-MS (ESI) m/z 414 and 416 (M+H)$^+$.

Example 59

Preparation 2-(2-(4-fluorophenyl)-1,3-dioxolan-2-yl)-N-(5-methyl-1H-pyrazol-3-yl)quinazolin-4-amine

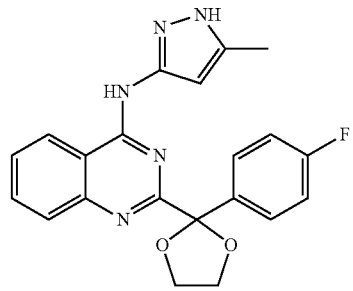 [SMILES: Cc1cc(Nc2nc(C3(c4ccc(F)cc4)OCCO3)nc3ccccc23)n[nH]1]

To (4-fluorophenyl)(4-(5-methyl-1H-pyrazol-3-ylamino)quinazolin-2-yl)methanone from Example 3 (0.20 g, 0.58 mmol) in toluene (20 mL) were added ethylene glycol (0.2 mL) and p-toluenesulfonic acid monohydrate (catalytic quantity). The mixture was heated under reflux overnight while collecting water in a Dean-Stark trap. Additional ethylene glycol (1.5 mL) and p-toluenesulfonic acid monohydrate (50 mg) were added and mixture was heated at reflux overnight with collection of water. After cooling, the mixture was evaporated to dryness, and then dissolved in DMSO (8 mL). A 5 mL aliquot of this solution was purified by preparative reverse-phase HPLC (Varian diphenyl reverse phase column eluting with gradient of solvent B=0.05% HOAC/ACN and solvent A=0.05% HOAc/H$_2$O) followed by additional purification by preparative reverse-phase HPLC (Phenomenex C-18 reverse phase column, eluted with gradient of solvent B=0.05% HOAC/ACN and solvent A=0.05% HOAc/H$_2$O) to afford 2-(2-(4-fluorophenyl)-1,3-dioxolan-2-yl)-N-(5-methyl-1H-pyrazol-3-yl)quinazolin-4-amine (2 mg, 1%). $^1$H NMR (300 MHz, DMSO-$d_6$) δ 2.20 (s, 3H) 4.05-4.22 (m, 4H)

6.2 (s, 1H) 7.19 (t, 2H) 7.5-7.65 (m, 3H) 7.81 (m, 2H) 8.59 (d, 1H) 10.38 (s, 1H) 12.08 (s, 1H); LC-MS (ESI) m/z 392 (M+H)⁺.

Example 60

Preparation of (8-fluoro-4-(5-methyl-1H-pyrazol-3-ylamino)quinazolin-2-yl)(4-fluorophenyl)methanone

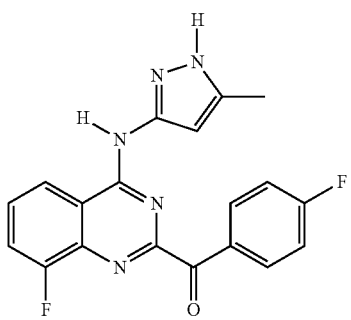 [SMILES: Cc1cc(Nc2nc(C(=O)c3ccc(F)cc3)nc3c(F)cccc23)n[nH]1]

Step A

Ethyl 2-(2-carbamoyl-6-fluorophenylamino)-2-oxoacetate was prepared with reference to procedures analogous to those described in Example 46 Steps A and B, in which 2-amino-3-fluorobenzoic acid may be substituted for the 2-amino-3-methylbenzoic acid used in Example 46.

Step B

A mixture of ethyl 2-(2-carbamoyl-6-fluorophenylamino)-2-oxoacetate (600 mg, 2.4 mmol) and potassium t-butoxide (300 mg, 6.7 mmol) in EtOH (10 mL) was stirred at rt for 5 h. Saturated aq NaCl (50 mL) and HOAc (0.5 mL) were added and the mixture was extracted with EtOAc (3×80 mL). The combined organic layers were washed with brine (80 mL), dried over Na$_2$SO$_4$, filtered, and concentrated under reduced pressure to afford ethyl 8-fluoro-4-hydroxyquinazoline-2-carboxylate (530 mg, 93%). $^1$H NMR (300 MHz, DMSO-d$_6$) δ 1.39 (t, J=7.2 Hz, 3H), 4.40 (q, J=7.2 Hz, 2H), 7.57-7.70 (m, 1H), 7.78 (t, J=9.2 Hz, 1H), 7.99 (d, J=8.1 Hz, 1H), 12.86 (s, 1H); LC-MS (ESI) m/z 237 (M+H)⁺.

Step C

A mixture of ethyl 8-fluoro-4-hydroxyquinazoline-2-carboxylate (530 mg, 2.2 mmol) and POCl$_3$ (3 mL) was heated under reflux for 5 h. The mixture was concentrated under reduced pressure, and then toluene was twice added and concentrated under reduced pressure. The residue was purified by silica gel chromatography eluting with 0-25% EtOAc/hexanes to afford ethyl 4-chloro-8-fluoroquinazoline-2-carboxylate (365 mg, 65%). $^1$H NMR (300 MHz, DMSO-d$_6$) δ 1.39 (t, J=7.1 Hz, 3H), 4.46 (q, J=7.1 Hz, 2H), 7.97-8.06 (m, 1H), 8.07-8.16 (m, 1H), 8.18-8.24 (m, 1H).

Step D

To a solution of ethyl 4-chloro-8-fluoroquinazoline-2-carboxylate (360 mg, 1.42 mmol) in THF (20 mL) at −40° C. was added 1M 4-fluorophenylmagnesium bromide/THF (1.7 mL, 1.7 mmol) and the mixture was stirred at −40° C. for 3 h. After this time, and additional portion of 1M 4-fluorophenylmagnesium bromide/THF (0.3 mL, 0.3 mmol) was added and the mixture was stirred at −40° C. for 2 h. To the mixture was added 0.5N HCl to give pH 2, and then saturated aq NaCl (50 mL) was added, and the mixture was extracted with EtOAc (3×50 mL). The combined organic layers were washed with brine (80 mL), dried over Na2SO4, filtered, and concentrated under reduced pressure to afford (4-chloro-8-fluoroquinazolin-2-yl)(4-fluorophenyl)methanone (0.4 g, 93%). $^1$H NMR (300 MHz, DMSO-d$_6$) δ 7.04-7.25 (m, 1H), 7.31-7.58 (m, 2H), 7.70-8.36 (m, 4H); LC-MS (ESI) m/z 305 (M+H)⁺, 327 (M+Na)⁺.

Step E

A mixture of (4-chloro-8-fluoroquinazolin-2-yl)(4-fluorophenyl)methanone (0.4 g, 1.32 mmol), 5-methyl-1H-pyrazol-3-amine (0.15 g, 1.58 mmol), DIEA (0.69 mL, 4.0 mmol), and KI (0.24 g, 1.45 mmol) in DMF (8 mL) was stirred at rt for 20 h. The mixture was diluted with H$_2$O (35 mL), and the precipitated solid was collected by filtration, washed with H$_2$O, and triturated with MeOH at 0° C. A portion of the resulting solid was purified by preparative reverse phase HPLC to afford (8-fluoro-4-(5-methyl-1H-pyrazol-3-ylamino)quinazolin-2-yl)(4-fluorophenyl)methanone. $^1$H NMR (300 MHz, DMSO-d$_6$) δ 2.19 (s, 3H), 6.52 (s, 1H), 7.41 (t, 2H), 7.64-7.80 (m, 2H), 8.11 (t, 2H), 8.57 (d, 1H), 10.84 (s, 1H), 12.27 (br s, 1H); LC-MS (ESI) m/z 366 (M+H)⁺.

Example 61

Preparation of (R,S)-(8-fluoro-4-(5-methyl-1H-pyrazol-3-ylamino)quinazolin-2-yl)(4-fluorophenyl)methanol

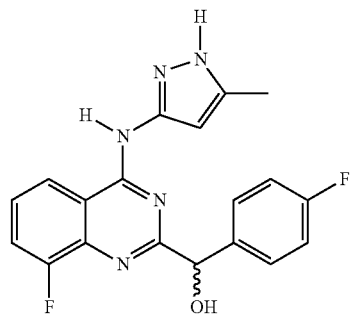 [SMILES: Cc1cc(Nc2nc(C(O)c3ccc(F)cc3)nc3c(F)cccc23)n[nH]1]

To a suspension of (8-fluoro-4-(5-methyl-1H-pyrazol-3-ylamino)quinazolin-2-yl)(4-fluorophenyl)methanone (233 mg, 0.64 mmol) in 2:1 MeOH/THF (15 mL) at 0° C. was added sodium borohydride (36 mg, 0.96 mmol), and the mixture was stirred at 0° C. for 1 h and at rt overnight. The mixture was cooled to 0° C. and 1N HCl was added to give pH<2, then saturated aqueous NaHCO$_3$ and brine were added. The precipitated solid was collected by filtration, washed with H$_2$O, and purified by preparative reverse phase HPLC to afford (R,S)-(8-fluoro-4-(5-methyl-1H-pyrazol-3-ylamino)quinazolin-2-yl)(4-fluorophenyl)methanol (141 mg, 60%). $^1$H NMR (300 MHz, DMSO-d$_6$) δ 2.24 (s, 3H), 5.69 (s, 1H), 5.86 (bs, 1H), 6.41 (bs, 1H), 7.15 (t, 2H), 7.47-7.65 (m, 4H), 8.34 (bs, 1H), 10.53 (bs, 1H), 12.18 (bs, 1H); LC-MS (ESI) m/z 368 (M+H)⁺.

Example 62

Preparation of (2-methoxyphenyl)(4-(5-methyl-1H-pyrazol-3-ylamino)quinazolin-2-yl)methanone

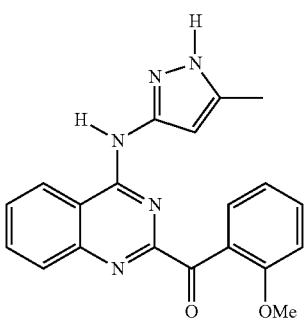 [SMILES: COc1ccccc1C(=O)c1nc(Nc2cc(C)[nH]n2)c2ccccc2n1]

To a solution of ethyl 4-chloroquinazoline-2-carboxylate (500 mg, 2.11 mmol) in THF (20 mL) at −40° C. was added dropwise 1M 2-methoxyphenylmagnesum bromide (2.6 mL, 2.5 mmol) and the mixture was stirred at −40° C. for 4 h. To the mixture were added 1N HCl to pH<2 and saturated aq NaCl (50 mL), and the mixture was extracted with EtOAc (3×80 mL). The combined organic layers were washed with brine (50 mL), dried over Na$_2$SO$_4$, filtered, and concentrated under reduced pressure. To the residue (673 mg) were added a solution of 5-methyl-1H-pyrazol-3-amine (247 mg, 2.84 mmol) in DMF (8 mL), potassium iodide (387 mg, 2.33 mmol), and DIEA (822 mg, 6.36 mmol), and the mixture was stirred at rt overnight and then at 50° C. for 5 h and then at 80° C. for 2 h. The mixture was allowed to cool to rt and then H$_2$O (30 mL) was added. The mixture was stirred and cooled to 0° C., and the precipitated solid was collected by filtration and washed with MeOH. A portion of the solid was purified by preparative reverse phase HPLC to afford (2-methoxyphenyl)(4-(5-methyl-1H-pyrazol-3-ylamino)quinazolin-2-yl)methanone. $^1$H NMR (300 MHz, DMSO-d$_6$) δ 2.11 (s, 3H), 3.48 (s, 3H), 6.15 (s, 1H), 7.11-7.18 (m, 2H), 7.56-7.64 (m, 3H), 7.56 (bs, 2H), 8.70 (d, 1H), 10.58 (s, 1H), 12.11 (s, 1H); LC-MS (ESI) m/z 360 (M+H)$^+$.

Example 63

Preparation of (R,S)-(2-methoxyphenyl)(4-(5-methyl-1H-pyrazol-3-ylamino)quinazolin-2-yl)methanol

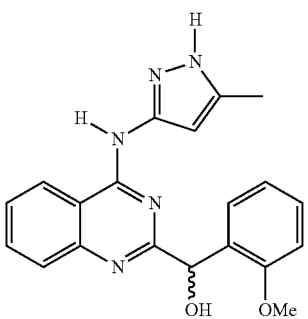

To a suspension of (2-methoxyphenyl)(4-(5-methyl-1H-pyrazol-3-ylamino)quinazolin-2-yl)methanone (420 mg, 1.17 mmol) in 2:1 MeOH/THF (15 mL) at 0° C. was added NaBH$_4$ (53 mg, 1.40 mmol) and the mixture was stirred at 0° C. for 1 h and at rt overnight. The mixture was cooled to 0° C. and 1N HCl was added to pH<2. Then saturated aq NaHCO$_3$ (50 mL) was added and the mixture was extracted with EtOAc (3×80 mL). The combined organic layers were washed with brine, dried over Na$_2$SO$_4$, filtered, and concentrated under reduced pressure. The residue was purified by preparative reverse phase HPLC to afford (R,S)-(2-methoxyphenyl)(4-(5-methyl-1H-pyrazol-3-ylamino)quinazolin-2-yl)methanol (55.3 mg, 15%). $^1$H NMR (300 MHz, DMSO-d$_6$) δ 2.19 (s, 3H), 3.76 (s, 3H), 5.65 (s, 1H), 6.00 (s, 1H), 6.24 (s, 1H), 6.92-7.01 (m, 3H), 7.25 (t, 1H), 7.45-7.52 (m, 2H), 7.80 (s, 2H), 8.57 (d, 1H), 10.36 (s, 1H), 12.05 (s, 1H); LC-MS (ESI) m/z 362 (M+H)$^+$.

Example 64

Preparation (3-fluorophenyl)(4-(5-methyl-1H-pyrazol-3-ylamino)quinazolin-2-yl)methanol

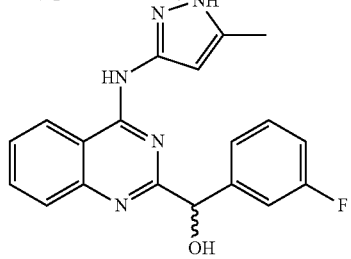

To (3-fluorophenyl)(4-(5-methyl-1H-pyrazol-3-ylamino)quinazolin-2-yl)methanone from Example 1 (0.15 g, 0.43 mmol) in 1:1 THF/MeOH (4 mL) at 0° C. was added sodium borohydride (0.02 g, 0.58 mmol) and the mixture was stirred at 0° C. for 30 min. To the mixture were added 6 N HCl and DMSO (3 mL), and the mixture was purified by preparative HPLC (Varian diphenyl reverse phase column eluting with gradient of solvent B=0.05% HOAC/MeOH and solvent A=0.05% HOAc/H$_2$O) to afford (3-fluorophenyl)(4-(5-methyl-1H-pyrazol-3-ylamino)quinazolin-2-yl)methanol (50 mg, 32%). $^1$H NMR (300 MHz, DMSO-d$_6$) δ 2.26 (s, 3H) 5.7 (s, 1H) 5.93 (s, 1H) 6.44 (s, 1H) 7.07 (m, 1H) 7.34-7.39 (m, 3H) 7.54 (m, 1H) 7.81 (s, 2H) 8.59 (d, 1H) 10.42 (s, 1H) 12.15 (s, 1H); LC-MS (ESI) m/z 350 (M+H)$^+$.

Example 65

Preparation N-((4-fluorophenyl)(4-(5-methyl-1H-pyrazol-3-ylamino)quinazolin-2-yl)methyl)formamide

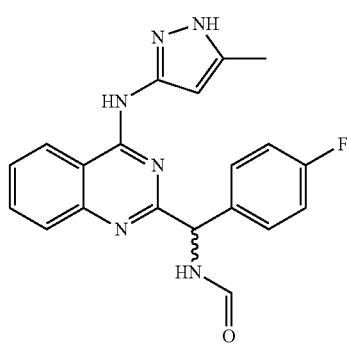 [SMILES: Cc1cc(Nc2nc(C(NC=O)c3ccc(F)cc3)nc3ccccc23)n[nH]1]

To 2-(amino(4-fluorophenyl)methyl)-N-(5-methyl-1H-pyrazol-3-yl)quinazolin-4-amine from Example 45 Step B (0.1 g, 0.28 mmol) in ethyl formate (4 mL) were added TEA (0.2 mL) and EtOH (0.5 mL), and the mixture was heated to 120° C. for 30 min in a Biotage microwave reactor and then concentrated under reduced pressure. The residue was diluted with DMSO (5 mL) and purified by reverse-phase preparative HPLC (Varian diphenyl reverse phase column, eluted with gradient of solvent B=0.05% HOAC/MeOH and solvent A=0.05% HOAc/H$_2$O) to afford N-((4-fluorophenyl)(4-(5-methyl-1H-pyrazol-3-ylamino)quinazolin-2-yl)methyl)formamide (8 mg, 8%). $^1$H NMR (300 MHz, DMSO-d$_6$) δ 2.26 (s, 3H) 6.07 (d, 1H) 6.44 (s, 1H) 7.16 (t, 2H) 7.4-7.6 (m, 3H) 7.8 (m, 2H) 8.21 (s, 1H) 8.62 (d, 1H) 9.06 (d, 1H) 10.48 (bs, 1H) 12.17 (bs, 1H); LC-MS (ESI) m/z 377 (M+H)$^+$.

Example 66

Preparation (R,S)-(3,4-difluorophenyl)(4-(5-methyl-1H-pyrazol-3-ylamino)quinazolin-2-yl)methanol

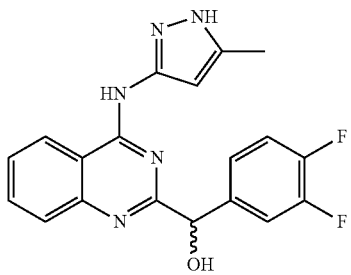 [SMILES: Cc1cc(Nc2nc(C(O)c3ccc(F)c(F)c3)nc3ccccc23)n[nH]1]

Step A

A mixture of ethyl 4-chloroquinazoline-2-carboxylate (1 g, 4.2 mmol) in THF (50 mL) was filtered, and to the filtrate at −30° C. under Ar was added 0.5M (3,4-difluorophenyl)magnesium bromide/THF (10.4 mL, 5.2 mmol). The mixture was stirred at −30° C. for 1.5 h., at which time additional 0.5M (3,4-difluorophenyl)magnesium bromide/THF (3 mL) was added. After a further 1.5 h, additional 0.5M (3,4-difluorophenyl)magnesium bromide/THF (3 mL) was added. To the mixture was added saturated aq ammonium chloride and the mixture was allowed to warm to rt. The mixture was extracted with EtOAc (2×) and the combined organic layers were dried over Na$_2$SO$_4$, filtered, and concentrated under reduced pressure to afford (4-chloroquinazolin-2-yl)(3,4-difluorophenyl)methanone (330 mg, 26%), which was used directly in the next step.

Step B

To a mixture of 5-methyl-1H-pyrazol-3-amine (0.18 g, 1.8 mmol), potassium iodide (0.18 g, 1.1 mmol), and TEA (0.16 mL, 1.1 mmol) in DMF (5 mL) was added a solution of (4-chloroquinazolin-2-yl)(3,4-difluorophenyl)methanone (0.33 g, 1.1 mmol) in DMF (5 mL) and the mixture was stirred at rt overnight. Water was added and the precipitated solid was collected by filtration. The yellow solid (553 mg) containing (3,4-difluorophenyl)(4-(5-methyl-1H-pyrazol-3-ylamino)quinazolin-2-yl)methanone was used directly in the next step. LC-MS (ESI) m/z 366 (M+H)$^+$.

Step C

To crude (3,4-difluorophenyl)(4-(5-methyl-1H-pyrazol-3-ylamino)quinazolin-2-yl)methanone (553 mg, 1.5 mmol) in 1:1 MeOH/THF (40 mL) at 0° C. was added sodium borohydride (0.09 g, 2.4 mmol), and the solution was stirred for 30 min, after which 6N HCl was added. The mixture was concentrated to dryness, and ca. 2/3 of the residue was purified by silica gel chromatography eluting with 0-15% MeOH/DCM to afford (3,4-difluorophenyl)(4-(5-methyl-1H-pyrazol-3-ylamino)quinazolin-2-yl)methanol (34 mg). $^1$H NMR (300 MHz, DMSO-d$_6$) δ 2.26 (s, 3H) 6.03 (s, 1H) 6.22 (s, 1H) 7.45-7.55 (m, 2H) 7.66 (t, 1H) 7.78 (t, 1H) 8.07 (t, 1H) 8.19 (t, 1H) 8.82 (d, 1H) 12.09 (bs, 1H) 12.67 (bs, 1H); LC-MS (ESI) m/z 368 (M+H)$^+$.

Example 67

Preparation (3-chloro-4-fluorophenyl)(4-(5-methyl-1H-pyrazol-3-ylamino)quinazolin-2-yl)methanol

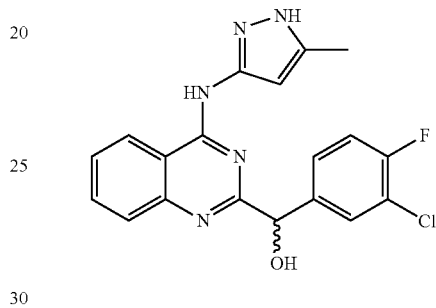

Step A

A mixture of ethyl 4-chloroquinazoline-2-carboxylate (1 g, 4.2 mmol) in THF (50 mL) was filtered, and to the filtrate at −30° C. under Ar was added 0.5 M (3-chloro-4-fluorophenyl)magnesium bromide/THF (10.4 mL, 5.2 mmol). After stirring at −30° C. for 0.75 h, additional 0.5 M (3-chloro-4-fluorophenyl)magnesium bromide/THF (4.2 mL). After 1 h, the reaction was quenched by addition of saturated aq ammonium chloride and allowed to warm to rt. The mixture was extracted with EtOAc, and the extracts were dried over sodium sulfate, filtered, and concentrated under reduced pressure to afford (3-chloro-4-fluorophenyl)(4-chloroquinazolin-2-yl)methanone (495 mg, 37%) which was used directly in the next step. LC-MS (ESI) m/z 321 (M+H)$^+$.

Step B

To a mixture of 5-methyl-1H-pyrazol-3-amine (0.26 g, 2.68 mmol), potassium iodide (0.26 g, 1.57 mmol), and TEA (0.45 mL, 3.23 mmol) in DMF (30 mL) was added (3-chloro-4-fluorophenyl)(4-chloroquinazolin-2-yl)methanone (0.495 g, 1.54 mmol) and the mixture was stirred at rt overnight. Water was added and the precipitated solid was collected by filtration to afford crude (3-chloro-4-fluorophenyl)(4-(5-methyl-1H-pyrazol-3-ylamino)quinazolin-2-yl)methanone (458 mg) which was used directly in the next step. LC-MS (ESI) m/z 382 (M+H)$^+$.

Step C

To crude (3-chloro-4-fluorophenyl)(4-(5-methyl-1H-pyrazol-3-ylamino)quinazolin-2-yl)methanone (458 mg, 1.2 mmol) in 1:1 MeOH/THF (60 mL) at 0° C. was added sodium borohydride (0.048 g, 1.3 mmol) and the solution was stirred for 30 min. The reaction was quenched by addition of 6 N HCl and the mixture was concentrated to dryness. The residue was purified by silica gel chromatography eluting with 0-15% MeOH/DCM. The resulting solid was triturated with methanol to afford (3-chloro-4-fluorophenyl)(4-(5-methyl-1H-pyrazol-3-ylamino)quinazolin-2-yl)methanol (42 mg). $^1$H NMR (300 MHz, DMSO-$d_6$) δ 2.27 (s, 3H) 5.70 (s, 1H) 6.01 (s, 1H) 6.41 (s, 1H) 7.36 (t, 1H) 7.47-7.52 (m, 2H) 7.79-7.82 (m, 3H) 8.59 (d, 1H) 10.42 (bs, 1H) 12.16 (bs, 1H); LC-MS (ESI) m/z 384 (M+H)$^+$.

Example 68

Preparation 3-(4-fluorophenyl)-3-(4-(5-methyl-1H-pyrazol-3-ylamino)quinazolin-2-yl)propanenitrile

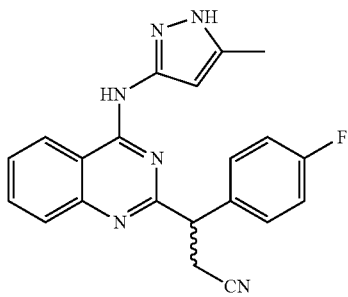 [SMILES: Cc1cc(Nc2nc(C(CC#N)c3ccc(F)cc3)nc3ccccc23)n[nH]1]

To a suspension of 60% sodium hydride/mineral oil (173 mg, 4.32 mmol) in THF (10 mL) at 0° C. under Ar was added diethyl cyanomethylphosphonate (0.68 mL, 4.32 mmol) and the mixture was stirred for 10 min. A suspension of (4-fluorophenyl)(4-(5-methyl-1H-pyrazol-3-ylamino)quinazolin-2-yl)methanone from Example 3 (500 mg, 1.44 mmol) in THF (20 mL) was then added and the mixture was stirred at rt for 30 min. Then AcOH (0.5 mL) and Celite were added and the mixture was concentrated under reduce pressure. The mixture was eluted onto a silica gel column and further eluted with EtOAc/hexanes. To the isolated material were added EtOH (100 mL) and 10% Pd—C (180 mg) and the mixture was heated at 70° C. overnight under a hydrogen atmosphere. The mixture was concentrated and subjected to silica gel chromatography eluting with EtOAc/hexanes to give 360 mg of impure material. One half of this material was further purified by preparative HPLC (Varian diphenyl reverse phase column, eluting with a gradient of solvent B=0.05% HOAc/MeOH and solvent A=0.05% HOAc/H$_2$O) to afford 3-(4-fluorophenyl)-3-(4-(5-methyl-1H-pyrazol-3-ylamino)quinazolin-2-yl)propanenitrile (65 mg, 24%). $^1$H NMR (300 MHz, DMSO-$d_6$) δ 2.25 (s, 3H) 3.24-3.48 (m, 2H) 4.57 (m, 1H) 6.36 (s, 1H) 7.17 (m, 2H) 7.46-7.55 (m, 3H) 7.77-7.81 (m, 2H) 8.60 (d, 1H) 10.41 (s, 1H) 12.13 (s, 1H); LC-MS (ESI) m/z 373 (M+H)$^+$.

Example 69

Preparation 2-((cyclopropylamino)(4-fluorophenyl)methyl)-N-(5-methyl-1H-pyrazol-3-yl)quinazolin-4-amine

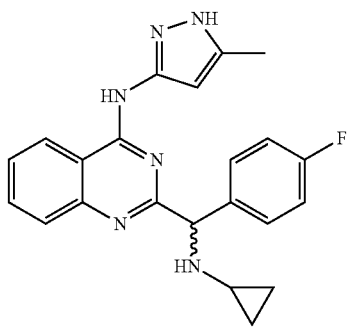 [SMILES: Cc1cc(Nc2nc(C(NC3CC3)c3ccc(F)cc3)nc3ccccc23)n[nH]1]

To (4-fluorophenyl)(4-(5-methyl-1H-pyrazol-3-ylamino) quinazolin-2-yl)methanone from Example 3 (100 mg, 0.28 mmol) in 2-propanol (3 mL) were added cyclopropylamine (0.1 mL) and 3 Å (8-12 mesh) molecular sieves, and the mixture was heated at 140° C. in a Biotage microwave reactor. Additional cyclopropylamine (0.15 mL) was added and the mixture in a sealed vial was heated conventionally at 90° C. for 4 d. Then a suspension of sodium borohydride (140 mg) in 2-propanol was added dropwise and the mixture was stirred at rt for 1 h. Then MeOH (0.1 mL), sodium borohydride (100 mg), and more MeOH (2 mL) were added, and the mixture was filtered and the filtrate was concentrated. To the residue were added THF (5 mL), MeOH (2 mL) and sodium borohydride (100 mg) and the mixture was stirred for 1 h at rt. AcOH (0.4 mL) was then added and the mixture was concentrated. DMSO (3 mL) was added and the mixture was purified by preparative HPLC (Varian diphenyl reverse phase column, eluting with a gradient of solvent B=0.05% HOAc/MeOH and solvent A=0.05% HOAc/H$_2$O) followed by further purification by preparative HPLC (Phenomonex C-18 reverse phase column, eluting with a gradient of solvent B=0.05% HOAc/MeOH and solvent A=0.05% HOAc/H$_2$O) to afford 2-((cyclopropylamino)(4-fluorophenyl)methyl)-N-(5-methyl-1H-pyrazol-3-yl)quinazolin-4-amine (5.5 mg, 9%). $^1$H NMR (300 MHz, DMSO-$d_6$) δ 0.34 (m, 4H) 1.24 (m, 1H) 2.03 (m, 1H) 2.26 (s, 3H) 4.91 (s, 1H) 6.41 (m, 1H) 7.11 (t, 2H) 7.4-7.6 (m, 3H) 7.76 (m, 2H) 8.56 (d, 1H) 10.38 (bs, 1H) 12.15 (bs, 1H); LC-MS (ESI) m/z 389 (M+H)$^+$.

Example 70

Preparation 2-(1-(4-fluorophenyl)-2-(methylsulfonyl)ethyl)-N-(5-methyl-1H-pyrazol-3-yl)quinazolin-4-amine

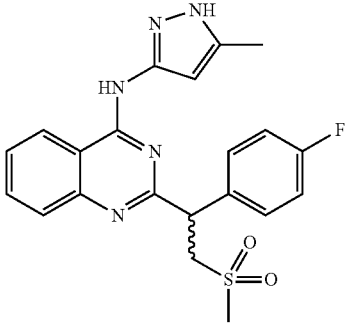 [SMILES: Cc1cc(Nc2nc(C(CS(C)(=O)=O)c3ccc(F)cc3)nc3ccccc23)n[nH]1]

Step A

To 3-chlorobenzoperoxoic acid (77%, 11.21 g, 50 mmol) in DCM (150 mL) was added diethyl methylthiomethylphosphonate (4.4 mL, 25 mmol) and the mixture was allowed to stir at rt overnight. Additional 3-chlorobenzoperoxoic acid (5.6 g) was then added and stirring was continued for 4 h at rt. The solution was washed with saturated aq potassium carbonate and concentrated. The residue was dissolved in DCM and washed again with a saturated potassium carbonate solution. The organic layer was concentrated to afford diethyl methylsulfonylmethylphosphonate (4.51 g, 39%). $^1$H NMR (300 MHz, DMSO-d$_6$) δ 1.25 (t, 6H) 3.13 (s, 3H) 4.09 (m, 4H) 4.20 (d, 2H); LC-MS (ESI) m/z 231 (M+H)$^+$.

Step B

To diethyl methylsulfonylmethylphosphonate (746 mg, 3.24 mmol) in THF (20 mL) at 0° C. was added potassium t-butoxide (1.0 M in THF, 3.25 mL, 3.25 mmol) and the mixture was stirred for 5 min. Then (4-fluorophenyl)(4-(5-methyl-1H-pyrazol-3-ylamino)quinazolin-2-yl)methanone from Example 3 (375 mg, 1.08 mmol) was added and the mixture was stirred at rt for 4 h. The mixture was treated with 1 N HCl and the resulting mixture was extracted with EtOAc. The organic layer was washed with brine and then concentrated to a residue (700 mg), which was subjected to silica gel chromatography eluting with 1-10% MeOH/DCM to give impure material. To a portion of this material (166 mg) in EtOAc (5 mL) was added 10% Pd—C (166 mg) and the mixture was stirred under a hydrogen atmosphere at rt overnight. The mixture was filtered and to the filtrate was added palladium on carbon (10%). The mixture was stirred under a hydrogen atmosphere for several hours, and then filtered. The filtrate was concentrated to a solid, which was triturated with ether to afford 2-(1-(4-fluorophenyl)-2-(methylsulfonyl)ethyl)-N-(5-methyl-1H-pyrazol-3-yl)quinazolin-4-amine (22 mg). $^1$H NMR (300 MHz, DMSO-d$_6$) δ 2.28 (s, 3H) 2.87 (s, 3H) 3.85 (m, 1H) 4.34 (m, 1H) 4.68 (bs, 1H) 6.45 (s, 1H) 7.15 (t, 2H) 7.49 (m, 3H) 7.76 (m, 2H) 8.56 (d, 1H) 10.36 (s, 1H) 12.17 (s, 1H); LC-MS (ESI) m/z 426 (M+H)$^+$.

Example 71

Preparation 2-(3-amino-1-(4-fluorophenyl)propyl)-N-(5-methyl-1H-pyrazol-3-yl)quinazolin-4-amine

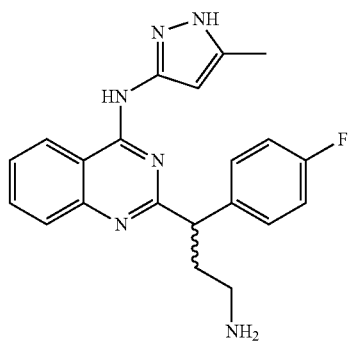 [SMILES: Cc1cc(Nc2nc(C(CCN)c3ccc(F)cc3)nc3ccccc23)n[nH]1]

To 3-(4-fluorophenyl)-3-(4-(5-methyl-1H-pyrazol-3-ylamino)quinazolin-2-yl)propanenitrile from Example 68 (80 mg, 0.21 mmol) in THF (3 mL) at 0° C. was added lithium aluminum hydride (20 mg) and the mixture was stirred for 5 min, then allowed to warm to rt and stir for 2-3 h. An additional amount of lithium aluminum hydride (40 mg) was then added and stirring was continued for 45 min. To the solution was slowly added 1 N NaOH (0.5 mL) followed by MeOH (2 mL). The mixture was stirred for 5 min and then AcOH (0.5 mL) was added, followed by DMSO (2 mL). The resulting solution was purified by preparative HPLC (Varian Diphenyl reverse phase column, eluting with a gradient of solvent B=0.05% HOAc/ACN and solvent A=0.05% HOAc/H$_2$O) to afford 2-(3-amino-1-(4-fluorophenyl)propyl)-N-(5-methyl-1H-pyrazol-3-yl)quinazolin-4-amine as the acetate salt (21 mg, 25%). $^1$H NMR (300 MHz, DMSO-d$_6$) δ 1.81 (s, 3H) 2.2-2.6 (m, 7H) 4.26 (t, 1H) 6.46 (s, 1H) 7.12 (t, 2H) 7.46-7.51 (m, 3H) 7.73-7.78 (m, 2H) 8.57 (d, 1H); LC-MS (ESI) m/z 377 (M+H)$^+$.

Example 72

Preparation of (R,S) (4-fluorophenyl)(4-(5-methyl-1H-pyrazol-3-ylamino)quinazolin-2-yl)methanol-1-d

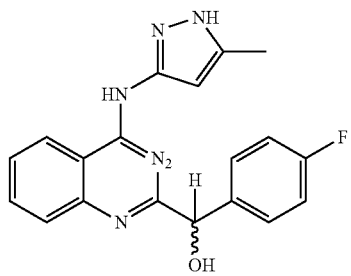

To (4-fluorophenyl)(4-(5-methyl-1H-pyrazol-3-ylamino)quinazolin-2-yl)methanone from Example 3 (200 mg, 0.57 mmol) in THF (5 mL) and MeOH-d$_4$ (2 mL) at 0° C. was added sodium borodeuteride (50 mg, 98%). The solution was stirred at 0° C. for 1 h and then allowed to warm to rt for 30 min. 2N HCl (0.4 mL) was then added and the solution was concentrated. The residue was purified by preparative HPLC (Varian diphenyl reverse phase column, eluting with a gradient of solvent B=0.05% HOAc/ACN and solvent A=0.05% HOAc/H$_2$O) to afford (R,S) (4-fluorophenyl)(4-(5-methyl-1H-pyrazol-3-ylamino)quinazolin-2-yl)methanol-1-d (60 mg, 30%). $^1$H NMR (300 MHz, DMSO-d$_6$) δ 2.25 (s, 3H) 5.80 (s, 1H) 6.41 (s, 1H) 7.14 (t, 2H) 7.53-7.55 (m, 3H) 7.79 (m, 2H) 8.58 (d, 1H) 10.41 (bs, 1H) 12.15 (bs, 1H); LC-MS (ESI) m/z 351 (M+H)$^+$.

Example 73

Preparation (4-fluorophenyl)(4-(5-methoxy-1H-pyrazol-3-ylamino)quinazolin-2-yl)methanone

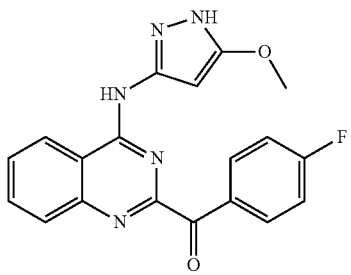 [SMILES: COc1cc(Nc2nc(C(=O)c3ccc(F)cc3)nc3ccccc23)n[nH]1]

Step A

To 3,5-dinitro-1H-pyrazole (517 mg, 3.27 mmol) in DMF (15 mL) were added potassium carbonate (903 mg, 6.54 mmol) and (2-(chloromethoxy)ethyl)trimethylsilane (0.64 mL, 3.59 mmol) and the mixture was stirred at rt for 2 h. The mixture was concentrated, and the residue was purified by silica gel chromatography eluting with 0-20% ethyl acetate/hexanes to give an oil (840 mg). To the oil in MeOH (20 mL) was added 25% NaOMe/MeOH (1.25 mL, 5.83 mmol) and the mixture was heated to 60° C. for 3-4 h. AcOH (0.3 mL) was then added and the mixture was purified by silica gel chromatography (ethyl acetate/hexanes 0-30%) to afford a single compound (3-methoxy-5-nitro-1-((2-(trimethylsilyl)ethoxy)methyl)-1H-pyrazole or 5-methoxy-3-nitro-1-((2-(trimethylsilyl)ethoxy)methyl)-1H-pyrazole) (610 mg, 68%). $^1$H NMR (300 MHz, CDCl$_3$) δ 0.00 (s, 9H) 0.94 (t, 2H) 3.67 (t, 2H) 4.02 (s, 3H) 5.41 (s, 2H), 6.23 (s, 1H); LC-MS (ESI) m/z 296 (M+H)$^+$.

Step B

To the product of Example 73 Step A (150 mg, 0.55 mmol) in EtOH (10 mL) was added palladium on carbon (10%, 30 mg) and the mixture was stirred under a hydrogen atmosphere for 1-2 h. The mixture was filtered and the filtrate was concentrated to an oil. To this oil in DMF (4 mL) were added DIEA (0.96 mL), potassium iodide (65 mg) and (4-chloroquinazolin-2-yl)(4-fluorophenyl)methanone from Example 3 Step A (112 mg, 0.39 mmol). The mixture was heated at 65° C. overnight, and then diluted with EtOAc and washed with water (3×), dried over sodium sulfate, filtered, and concentrated under reduced pressure. The residue was dissolved in THF (5 mL) and a portion (3 mL) was concentrated, treated with TFA (3 mL) at rt for 45 min. The mixture was concentrated, and then MeOH was added and evaporated. The residue was dissolved in DMSO and recombined with the second portion of the sample which had been treated in an analogous fashion. The mixture was purified by preparative HPLC (Varian diphenyl reverse phase column, eluted with gradient of solvent B=0.05% HOAC/ACN and solvent A=0.05% HOAc/H$_2$O) to afford (4-fluorophenyl)(4-(5-methoxy-1H-pyrazol-3-ylamino)quinazolin-2-yl)methanone (12 mg). $^1$H NMR (300 MHz, DMSO-d$_6$) δ 3.73 (s, 3H) 5.78 (bs, 1H) 7.40 (t, 2H) 7.78 (m, 1H) 7.94 (m, 2H) 8.12 (m, 2H) 8.59 (bs, 1H) 10.88 (bs, 1H) 11.77 (bs, 1H); LC-MS (ESI) m/z 364 (M+H)$^+$.

Example 74

Preparation (R,S)-(4-(5-ethyl-1H-pyrazol-3-ylamino)quinazolin-2-yl)(4-fluorophenyl)methanol

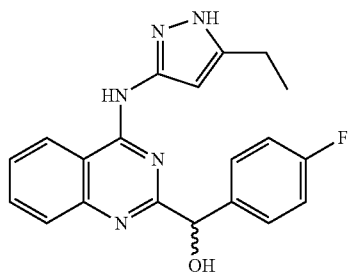 [SMILES: CCc1cc(Nc2nc(C(O)c3ccc(F)cc3)nc3ccccc23)n[nH]1]

Step A

To a mixture of 5-ethyl-1H-pyrazol-3-amine (101 mg, 0.91 mmol), potassium iodide (117 mg, 0.7 mmol), and DIEA (0.15 mL, 0.84 mmol) in DMF (4 mL) was added (4-chloroquinazolin-2-yl)(4-fluorophenyl)methanone from Example 3 Step A (200 mg, 0.7 mmol) and the mixture was stirred at rt overnight. Water was added and the precipitated solid was collected by filtration. The yellow solid (226 mg) containing (4-(5-ethyl-1H-pyrazol-3-ylamino)quinazolin-2-yl)(4-fluorophenyl)methanone was used directly in the next step. LC-MS (ESI) m/z 362 (M+H)$^+$.

Step B

To crude (4-(5-ethyl-1H-pyrazol-3-ylamino)quinazolin-2-yl)(4-fluorophenyl)methanone (104 mg, 0.28 mmol) in 1:1 MeOH/THF (4 mL) at rt was added sodium borohydride (22 mg, 0.57 mmol), and the solution was stirred for 30 min, after which 4N HCl (0.1 mL) was added. The mixture was concentrated to dryness, and the residue was purified by preparative HPLC (Varian diphenyl reverse phase column, eluting with a gradient of solvent B=0.05% HOAc/ACN and solvent A=0.05% HOAc/H$_2$O) to afford (4-(5-ethyl-1H-pyrazol-3-ylamino)quinazolin-2-yl)(4-fluorophenyl)methanol (7 mg). $^1$H NMR (300 MHz, DMSO-d$_6$) δ 1.24 (t, 3H) 2.62 (q, 2H) 5.67 (m, 1H) 5.83 (s, 1H) 6.45 (s, 1H) 7.13 (t, 2H) 7.53-7.57 (m, 3H) 7.81 (s, 2H) 8.59 (d, 1H) 10.42 (bs, 1H) 12.15 (bs, 1H); LC-MS (ESI) m/z 364 (M+H)$^+$.

Example 75

Preparation of (4-Fluorophenyl)(4-(5-methoxy-1H-pyrazol-3-ylamino)quinazolin-2-yl)methanol

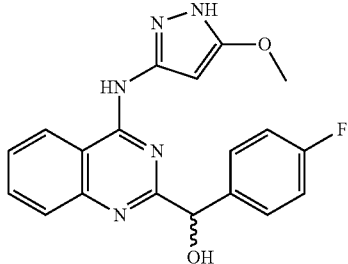 [SMILES: COc1cc(Nc2nc(C(O)c3ccc(F)cc3)nc3ccccc23)n[nH]1]

(4-Fluorophenyl)(4-(5-methoxy-1H-pyrazol-3-ylamino)quinazolin-2-yl)methanol is prepared using a procedure analogous to that described in Example 6, substituting (4-fluorophenyl)(4-(5-methoxy-1H-pyrazol-3-ylamino)quinazolin-2-yl)methanone from Example 75 for the (4-(1H-pyrazol-3-ylamino)quinazolin-2-yl)(4-fluorophenyl)methanone used in Example 6.

Example 76

Preparation of (4-fluoro-3-methoxyphenyl)(4-(5-methyl-1H-pyrazol-3-ylamino)quinazolin-2-yl) methanone

Step A

To a stirred mixture of ethyl 4-chloroquinazoline-2-carboxylate (500 mg, 2.11 mmol) in THF (17 mL) at −40° C. was added dropwise 1 M 4-fluoro-3-methoxyphenylmagnesium bromide/2-methyltetrahydrofuran (2.53 mL, 2.53 mmol). The reaction mixture was stirred at −30 to −40° C. for 3 h. Additional 1 M 4-fluoro-3-methoxyphenylmagnesium bromide/2-methyltetrahydrofuran (1.05 mL, 1.05 mmol) was added and stirring was continued at −30 to −40° C. for an additional 1.5 h. To the mixture was added saturated aq ammonium chloride (25 mL) and the mixture was allowed to warm to rt. The mixture was extracted with EtOAc (2×) and the combined organic layers were dried over magnesium sulfate, filtered, and concentrated under reduced pressure. The residue was triturated with diethyl ether and the resulting solid was collected by filtration and dried to afford (4-chloroquinazolin-2-yl)(4-fluoro-3-methoxyphenyl)methanone as a colorless solid (417 mg, 62%). $^1$H NMR (300 MHz, DMSO-$d_6$) δ ppm 3.92 (s, 3H), 7.42 (dd, J=11.1, 8.7 Hz, 1H), 7.64 (m, 1H), 7.85 (d, J=8.4 Hz, 1H), 8.04 (m, 1H), 8.23-8.25 (m, 2H), 8.43 (d, J=8.4 Hz, 1H); LC-MS (ESI) m/z 317 (M+H)$^+$.

Step B

A mixture of (4-chloroquinazolin-2-yl)(4-fluoro-3-methoxyphenyl)methanone (337 mg, 1.06 mmol), 5-methyl-1H-pyrazol-3-amine (206 mg, 2.12 mmol), potassium iodide (528 mg, 3.18 mmol) and DIEA (0.37 mL, 2.13 mmol) in DMF (10 mL) was stirred at rt for 20 h. To the mixture was added water (80 mL) and the resulting solid was collected by filtration and washed with water and then diethyl ether. The solid was dried to afford (4-fluoro-3-methoxyphenyl)(4-(5-methyl-1H-pyrazol-3-ylamino)quinazolin-2-yl)methanone as a yellow solid (300 mg, 75%). $^1$H NMR (300 MHz, DMSO-$d_6$) δ ppm 2.19 (s, 3H), 3.90 (s, 3H), 6.55 (s, 1H), 7.38 (dd, J=11.1, 8.4 Hz, 1H), 7.59 (m, 1H), 7.68 (dd, J=7.8, 7.8 Hz, 1H), 7.77-7.94 (m, 3H), 8.75 (d, J=7.8 Hz, 1H), 10.69 (br s, 1H), 12.23 (br s, 1H); LC-MS (ESI) m/z 378 (M+H)$^+$.

Example 77

Preparation of (4-fluoro-3-hydroxyphenyl)(4-(5-methyl-1H-pyrazol-3-ylamino)quinazolin-2-yl) methanone

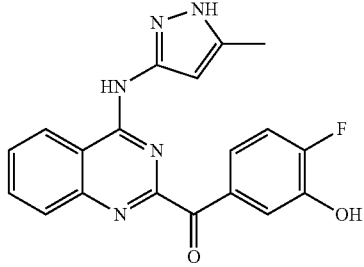 [SMILES: Cc1cc(Nc2nc(C(=O)c3ccc(F)c(O)c3)nc3ccccc23)n[nH]1]

To a stirred suspension of (4-fluoro-3-methoxyphenyl)(4-(5-methyl-1H-pyrazol-3-ylamino)quinazolin-2-yl)methanone from Example 76 (100 mg, 0.265 mmol) in DCM (4 mL) at 0° C., was added dropwise 1.0 M boron tribromide/DCM (2.12 mL, 2.12 mmol). The mixture was stirred at 0° C. for 30 min. Additional 1.0 M boron tribromide/DCM (1.50 mL, 1.50 mmol) was added and the mixture was allowed to warm to rt and stir for a further 2.5 h. Water (10 mL) was added, and the mixture was extracted with 25% 2-propanol/DCM (2×). The combined organic layers were dried over magnesium sulfate, filtered, and concentrated under reduced pressure. The residue was triturated with diethyl ether and the resulting solid was collected by filtration and dried. The solid was further purified by reverse-phase HPLC eluting with a mixture of water and acetonitrile to afford (4-fluoro-3-hydroxyphenyl)(4-(5-methyl-1H-pyrazol-3-ylamino)quinazolin-2-yl) methanone as a yellow solid (20 mg, 21%). $^1$H NMR (300 MHz, DMSO-$d_6$) δ ppm 2.19 (s, 3H), 6.51 (s, 1H), 7.28 (dd, J=10.8, 8.4 Hz, 1H), 7.39 (m, 1H), 7.58 (dd, J=8.7, 1.8 Hz, 1H), 7.67 (ddd, J=8.1, 8.1, 1.5 Hz, 1H), 7.83-7.92 (m, 2H), 8.73 (d, J=8.4 Hz, 1H), 10.65 (br s, 1H), 12.22 (br s, 1H); LC-MS (ESI) m/z 364 (M+H)$^+$.

Example 78

Preparation of (R,S)-(2-fluoro-5-(hydroxy(4-(5-methyl-1H-pyrazol-3-ylamino)quinazolin-2-yl)methyl) phenol acetate

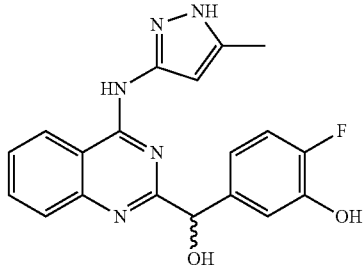 [SMILES: Cc1cc(Nc2nc(C(O)c3ccc(F)c(O)c3)nc3ccccc23)n[nH]1]

To a stirred solution of (4-fluoro-3-hydroxyphenyl)(4-(5-methyl-1H-pyrazol-3-ylamino)quinazolin-2-yl)methanone from Example 77 (20 mg, 0.055 mmol) in a mixture of THF (0.3 mL) and MeOH (0.3 mL) at 0° C. was added sodium borohydride (3 mg, 0.079 mmol) and the mixture was stirred at 0° C. for 15 min. To the mixture was added concentrated hydrochloric acid solution to pH 1. This mixture was combined with a mixture obtained analogously starting with (4-fluoro-3-hydroxyphenyl)(4-(5-methyl-1H-pyrazol-3-ylamino)quinazolin-2-yl)methanone (60 mg, 0.165 mmol). The resulting mixture was purified by reverse-phase HPLC eluting with a mixture of water in acetonitrile to afford (R,S)-(2-fluoro-5-(hydroxy(4-(5-methyl-1H-pyrazol-3-ylamino) quinazolin-2-yl)methyl)phenol acetate as a solid (26 mg, 28%). $^1$H NMR (300 MHz, DMSO-$d_6$) δ ppm 1.89 (s, 3H), 2.25 (s, 3H), 5.55 (s, 1H), 5.75 (br s, 1H), 6.43 (br s, 1H), 6.92 (m, 1H), 7.02-7.11 (m, 2H), 7.52 (m, 1H), 7.70-7.79 (br m, 2H), 8.58 (m, 1H), 10.44 (br s, 1H), 12.10 (br s, 1H); LC-MS (ESI) m/z 366 (M+H)$^+$.

Example 79

Competition Binding Assay to Determine Binding Constants ($K_d$) of the Compounds Against JAK Kinases Competition binding assays used herein were developed, validated and performed as described in Fabian et al., *Nature Biotechnology* 2005, 23, 329-336. Kinases were produced as fusions to T7 phage (See, Fabian et al. or WO04/015142) or alternatively, the kinases were expressed in HEK-293 cells and subsequently tagged with DNA for PCR detection (See, WO08/005,310). For the binding assays, streptavidin-coated magnetic beads were treated with biotinylated affinity ligands for 30 min at rt to generate affinity resins. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinase, liganded affinity beads, and test compounds in 1× binding buffer (20% SeaBlock, 0.17×PBS, 0.05% Tween 20, 6 mM DTT). Test compounds were prepared as 100× stocks in DMSO and rapidly diluted into the aqueous environment. DMSO was added to control assays lacking a test compound. Primary screen interactions were performed in polypropylene 384-well plates in a final volume of 34 µL, while Kd determinations were performed in polystyrene 96-well plates in a final volume of 135 pt. The assay plates were incubated at room temperature with shaking for 1 hour, long enough for binding reactions to reach equilibrium, and the affinity beads were washed extensively with wash buffer (1×PBS, 0.05% Tween 20) to remove unbound protein. The beads were then resuspended in elution buffer (1×PBS, 0.05% Tween 20, 2 µM non-biotinylated affinity ligand) and incubated at room temperature with shaking for 30 min. The kinase concentration in the eluates was measured by quantitative PCR. Each kinase was tested individually against each compound. Kds were determined using eleven serial threefold dilutions. A selectivity score, which is a quantitative measure of selectivity of a compound against a panel of enzymes, may be calculated for a compound by dividing the number of enzymes for which a compound meets a set criteria, (for example, a binding constant of 100 nM or less), by the total number of enzymes tested. A kinase selectivity score, S10, for example, is calculated for each compound by dividing the number of kinases for which a compound at a certain concentration (for example, 10 µM) displayed inhibition of 90% or greater compared to negative control lacking inhibitors (DMSO only), divided by the 321 distinct kinases tested excluding mutant variants.

In one embodiment, the compounds provided herein were found to have Kds of less than about 20 µM against JAK2. In another embodiment, the compounds provided herein were found to have Kds of less than about 10 µM against JAK2. In another embodiment, the compounds provided herein were found to have Kds of less than about 1 µM against JAK2.

In another embodiment, the compounds provided herein were found to have Kds of less than about 20 µM against JAK3. In another embodiment, the compounds provided herein were found to have Kds of less than about 10 µM against JAK3. In another embodiment, the compounds provided herein were found to have Kds of less than about 1 µM against JAK3.

Example 80 csTF-1 Cell-Based Reporter Assay csTF-1 cells are derived from the human erythroleukemia cell line that is growth dependent on GM-CSF and has an intact GM-CSFR/JAK2/STAT5 pathway. The cell line contains stably integrated beta-lactamase reporter gene under the control of the regulatory factor 1 (irf 1) response element recognized by the activated transcription factor STAT5. csTF-1 cells (Invitrogen K1219) were washed with assay media (97% OPTIMEM/0.5% dialyzed FBS/0.1 mM NEAA/1 mM Na pyr/P/S) and seeded in the same media at $5 \times 10^5$ cell/mL in T150 flask. After 16 hour incubation, cells were seeded at $2 \times 10^5$ cell/well in 50 µl volume, into Costar, clear bottom, 96-well assay plates. Serial dilutions of compounds were added to the plates with final DMSO concentration at 0.5% and GM-CSF at 2 ng/mL and the plates were then incubated at 30° C. and 5% $CO_2$ for 4 hours. The plates were brought to room temperature before adding Substrate Mixture according to manufacturer's protocol (Invitrogen, Catalog #K1085). The assay plates containing the substrate mixture were incubated in the dark at room temperature for 2 hours. Blue and green fluorescence was measured with excitation at 409 nm and emission at 460 nm (for blue) and excitation at 409 nm and emission at 530 nm (for green) using Spectra Max Gemini EM. The compounds provided herein were found to have $IC_{50}$ of less than about 5 µM. In another embodiment, the compounds provided herein were found to have activity $IC_{50}$ of less than about 500 nM.

The compounds provided herein were found to have the following activity shown in Table 1:

TABLE 1

| Compound | Cell Assay: CS0017: CS TF-1 reporter assay: $IC_{50}$ | Binding Assay: JAK3 (active_KD, ENZ) | Binding Assay: JAK2 (active_KD) | Binding Assay: AuroraB KD | S Score (at 10 µM) |
|---|---|---|---|---|---|
| 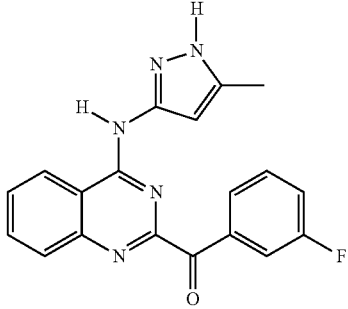 [SMILES: Cc1cc(Nc2nc(C(=O)c3cccc(F)c3)nc3ccccc23)n[nH]1] | B | B | B | D | A |

TABLE 1-continued
| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 μM) |
|---|---|---|---|---|---|
| 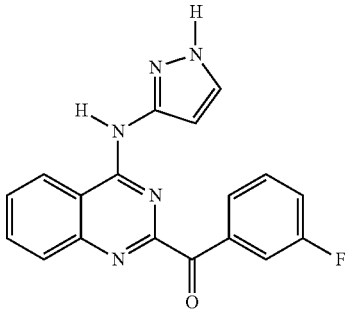 [SMILES: O=C(c1cccc(F)c1)c1nc(Nc2cc[nH]n2)c2ccccc2n1] | C | C | C | D | A |
| 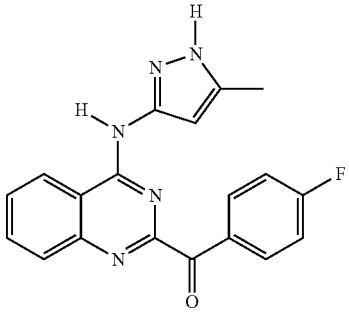 [SMILES: Cc1cc(Nc2nc(C(=O)c3ccc(F)cc3)nc3ccccc23)n[nH]1] | A | B | A | D | A |
| 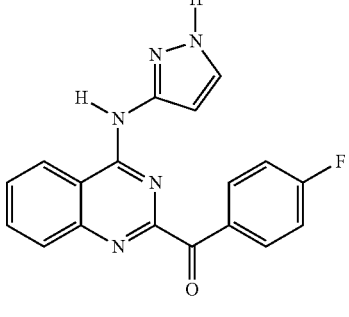 | A | B | A | D | A |
| 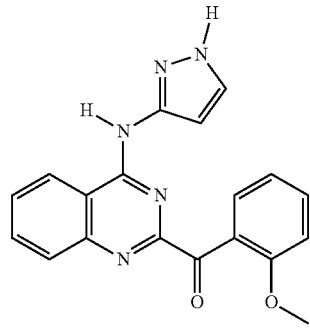 [SMILES: COc1ccccc1C(=O)c1nc(Nc2cc[nH]n2)c2ccccc2n1] | B | C | B | D | A |

TABLE 1-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 μM) |
|---|---|---|---|---|---|
| [pyrazole-NH-quinazoline-CH(OH)-(4-fluorophenyl)] | A | B | A | D | A |
| [pyrazole-NH-quinazoline-CHF-(4-fluorophenyl)] | B | B | A | D | A |
| [5-methylpyrazole-NH-quinazoline-CF$_2$-(4-fluorophenyl)] | A | A | A | D | A |
| [pyrazole-NH-quinazoline-CF$_2$-(4-fluorophenyl)] | A | B | A | D | A |
| [5-cyclopropylpyrazole-NH-quinazoline-CF$_2$-(4-fluorophenyl)] | A | A | B | D | D |

TABLE 1-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 μM) |
|---|---|---|---|---|---|
| (pyrazole-CN / quinazoline / CF$_2$-4-F-phenyl) | C | C | C | D | A |
| (5-methylpyrazole / quinazoline / CH(OH)-4-F-phenyl) | A | B | A | C | A |
| (5-methylpyrazole / quinazoline / CH(OMe)-4-F-phenyl) | B | B | A | D | A |
| (5-methylpyrazole / quinazoline / CH(NH$_2$)-4-F-phenyl) | B | B | B | D | A |
| (pyrazole-CN / quinazoline / CH(OH)-4-F-phenyl) | C | C | C | D | A |

TABLE 1-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 µM) |
|---|---|---|---|---|---|
| (5-fluoroquinazoline with pyrazolylamino and (4-fluorophenyl)(hydroxy)methyl) | B | C | C | D | A |
| (7-trifluoromethylquinazoline with pyrazolylamino and 4-fluorobenzoyl) | B | C | C | D | A |
| (7-trifluoromethylquinazoline with pyrazolylamino and (4-fluorophenyl)(hydroxy)methyl) | B | B | B | D | A |
| (7-fluoroquinazoline with pyrazolylamino and 4-fluorobenzoyl) | A | B | B | D | A |
| (7-fluoroquinazoline with pyrazolylamino and difluoro(4-fluorophenyl)methyl) | A | B | A | D | A |

TABLE 1-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 μM) |
|---|---|---|---|---|---|
| (7-fluoro-2-[difluoro(4-fluorophenyl)methyl]-N-(1H-pyrazol-3-yl)quinazolin-4-amine) | B | B | B | ND | A |
| (7-iodo-2-(4-fluorobenzoyl)-N-(1H-pyrazol-3-yl)quinazolin-4-amine) | B | C | B | ND | A |
| (7-iodo-2-[(4-fluorophenyl)(hydroxy)methyl]-N-(1H-pyrazol-3-yl)quinazolin-4-amine) | B | C | B | D | A |
| (2-(4-fluorobenzoyl)-7-methyl-N-(5-methyl-1H-pyrazol-3-yl)quinazolin-4-amine) | A | B | A | D | A |
| (2-[(4-fluorophenyl)(hydroxy)methyl]-7-methyl-N-(5-methyl-1H-pyrazol-3-yl)quinazolin-4-amine) | A | B | A | D | A |

TABLE 1-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 μM) |
|---|---|---|---|---|---|
| [structure: 7-methyl-quinazoline with 5-methyl-1H-pyrazol-3-ylamino and CF$_2$-(4-fluorophenyl)] | A | A | A | D | A |
| [structure: 7-methyl-quinazoline with 1H-pyrazol-3-ylamino and CF$_2$-(4-fluorophenyl)] | A | B | A | ND | A |
| [structure: 7-methoxy-quinazoline with 1H-pyrazol-3-ylamino and C(=O)-(4-fluorophenyl)] | B | C | B | D | A |
| [structure: 7-methoxy-quinazoline with 1H-pyrazol-3-ylamino and CH(OH)-(4-fluorophenyl)] | A | B | A | D | A |
| [structure: 7-methoxy-quinazoline with 5-methyl-1H-pyrazol-3-ylamino and C(=O)-(4-fluorophenyl)] | A | B | B | D | A |

TABLE 1-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 μM) |
|---|---|---|---|---|---|
| *structure* | A | B | A | D | A |
| *structure* | A | B | A | D | A |
| *structure* | B | C | B | C | A |
| *structure* | A | B | A | D | B |
| *structure* | C | C | C | C | A |

TABLE 1-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 μM) |
|---|---|---|---|---|---|
| (structure) | A | B | A | B | A |
| (structure) | A | B | A | D | A |
| (structure) | B | A | A | D | C |
| (structure) | A | A | A | D | B |
| (structure) | A | A | A | D | B |

TABLE 1-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 μM) |
|---|---|---|---|---|---|
| *(structure)* | B | A | A | D | D |
| *(structure)* | A | A | A | D | D |
| *(structure)* | B | B | A | D | C |
| *(structure)* | C | A | A | D | A |
| *(structure)* | B | B | A | D | A |

TABLE 1-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: AuroraB KD | S Score (at 10 μM) |
|---|---|---|---|---|---|
| [structure] | C | C | C | D | A |

Further exemplary compounds provided herein were found to have the following activity shown in Table 2:

TABLE 2

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: Aurora B (Kd) | S Score (at 10 μM) |
|---|---|---|---|---|---|
| [structure] | B | B | A | D | A |
| [structure] | B | B | A | D | A |

TABLE 2-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: Aurora B (Kd) | S Score (at 10 μM) |
|---|---|---|---|---|---|
| *(7-fluoro-quinazoline with 4-(5-methyl-1H-pyrazol-3-ylamino) and 2-[(4-fluorophenyl)(hydroxy)methyl])* | B | B | A | D | A |
| *(quinazoline with 4-(5-methyl-1H-pyrazol-3-ylamino) and 2-[bis(4-fluorophenyl)(hydroxy)methyl])* | C | C | C | D | A |
| *(7-hydroxymethyl-quinazoline with 4-(5-methyl-1H-pyrazol-3-ylamino) and 2-[difluoro(4-fluorophenyl)methyl])* | A | A | A | ND | D |
| *(7-(methylsulfonylmethyl)-quinazoline with 4-(5-methyl-1H-pyrazol-3-ylamino) and 2-[difluoro(4-fluorophenyl)methyl])* | A | A | A | D | C |

TABLE 2-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: Aurora B (Kd) | S Score (at 10 µM) |
|---|---|---|---|---|---|
| [structure] | A | A | A | C | B |
| [structure] | A | B | B | D | A |
| [structure] | B | C | B | ND | A |
| [structure] | B | C | B | ND | A |

TABLE 2-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: Aurora B (Kd) | S Score (at 10 μM) |
|---|---|---|---|---|---|
| [structure: 6-F quinazoline, 4-NH-pyrazole, 2-CH(OH)-(4-F-phenyl)] | C | C | B | ND | A |
| [structure: 7-Br quinazoline, 4-NH-(5-methylpyrazole), 2-C(=O)-(4-F-phenyl)] | B | B | B | ND | A |
| [structure: 7-Br quinazoline, 4-NH-(5-methylpyrazole), 2-CH(OH)-(4-F-phenyl)] | B | TBD | B | ND | A |
| [structure: 7-Br quinazoline, 4-NH-pyrazole, 2-CH(OH)-(4-F-phenyl)] | B | C | B | ND | A |

TABLE 2-continued
| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: Aurora B (Kd) | S Score (at 10 µM) |
|---|---|---|---|---|---|
| 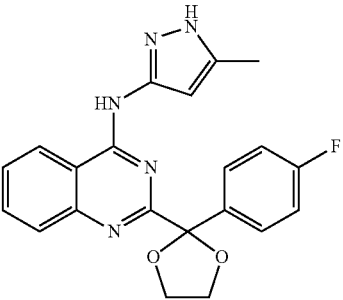 [SMILES: Cc1cc(Nc2nc(C3(c4ccc(F)cc4)OCCO3)nc3ccccc23)n[nH]1] | A | B | A | ND | B |
| 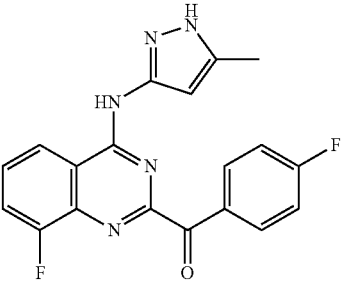 [SMILES: Cc1cc(Nc2nc(C(=O)c3ccc(F)cc3)nc3c(F)cccc23)n[nH]1] | B | C | B | ND | A |
| 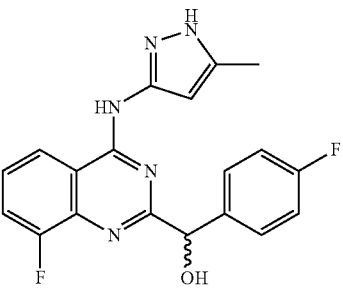 [SMILES: Cc1cc(Nc2nc(C(O)c3ccc(F)cc3)nc3c(F)cccc23)n[nH]1] | B | B | A | ND | A |
| 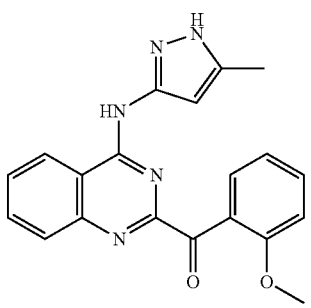 [SMILES: COc1ccccc1C(=O)c1nc(Nc2cc(C)[nH]n2)c2ccccc2n1] | B | C | B | ND | A |

TABLE 2-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: Aurora B (Kd) | S Score (at 10 μM) |
|---|---|---|---|---|---|
| [quinazoline with 4-(5-methyl-1H-pyrazol-3-ylamino), 2-((2-methoxyphenyl)(hydroxy)methyl)] | B | B | B | ND | A |
| [quinazoline with 4-(5-methyl-1H-pyrazol-3-ylamino), 2-((3-fluorophenyl)(hydroxy)methyl)] | B | B | B | ND | A |
| [quinazoline with 4-(5-methyl-1H-pyrazol-3-ylamino), 2-((4-fluorophenyl)(formamido)methyl)] | B | B | A | ND | A |
| [quinazoline with 4-(5-methyl-1H-pyrazol-3-ylamino), 2-((3,4-difluorophenyl)(hydroxy)methyl)] | B | A | A | ND | A |

TABLE 2-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: Aurora B (Kd) | S Score (at 10 µM) |
|---|---|---|---|---|---|
| (quinazoline with pyrazolylamino, CH(OH)-(3-Cl-4-F-phenyl)) | B | A | A | ND | B |
| (quinazoline with pyrazolylamino, CH(4-F-phenyl)-CH$_2$CN) | A | B | B | ND | A |
| (quinazoline with pyrazolylamino, CH(4-F-phenyl)-NH-cyclopropyl) | B | B | A | ND | A |
| (quinazoline with pyrazolylamino, CH(4-F-phenyl)-CH$_2$-S(O)$_2$-CH$_3$) | B | B | A | ND | A |

TABLE 2-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: Aurora B (Kd) | S Score (at 10 μM) |
|---|---|---|---|---|---|
| [quinazoline with 4-NH-(5-methyl-1H-pyrazol-3-yl), 2-position bearing CH(4-F-phenyl)CH2NH2] | C | B | B | ND | A |
| [quinazoline with 4-NH-(5-methyl-1H-pyrazol-3-yl), 2-position bearing C(D)(OH)(4-F-phenyl)] | A | A | A | ND | A |
| [quinazoline with 4-NH-(5-methoxy-1H-pyrazol-3-yl), 2-position bearing C(=O)(4-F-phenyl)] | B | B | A | ND | ND |
| [quinazoline with 4-NH-(5-ethyl-1H-pyrazol-3-yl), 2-position bearing CH(OH)(4-F-phenyl)] | ND | ND | A | ND | ND |

TABLE 2-continued

| Compound | Cell Assay: CS0017: CS TF-1 reporter assay: IC$_{50}$ | Binding Assay: JAK3 (active_KD, ENZ) | Binding Assay: JAK2 (active_KD) | Binding Assay: Aurora B (Kd) | S Score (at 10 µM) |
|---|---|---|---|---|---|
| [structure] | ND | ND | C | ND | ND |
| [structure] | ND | ND | C | ND | ND |
| [structure] | ND | ND | A | ND | ND |

In Tables 1 and 2,

CSTF-1 reporter assay IC$_{50}$ (nM): A≤100, 100<B≤500, C>500;

JAK2 Kd (nM): A≤1, 1<B≤10, C>10; JAK3 Kd (nM): A≤10, 10<B≤100, C>100;

AuroraB Kd (nM) A≤20, 20<B≤50, 50<C≤200 D>200

S score: A≤0.3, 0.3<B≤0.4, 0.4<C≤0.5, D>0.5; and ND=no data.

In certain embodiments, the compounds provided herein bind to JAK2 kinase with higher specificity as compared to non-mutant and non-JAK family kinases. For certain compounds provided herein, binding constants for less than 10 non-mutant and non-JAK family kinases are within 100-fold of the binding constant for JAK2 kinase for compounds provided herein. For certain compounds provided herein, binding constants for less than 8 non-mutant and non-JAK family kinases are within 100-fold of the binding constant for JAK2 kinase for compounds provided herein. For certain compounds provided herein, binding constants for 6 non-mutant and non-JAK family kinases are within 100-fold of the binding constant for JAK2 kinase.

Example 81

Dose Responsive Effects of a Compound of Formula I in Rat Type II Collagen-Induced Arthritis (CIA) Model On Day 0 of the experiment, female Lewis rats (Charles River) were injected subcutaneously at three different sites on the back each with 300 µL of bovine Type II collagen emulsified in Freund's incomplete adjuvant, for a total of 1.2 mg of collagen administered per animal. The animals received a boost at Day 6. Caliper measures of normal (pre-disease) right and left ankle joints were done on Day 8. Upon onset of arthritis (Day 9), the rats were randomized into treatment groups of 8 animals per each arthritic group (with 4 animals having been initially reserved for the normal control group). Starting on Day 9, a compound of Formula I was diluted in Pharmatek#6 and treatment was initiated with the oral administration of a compound of Formula I at 5 mg/kg, 20 mg/kg or 60 mg/kg BID at 12 hour intervals or at 60 mg/kg QD. The control arthritic groups included a vehicle control, a water control, a no treatment control and a positive control group given an oral administration of dexamethasone at 0.03 mg/kg QD. Treatment continued for a total of 6 days. Caliper measurements of the ankles were taken every day starting from Day 9 through Day 16. Results of the assay are provided in FIG. 1.

An exemplary compound of Formula I provided a statistically significant improvement in ankle thickness at ≥5 mg/kg BID as early as treatment Day 2. Maximum efficacy for the compound in the CIA rat model was observed at 60 mg/kg (QD or BID). A correlation between the clinical paw swelling score and histology was observed.

Figure 2:
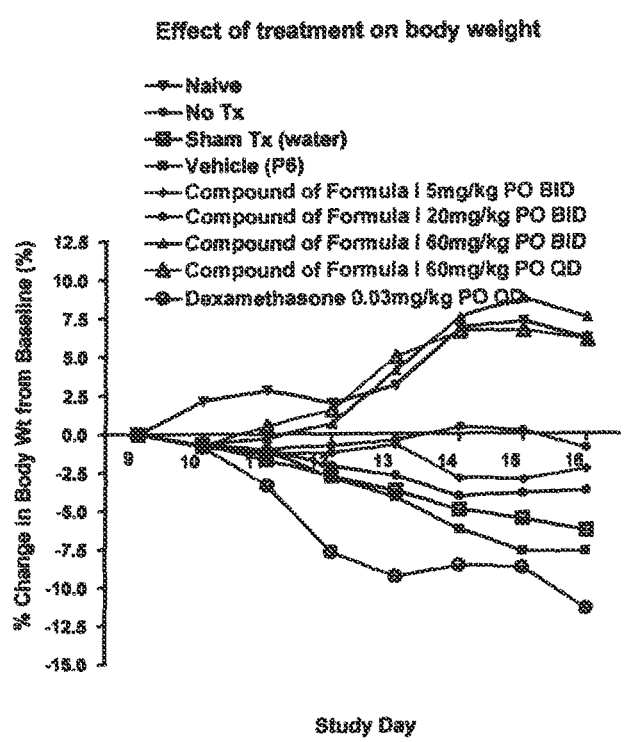
FIG. 2 provides effects of administration of various doses of a compound of Formula I and control on body weight in the rat Type II Collagen-Induced Arthritis (CIA) model.

Effect of the treatment on body weight of rats was measured from Day 9 through Day 16 as percent change in the body weight from the baseline. Results are provided in FIG. 2.

Example 82

In Vivo Efficacy Study in the Mouse TELJAK Mouse Model

Figure 3:
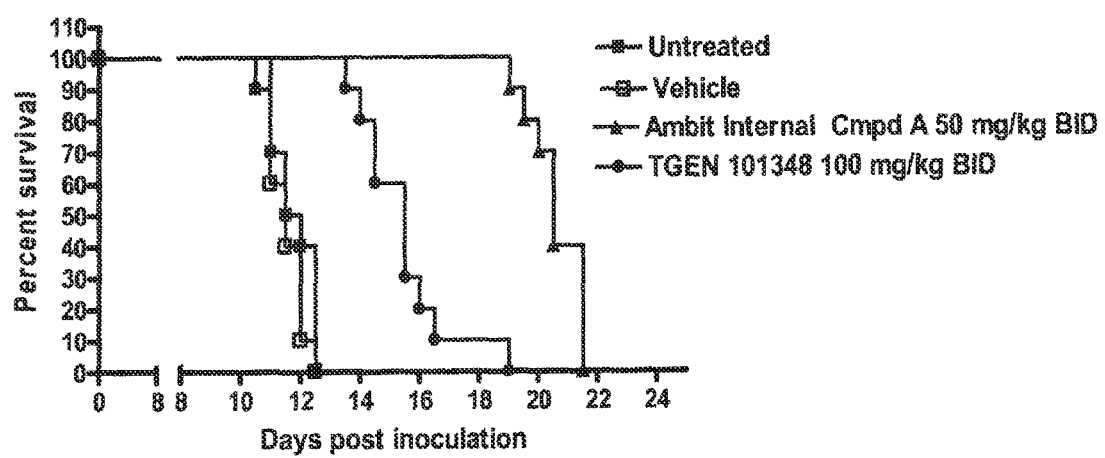
FIG. 3 provides a Kaplan Meier survival analysis for an Ambit internal compound, TGEN101348 and control in the mouse TELJAK mouse model.

This study was conducted to determine the effect of a selected compound of Formula I on tumor progression and survival. CB17 SCID mice (Harlan Laboratories) were inoculated with 5e5 TEL-JAK cells via tail vein on day 0. Cells were allowed to establish in the animal, and on day 3, dosing was initiated as follows: Vehicle (Pharmatek#6) administered 50 uL at BID to a first group, Ambit Internal Compound prepared in Pharmatek #6 and administered at 50 mg/kg BID to a second group and TGEN101348 prepared in Pharmatek #6 to a third group at 100 mg/kg BID. Each treatment group (16 animals per group) received a twice daily dosing for a two week period. An untreated group of 10 animals also served as control. FIG. 3 shows the results of the Kaplan Meier survival analysis.

Figure 4:
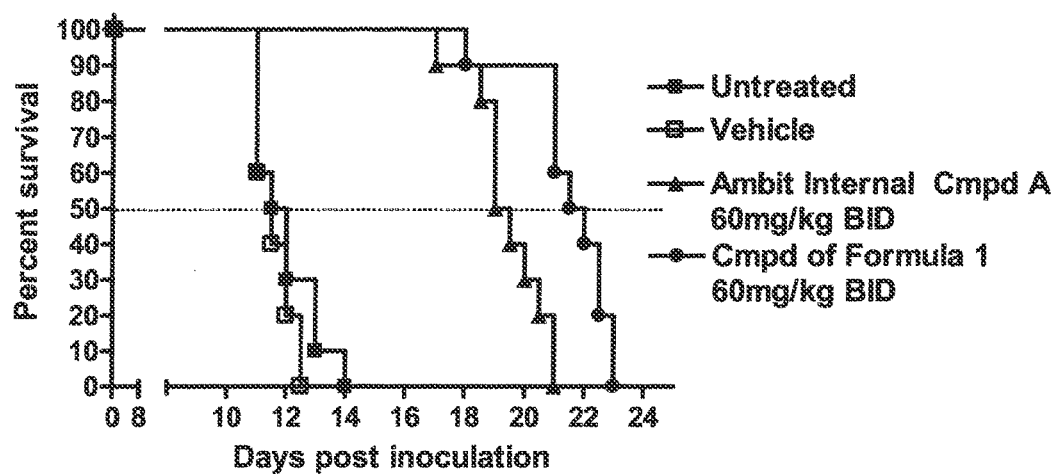
FIG. 4 provides a Kaplan Meier survival analysis for an Ambit internal compound, a compound of Formula I and control in the mouse TELJAK mouse model.

A second study was conducted using the same protocol, with the same controls and the following treatment groups: Ambit Internal Compound A prepared in Pharmatek #6 administered at 60 mg/kg BID and a selected compound of Formula I prepared in Pharmatek#6 at 60 mg/kg BID. FIG. 4 shows the results of the Kaplan Meier survival analysis.

The data shows that Ambit Internal Compound provides greater than 70% increased life span (ILS) while TGEN101348 provides 30% ILS. The selected compound of Formula I is shown to perform better than Ambit Internal Compound and is therefore expected to perform better than TGEN101348 preclinically.

Example 83

In Vivo Efficacy Study in the Mouse HELV617F Liquid Tumor Mouse Model

Figure 5:
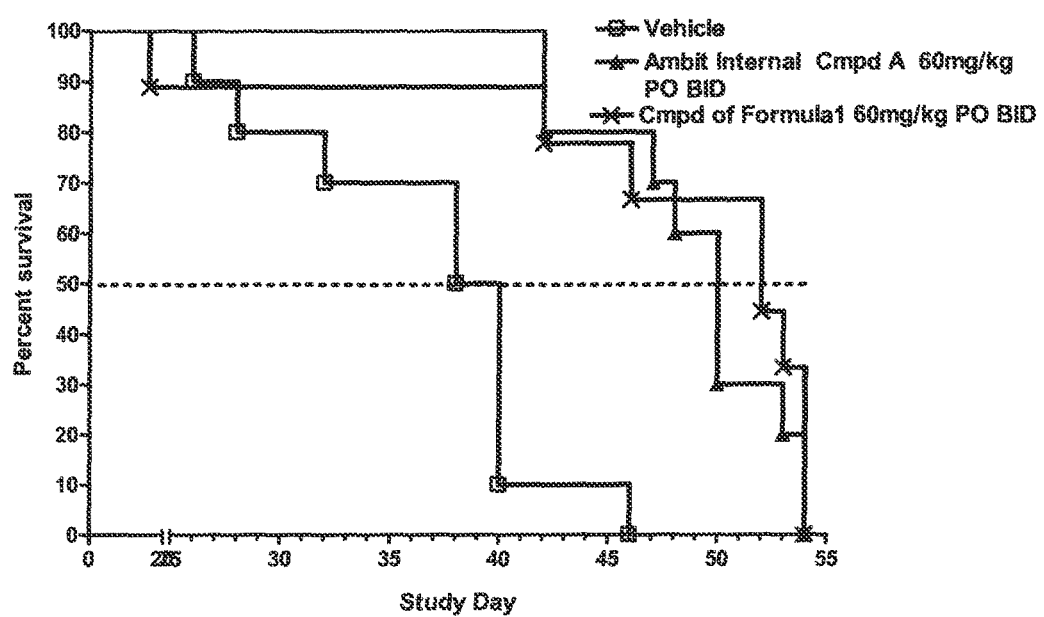
FIG. 5 provides a Kaplan Meier survival analysis for an Ambit internal compound, a compound of Formula I and control in the mouse HELV617F liquid tumor model.

This study was conducted to determine the effect of a selected compound of Formula I on tumor progression and survival. CB17 SCID mice (Charles River Labs) were pretreated with cyclophosphamide IP QD at 150 mg/kg for two consecutive days before being injected with cells. On Day 0, 75 mice were inoculated IV with 5e6 HEL 92.1.7 cells suspended in sterile saline. Animals were weighed on Day 8, and assigned to groups with similar mean body weights and similar standard deviations from the mean. Animals were dosed on Day 8 for a 21 day dosing period. Treatment groups were as follows (10 animals per group): First group was administered vehicle (Pharmatek#6), PO, BID; a second group was administered Ambit Internal Compound A prepared in Pharmatek#6, at 50 mg/kg PO, BID; and a third group was administered TGEN101348 prepared in Pharmatek#6, at 120 mg/kg PO, BID. An untreated group of 10 animals also served as control. FIG. 5 shows the results of the Kaplan Meier analysis.

Figure 6:
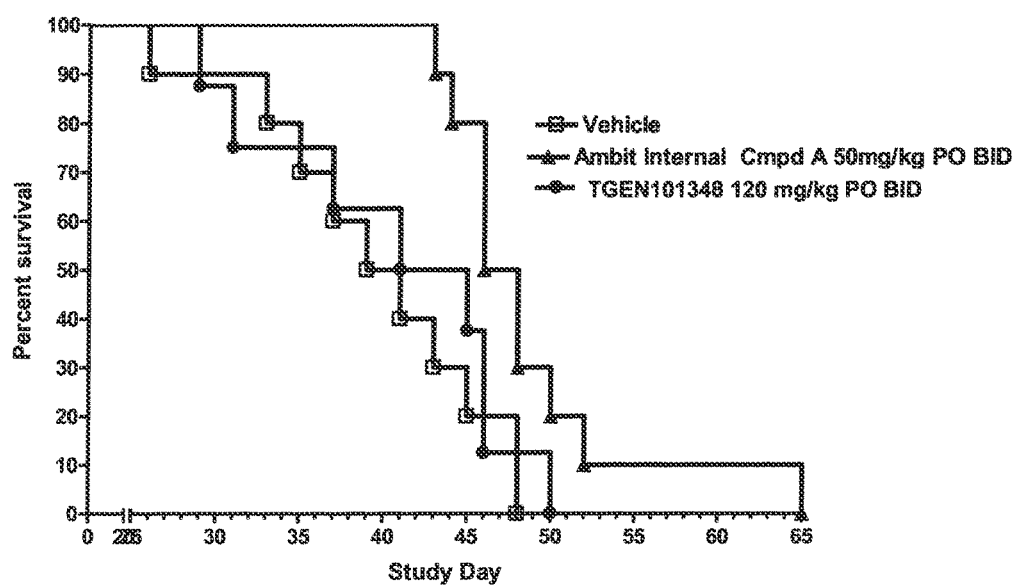
FIG. 6 provides a Kaplan Meier survival analysis for an Ambit internal compound, TGEN101348 and control in the mouse HELV617F liquid tumor model.

Another study was conducted using the same protocol, with the same controls and the following treatment groups: Ambit Internal Compound A prepared in Pharmatek #6 administered at 60 mg/kg BID and a selected compound of Formula I prepared in Pharmatek#6 at 60 mg/kg BID. FIG. 6 shows the results of the Kaplan Meier analysis. FIGS. 5 and 6 show that the Ambit Internal Compound and the selected compound of Formula I provide approximately a 30% increased life span (ILS) while TGEN101348 provides no survival benefit (approximately 5% ILS).

Example 84

Other Cell-Based Assays

Compounds of Formula I were also tested in other cell-based assays, for example, pSTAT5 electrochemiluminescence immunoassays (Meso Scale Discovery) in csTF-1 and HEL cell lines, and found to be potent in those assays. The effects of the compounds of Formula I on BaF3 cell proliferation were also tested using the CellTiter-Blue® assay (Promega).

Inhibition of DTH Response to Ovalbumin in CD-1 Mice

A study was conducted to evaluate the effect of a compound of Formula I in a mouse model of ovalbumin-induced delayed-type hypersensitivity (type IV hypersensitivity, DTH) using two dosing schedules. Delayed-type hypersensitivity is characterized by antigen specific T-cell production of cytokines, resulting in increased vascular permeability, infiltration by mononuclear and polymorphonuclear cells, edema and induration. Primary exposure to antigen (sensitization phase) elicits development of antigen specific memory T-cells that are activated upon secondary exposure (challenge).

The biphasic nature of Type IV hypersensitivity provides a model to differentiate the immunopharmacological activity of compounds with immunomodulatory properties. Compounds that are immunosuppressive (suppress the primary immune response) would be expected to be effective when administered during the sensitization phase. Compounds that are anti-inflammatory would be expected to be effective when administered during the recall phase, preventing or down regulating the antigen recognition and/or activation of memory T-cells, or by interrupting the secondary signaling cascades induced by T-cell produced cytokines and growth factors (thereby reducing/preventing increased vascular permeability and inflammatory cell motility/recruitment). Compounds that are immunostimulatory would be expected to increase the DTH response when administered during sensitization (increased antigen presentation or memory T-cell expansion), or during recall phase (increased T-cell activation and cytokine/chemokine production, and/or inflammatory cell motility/recruitment/activation).

Since modifications will be apparent to those of skill in the art, it is intended that the claimed subject matter be limited only by the scope of the appended claims.

What is claimed is:
1. A method of treatment of an inflammatory or autoimmune disease comprising administering a therapeutically effective amount of a compound having formula (I):

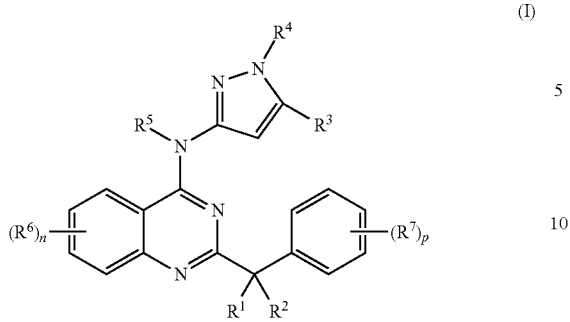

(I)

or pharmaceutically acceptable salts, solvates or hydrates thereof, wherein $R^1$ and $R^2$ are selected from (i), (ii), (iii), (iv) and (v) as follows:
 (i) $R^1$ and $R^2$ together form =O, =S, =$NR^9$ or =$CR^{10}R^{11}$;
 (ii) $R^1$ and $R^2$ are both —$OR^8$, or $R^1$ and $R^2$, together with the carbon atom to which they are attached, form dioxacycloalkyl;
 (iii) $R^1$ is hydrogen or halo; and $R^2$ is halo; and
 (iv) $R^1$ is alkyl, alkenyl, alkynyl, cycloalkyl or aryl, wherein the alkyl, alkenyl, alkynyl, cycloalkyl and aryl is optionally substituted with one or more substituents selected from halo, cyano, alkyl, —$R^x$-$OR^w$, —$R^xS(O)_qR^v$, —$R^xNR^yR^z$ and —$C(O)OR^w$; and $R^2$ is hydrogen, halo or —$OR^8$; and
 (v) $R^1$ is halo, deutero, —$OR^{12}$, —$NR^{13}R^{14}$, or —$S(O)_qR^{15}$; and $R^2$ is hydrogen, deutero, alkyl, alkenyl, alkynyl, cycloalkyl or aryl, wherein the alkyl, alkenyl, alkynyl, cycloalkyl and aryl, is optionally substituted with one or more substitutents selected from halo, cyano, alkyl, —$R^xOR^w$, —$R^xS(O)_qR^v$ and —$R^xNR^yR^z$;

$R^3$ is hydrogen, halo, alkyl, cyano, haloalkyl, cycloalkyl, cycloalkylalkyl, hydroxy or alkoxy;

$R^4$ and $R^5$ are each independently hydrogen or alkyl;

each $R^6$ is independently selected from halo, alkyl, alkenyl, alkynyl, haloalkyl, cycloalkyl, —$R^xOR^{18}$, —$R^xNR^{19}R^{20}$, and —$R^xS(O)_qR^v$;

each $R^7$ is independently halo, alkyl, haloalkyl or —$R^x$-$OR^w$;

$R^8$ is alkyl, alkenyl or alkynyl;

$R^9$ is hydrogen, alkyl, haloalkyl, hydroxy, alkoxy or amino;

$R^{10}$ is hydrogen or alkyl;

$R^{11}$ is hydrogen, alkyl, haloalkyl or —$C(O)OR^8$;

$R^{12}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —$C(O)R^v$, —$C(O)OR^w$ and —$C(O)NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;

$R^{13}$ and $R^{14}$ are selected as follows:
 (i) $R^{13}$ is hydrogen or alkyl; and $R^{14}$ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —$C(O)R^v$, —$C(O)OR^w$, —$C(O)NR^yR^z$ and —$S(O)_qR^v$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio; or
 (ii) $R^{13}$ and $R^{14}$, together with the nitrogen atom to which they are attached, form heterocyclyl or heteroaryl wherein the heterocyclyl or heteroaryl is optionally substituted with one or more substituents independently selected from halo, alkyl, hydroxy, alkoxy, amino and alkylthio and wherein the heterocyclyl is also optionally substituted with oxo;

$R^{15}$ is alkyl, alkenyl, alkynyl, cycloalkyl, cycloalkylalkyl, heterocyclyl, heterocyclylalkyl, aryl, aralkyl, heteroaryl, heteroaralkyl, —$C(O)NR^yR^z$ or —$NR^yR^z$, wherein the alkyl, alkenyl, alkynyl, cycloalkyl, cycloalkylalkyl, heterocyclyl, heterocyclylalkyl, aryl, aralkyl, heteroaryl and heteroaralkyl are each optionally substituted with one or more substituents independently selected from halo, oxo, alkyl, hydroxy, alkoxy, amino and alkylthio;

$R^{18}$ is hydrogen, alkyl, haloalkyl, hydroxy$C_{2-6}$alkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups $Q^1$, each $Q^1$ independently selected from alkyl, hydroxyl, halo, haloalkyl, alkoxy, aryloxy, alkoxyalkyl, alkoxycarbonyl, alkoxysulfonyl, hydroxycarbonyl, cycloalkyl, heterocyclyl, aryl, heteroaryl, haloaryl and amino;

$R^{19}$ and $R^{20}$ are selected as follows:
 (i) $R^{19}$ and $R^{20}$ are each independently hydrogen or alkyl; or
 (ii) $R^{19}$ and $R^{20}$, together with the nitrogen atom to which they are attached, form a heterocyclyl or heteroaryl which is optionally substituted with 1 to 2 groups each independently selected from halo, alkyl, haloalkyl, hydroxyl and alkoxy;

each $R^x$ is independently alkylene or a direct bond;

$R^v$ is hydrogen, alkyl, alkenyl or alkynyl;

$R^w$ is independently hydrogen, alkyl, alkenyl, alkynyl or haloalkyl;

$R^y$ and $R^z$ are selected as follows:
 (i) $R^y$ and $R^z$ are each independently hydrogen, alkyl, alkenyl, alkynyl, cycloalkyl or haloalkyl;
 (ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy;

n is 0-4;

p is 0-5; and each q is independently 0, 1 or 2, wherein the disease is selected from graft-versus-host disease, kidney disease, multiple sclerosis, thyroiditis, type 1 diabetes, psoriasis, inflammatory bowel disease, Crohn's disease, ulcerative colitis, systemic lupus erythematosis, arthritis, osteoarthritis, rheumatoid arthritis, osteoporosis and asthma.

2. The method of claim 1, wherein the disease is asthma.

3. The method of claim 1, wherein the compound has formula (II)

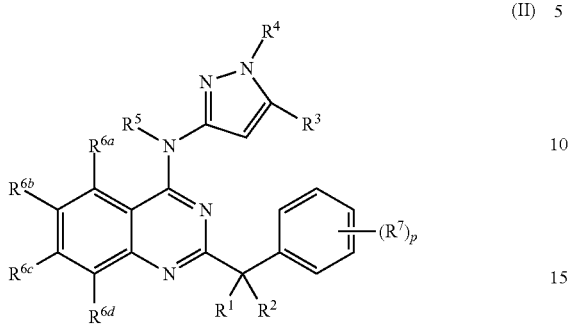

(II)

or a pharmaceutically acceptable salt, solvate or hydrate thereof, wherein
$R^1$ and $R^2$ are selected from (i), (ii), (iii), (iv) and (v) as follows:
(i) $R^1$ and $R^2$ together form =O, =S, =NR$^9$ or =CR$^{10}$R$^{11}$;
(ii) $R^1$ and $R^2$, are both —OR$^8$, or $R^1$ and $R^2$, together with the carbon atom to which they are attached, form dioxacycloalkyl;
(iii) $R^1$ is hydrogen or halo, and $R^2$ is halo;
(iv) $R^1$ is alkyl, alkenyl, alkynyl, cycloalkyl or aryl, wherein the alkyl, alkenyl, alkynyl, cycloalkyl and aryl is optionally substituted with one or more substituents selected from halo, alkyl, —R$^x$OR$^w$, —R$^x$S(O)$_q$R$^v$ and —R$^x$NR$^y$R$^z$, and $R^2$ is hydrogen, halo or —OR$^8$; and
(v) $R^1$ is halo, —OR$^{12}$, —NR$^{13}$R$^{14}$, or —S(O)$_q$R$^{15}$, and $R^2$ is hydrogen, alkyl, alkenyl, alkynyl, cycloalkyl or aryl, wherein the alkyl, alkenyl, alkynyl, cycloalkyl and aryl is optionally substituted with one or more substituents selected from halo, alkyl, —R$^x$OR$^w$, —R$^x$S(O)$_q$R$^v$ and —R$^x$NR$^y$R$^z$;
$R^3$ is hydrogen, alkyl or, cycloalkyl;
$R^4$ and $R^5$ are each independently hydrogen or alkyl;
$R^{6a}$, $R^{6b}$, $R^{6c}$, and $R^{6d}$ are each independently selected from halo, alkyl, haloalkyl and —R$^x$OR$^{18}$;
$R^7$ is halo, alkyl, haloalkyl or —R$^x$OR$^w$;
$R^8$ is alkyl, alkenyl or alkynyl;
$R^9$ is hydrogen, alkyl, haloalkyl, hydroxy, alkoxy or amino;
$R^{10}$ is hydrogen or alkyl;
$R^{11}$ is hydrogen, alkyl, haloalkyl or —C(O)OR$^8$;
each $R^{12}$ is independently hydrogen, alkyl, haloalkyl, hydroxyalkyl, alkoxyalkyl, aminoalkyl, thioalkyl, heterocyclylalkyl or —C(O)NR$^y$R$^z$;
$R^{13}$ and $R^{14}$ are selected as follows:
(i) $R^{13}$ is hydrogen or alkyl, and $R^{14}$ is selected from hydrogen, alkyl, haloalkyl, hydroxyalkyl, alkoxyalkyl, aminoalkyl, thioalkyl, heterocyclylalkyl, —C(O)OR$^w$, —C(O)NR$^y$R$^z$ and —S(O)$_q$R$^v$; or
(ii) $R^{13}$ and $R^{14}$, together with the nitrogen atom to which they are attached, form heterocyclyl optionally substituted with one more substituents independently selected from halo, oxo, alkyl, hydroxy, alkoxy, amino and alkylthio;
$R^{15}$ is selected from alkyl, haloalkyl, hydroxyalkyl, alkoxyalkyl, aminoalkyl, thioalkyl, heterocycylalkyl, —C(O)NR$^y$R$^z$ or —NR$^y$R$^z$;

$R^{18}$ is hydrogen, alkyl, haloalkyl, hydroxyC$_{2-6}$alkyl, alkenyl, alkynyl, cycloalkyl, cycloalkylalkyl, heterocyclyl, heterocyclylalkyl, aryl, aralkyl, heteroaryl or heteroarylalkyl; wherein $R^{18}$ is optionally substituted with 1 to 3 groups Q$^1$, where each Q$^1$ independently selected from alkyl, hydroxyl, halo, haloalkyl, alkoxy, aryloxy, alkoxyalkyl, alkoxycarbonyl, hydroxycarbonyl, cycloalkyl, heterocyclyl, aryl, heteroaryl, haloaryl and amino;
$R^v$ is alkyl, alkenyl or alkynyl;
each $R^x$ is independently alkylene or a direct bond;
$R^w$ is independently hydrogen or alkyl;
$R^y$ and $R^z$ are selected as follows:
(i) $R^y$ and $R^z$ are each independently hydrogen, alkyl, alkenyl, alkynyl, cycloalkyl or haloalkyl; or
(ii) $R^y$ and $R^z$, together with the nitrogen atom to which they are attached, form a heterocyclyl or heteroaryl which is optionally substituted with 1 to 2 groups each independently selected from halo, alkyl, haloalkyl, hydroxyl and alkoxy; and
each q is independently 0, 1 or 2.

4. The method of claim 1, wherein $R^1$ and $R^2$ together form =O.

5. The method of claim 1, wherein $R^1$ is hydrogen or fluoro, and $R^2$ is fluoro.

6. The method of claim 1, wherein $R^1$ is hydroxyl, methoxy, amino or methoxycarbonylamino, and $R^2$ is hydrogen, phenyl or fluorophenyl.

7. The method of claim 1, wherein $R^3$ is hydrogen, alkyl or alkoxy.

8. The method of claim 1, wherein each $R^6$ is independently selected from halo, alkyl, hydroxyl and alkoxy.

9. The method of claim 1, wherein $R^7$ is halo.

10. The method of claim 1, wherein p is 1 or 2.

11. The method of claim 1, wherein the compound has formula (III) or (IIIa)

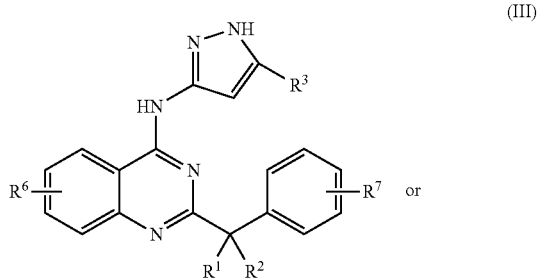

(III)

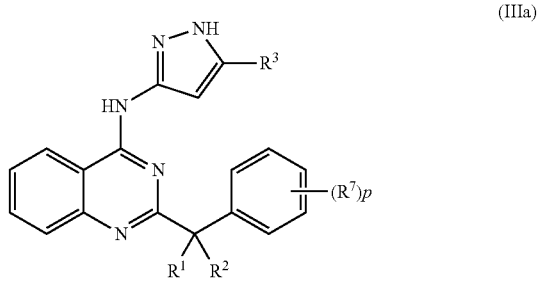

(IIIa)

or a pharmaceutically acceptable salt thereof, wherein:
$R^1$ and $R^2$ are selected from (i) and (ii) as follows:
(i) $R^1$ and $R^2$ are both alkoxy or $R^1$ and $R^2$, together form =O; and
(ii) $R^1$ is —OR$^{12}$ or —NR$^{13}$R$^{14}$, and $R^2$ is hydrogen, alkyl, aryl or haloaryl;

R¹² is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, —C(O)R$^v$, —C(O)OR$^w$ and —C(O)NR$^y$R$^z$, wherein the alkyl, alkenyl, alkynyl, cycloalkyl, cycloalkylalkyl, heterocyclyl, heterocyclylalkyl, aryl, aralkyl, heteroaryl or heteroaralkyl are each optionally substituted with one or more substituents independently selected from halo, oxo, alkyl, hydroxy, alkoxy, amino and alkylthio;

R¹³ and R¹⁴ are selected as follows:
(i) R¹³ is hydrogen or alkyl and R¹⁴ is selected from hydrogen, alkyl, alkenyl, alkynyl, cycloalkyl, cycloalkylalkyl, heterocyclyl, heterocyclylalkyl, aryl, aralkyl, heteroaryl, heteroaralkyl, alkoxy, —C(O)R$^v$, —C(O)OR$^w$, —C(O)NR$^y$R$^z$ and —S(O)$_q$R$^v$ wherein the alkyl, alkenyl, alkynyl, cycloalkyl, cycloalkylalkyl, heterocyclyl, heterocyclylalkyl, aryl, aralkyl, heteroaryl or heteroaralkyl are each optionally substituted with one or more substituents independently selected from halo, oxo, alkyl, hydroxy, alkoxy, amino and alkylthio; or
(ii) R¹³ and R¹⁴, together with the nitrogen atom to which they are attached, form heterocyclyl or heteroaryl wherein the heterocyclyl or heteroaryl is optionally substituted with one or more substituents independently selected from halo, alkyl, hydroxy, alkoxy, amino and alkylthio and wherein the heterocyclyl is also optionally substituted with oxo;

R³ is hydrogen or alkyl;
R⁶ is selected from halo, alkyl, haloalkyl and —R$^x$OR¹⁸; where R¹⁸ is hydrogen, alkyl, haloalkyl, hydroxyalkyl or heterocyclyl; wherein R¹⁸ is optionally substituted with group Q', where Q¹ is selected from hydroxyl, alkoxy, alkoxycarbonyl, hydroxycarbonyl, heterocyclyl and amino;
R⁷ is halo, alkyl, haloalkyl, hydroxyl or alkoxy;
R$^v$ is hydrogen, alkyl, alkenyl or alkynyl;
R$^w$ is independently hydrogen, alkyl, alkenyl, alkynyl or haloalkyl;
R$^y$ and R$^z$ are selected as follows:
(i) R$^y$ and R$^z$ are each independently hydrogen, alkyl, alkenyl, alkynyl, cycloalkyl or haloalkyl; or
(ii) R$^y$ and R$^z$, together with the nitrogen atom to which they are attached, form a heterocyclyl or heteroaryl which is optionally substituted with 1 to 2 groups each independently selected from halo, alkyl, haloalkyl, hydroxyl and alkoxy;
and q is 0, 1 or 2.

12. The method of claim 1, wherein the compound has formula (IV) or (IVa)

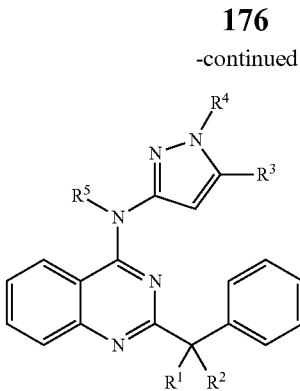

(IV)

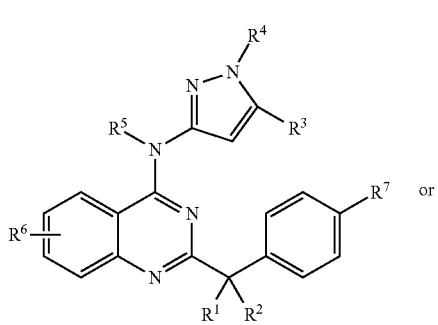

(IVa)

or a pharmaceutically acceptable salt thereof.

13. The method of claim 1, wherein the compound has formula (VI)

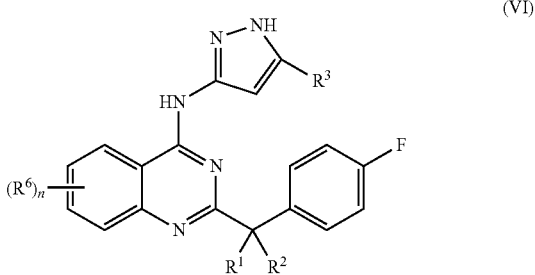

(VI)

or a pharmaceutically acceptable salt thereof.

14. The method of claim 1, wherein the compound has formula (VII)

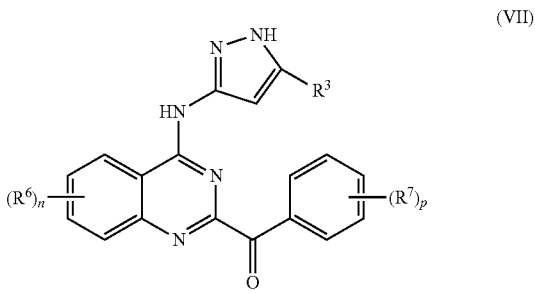

(VII)

or a pharmaceutically acceptable salt thereof.

15. The method of claim 1, wherein the compound has formula (VIII)

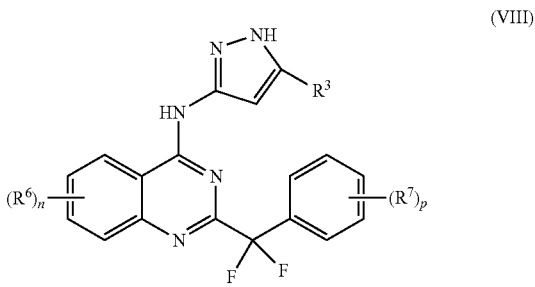

(VIII)

or a pharmaceutically acceptable salt thereof.

16. The method of claim 1, wherein the compound has formula (IX)

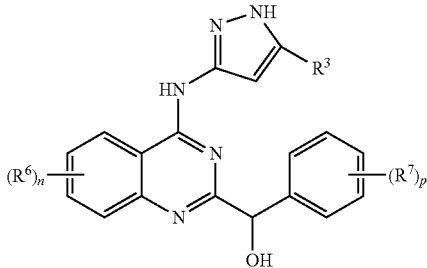

or a pharmaceutically acceptable salt thereof.

17. The method of claim 1, wherein the compound has formula (X)

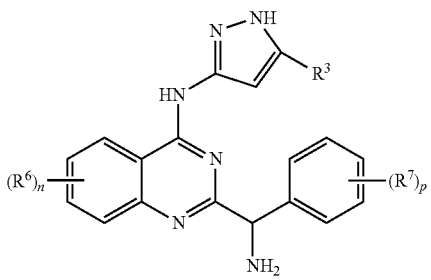

or a pharmaceutically acceptable salt thereof.

18. The method of claim 1, wherein the compound is selected from:
- (3-fluorophenyl)(4-(5-methyl-1H-pyrazol-3-ylamino) quinazolin-2-yl)methanone;
- (4-(1H-pyrazol-3-ylamino)quinazolin-2-yl)(3-fluorophenyl)methanone;
- (4-fluorophenyl)(4-(5-methyl-1H-pyrazol-3-ylamino) quinazolin-2-yl)methanone;
- (4-(1H-pyrazol-3-ylamino)quinazolin-2-yl)(4-fluorophenyl)methanone;
- (4-(1H-pyrazol-3-ylamino)quinazolin-2-yl)(2-methoxyphenyl) methanone;
- (4-(1H-pyrazol-3-ylamino)quinazolin-2-yl)(4-fluorophenyl)methanol;
- 2-(fluoro(4-fluorophenyl)methyl)-N-(1H-pyrazol-3-yl) quinazolin-4-amine;
- 2-(difluoro(4-fluorophenyl)methyl)-N-(5-methyl-1H-pyrazol-3-yl)quinazolin-4-amine;
- 2-(difluoro(4-fluorophenyl)methyl)-N-(1H-pyrazol-3-yl) quinazolin-4-amine;
- N-(5-cyclopropyl-1H-pyrazol-3-yl)-2-(difluoro(4-fluorophenyl)methyl) quinazolin-4-amine;
- 3-(2-(4-fluorobenzoyl)quinazolin-4-ylamino)-1H-pyrazole-5-carbonitrile;
- (4-fluorophenyl)(4-(5-methyl-1H-pyrazol-3-ylamino) quinazolin-2-yl)methanol;
- 2((4-fluorophenyl)(methoxy)methyl)-N-(5-methyl-1H-pyrazol-3-yl)quinazolin-4-amine;
- 2-(amino(4-fluorophenyl)methyl)-N-(5-methyl-1H-pyrazol-3-yl)quinazolin-4-amine;
- 3-(2-((4-fluorophenyl)(hydroxy)methyl)quinazolin-4-ylamino)-1H-pyrazole-5-carbonitrile;
- (5-fluoro-4-(5-methyl-1H-pyrazol-3-ylamino) quinazolin-2-yl) (4-fluorophenyl) methanol;
- (4-fluorophenyl) (4-(5-methyl-1H-pyrazol-3-ylamino)-7-(trifluoromethyl) quinazolin-2-yl) methanone;
- (4-fluorophenyl) (4-(5-methyl-1H-pyrazol-3-ylamino)-7-(trifluoromethyl) quinazolin-2-yl) methanol;
- (7-fluoro-4-(5-methyl-1H-pyrazol-3-ylamino)quinazolin-2-yl)(4-fluorophenyl)methanone;
- 2-(difluoro(4-fluorophenyl)methyl)-7-fluoro-N-(5-methyl-1H-pyrazol-3-yl)quinazolin-4-amine;
- 2-(difluoro(4-fluorophenyl)methyl)-7-fluoro-N-(1H-pyrazol-3-yl) quinazolin-4-amine;
- (4-(1H-pyrazol-3-ylamino)-7-iodoquinazolin-2-yl)(4-fluorophenyl)methanone;
- (4-(1H-pyrazol-3-ylamino)-7-iodoquinazolin-2-yl)(4-fluorophenyl)methanol;
- (4-fluorophenyl)(7-methyl-4-(5-methyl-1H-pyrazol-3-ylamino)quinazolin-2-yl)methanone;
- (4-fluorophenyl)(7-methyl-4-(5-methyl-1H-pyrazol-3-ylamino)quinazolin-2-yl)methanol;
- 2-(difluoro(4-fluorophenyl)methyl)-7-methyl-N-(5-methyl-1H-pyrazol-3-yl)quinazolin-4-amine;
- 2-(difluoro(4-fluorophenyl)methyl)-7-methyl-N-(1H-pyrazol-3-yl)quinazolin-4-amine;
- (4-(1H-pyrazol-3-ylamino)-7-methoxyquinazolin-2-yl) (4-fluorophenyl)methanone;
- (4-(1H-pyrazol-3-ylamino)-7-methoxyquinazolin-2-yl) (4-fluorophenyl)methanol;
- (4-fluorophenyl)(7-methoxy-4-(5-methyl-1H-pyrazol-3-ylamino)quinazolin-2-yl)methanone;
- (4-fluorophenyl)(7-methoxy-4-(5-methyl-1H-pyrazol-3-ylamino)quinazolin-2-yl)methanol;
- 2-(difluoro(4-fluorophenyl)methyl)-7-methoxy-N-(5-methyl-1H-pyrazol-3-yl)quinazolin-4-amine;
- 2-(difluoro(4-fluorophenyl)methyl)-7-methoxy-N-(1H-pyrazol-3-yl)quinazolin-4-amine;
- 2-(difluoro(4-fluorophenyl)methyl)-8-fluoro-N-(5-methyl-1H-pyrazol-3-yl)quinazolin-4-amine;
- (4-(1H-pyrazol-3-ylamino)-8-methoxyquinazolin-2-yl) (4-fluorophenyl)methanone;
- 2-((4-fluorophenyl)(hydroxy)methyl)-4-(5-methyl-1H-pyrazol-3-ylamino)quinazolin-7-ol;
- (4-fluorophenyl)(7-hydroxy-4-(5-methyl-1H-pyrazol-3-ylamino)quinazolin-2-yl)methanone;
- (4-fluorophenyl)(4-(5-methyl-1H-pyrazol-3-ylamino)-7-(2-morpholinoethoxy)quinazolin-2-yl)methanol;
- 2-(2-((4-fluorophenyl)(hydroxy)methyl)-4-(5-methyl-1H-pyrazol-3-ylamino)quinazolin-7-yloxy)ethanol;
- 3-(2-((4-fluorophenyl)(hydroxy)methyl)-4-(5-methyl-1H-pyrazol-3-ylamino)quinazolin-7-yloxy)propan-1-ol;
- (4-fluorophenyl)(4-(5-methyl-1H-pyrazol-3-ylamino)-7-(piperidin-4-yloxy)quinazolin-2-yl)methanol;
- (4-fluorophenyl)(7-(2-methoxyethoxy)-4-(5-methyl-1H-pyrazol-3-ylamino)quinazolin-2-yl)methanol;
- tert-butyl 2-(2-((4-fluorophenyl)(hydroxy)methyl)-4-(5-methyl-1H-pyrazol-3-ylamino)quinazolin-7-yloxy)acetate;
- 2-(2-((4-fluorophenyl)(hydroxy)methyl)-4-(5-methyl-1H-pyrazol-3-ylamino)quinazolin-7-yloxy)acetic acid;
- {(4-fluoro-phenyl)-[4-(5-methyl-1H-pyrazol-3-ylamino)-quinazolin-2-yl]-methyl}-carbamic acid methyl ester;
- bis-(4-fluoro-phenyl)-[4-(5-methyl-1H-pyrazol-3-ylamino)-quinazolin-2-yl]-methanol;

methyl (4-fluorophenyl)(4-(5-methyl-4H-pyrazol-3-ylamino) quinazolin-2-yl) methylcarbamate;
(4-fluorophenyl)(8-methyl-4-(5-methyl-1H-pyrazol-3-ylamino)quinazolin-2-yl)methanol;
(7-fluoro-4-(5-methyl-1H-pyrazol-3-ylamino)quinazolin-2-yl)(4-fluorophenyl)methanol;
(4-(1H-pyrazol-3-ylamino)quinazolin-2-yl)bis(4-fluorophenyl)methanol;
(2-(difluoro(4-fluorophenyl)methyl)-4-(5-methyl-1H-pyrazol-3-ylamino)quinazolin-7-yl)methanol;
2-(difluoro(4-fluorophenyl)methyl)-N-(5-methyl-1H-pyrazol-3-yl)-7-(methylsulfonylmethyl)quinazolin-4-amine;
2-(Difluoro(4-fluorophenyl)methyl)-7-(ethoxymethyl)-N-(5-methyl-1H-pyrazol-3-yl)quinazolin-4-amine;
(7-chloro-4-(5-methyl-1H-pyrazol-3-ylamino)quinazolin-2-yl)(4-fluorophenyl)methanol;
(6-fluoro-4-(5-methyl-1H-pyrazol-3-ylamino)quinazolin-2-yl)(4-fluorophenyl)methanone-(6-fluoro-4-(5-methyl-1H-pyrazol-3-ylamino)quinazolin-2-yl)(4-fluorophenyl)methanol;
(4-(1H-pyrazol-3-ylamino)-6-fluoroquinazolin-2-yl)(4-fluorophenyl)methanol;
(7-bromo-4-(5-methyl-1H-pyrazol-3-ylamino)quinazolin-2-yl)(4-fluorophenyl)methanone;
(7-bromo-4-(5-methyl-1H-pyrazol-3-ylamino)quinazolin-2-yl)(4-fluorophenyl)methanol;
(4-(1H-pyrazol-3-ylamino)-7-bromoquinazolin-2-yl)(4-fluorophenyl)methanol;
2-(2-(4-fluorophenyl)-1,3-dioxolan-2-yl)-N-(5-methyl-1H-pyrazol-3-yl)quinazolin-4-amine;
(8-fluoro-4-(5-methyl-1H-pyrazol-3-ylamino)quinazolin-2-yl)(4-fluorophenyl)methanone;
(8-fluoro-4-(5-methyl-1H-pyrazol-3-ylamino)quinazolin-2-yl)(4-fluorophenyl)methanol;
(2-methoxyphenyl)(4-(5-methyl-1H-pyrazol-3-ylamino)quinazolin-2-yl)methanone;
(2-methoxyphenyl)(4-(5-methyl-1H-pyrazol-3-ylamino)quinazolin-2-yl)methanol;
(3-fluorophenyl)(4-(5-methyl-1H-pyrazol-3-ylamino)quinazolin-2-yl)methanol;
N-((4-fluorophenyl)(4-(5-methyl-1H-pyrazol-3-ylamino)quinazolin-2-yl)methyl)formamide;
(3,4-difluorophenyl)(4-(5-methyl-1H-pyrazol-3-ylamino)quinazolin-2-yl)methanol;
(3-chloro-4-fluorophenyl)(4-(5-methyl-1H-pyrazol-3-ylamino)quinazolin-2-yl)methanol;
3-(4-fluorophenyl)-3-(4-(5-methyl-1H-pyrazol-3-ylamino)quinazolin-2-yl)propanenitrile;
2-((cyclopropylamino)(4-fluorophenyl)methyl)-N-(5-methyl-1H-pyrazol-3-yl)quinazolin-4-amine;
2-(1-(4-fluorophenyl)-2-(methylsulfonyl)ethyl)-N-(5-methyl-1H-pyrazol-3-yl)quinazolin-4-amine;
2-(3-amino-1-(4-fluorophenyl)propyl)-N-(5-methyl-1H-pyrazol-3-yl)quinazolin-4-amine;
(4-fluorophenyl)(4-(5-methyl-1H-pyrazol-3-ylamino)quinazolin-2-yl)methanol-1-d;
(4-fluorophenyl)(4-(5-methoxy-1H-pyrazol-3-ylamino)quinazolin-2-yl)methanone;
(4-(5-ethyl-1H-pyrazol-3-ylamino)quinazolin-2-yl)(4-fluorophenyl)methanol;
(4-Fluorophenyl)(4-(5-methoxy-1H-pyrazol-3-ylamino)quinazolin-2-yl)methanol;
(4-fluoro-3-methoxyphenyl)(4-(5-methyl-1H-pyrazol-3-ylamino)quinazolin-2-yl)methanone;
(4-fluoro-3-hydroxyphenyl)(4-(5-methyl-1H-pyrazol-3-ylamino)quinazolin-2-yl)methanone; and
(2-fluoro-5-(hydroxy(4-(5-methyl-1H-pyrazol-3-ylamino)quinazolin-2-yl)methyl)phenol acetate.

19. The method of claim 1, further comprising administering a second pharmaceutical agent selected from anti-inflammatory agent, immunomodulatory agent and immunosuppressive agent.

* * * * *